US012611447B2

(12) United States Patent
Petryk et al.

(10) Patent No.: US 12,611,447 B2
(45) Date of Patent: Apr. 28, 2026

(54) METHODS FOR TREATING BONE MINERALIZATION DISORDERS

(71) Applicant: Alexion Pharmaceuticals, Inc., Boston, MA (US)

(72) Inventors: Anna Petryk, Boston, MA (US); Loredana Cuccia, Newton, MA (US)

(73) Assignee: Alexion Pharmaceuticals, Inc., Boston, MA (US)

( * ) Notice: Subject to any disclaimer, the term of this patent is extended or adjusted under 35 U.S.C. 154(b) by 554 days.

(21) Appl. No.: 18/024,404

(22) PCT Filed: Sep. 2, 2021

(86) PCT No.: PCT/US2021/048792
§ 371 (c)(1),
(2) Date: Mar. 2, 2023

(87) PCT Pub. No.: WO2022/051452
PCT Pub. Date: Mar. 10, 2022

(65) Prior Publication Data
US 2023/0372456 A1    Nov. 23, 2023

Related U.S. Application Data

(60) Provisional application No. 63/074,917, filed on Sep. 4, 2020.

(51) Int. Cl.
*A61K 38/46*        (2006.01)
*A61B 5/00*         (2006.01)
*A61B 5/11*         (2006.01)

(52) U.S. Cl.
CPC .......... *A61K 38/465* (2013.01); *A61B 5/1118* (2013.01); *A61B 5/4848* (2013.01); *A61B 5/681* (2013.01); *C12Y 301/03001* (2013.01)

(58) Field of Classification Search
None
See application file for complete search history.

(56) References Cited

U.S. PATENT DOCUMENTS

| | | |
|---|---|---|
| 5,336,759 A | 8/1994 | Matsuo et al. |
| 5,338,830 A | 8/1994 | Matsuo et al. |
| 5,340,920 A | 8/1994 | Matsuo et al. |
| 5,352,770 A | 10/1994 | Matsuo |
| 5,428,130 A | 6/1995 | Capon et al. |
| 5,434,133 A | 7/1995 | Tanaka et al. |
| 5,583,108 A | 12/1996 | Wei et al. |
| 5,665,704 A | 9/1997 | Lowe et al. |
| 5,714,147 A | 2/1998 | Capon et al. |
| 5,767,239 A | 6/1998 | Immer et al. |
| 5,846,932 A | 12/1998 | Lowe et al. |
| 5,948,761 A | 9/1999 | Seilhamer et al. |
| 5,973,134 A | 10/1999 | Matsuo et al. |
| 6,020,168 A | 2/2000 | Matsuo et al. |
| 6,028,055 A | 2/2000 | Lowe et al. |
| 6,034,231 A | 3/2000 | Tanaka et al. |
| 6,290,952 B1 | 9/2001 | Poelstra et al. |
| 6,406,697 B1 | 6/2002 | Capon et al. |
| 6,407,211 B1 | 6/2002 | Burnett, Jr. et al. |
| 6,420,384 B2 | 7/2002 | Weigele et al. |
| 6,436,386 B1 | 8/2002 | Roberts et al. |
| 6,455,495 B1 | 9/2002 | Orgel et al. |
| 6,458,579 B2 | 10/2002 | Hopwood et al. |
| 6,525,022 B1 | 2/2003 | Lowe et al. |
| 6,541,610 B1 | 4/2003 | Smith |
| 6,743,425 B2 | 6/2004 | Nakao |
| 6,790,649 B1 | 9/2004 | Crine et al. |
| 6,818,619 B2 | 11/2004 | Burnett, Jr. et al. |
| 6,830,885 B1 | 12/2004 | Lanctot et al. |
| 6,849,714 B1 | 2/2005 | Bridon et al. |
| 6,887,470 B1 | 5/2005 | Bridon et al. |
| 6,905,689 B2 | 6/2005 | Schneidinger et al. |
| 6,946,484 B2 | 9/2005 | Adams et al. |
| 7,026,293 B2 | 4/2006 | Kitakaze |
| 7,033,997 B2 | 4/2006 | Forssmann et al. |
| 7,070,974 B1 | 7/2006 | Desgroseillers et al. |
| 7,105,539 B2 | 9/2006 | Gravel et al. |
| 7,112,341 B1 | 9/2006 | Nagarajan et al. |
| 7,179,903 B2 | 2/2007 | McArthur et al. |
| 7,256,253 B2 | 8/2007 | Bridon et al. |
| 7,271,149 B2 | 9/2007 | Glaesner et al. |
| 7,276,481 B2 | 10/2007 | Golembo et al. |
| 7,341,838 B2 | 3/2008 | Buechler et al. |
| 7,365,091 B2 | 4/2008 | Gravel et al. |

(Continued)

FOREIGN PATENT DOCUMENTS

| | | |
|---|---|---|
| CA | 3161266 A1 | 6/2021 |
| EP | 0478797 B1 | 4/1995 |

(Continued)

OTHER PUBLICATIONS

Sharma et al., "Alkaline phosphatase: An Overview", Indian Journal of Clinical Biochemistry, Jul.-Sep. 2014, 29(3):269-278. DOI 10.1007/s12291-013-0408-y.*

Magdaleno et al., "Adult-Onset Hypophosphatasia: Before and After Treatment With Asfotase Alfa", AACE AACE Clin Case Rep. Aug. 15, 2019;5(6):e344-e348. doi: 10.4158/ACCR-2019-0143.*

Bowden et al., "Reappearance of hypomineralized bone after discontinuation of asfotase alfa treatment for severe childhood hypophosphatasia", Osteoporosis International (2018) 29:2155-2156. https://doi.org/10.1007/s00198-018-4613-7.*

Rockman-Greenberg, C. "Letter to the Editor: "Efficacy and Safety of Asfotase Alfa in Infants and Young Children With Hypophosphatasia: A Phase 2 Open-Label Study"", Clin Endocrinol Metab, Aug. 2019, 104(8):3146-3147. doi: 10.1210/jc.2018-02413.*

(Continued)

*Primary Examiner* — Suzanne M Noakes
(74) *Attorney, Agent, or Firm* — Clark & Elbing LLP

(57) ABSTRACT

Featured are compositions and methods for treating bone mineralization disorders, such as hypophosphatasia (HPP). In some embodiments, the methods described herein are useful for treating adult subjects with HPP and/or treating or preventing bone fractures.

19 Claims, 16 Drawing Sheets
Specification includes a Sequence Listing.

(56)                    References Cited

U.S. PATENT DOCUMENTS 7,384,917 B2    6/2008   Burnett, Jr. et al.
    7,399,466 B2    7/2008   Boileau
    7,414,107 B2    8/2008   Larsen
    7,425,531 B2    9/2008   Lanctot et al.
    7,427,498 B2    9/2008   Crine et al.
    7,470,668 B2   12/2008   Lanctot et al.
    7,488,713 B2    2/2009   Vesely
    7,527,939 B2    5/2009   Davey et al.
    7,563,769 B2    7/2009   Bogin et al.
    7,625,564 B2   12/2009   Wang et al.
    7,642,243 B2    1/2010   Nakao et al.
    7,648,962 B2    1/2010   James et al.
    7,662,773 B2    2/2010   James et al.
    7,678,391 B2    3/2010   Graham et al.
    7,732,406 B2    6/2010   Mitrovic et al.
    7,736,653 B2    6/2010   Kim et al.
    7,754,852 B2    7/2010   Burnett, Jr. et al.
    7,763,712 B2    7/2010   Crine et al.
    7,803,769 B2    9/2010   Sullivan et al.
    7,803,901 B2    9/2010   Burnett, Jr. et al.
    7,825,092 B2   11/2010   Vesely
    7,846,900 B2   12/2010   Vesely
    7,858,560 B2   12/2010   Koster et al.
    7,919,591 B2    4/2011   Sheffer et al.
    7,943,126 B2    5/2011   Tomatsu et al.
    7,960,529 B2    6/2011   Crine et al.
    8,058,242 B2   11/2011   Alewood et al.
    8,691,208 B2    4/2014   Tomatsu et al.
    9,266,939 B2    2/2016   Crine et al.
    9,650,412 B2    5/2017   Konstantinov et al.
    9,650,413 B2    5/2017   Konstantinov et al.
    9,908,932 B2    3/2018   Malanson et al.
    9,988,620 B2    6/2018   Crine et al.
   10,000,532 B2    6/2018   Crine et al.
   10,052,366 B2    8/2018   Crine et al.
   10,449,236 B2   10/2019   Marozsan et al.
   10,603,361 B2    3/2020   Odrljin
   10,822,596 B2   11/2020   Hatch
   10,898,549 B2    1/2021   Fujita et al.
   10,988,744 B2    4/2021   Rajendran et al.
   11,065,306 B2    7/2021   Fujita et al.
   11,116,821 B2    9/2021   Saal
   11,186,832 B2   11/2021   Marozsan
   11,224,637 B2    1/2022   Moseley et al.
   11,224,638 B2    1/2022   Marozsan et al.
   11,229,686 B2    1/2022   Pradhan et al.
   11,248,021 B2    2/2022   Crine et al.
   11,352,612 B2    6/2022   Jaluria et al.
   11,400,140 B2    8/2022   Saal et al.
   11,564,978 B2    1/2023   Odrijin
   11,913,039 B2    2/2024   Godawat et al.
   12,083,169 B2    9/2024   Voegtli et al.
   12,268,733 B2    4/2025   Petryk
   12,433,938 B2   10/2025   Voegtli et al.
 2002/0183276 A1   12/2002   Millan et al.
 2003/0158132 A1    8/2003   Kovesdi
 2004/0023916 A1    2/2004   Millan et al.
 2004/0077537 A1    4/2004   Schreiner
 2004/0234518 A1   11/2004   Crine et al.
 2005/0113286 A1    5/2005   Schreiner et al.
 2005/0142217 A1    6/2005   Adams et al.
 2005/0202442 A1    9/2005   Morris et al.
 2005/0244904 A1   11/2005   Ng
 2005/0276796 A1   12/2005   Tomatsu et al.
 2006/0014687 A1    1/2006   Crine et al.
 2006/0019890 A1    1/2006   Kapoun et al.
 2006/0074009 A1    4/2006   James et al.
 2006/0110359 A1    5/2006   Sanchez-Ramos et al.
 2006/0172929 A1    8/2006   Rappold-Hoerbrand et al.
 2006/0228710 A1   10/2006   Morris et al.
 2007/0041972 A1    2/2007   Rother et al.
 2007/0042957 A1    2/2007   Burnett et al.
 2007/0081984 A1    4/2007   Tomatsu et al.
 2007/0081986 A1    4/2007   Tomatsu et al.
 2007/0197434 A1    8/2007   Nakao et al.
 2007/0281887 A1   12/2007   Pan
 2007/0292966 A1   12/2007   Prickett et al.
 2007/0293418 A1   12/2007   Larsen
 2008/0032933 A1    2/2008   Burnett et al.
 2008/0081768 A1    4/2008   Watt et al.
 2008/0085862 A1    4/2008   Kim et al.
 2008/0113411 A1    5/2008   Sheffer et al.
 2008/0113412 A1    5/2008   Sheffer et al.
 2008/0125574 A1    5/2008   Sheffer et al.
 2008/0153747 A1    6/2008   Alewood et al.
 2008/0161243 A1    7/2008   Rosen et al.
 2008/0181903 A1    7/2008   Bhaskar et al.
 2008/0182299 A1    7/2008   Colocaru et al.
 2008/0194481 A1    8/2008   Rosen et al.
 2008/0194682 A1    8/2008   Golembo et al.
 2008/0227713 A1    9/2008   Protter
 2008/0293632 A1   11/2008   Rappold-Hoerbrand et al.
 2008/0312142 A1   12/2008   Nakao et al.
 2009/0011997 A1    1/2009   Peri et al.
 2009/0022728 A1    1/2009   Lin
 2009/0023652 A1    1/2009   Bell et al.
 2009/0053192 A1    2/2009   Millan et al.
 2009/0069243 A1    3/2009   Burnett, Jr. et al.
 2009/0092582 A1    4/2009   Bogin et al.
 2009/0142347 A1    6/2009   Millan
 2009/0170756 A1    7/2009   Burnett, Jr. et al.
 2009/0221803 A1    9/2009   Dall'Acqua et al.
 2009/0238814 A1    9/2009   Tomatsu et al.
 2009/0240031 A1    9/2009   Immer et al.
 2009/0247462 A1   10/2009   Bogin et al.
 2009/0252729 A1   10/2009   Farrington et al.
 2009/0258018 A1   10/2009   Medich et al.
 2009/0275506 A1   11/2009   Bakis et al.
 2009/0325195 A1   12/2009   Davey et al.
 2010/0008979 A1    1/2010   Tomatsu et al.
 2010/0055150 A1    3/2010   Golembo et al.
 2010/0093678 A1    4/2010   Della-Fera et al.
 2010/0160212 A1    6/2010   Sheffer et al.
 2010/0168443 A1    7/2010   Geysen
 2010/0184680 A1    7/2010   Bevec
 2010/0197574 A1    8/2010   Chen et al.
 2010/0204094 A1    8/2010   Simari et al.
 2010/0204109 A1    8/2010   Bevec
 2010/0204446 A1    8/2010   Forssmann
 2010/0209958 A1    8/2010   Nakao et al.
 2010/0216714 A1    8/2010   James et al.
 2010/0221234 A1    9/2010   Crine et al.
 2010/0240125 A1    9/2010   Crine et al.
 2010/0249017 A1    9/2010   Bevec et al.
 2010/0260706 A1   10/2010   Bogin et al.
 2010/0261248 A1   10/2010   Kim et al.
 2010/0297021 A1   11/2010   Wendt et al.
 2010/0297119 A1   11/2010   Crine et al.
 2010/0305031 A1   12/2010   Wakabayashi et al.
 2010/0305051 A1   12/2010   Burnett, Jr. et al.
 2010/0310561 A1   12/2010   Canada et al.
 2010/0311660 A1   12/2010   Simari et al.
 2010/0317600 A1   12/2010   Immer et al.
 2010/0331256 A1   12/2010   Wendt et al.
 2011/0152194 A1    6/2011   Burnett, Jr. et al.
 2011/0250187 A1   10/2011   Tomatsu et al.
 2011/0269684 A1   11/2011   Burnett, Jr. et al.
 2011/0300143 A1   12/2011   Sly et al.
 2012/0088771 A1    4/2012   Millan
 2012/0164142 A1    6/2012   Crine et al.
 2013/0108635 A1    5/2013   Crine et al.
 2013/0323244 A1   12/2013   Crine et al.
 2014/0004096 A1    1/2014   Nichols
 2014/0193388 A1    7/2014   Velders et al.
 2014/0194484 A1    7/2014   Coats et al.
 2015/0353633 A1   12/2015   Kakkis et al.
 2016/0015784 A1    1/2016   Shaw et al.
 2016/0052968 A1    2/2016   Crine et al.
 2016/0097100 A1    4/2016   Trent et al.
 2017/0175094 A1    6/2017   Hatch
 2017/0360899 A1   12/2017   Marozsan et al.
 2018/0072986 A1    3/2018   Park et al.
 2018/0230445 A1    8/2018   Jaluria et al.
 2019/0043501 A1    2/2019   Ramaci

(56) References Cited

U.S. PATENT DOCUMENTS

| | | | |
|---|---|---|---|
| 2019/0099473 | A1 | 4/2019 | Fujita et al. |
| 2020/0101141 | A1 | 4/2020 | Moseley et al. |
| 2020/0121767 | A1 | 4/2020 | Tomazos et al. |
| 2020/0224182 | A1 | 7/2020 | Rajendran et al. |
| 2020/0282012 | A1 | 9/2020 | Francois |
| 2020/0306350 | A1 | 10/2020 | Fujita et al. |
| 2021/0169994 | A1 | 6/2021 | Voegtli et al. |
| 2021/0317425 | A1 | 10/2021 | Godawat et al. |
| 2022/0154155 | A1 | 5/2022 | Godawat et al. |
| 2023/0201318 | A1 | 6/2023 | Fujita et al. |
| 2023/0372456 | A1 | 11/2023 | Petryk et al. |
| 2024/0052327 | A1 | 2/2024 | DeWitt et al. |
| 2024/0382568 | A1 | 11/2024 | Voegtli et al. |

FOREIGN PATENT DOCUMENTS

| | | | |
|---|---|---|---|
| EP | 0769554 A2 | 4/1997 |
| EP | 0466174 B1 | 6/1997 |
| EP | 0475394 B1 | 6/1997 |
| EP | 0466175 B1 | 1/1998 |
| EP | 0477971 B1 | 1/1998 |
| EP | 0475290 B1 | 12/1998 |
| EP | 0475291 B1 | 12/1998 |
| EP | 0497368 B1 | 6/2002 |
| EP | 1492567 A0 | 9/2003 |
| EP | 1488802 A2 | 12/2004 |
| EP | 1502604 A1 | 2/2005 |
| EP | 1623994 A2 | 2/2006 |
| EP | 1759710 A1 | 3/2007 |
| EP | 0771875 B1 | 2/2008 |
| EP | 1985697 A1 | 10/2008 |
| EP | 2158319 A0 | 11/2008 |
| EP | 1759001 B1 | 4/2011 |
| EP | 2158319 B1 | 12/2011 |
| EP | 3250227 A2 | 12/2017 |
| JP | H08-70875 A | 3/1996 |
| JP | 2000-327583 A | 11/2000 |
| JP | 2002-541776 A | 12/2002 |
| JP | 2007-511209 A | 5/2007 |
| JP | 2007-537725 A | 12/2007 |
| JP | 2010-501026 A | 1/2010 |
| JP | 2010-526543 A | 8/2010 |
| JP | 2010-530222 A | 9/2010 |
| JP | 2011-504506 A | 2/2011 |
| JP | 2014-181229 A | 9/2014 |
| JP | 2015-502336 A | 1/2015 |
| WO | WO-92/20371 A1 | 11/1992 |
| WO | WO-94/20534 A1 | 9/1994 |
| WO | WO-95/05456 A1 | 2/1995 |
| WO | WO-95/13296 A1 | 5/1995 |
| WO | WO-95/33769 A1 | 12/1995 |
| WO | WO-98/17690 A1 | 4/1998 |
| WO | WO-98/35703 A2 | 8/1998 |
| WO | WO-99/46283 A1 | 9/1999 |
| WO | WO-00/18954 A2 | 4/2000 |
| WO | WO-00/50580 A2 | 8/2000 |
| WO | WO-00/53755 A2 | 9/2000 |
| WO | WO-00/64486 A2 | 11/2000 |
| WO | WO-00/69900 A2 | 11/2000 |
| WO | WO-01/36620 A2 | 5/2001 |
| WO | WO-01/44284 A2 | 6/2001 |
| WO | WO-01/80890 A2 | 11/2001 |
| WO | WO-02/15918 A2 | 2/2002 |
| WO | WO-02/47871 A1 | 6/2002 |
| WO | WO-02/067639 A1 | 8/2002 |
| WO | WO-02/068579 A2 | 9/2002 |
| WO | WO-02/074234 A2 | 9/2002 |
| WO | WO-03/074082 A1 | 9/2003 |
| WO | WO-03/079979 A2 | 10/2003 |
| WO | WO-03/092581 A2 | 11/2003 |
| WO | WO-03/094835 A2 | 11/2003 |
| WO | WO-2004/011498 A2 | 2/2004 |
| WO | WO-2004/022579 A2 | 3/2004 |
| WO | WO-2004/046194 A2 | 6/2004 |
| WO | WO-2004/047871 A2 | 6/2004 |
| WO | WO-2004/062555 A2 | 7/2004 |
| WO | WO-2004/074320 A2 | 9/2004 |
| WO | WO-2004/094460 A2 | 11/2004 |
| WO | WO-2005/000095 A2 | 1/2005 |
| WO | WO-2005/007809 A2 | 1/2005 |
| WO | WO-2005/042034 A1 | 5/2005 |
| WO | WO-2005/047337 A1 | 5/2005 |
| WO | WO-2005/070446 A1 | 8/2005 |
| WO | WO-2005/072055 A2 | 8/2005 |
| WO | WO-2005/087802 A2 | 9/2005 |
| WO | WO-2005/094890 A1 | 10/2005 |
| WO | WO-2005/098490 A1 | 10/2005 |
| WO | WO-2005/103263 A1 | 11/2005 |
| WO | WO-2005/105156 A1 | 11/2005 |
| WO | WO-2005/110435 A1 | 11/2005 |
| WO | WO-2006/005140 A2 | 1/2006 |
| WO | WO-2006/026663 A1 | 3/2006 |
| WO | WO-2006/039480 A2 | 4/2006 |
| WO | WO-2006/060641 A2 | 6/2006 |
| WO | WO-2006/110743 A1 | 10/2006 |
| WO | WO-2006/116260 A2 | 11/2006 |
| WO | WO-2007/041645 A2 | 4/2007 |
| WO | WO-2007/071295 A1 | 6/2007 |
| WO | WO-2007/097923 A2 | 8/2007 |
| WO | WO-2007/130113 A2 | 11/2007 |
| WO | WO-2008/021872 A1 | 2/2008 |
| WO | WO-2008/030558 A2 | 3/2008 |
| WO | WO-2008/031045 A2 | 3/2008 |
| WO | WO-2008/053362 A2 | 5/2008 |
| WO | WO-2008/058016 A2 | 5/2008 |
| WO | WO-2008/079400 A2 | 7/2008 |
| WO | WO-2008/079995 A2 | 7/2008 |
| WO | WO-2008/088422 A2 | 7/2008 |
| WO | WO-2008/109903 A1 | 9/2008 |
| WO | WO-2008/133511 A2 | 11/2008 |
| WO | WO-2008/136611 A1 | 11/2008 |
| WO | WO-2008/138131 A1 | 11/2008 |
| WO | WO-2008/154226 A1 | 12/2008 |
| WO | WO-2009/006520 A1 | 1/2009 |
| WO | WO-2009/015011 A1 | 1/2009 |
| WO | WO-2009/023270 A2 | 2/2009 |
| WO | WO-2009/006732 A9 | 3/2009 |
| WO | WO-2009/033680 A2 | 3/2009 |
| WO | WO-2009/033724 A1 | 3/2009 |
| WO | WO-2009/033796 A1 | 3/2009 |
| WO | WO-2009/033807 A2 | 3/2009 |
| WO | WO-2009/034134 A2 | 3/2009 |
| WO | WO-2009/036448 A2 | 3/2009 |
| WO | WO-2009/040030 A1 | 4/2009 |
| WO | WO-2009/040031 A2 | 4/2009 |
| WO | WO-2009/040083 A2 | 4/2009 |
| WO | WO-2009/046861 A1 | 4/2009 |
| WO | WO-2009/058322 A1 | 5/2009 |
| WO | WO-2009/067639 A2 | 5/2009 |
| WO | WO-2009/086126 A2 | 7/2009 |
| WO | WO-2009/090553 A2 | 7/2009 |
| WO | WO-2009/142307 A1 | 11/2009 |
| WO | WO-2009/149161 A9 | 12/2009 |
| WO | WO-2009/156481 A1 | 12/2009 |
| WO | WO-2009/158035 A2 | 12/2009 |
| WO | WO-2010/002583 A2 | 1/2010 |
| WO | WO-2010/011096 A2 | 1/2010 |
| WO | WO-2010/048308 A2 | 4/2010 |
| WO | WO-2010/078325 A2 | 7/2010 |
| WO | WO-2010/082804 A2 | 7/2010 |
| WO | WO-2010/117760 A2 | 10/2010 |
| WO | WO-2010/129655 A2 | 11/2010 |
| WO | WO-2010/135541 A2 | 11/2010 |
| WO | WO-2011/130229 A1 | 10/2011 |
| WO | WO-2011/134084 A1 | 11/2011 |
| WO | WO-2012/088608 A1 | 7/2012 |
| WO | WO-2012/099851 A2 | 7/2012 |
| WO | WO-2013/058833 A1 | 4/2013 |
| WO | WO-2013/059491 A1 | 4/2013 |
| WO | WO-2013/071262 A1 | 5/2013 |
| WO | WO-2013/169397 A1 | 11/2013 |
| WO | WO-2015/112015 A1 | 7/2015 |
| WO | WO-2015/112017 A1 | 7/2015 |
| WO | WO-2016/007873 A1 | 1/2016 |

(56) References Cited

FOREIGN PATENT DOCUMENTS

| WO | WO-2016/090251 A1 | 6/2016 |
| WO | WO-2016/123342 A2 | 8/2016 |
| WO | WO-2016/153191 A1 | 9/2016 |
| WO | WO-2017/031114 A1 | 2/2017 |
| WO | WO-2017/058822 A1 | 4/2017 |
| WO | WO-2017/074466 A1 | 5/2017 |
| WO | WO-2017/155569 A1 | 9/2017 |
| WO | WO-2017/171871 A1 | 10/2017 |
| WO | WO-2017/173395 A1 | 10/2017 |
| WO | WO-2017/173413 A1 | 10/2017 |
| WO | WO-2017/214130 A1 | 12/2017 |
| WO | WO-2018/004517 A1 | 1/2018 |
| WO | WO-2018/035420 A1 | 2/2018 |
| WO | WO-2018/164995 A1 | 9/2018 |
| WO | WO 2018/183720 * | 10/2018 |
| WO | WO-2019/164978 A1 | 8/2019 |
| WO | WO-2019/183208 A1 | 9/2019 |
| WO | WO-2019/190752 A1 | 10/2019 |
| WO | WO-2020/247421 A1 | 12/2020 |
| WO | WO-2021/081026 A1 | 4/2021 |
| WO | WO-2021/119218 A1 | 6/2021 |
| WO | WO-2022/087229 A1 | 4/2022 |

OTHER PUBLICATIONS

Strensiq Perscribing information, dated Jun. 2020 < chrome-extension://efaidnbmnnnibpcajpcglclefindmkaj/https://alexion.us/-/media/alexion_global/documents/regulatory/north-america/usa/2024/english/strensiq_uspi.pdf > Retrieved on Nov. 12, 2025.*

"Effects of feeding strategy on CHO cell performance in fed-batch cultures using HyClone ActiPro medium and Cell Boost 7a and 7b supplements," Cytiva, <http://www.processdevelopmentforum.com/posters/effects-of-feeding-strategy-on-cho-cell-performance-in-fed-batch-cultures/>. Apr. 2017 (5 pages).

"Pharmaceutical and Food Safety Bureau Examination and Management Division / Pharmaceuticals and Medical Devices Agency, Review Report," published Oct. 26, 2015 (English Abstract) (64 pages).

"Scale-up of CHO fed-batch cultures in HyClone™ ActiPro™ medium supplemented with Cell Boost™ 7a and 7b," GE Healthcare Bio-Sciences AB, dated Sep. 2016 (4 pages).

"Sequence 4," SCORE Search Results for U.S. Appl. No. 12/599,679, retrieved Nov. 17, 2018 (2 pages).

"Strensiq: Assessment Report," European Medicines Agency, dated Jun. 25, 2015 (92 pages).

"View of NCT02235493 on Nov. 19, 2025," ClinicalTrials.gov archive, updated Nov. 19, 2015, retrieved Jan. 27, 2017 (4 pages).

"Xcellerex™ XDR cell culture bioreactor systems," GE Healthcare Life Sciences, retrieved from <https://www.cytivallifesciences.co.jp/catalog/pdf/29092925AA.pdf>, published Feb. 2014 (4 pages).

Abbruzzese, "The Tinetti Performance-Oriented Mobility Assessment Tool," Am J Nursing. 98(12):16J-16L (1998) (3 pages).

Abrams et al., "Calcium and Vitamin D Requirements of Enterally Fed Preterm Infants," Pediatrics. 131(5): e1676-e1683 (2013) (9 pages).

Achord et al., "Human beta-glucuronidase: in vivo clearance and in vitro uptake by a glycoprotein recognition system on reticuloendothelial cells," Cell. 15(1):269-278 (1978).

Addison et al., "Pyrophosphate inhibits mineralization of osteoblast cultures by binding to mineral, up-regulating osteopontin, and inhibiting alkaline phosphatase activity," J Biol Chem. 282(21):15872-83 (2007).

Advisory Action for U.S. Appl. No. 11/484,870, mailed Dec. 20, 2007 (4 pages).

Agochukwu et al., "Hearing loss in syndromic craniosynostoses: Introduction and consideration of mechanisms," available in PMC Aug. 13, 2014, published in final edited form as: Am J Audiol. 23(2):135-41 (2014) (13 pages).

Ahn et al., "Idiopathic calcium pyrophosphate dihydrate (CPPD) crystal deposition disease in a young male patient: a case report," J Korean Med Sci. 18(6):917-20 (2003).

Alexion Pharma International, "Product Monograph, Including Patient Medication Information. Strensiq™ (asfotase alfa), Solution for Injection 40 mg/mL & 100 mg/mL," <http://alexionpharma.ca/documents/Strensiq-PM-asfotase-alfa-14Aug2015.aspx>, prepared Aug. 14, 2015 (32 pages).

Alexion Pharmaceuticals, "Safety and Efficacy Study of Asfotase Alfa in Adolescents and Adults With Hypophosphatasia (HPP)," ClinicalTrials.gov. NCT01163149, <https://clinicaltrials.gov/ct2/show/NCT01163149>, last updated Mar. 13, 2019 (9 pages).

Alexion Pharmaceuticals, "Safety Study of Human Recombinant Tissue Non-Specific Alkaline Phosphatase Fusion Protein Asfotase Alfa in Adults With Hypophosphatasia (HPP)," ClinicalTrials.gov. NCT00739505, <https://www.clinicaltrials.gov/ct2/show/NCT00739505>, last updated Mar. 29, 2019 (8 pages).

Alexion Pharmaceuticals, "Strensiq™ (asfotase alfa) for injection," retrieved from <globalgenes.org/2015/11/05/alexion-announces-fda-approval-for--strensiq/?gclid=CjwKCAjwwqaGBhBKEiwAMk-FtFQOKvuVN-WmNcDVyu9Q9X3f6QB-V0Two0x216TR2H4_Qc6jSIhvxoCILMQAvD_BWE>, dated Nov. 5, 2015 (1 page).

Alexion Third Quarter 2017 Earnings Call, "http://files.shareholder.com/downloads/ALXN/5636824573x0x961197/3B361D6E-80E2-463E-B0E5-3EAD7FC5B9D0/Alexion_Q3_2017_Earnings_Slides.pdf" (43 pages).

Alexion, "Highlights of Prescribing Information" for Strensiq®, 2018 (8 pages).

Ali et al., "Isolation and characterization of calcifying matrix vesicles from epiphyseal cartilage," Proc Natl Acad Sci USA. 67(3):1513-20 (1970).

Altarescu et al., "The efficacy of enzyme replacement therapy in patients with chronic neuronopathic Gaucher's disease," J Pediatr. 138(4):539-547 (2001).

An et al., "IgG2m4, an engineered antibody isotype with reduced Fc function," mAbs. 1(6): 572-579 (2009).

Anderson et al., "Impaired calcification around matrix vesicles of growth plate and bone in alkaline phosphatase-deficient mice," Am J Pathol. 164(3):841-7 (2004).

Anderson et al., "Matrix vesicles in osteomalacic hypophosphatasia bone contain apatite-like mineral crystals," Am J Pathol. 151(6):1555-61 (1997).

Anderson et al., "Pyrophosphate stimulation of calcium uptake into cultured embryonic bones. Fine structure of matrix vesicles and their role in calcification," Dev Biol. 34:211-227 (1973).

Anderson et al., "Sustained osteomalacia of long bones despite major improvement in other hypophosphatasia-related mineral deficits in tissue nonspecific alkaline phosphatase/nucleotide pyrophosphatase phosphodiesterase 1 double-deficient mice," Am J Pathol. 166(6):1711-1720 (2005).

Anderson et al., "The role of matrix vesicles in growth plate development and biomineralization," Front Biosci. 10:822-37 (2005).

Anderson, "Mechanism of Mineral Formation in Bone," Pathology Reviews. Emanuel Rubin and Ivan Damjanov (eds.), 13-23 (1990).

Appeal Brief as Filed in U.S. Appl. No. 12/638,527, dated Oct. 9, 2015 (101 pages).

Attwood, "The Babel of Bioinformatics," Science. 290(5491):471-3 (2000).

Balasubramaniam et al., "Perinatal hypophosphatasia presenting as neonatal epileptic encephalopathy with abnormal neurotransmitter metabolism secondary to reduced co-factor pyridoxal-5'-phosphate availability," J Inherit Metab Dis. 33(Suppl 3):S25-33 (2010).

Barcia et al., "Infantile hypophosphatasia: treatment options to control hypercalcemia, hypercalciuria, and chronic bone demineralization," J Pediatr. 130(5):825-8 (1997).

Barranger et al., "Lessons learned from the development of enzyme therapy for Gaucher disease," J Inherit Metab Dis. 24(Suppl. 2):89-96 (2001).

Barton et al., "Replacement therapy for inherited enzyme deficiency—macrophage-targeted glucocerebrosidase for Gaucher's disease," N Engl J Med. 324(21):1464-70 (1991) (1 page) (Abstract only).

(56)             References Cited

OTHER PUBLICATIONS

Barvencik et al., "Skeletal mineralization defects in adult hypophosphatasia—a clinical and histological analysis," Osteoporosis Int. 22(10):2667-75 (2011).

Baumgartner-Sigl et al., "Pyridoxine-responsive seizures as the first symptom of infantile hypophosphatasia caused by two novel missense mutations (c.677T>C, p.M226T; c.1112C>T, p.T371l) of the tissue-nonspecific alkaline phosphatase gene," Bone. 40(6):1655-61 (2007).

Beck et al., "Whole-body MRI in the childhood form of hypophosphatasia," Rheumatol Int. 31(10):1315-20 (2011).

Beederman et al., "Molecular basis of cranial suture biology and disease: osteoblastic and osteoclastic perspectives," Genes Dis. 1(1):120-5 (2014).

Beertsen et al., "Root development in mice lacking functional tissue non-specific alkaline phosphatase gene: Inhibition of acellular cementum formation," J Dent Res. 78(6):1221-1229 (1999) (10 pages).

Belachew et al., "Infantile hypophosphatasia secondary to a novel compound heterozygous mutation presenting with pyridoxine-responsive seizures," JIMD Rep. 11:17-24 (2013).

Belkhouribchia et al., "Osteomalacia with low alkaline phosphatase: a not so rare condition with important consequences," BMJ Case Rep. doi: 10.1136/bcr-2015-212827 (Jan. 2016) (4 pages).

Bennett et al., "Extracellular domain-IgG fusion proteins for three human natriuretic peptide receptors," J Biol Chem. 266(34):23060-23067 (1991).

Berkseth et al., "Clinical spectrum of hypophosphatasia diagnosed in adults," Bone. 54(1):21-7 (2013).

Bernard, "Ultrastructural localization of alkaline phosphatase in initial intramembranous osteogenesis," Clin Orthop Relat Res. 135:218-25 (1978).

Bernardi, "Chromatography of proteins on hydroxyapatite," Methods Enzymol. 27:471-9 (1973).

Bhattacharyya et al., "Hypophosphatasia and the risk of atypical femur fractures: a case-control study," BMC Muscoloskelet Disord. 17:332 (Aug. 2016) (4 pages).

Bianchi, "Hypophosphatasia: an overview of the disease and its treatment," Osteoporos Int. 26(12):2743-57 (2015).

Bishop et al., "Life-threatening hypophosphatasia (HPP): Results of up to two years bone-targeted Enzyme Replacement Therapy (ERT) in infants and young children," Bone. 48:S82 (2011) (1 page) (Abstract only).

Bishop et al., "Transformative therapy in hypophosphatasia," Arch Dis Child. 101(6):514-5 (Jun. 2016).

Bishop, "Asfotase alfa for hypophosphatasia," Horizon Scanning Centre. National Institute for Health Research. http://www.hsric.nihr.ac.uk/topics/asfotase-alfa-for-hypophosphatasia/download, retrieved Oct. 20, 2013 (9 pages).

Bishop, "Clinical management of hypophosphatasia," Clin Cases Miner Bone Metab. 12(2):170-3 (2015).

Bloch-Zupan, "Hypophosphatasia: diagnosis and clinical signs—a dental surgeon perspective," Int J Paediatr Dent. 26(6):426-438 (Nov. 2016).

Bobryshev et al., "Role of bone-type tissue-nonspecific alkaline phosphatase and PHOSPO1 in vascular calcification," Curr Pharm Des. 20(37):5821-8 (2014).

Bobyr et al., "High-resolution analysis of Zn(2+) coordination in the alkaline phosphatase superfamily by EXAFS and x-ray crystallography," J Mol Biol. 415(1):102-17 (2012).

Bobé et al., "Fas-mediated liver damage in MRL hemopoietic chimeras undergoing lpr-mediated graft-versus-host disease," J Immunol. 159(9):4197-4204 (1997).

Bocciardi et al., "Overexpression of the C-type natriuretic peptide (CNP) is associated with overgrowth and bone anomalies in an individual with balanced t(2;7) translocation," Hum Mutat. 28(7):724-31 (2007).

Bonilla, "Pharmacokinetics of immunoglobulin administered via intravenous or subcutaneous routes," Immunol Allergy Clin N Am. 28:803-19 (2008).

Boskey et al., "Matrix vesicles promote mineralization in a gelatin gel," Calcif Tissue Int. 60(3):309-15 (1997).

Boskey, "Amorphous calcium phosphate: The contention of bone," J Dent Res. 76(8):1433-1436 (1997).

Boulet et al., "A population-based study of craniosynostosis in metropolitan Atlanta, 1989-2003," Am J Med Genet A. 146A(8): 984-91 (2008).

Bowden et al., "Asfotase alfa treatment for 1 year in a 16 year-old male with severe childhood hypophosphatasia," Osteoporos Int. 29(2):511-5 (2018).

Braunstein, "Multiple fractures, pain, and severe disability in a patient with adult-onset hypophosphatasia," Bone Rep. 4:1-4 (Jun. 2016).

Brenner et al., "Diverse biological actions of atrial natriuretic peptide," Physiol Rev. 70(3):665-699 (1990).

Briot et al., "Adult hypophosphatasia," Curr Opin Rheumatol. 28(4):448-51 (Jul. 2016).

Buchet et al., "Chapter 3: Multisystemic functions of alkaline phosphatases," *Phosphatase Modulators, Methods in Molecular Biology*, vol. 1053. José Luis Millán (ed.), 27-51 (2013).

Byers et al., "Effect of enzyme replacement therapy on bone formation in a feline model of mucopolysaccharidosis type VI," Bone. 21(5):425-31 (1997).

Cahill et al., "Infantile hypophosphatasia: transplantation therapy trial using bone fragments and cultured osteoblasts," J. Clin Endocrinol Metab. 92(8): 2923-30 (2007).

Cameron et al., "Minireview: Natriuretic peptides during development of the fetal heart and circulation," Endocrinology. 144(6):2191-4 (2003).

Campbell et al., "Insulin-like growth factor (IGF)-binding protein-5-(201-218) region regulates hydroxyapatite and IGF-I binding," Am J Physiol Endocrinol Metab. 273:E1005-1013 (1997).

Carden et al. "Tracheomalacia and tracheobronchomalacia in children and adults: an in-depth review," Chest. 127(3):984-1005 (2005).

Center for Drug Evaluation and Research, "Application No. 125513Orig1s000," <http://www.accessdata.fda.gov/drugsatfda_docs/nda/2015/125513Orig1s000MedR.pdf>, review completed Oct. 20, 2015; retrieved on Jun. 1, 2016 (254 pages).

Chan et al., "Endoscope-assisted versus open repair of craniosynostosis: a comparison of perioperative cost and risk," J Craniofac Surg. 24(1):170-4 (2013).

Chen et al., "Gly369Cys mutation in mouse FGFR3 causes achondroplasia by affecting both chondrogenesis and osteogenesis," J Clin Invest. 104(11):1517-25 (1999).

Choe et al., "Substrate profiling of cysteine proteases using a combinatorial peptide library identifies functionally unique specificities," J Biol Chem. 281(18):12824-32 (2006).

Choi et al., "Craniosynostosis in growing children: pathophysiological changes and neurosurgical problems," J Korean Neurosurg Soc. 59(3):197-203 (May 2016).

Chong et al., "Minimally invasive suturectomy and postoperative helmet therapy: advantages and limitations," J Korean Neurosurg Soc. 59(3):227-32 (May 2016).

Chusho et al., "Dwarfism and early death in mice lacking C-type natriuretic peptide," Proc Natl Acad Sci U S A. 98(7):4016-21 (2001).

Ciancaglini et al., "Contribution of matrix vesicles and alkaline phosphatase to ectopic bone formation," Braz J Med Biol Res. 39(5):603-10 (2006).

Clarke, "Normal bone anatomy and physiology," Clin J Am Soc Nephrol. 3(Suppl 3):S131-9 (2008).

Cleland et al., "Emerging protein delivery methods," Curr Opin Biotechnol. 12:212-9 (2001).

Clemens et al., "Pharmacokinetics and biological actions of subcutaneously administered human brain natriuretic peptide," J Pharmacol Exp Ther. 287(1):67-71 (1998).

Colantonio et al., "Closing the gaps in pediatric laboratory reference intervals: a CALIPER database of 40 biochemical markers in a healthy and multiethnic population of children," Clin Chem. 58(5):854-68 (2012).

Collmann et al., "Neurosurgical aspects of childhood hypophosphatasia," Childs Nerv Syst. 25(2):217-23 (2009).

(56) References Cited

OTHER PUBLICATIONS

Communication from Examining Division for European Application No. 05739065.0, dated Jun. 11, 2010 (5 pages).
Communication from Examining Division for European Application No. 05739065.0, dated Jun. 18, 2009 (6 pages).
Communication from Examining Division for European Application No. 08757088.3, dated Apr. 20, 2011 (4 pages).
Communication pursuant to Article 94(3) EPC for European Patent Application No. 15825878.0, dated Apr. 4, 2022 (5 pages).
Communication pursuant to Article 94(3) EPC for European Patent Application No. 16739617.5, dated May 11, 2020 (10 pages).
Communication pursuant to Article 94(3) EPC for European Patent Application No. 16758322.8, dated Jan. 25, 2022 (3 pages).
Communication pursuant to Article 94(3) EPC for European Patent Application No. 16852428.8, dated Dec. 8, 2021 (4 pages).
Communication pursuant to Article 94(3) EPC for European Patent Application No. 18775045.0, dated Jan. 25, 2022 (6 pages).
Communication pursuant to Rule 164(2)(b) and Article 94(3) EPC for European Patent Application No. 16707571.2, dated Feb. 26, 2019 (12 pages).
Crawley et al., "Enzyme replacement therapy in a feline model of Maroteaux-Lamy syndrome," J Clin Invest. 97(8):1864-73 (1996).
Cuzick et al., "Overview of the main outcomes in breast-cancer prevention trials," Lancet. 361(9354):296-300 (2003).
Czerwinski et al., "Major morbidity and mortality rates in craniofacial surgery: an analysis of 8101 major procedures," Plast Reconstr Surg. 126(1):181-6 (2010).
Daggubati et al., "Adrenomedullin, endothelin, neuropeptide Y, atrial, brain, and C-natriuretic prohormone peptides compared as early heart failure indicators," Cardiovasc Res. 36:246-55 (1997).
Data Sheet for pFUSE-SEAP-hFc "Plasmid designed for the expression of a SEAP-Fc Fusion protein," Invivogen, San Diego, CA (1 page) (1989).
Dbfetch, "Bone targeted alkaline phosphatase, kits and methods of use thereof," Database No. HI520929, last updated Nov. 2, 2010 (1 page).
De la Croix Ndong et al., "Asfotase-alpha improves bone growth, mineralization and strength in mouse models of neurofibromatosis type-1," Nat Med. 20(8):904-10 (2014) (10 pages).
De Plater et al., "The natriuretic peptide (OVCNP-39) from platypus (*Ornithorhynchus anatinus*) venom relaxes the isolated rat uterus and promotes oedema and mast cell histamine release," Toxicon. 36(6):847-57 (1998).
De Roo et al., "Infantile hypophosphatasia without bone deformities presenting with severe pyridoxine-resistant seizures," Mol Genet Metab. 111(3):404-7 (2014).
Decision on Rejection for Chinese Patent Application No. 201680048588.5, issued Jan. 20, 2022 (19 pages).
Declaration of Dr. Philippe Crine for European Patent Application No. 08757088.3, executed Jan. 14, 2011 (6 pages).
Deeb et al., "Could alerting physicians for low alkaline phosphatase levels be helpful in early diagnosis of hypophosphatasia?," J Clin Res Pediatr Endocrinol. 10(1):19-24 (2018).
Del Angel et al., "Birth prevalence estimation of severe Hypophosphatasia in European populations using large-scale protein-coding genetic variation databases," American Society of Human Genetics 66th Annual Meeting, Oct. 18-22, Vancouver, Canada. Poster abstract 1670T (2016) (2 pages).
Di Mauro et al., "Kinetic characterization of hypophosphatasia mutations with physiological substrates," J Bone Miner Res. 17(8):1383-91 (2002).
Di Rocco et al. "Craniosynostosis and hypophosphatasia," Arch Pediatr. 24(5S2):5S89-5S92 (May 2017).
Dortschy et al., "Bevölkerungsbezogene verteilungswerte ausgewählter laborparameter aus der studie zur gesundheit von kindern und jugendlichen in Deutschland (KIGGS)," Gesundheitsberichterstattung des Bundes, Robert Koch Institute (2009) (136 pages).
Dumont et al., "Monomeric Fc fusions: impact on pharmacokinetic and biological activity of protein therapeutics," BioDrugs. 20(3):151-60 (2006).

Durussel et al., "Bone mineralization-dependent craniosynostosis and craniofacial shape abnormalities in the mouse model of infantile hypophosphatasia," Dev Dyn. 245(2):175-82 (Feb. 2016).
Dutta et al., "Men and mice: Relating their ages," Article in Press, published in final edited form as: Life Sci. 152:244-8 (May 2016) (5 pages).
Eade et al., "Pyrophosphate arthropathy in hypophosphatasia," Ann Rheum Dis. 40(2):164-70 (1981).
EBI Blast for Accession No. ATD17216. Entered Oct. 16, 2008 (1 page).
Eng et al., "Safety and efficacy of recombinant human alpha-galactosidase A replacement therapy in Fabry's disease," N Engl J Med. 345(1):9-16 (2001).
Engel et al., "Characterization of the hormone binding site of natriuretic peptide receptor-C," FEBS Lett. 360(2):169-72 (1995).
Esparza et al., "Complications in the surgical treatment of craniosynostosis and craniofacial syndromes: apropos of 306 transcranial procedures," Childs Nerv Syst. 24(12):1421-30 (2008).
Esparza et al., "Surgical treatment of isolated and syndromic craniosynostosis. Results and complications in 283 consecutive cases," Neurocirugía. 19(6):509-29 (2008).
European Collection of Authenticated Cell Cultures (ECACC), General Cell Collection: NS0, Catalogue No. 85110503. Retrieved May 2, 2018 (3 pages).
European Medicines Agency, "Strensiq: Asfotase Alfa," <www.ema.europa.eu/en/medicines/human/EPAR/strensiq>, last updated Mar. 25, 2021 (8 pages).
Evans et al., "Vaccine therapy for cancer—fact or fiction?," QJM. 92(6):299-307 (1999).
Examination Report for Canadian Patent Application No. 2,967,851, dated Dec. 21, 2021 (4 pages).
Examination Report for Canadian Patent Application No. 2,973,883, dated Mar. 24, 2022 (6 pages).
Examination Report No. 1 for Australian Patent Application No. 2016308624, dated Aug. 27, 2021 (6 pages).
Examination Report No. 2 for Australian Patent Application No. 2016308624, dated Apr. 7, 2022 (4 pages).
Examiner's Answer to Appeal Brief for U.S. Appl. No. 12/638,527, mailed Feb. 23, 2016 (9 pages).
Extended European Search Report for European Application No. 08757088.3, dated Jun. 21, 2010 (6 pages).
Extended European Search Report for European Application No. 11000196.3, mailed Jun. 22, 2011 (6 pages).
Extended European Search Report for European Application No. 11004496.3, mailed Aug. 26, 2011 (7 pages).
Extended European Search Report for European Application No. 11774253.6, dated Oct. 14, 2013 (8 pages).
Extended European Search Report for European Application No. 15907550.6, dated Jun. 4, 2019 (7 pages).
Extended European Search Report for European Application No. 18173111.8, dated Aug. 21, 2018 (9 pages).
Extended European Search Report for European Patent Application No. 12842640.0, mailed Mar. 13, 2015 (7 pages).
Farley et al., "Effects of tunicamycin, mannosamine, and other inhibitors of glycoprotein processing on skeletal alkaline phosphatase in human osteoblast-like cells," Calcif Tissue Int. 76:63-74 (2005).
Farnum et al., "In vivo delivery of fluoresceinated dextrans to the murine growth plate: imaging of three vascular routes by multiphoton microscopy," available in PMC Oct. 28, 2008, published in final edited form as: Anat Rec A Discov Mol Cell Evol Biol. 288(1):91-103 (2006) (22 pages).
Fedde et al., "Alkaline phosphatase knock-out mice recapitulate the metabolic and skeletal defects of infantile hypophosphatasia," available in PMC Mar. 7, 2011, published in final edited form as: J Bone Miner Res. 14(12):2015-26 (1999) (19 pages).
Fodor et al., "Differencial diagnosis of the low alkaline phosphatase activities," Orv Hetil. 158(26):1003-7 (Jul. 2017) (Article in Hungarian) (English Abstract included).
Fong et al., "Hypocalcemia: Updates in diagnosis and management for primary care," Can Fam Physician. 58(2):158-62 (2012).
Fraser, "Hypophosphatasia," Am J Med. 22(5):730-46 (1957).
Fujisaki et al., "Osteotropic Drug Delivery System (ODDS) based on bisphosphonic prodrug. IV effects of osteotropic estradiol on

(56) References Cited

OTHER PUBLICATIONS bone mineral density and uterine weight in ovariectomized rats," J Drug Target. 5(2):129-38 (1997) (11 pages).

Fujisawa et al., "Acidic amino acid-rich sequences as binding sites of osteonectin to hydroxyapatite crystals," Biochim Biophys Acta. 1292:53-60 (1996).

Furbish et al., "Uptake and distribution of placental glucocerebrosidase in rat hepatic cells and effects of sequential deglycosylation," Biochim Biophys Acta. 673:425-434 (1981).

Furuya et al., "Structural requirements of C-type natriuretic peptide for elevation of cyclic GMP in cultured vascular smooth muscle cells," Biochem Biophys Res Commun. 183(3):964-9 (1992).

Garber et al., "Comparing outcomes and cost of 3 surgical treatments for sagittal synostosis: a retrospective study including procedure-related cost analysis," Neurosurgery. 81(4):680-7 (Oct. 2017).

Garg, "Investigation of the role of FcRn in the absorption, distribution, and elimination of monoclonal antibodies," Dissertation: State University of New York at Buffalo, 2007 (Abstract only) (2 pages).

Gasque et al., "Improvement of the skeletal and dental hypophosphatasia phenotype in Alpl-/- mice by administration of soluble (non-targeted) chimeric alkaline phosphatase," Available in PMC Mar. 1, 2016, published in final edited form as: Bone. 72:137-147 (2015) (25 pages).

Gates et al., "Effects of age, sex, and comorbidities on the pediatric outcomes data collection instrument (PODCI) in the general population," J Pediatr Orthop. 35(2):203-9 (2015).

GenBank NM_000478.2, "*Homo sapiens* alkaline phosphatase, liver/bone/kidney (ALPL), mRNA," <https://www.ncbi.nlm.nih.gov/nuccore/NM_000478.2>, dated Sep. 17, 2006, retrieved on Feb. 23, 2021 (7 pages).

Gilbert et al., "Chimeric peptides of statherin and osteopontin that bind hydroxyapatite and mediate cell adhesion," J Biol Chem. 275(21):16213-8 (2000).

Ginelliová et al., "Sudden death associated with syndromic craniosynostosis," Forensic Sci Med Pathol. 12(4):506-9 (Dec. 2016).

Glass et al., "The infant skull: a vault of information," Radiographics. 24(2):507-22 (2004).

Graham et al., "Characteristics of a Human Cell Line Transformed by DNA from Human Adenovirus Type 5," J Gen Virol. 36(1):59-72 (1977).

Greenberg et al., "A homoallelic Gly[317] to Asp mutation in ALPL causes the perinatal (lethal) form of hypophosphatasia in Canadian Mennonites," Genomics. 17:215-7 (1993).

Greenwood et al., "Familial incidence and associated symptoms in a population of individuals with nonsyndromic craniosynostosis," Genet Med. 16(4):302-10 (2014).

Guañabens et al., "Calcific periarthritis as the only clinical manifestation of hypophosphatasia in middle-aged sisters," J Bone Miner Res. 29(4):929-34 (2014).

Guo et al. "Protein tolerance to random amino acid change," Proc Natl Acad Sci USA. 101(25):9205-10 (2004).

Güzel Nur et al., "Pyridoxine-responsive seizures in infantile hypophosphatasia and a novel homozygous mutation in ALPL gene," J Clin Res Pediatr Endocrinol. 8(3):360-4 (Sep. 2016).

Hagiwara et al., "Autocrine regulation of rat chondrocyte proliferation by natriuretic peptide C and its receptor, natriuretic peptide receptor-B," J Biol Chem. 269(14):10729-33 (1994).

Hagiwara et al., "cGMP produced in response to ANP and CNP regulates proliferation and differentiation of osteoblastic cells," Am J Physiol Cell Physiol. 270:C1311-18 (1996) (9 pages).

Halling Linder et al., "Glycosylation differences contribute to distinct catalytic properties among bone alkaline phosphatase isoforms," available in PMC Nov. 1, 2010, published in final edited form as: Bone. 45(5):987-993 (2009) (17 pages).

Hancarova et al. "Hypophosphatasia due to uniparental disomy," Bone. 81:765-766 (2015).

Hardy et al., "Dissection of a carboxy-terminal region of the yeast regulatory protein RAP1 with effects on both transcriptional activation and silencing," Mol Cell Biol. 12(3):1209-17 (1992).

Harmey et al., "Concerted regulation of inorganic pyrophosphate and osteopontin by Akp2, Enpp1, and Ank," Am J Pathol. 164(4):1199-209 (2004).

Harmey et al., "Elevated skeletal osteopontin levels contribute to the hypophosphatasia phenotype in Akp2[-/-] mice," J Bone Miner Res. 21(9):1377-86 (2006).

Harris, "The human alkaline phosphatases: what we know and what we don't know," Clin Chim Acta. 186(2):133-50 (1989).

Hawrylak et al., "The solubilization of tetrameric alkaline phosphatase from human liver and its conversion into various forms by phosphatidylinositol phospholipase C or proteolysis," J Biol Chem. 263(28):14368-73 (1988).

Henthorn et al., "Different missense mutations at the tissue-nonspecific alkaline phosphatase gene locus in autosomal recessively inherited forms of mild and severe hypophosphatasia," Proc Natl Acad Sci USA. 89:9924-8 (1992).

Henthorn et al., "Missense mutations of the tissue-nonspecific alkaline phosphatase gene in hypophosphatasia," Clin Chem. 38(12):2501-5 (1992).

Herasse et al., "Molecular study of three cases of odontohypophosphatasia resulting from heterozygosity for mutations in the tissue non-specific alkaline phosphatase gene," J Med Genet. 40(8):605-9 (2003).

Hernández-Ledesma et al., "Lunasin, a novel seed peptide for cancer prevention," Peptides. 30(2):426-430 (2009).

Herring, "Mechanical influences on suture development and patency," Front Oral Biol. 12:41-56 (2008).

Hessle et al., "Tissue-nonspecific alkaline phosphatase and plasma cell membrane glycoprotein-1 are central antagonistic regulators of bone mineralization," Proc Natl Acad Sci USA. 99(14): 9445-9 (2002).

Highlights of Prescribing Information for Strensiq™ (asfotase alfa) Injection, Alexion Pharmaceuticals, Inc., <http://www.alexion.com/Documents/strensiq_pi-10-2015.aspx> (2015) (19 pages).

Hofmann et al., "Asfotase alfa: enzyme replacement for the treatment of bone disease in hypophosphatasia," Drugs Today (Barc). 52(5):271-85 (May 2016).

Hofmann et al., "Chapter 15: Recombinant enzyme replacement therapy in hypophosphatasia," *Neuronal Tissue-Nonespecific Alkaline Phosphatase (TNAP): Subcellular Biochemistry*. Caroline Fonta and Laszlo Negyessy, 76:323-41 (2015).

Hofmann et al., "Clinical aspects of hypophosphatasia: an update," Clinic Rev Bone Miner Metab. 11(2):60-70 (2013).

Hofmann et al., "Compound heterozygosity of two functional null mutations in the ALPL gene associated with deleterious neurological outcome in an infant with hypophosphatasia," Bone. 55:150-7 (2013).

Hofmann et al., "Efficacy and safety of asfotase alfa in infants and young children with hypophosphatasia: a phase 2 open-label study," J Clin Endocrinol Metab. 104(7): 2735-2747 (2019) (14 pages).

Hofmann et al., "Improvement in bone manifestations and respiratory status in infants and young children with HPP treated with asfotase alfa: an update on the ENB-010-10 trial," 7th International Conference on Children's Bone Health, Jun. 27-30, Salzburg, Austria. Bone Abstracts. 4:OC18 (2015) (3 pages).

Hollis et al., "Current concepts in hypophosphatasia: case report and literature review," Int J Paediatr Dent. 23(3):153-9 (2013).

Horton et al., "Achondroplasia," Lancet. 370:162-72 (2007).

Hosain et al., "Targeted delivery of antineoplastic agent to bone: biodistribution studies of technetium-99m-labeled gem-bisphosphonate conjugate of methotrexate," J Nucl Med. 37(1):105-7 (1996).

Hult et al., "Engineered enzymes for improved organic synthesis," Curr Opin Biotechnol. 14:395-400 (2003).

Hunter et al., "Modulation of crystal formation by bone phosphoproteins: structural specificity of the osteopontin-mediated inhibition of hydroxyapatite formation," Biochem J. 300:723-8 (1994).

Husain et al., "Fc site-specific labeling of immunoglobulins with calf intestinal alkaline phosphatase," Bioconjug Chem. 5(5):482-90 (1994).

(56) References Cited

OTHER PUBLICATIONS

Hwang et al., "Update of diagnostic evaluation of craniosynostosis with a focus on pediatric systematic evaluation and genetic studies," J Korean Neurosurg Soc. 59(3):214-8 (May 2016).

Ikezawa, "Glycosylphosphatidylinositol (GPI)-anchored proteins," Biol Pharm Bull. 25(4):409-17 (2002).

Inoue et al., "Four functionally distinct C-type natriuretic peptides found in fish reveal evolutionary history of the natriuretic peptide system," Proc Natl Acad Sci USA. 100(17):10079-84 (2003).

International Preliminary Report on Patentability for International Patent Application No. PCT/CA2011/050258, mailed Nov. 15, 2012 (9 pages).

International Preliminary Report on Patentability for International Patent Application No. PCT/US2012/039004, issued Apr. 22, 2014 (8 pages).

International Preliminary Report on Patentability for International Patent Application No. PCT/US2012/060869, issued Apr. 22, 2014 (7 pages).

International Preliminary Report on Patentability for International Patent Application No. PCT/US2016/015366, mailed Aug. 10, 2017 (10 pages).

International Preliminary Report on Patentability for International Patent Application No. PCT/US2016/049983, issued Sep. 11, 2018 (9 pages).

International Search Report and Written Opinion for International Application No. PCT/US18/26868, mailed Sep. 7, 2018 (30 pages).

International Search Report and Written Opinion for International Application No. PCT/US2019/045963, mailed Jan. 30, 2020 (26 pages).

International Search Report and Written Opinion for International Patent Application No. PCT/CA2005/000615, mailed Aug. 18, 2005 (14 pages).

International Search Report and Written Opinion for International Patent Application No. PCT/CA2008/000923, mailed Sep. 12, 2008 (11 pages).

International Search Report and Written Opinion for International Patent Application No. PCT/CA2011/050258, mailed Jul. 29, 2011 (14 pages).

International Search Report and Written Opinion for International Patent Application No. PCT/CA2011/050807, mailed Apr. 13, 2012 (18 pages).

International Search Report and Written Opinion for International Patent Application No. PCT/US20/64140, mailed Apr. 23, 2021 (16 pages).

International Search Report and Written Opinion for International Patent Application No. PCT/US2012/039004, mailed Nov. 2, 2012 (22 pages).

International Search Report and Written Opinion for International Patent Application No. PCT/US2015/039973, mailed Oct. 5, 2015 (12 pages).

International Search Report and Written Opinion for International Patent Application No. PCT/US2015/058498, mailed Jan. 22, 2016 (12 pages).

International Search Report and Written Opinion for International Patent Application No. PCT/US2015/064003, mailed Mar. 31, 2016 (13 pages).

International Search Report and Written Opinion for International Patent Application No. PCT/US2016/015366, mailed Aug. 9, 2016 (14 pages).

International Search Report and Written Opinion for International Patent Application No. PCT/US2016/025721, mailed Aug. 17, 2016 (18 pages).

International Search Report and Written Opinion for International Patent Application No. PCT/US2016/039595, mailed Feb. 21, 2017 (16 pages).

International Search Report and Written Opinion for International Patent Application No. PCT/US2016/047166, mailed Nov. 7, 2016 (15 pages).

International Search Report and Written Opinion for International Patent Application No. PCT/US2016/049983, mailed Nov. 29, 2016 (12 pages).

International Search Report and Written Opinion for International Patent Application No. PCT/US2016/054013, mailed Dec. 13, 2016 (19 pages).

International Search Report and Written Opinion for International Patent Application No. PCT/US2017/025590, mailed Jun. 29, 2017 (18 pages).

International Search Report and Written Opinion for International Patent Application No. PCT/US2017/025618, mailed Jul. 11, 2017 (22 pages).

International Search Report and Written Opinion for International Patent Application No. PCT/US2017/036133, mailed Aug. 24, 2017 (10 pages).

International Search Report and Written Opinion for International Patent Application No. PCT/US2017/047527, mailed Nov. 6, 2017 (10 pages).

International Search Report and Written Opinion for International Patent Application No. PCT/US2018/020859, mailed Jun. 19, 2018 (14 pages).

International Search Report and Written Opinion for International Patent Application No. PCT/US2018/025206, mailed Jul. 3, 2018 (25 pages).

International Search Report and Written Opinion for International Patent Application No. PCT/US2022/016031, mailed May 3, 2022 (9 pages).

International Search Report and Written Opinion for International Patent Application No. PCT/US2022/025648, mailed Jul. 22, 2022 (12 pages).

International Search Report and Written Opinion of the International Searching Authority for International Application No. PCT/US2020/064140, mailed Apr. 23, 2021 (12 pages).

International Search Report for International Patent Application No. PCT/US2012/060869, mailed Mar. 25, 2013 (5 pages).

Invitation to Pay Additional Fees for International Patent Application No. PCT/CA2011/050807, mailed Feb. 13, 2012 (2 pages).

Invitation to Pay Additional Fees for International Patent Application No. PCT/US2012/039004, mailed Aug. 29, 2012 (2 pages).

Invitation to Pay Additional Fees for International Patent Application No. PCT/US2016/015366, mailed Jun. 1, 2016 (7 pages).

Iqbal et al., "Recurrent Metatarsal Fractures in Postmenopausal Woman With Low Serum Alkaline Phosphatase: A Rare Diagnosis Not to Miss," J Investig Med High Impact Case Rep. 5(3):1-3 (Jul. 2017).

Ishida et al., "Tissue-nonspecific alkaline phosphatase with an Asp(289)-->Val mutation fails to reach the cell surface and undergoes proteasome-mediated degradation," J Biochem. 134(1):63-70 (2003).

Jansonius, "Structure, evolution and action of vitamin B6-dependent enzymes," Curr Opin Struct Biol. 8:759-769 (1998).

Jin et al., "Novel analog of atrial natriuretic peptide selective for receptor-A produces increased diuresis and natriuresis in rats," J Clin Invest. 98(4):969-976 (1996).

Johnson et al., "Craniosynostosis," Eur J Hum Genet. 19(4):369-76 (2011).

Johnson et al., "Matrix vesicle plasma cell membrane glycoprotein-1 regulates mineralization by murine osteoblastic MC3T3 cells," J Bone Miner Res. 14(6):883-892 (1999).

Johnson et al., "Motor proficiency in children with neurofibromatosis type 1," Pediatr Phys Ther. 22(4):344-8 (2010).

Kabbani et al., "Craniosynostosis," Am Fam Physician. 69(12):2863-70 (2004).

Kajdic et al., "Craniosynostosis—Recognition, clinical characteristics, and treatment," Bosn J Basic Med Sci. 18(2):110-6 (2018).

Kakkis et al., "Enzyme-replacement therapy in mucopolysaccharidosis I," N Engl J Med. 344(3):182-8 (2001).

Kalra et al., "The role of C-type natriuretic peptide in cardiovascular medicine," Eur Heart J. 22:997-1007 (2001).

Kasugai et al., "Selective drug delivery system to bone: small peptide $(Asp)_6$ conjugation," J Bone Miner Res. 15(5):936-943 (2000).

(56) References Cited

OTHER PUBLICATIONS

Katsianou et al., "Signaling mechanisms implicated in cranial sutures pathophysiology: Craniosynostosis," BBA Clin. 6:165-76 (Apr. 2016).

Kaufmann et al., "Influence of low temperature on productivity, proteome and protein phosphorylation of CHO cells," Biotechnol Bioeng. 63(5):573-82 (1999).

Khanna et al., "Pictorial essay: the many faces of craniosynostosis," Indian J Radiol Imaging. 21(1):49-56 (2011).

Kim et al., "CHO cells in biotechnology for production of recombinant proteins: current state and further potential," Appl Microbiol Biotechnol. 93(3):917-30 (2012).

Kim et al., "Comparison of phenylketonuria (PKU) patients' height, weight and body mass index (BMI) to the general population," Mol Genet Metab. 105:328-329 (2012).

Kim et al., "Craniosynostosis: Updates in radiologic diagnosis," J Korean Neurosurg Soc. 59(3):219-26 (May 2016).

Kishnani et al., "Biochemical and physical function outcomes in adolescents and adults with hypophosphatasia treated with asfotase alfa for up to 4 years: interim results from a phase II study," Endocrine Society's 98th Annual Meeting and Expo, Apr. 1-4, Boston, MA. Abstract OR26-3 (Apr. 2016) (2 pages).

Kishnani et al., "Five-year efficacy and safety of asfotase alfa therapy for adults and adolescents with hypophosphatasia," Bone. 121:149-162 (2019).

Kishnani et al., "Hypophosphatasia: enzyme replacement therapy (ENB-0040) decreases TNSALP substrate accumulation and improves functional outcome in affected adolescents and adults," Endocrine Society's 15th International & 14th European Congress of Endocrinology, May 5-9, Florence, Italy. Abstract OC8.1 (2012) (4 pages).

Kishnani et al., "Monitoring guidance for patients with hypophosphatasia treated with asfotase alfa," Mol Genet Metab. 122(1-2):4-17 (Sep. 2017).

Kishnani et al., "OR26-3 Biochemical and Physical Function Outcomes in Adolescents and Adults with Hypophosphatasia Treated with Asfotase Alfa for up to 4 Years: Interim Results from a Phase II Study," ENDO 2016, Boston, MA, Apr. 3, 2016 (22 pages).

Kitaoka et al., "Safety and efficacy of treatment with asfotase alfa in patients with hypophosphatasia: results from a Japanese clinical trial," Clin Endocrinol (Oxf). 87(1):10-19 (epub pp. 1-10) (Jul. 2017).

Klidaras et al., "Fracture Healing in Two Adult Patients With Hypophosphatasia After Asfotase Alfa Therapy," JBMR Plus. 2(5):304-307 (May 2018).

Kochanowski et al., "Medium and feed optimization for fed-batch production of a monoclonal antibody in CHO cells," BMC Proc. 5(Suppl 8):P75 (2011) (3 pages).

Kochendoerfer, "Protein & Peptide Drug Delivery—Third International Conference: Minimally invasive delivery methods, Sep. 22-23, Philadelphia, PA, USA," IDrugs. 6(11):1043-5 (2003).

Komaru et al., "Molecular and cellular basis of hypophosphatasia," J Oral Biosci. 61(3):141-148 (Sep. 2019).

Komenaka et al., "Immunotherapy for melanoma," Clin Dermatol. 22(3):251-265 (2004).

Kosnik-Infinger et al., "Enzyme replacement therapy for congenital hypophosphatasia allows for surgical treatment of related complex craniosynostosis: a case series," Neurosurg Focus. 38(5):E10 (2015) (6 pages).

Kostenuik et al., "Infrequent delivery of a long-acting PTH-Fc fusion protein has potent anabolic effects on cortical and cancellous bone," J Bone Miner Res. 22(10):1534-1547 (2007).

Kozlenkov et al., "Residues determining the binding specificity of uncompetitive inhibitors to tissue-nonspecific alkaline phosphatase," J Bone Miner Res. 19(11):1862-72 (2004).

Kozlowski et al., "Hypophosphatasia. Review of 24 Cases," Pediatr Radiol. 5(2):103-17 (1976) (15 pages).

Krakow et al., "Clinical and radiographic delineation of bent bone dysplasia-FGFR2 type or bent bone dysplasia with distinctive clavicles and angel-shaped phalanges," Am J Med Genet A. 170(10):2652-61 (Oct. 2016).

Kulikova et al., "Hypophosphatasia: the clinical description of 3 cases of the disease with the molecular-genetic verification of the diagnosis," Problems of Endocrinology. 61(3):37-42 (2015) (Article in Russian) (English Abstract included).

Lazdunski et al., "Structure-function relationships for some metalloalkaline phosphatases of E. coli," Eur J Biochem. 8(4):510-7 (1969).

Le Du et al., "Crystal structure of alkaline phosphatase from human placenta at 1.8 Å resolution. Implication for a substrate specificity," J Biol Chem. 276(12):9158-65 (2001) (9 pages).

Lee et al., "Disturbed osteoblastic differentiation of fibrous hamartoma cell from congenital pseudarthrosis of the tibia associated with neurofibromatosis type I," Clin Orthop Surg. 3(3):230-7 (2011).

Leone et al., "Allosteric modulation of pyrophosphatase activity of rat osseous plate alkaline phosphatase by magnesium ions," Int J Biochem Cell Biol. 30:89-97 (1998).

Leung et al. "Outcome of perinatal hypophosphatasia in Manitoba Mennonites: a retrospective cohort analysis," JIMD Rep. 11:73-78 (2013).

Li et al. "Timing of the initiation of bisphosphonates after surgery for fracture healing: a systematic review and meta-analysis of randomized controlled trials," Osteoporos Int. 26(2):431-41 (2015) (11 pages).

Li et al., "Standard reference for the six-minute-walk test in healthy children aged 7 to 16 years," Am J Respir Crit Care Med. 176(2):174-80 (2007).

Linglart et al., "Hypophosphatasia," Curr Osteoporos Rep. 14(3):95-105; DOI 10.1007/s11914-016-0309-0 (Jun. 2016) (11 pages).

Little et al., "Lineage tracking of myogenic progenitors in surgical models of tibial bone repair," Bone. 48(2):S82 (2011).

Liu et al., "Tissue-nonspecific alkaline phosphatase deficiency causes abnormal craniofacial bone development in the Alpl(-/-) mouse model of infantile hypophosphatasia," available in PMC Oct. 1, 2015, published in final edited form as: Bone. 67:81-94 (2014) (30 pages).

Lo et al., "High level expression and secretion of Fc-X fusion proteins in mammalian cells," Protein Eng. 11(6):495-500 (1998).

Luo et al., "Lower ultrafiltration temperature improves membrane performance and emulsifying properties of milk protein concentrates," Dairy Sci. & Technol. 95(1):15-31 (Sep. 2014).

López-Delgado et al., "Abnormal bone turnover in individuals with low serum alkaline phosphatase," Osteoporosis Int. 29(9):2147-2150; doi: 10.1007/s00198-018-4571-0 (Supplementary information included) (2018) (6 pages).

Madson et al., "Asfotase alfa: sustained efficacy and tolerability in children with hypophosphatasia treated for 5 years," ESPE Abstracts. 84:FC2.4 (2015) (2 pages).

Mahmood et al., "Selection of the first-time dose in humans: comparison of different approaches based on interspecies scaling of clearance," J Clin Pharmacol. 43:692-697 (2003).

Makras et al., "Medical treatment of Hypercalcaemia," Hormones. 8(2):83-95 (2009).

Martos-Moreno et al., "Hypophosphatasia: clinical manifestations, diagnostic recommendations and therapeutic options," An Pediatr (Barc). S1695-4033(17)30223-0 (Jul. 2017) (11 pages) (Article in Spanish) (English Abstract included).

Mather, "Establishment and characterization of two distinct mouse testicular epithelial cell lines," Biol Reprod. 23(1):243-52 (1980).

Mathijssen, "Guideline for care of patients with the diagnoses of craniosynostosis: working group on craniosynostosis," J Craniofac Surg. 26(6):1735-807 (2015).

Matsumoto et al., "Rescue of severe infantile hypophosphatasia mice by AAV-mediated sustained expression of soluble alkaline phosphatase," Hum Gene Ther. 22(11):1355-64 (2011).

Mayer, "Chapter 4: Immunoglobulins: Structure and Function," Microbiology and Immunology On-line, University of South Carolina School of Medicine, <http://pathmicro.med.sc.edu/mayer/IgStruct2000.htm> (2009) (12 pages).

(56)        References Cited

OTHER PUBLICATIONS

McCormack et al., "Is bigger better? An argument for very low starting doses," CMAJ. 183(1):65-9 (2011).

McKiernan et al., "Clinical and radiographic findings in adults with persistent hypophosphatasemia," J Bone Miner Res. 29(7):1651-60 (2014).

Mericq et al., "Regulation of fetal rat bone growth by C-type natriuretic peptide and cGMP," Pediatr Res. 47(2):189-193 (2000) (9 pages).

Merrill et al., "Bent bone dysplasia-FGFR2 type, a distinct skeletal disorder, has deficient canonical FGF signaling," Am J Hum Genet. 90(3):550-7 (2012).

Meyer, "Can biological calcification occur in the presence of pyrophosphate?" Arch Biochem Biophys. 231(1):1-8 (1984).

Michigami et al., "Common mutations F310L and T1559del in the tissue-nonspecific alkaline phosphatase gene are related to distinct phenotypes in Japanese patients with hypophosphatasia," Eur J Pediatr. 164:277-282 (2005).

Miller et al., "Ultrasound diagnosis of craniosynostosis," Cleft Palate Craniofac J. 39(1):73-80 (2002).

Millichap, "Cognitive Development of Children with Craniosynostosis," Pediatr Neurol Briefs. 29(6):47 (2015).

Millan et al., "Alkaline phosphatase and hypophosphatasia," Calcif Tissue Int. 98(4):398-416 (Apr. 2016).

Millan et al., "Enzyme replacement therapy for murine hypophosphatasia," J Bone Miner Res. 23(6):777-87 (2008).

Millan et al., "Hypophosphatasia—pathophysiology and treatment," available in PMC Sep. 22, 2014, published in final edited form as: Actual Osteol. 8(3):164-182 (2012) (21 pages).

Millán, "The role of phosphatases in the initiation of skeletal mineralization," Calcif Tissue Int. 93(4):299-306 (2013).

Millán, Chapter 7: The in vivo role of TNAP. Mammalian alkaline phosphatases: From Biology to Applications in Medicine and Biotechnology. Wiley-VCH Verlag Gmbh & Co., 107-185 (2006).

Millán, Mammalian Alkaline Phosphatases: From Biology to Applications in Medicine and Biotechnology, Wiley-VCH Verlag GmbH & Co., Weinheim, Germany (2006) (324 pages).

Miyazawa et al., "Cyclic GMP-dependent protein kinase II plays a critical role in C-type natriuretic peptide-mediated endochondral ossification," Endocrinology. 143(9):3604-3610 (2002).

Mohn et al., "Hypophosphatasia in a child with widened anterior fontanelle: lessons learned from late diagnosis and incorrect treatment," Acta Paediatr. 100(7):e43-6 (2011).

Mori et al., "Case series: odontohypophosphatasia or missed diagnosis of childhood/adult-onset hypophosphatasia?—Call for a long-term follow-up of premature loss of primary teeth," Bone Rep. 5:228-232 (Aug. 2016).

Mornet et al., "A molecular-based estimation of the prevalence of hypophosphatasia in the European population," Ann Hum Genet. 75(3):439-45 (2011).

Mornet et al., "Hypophosphatasia," GeneReviews. https://www.ncbi.nlm.nih.gov/books/NBK1150/, retrieved Dec. 6, 2017, initially published Nov. 20, 2007, last updated Feb. 4, 2016 (25 pages).

Mornet et al., "Identification of fifteen novel mutations in the tissue-nonspecific alkaline phosphatase (TNSALP) gene in European patients with severe hypophosphatasia," Eur J Hum Genet. 6(4):308-14 (1998).

Mornet et al., "Structural evidence for a functional role of human tissue nonspecific alkaline phosphatase in bone mineralization," J Biol Chem. 276(33):31171-8 (2001).

Mornet, "Chapter 2: Molecular genetics of hypophosphatasia and phenotype-genotype correlations," Subcell Biochem. 76:25-43 (2015).

Mornet, "Hypophosphatasia," Best Pract Res Clin Rheumatol. 22(1):113-27 (2008).

Mornet, "Hypophosphatasia," Metabolism. 82:142-155; DOI: 10.1016/j.metabol.2017.08.013 (2018) (30 pages).

Mornet, "Hypophosphatasia," Orphanet J Rare Dis. 2:(40) (2007) (8 pages).

Mornet, "The tissue nonspecific alkaline phosphatase gene mutations database," <www.sesep.uvsq.fr/03_hypo_mutations.php>, last updated Nov. 28, 2019 (14 pages).

Morris et al., "Immunolocalization of alkaline phosphatase in osteoblasts and matrix vesicles of human fetal bone," Bone Miner. 19:287-298 (1992).

Morrison et al. "Mitigation of tracheobronchomalacia with 3D-printed personalized medical devices in pediatric patients," available in PMC Apr. 29, 2016, published in final edited form as: Sci Transl Med. 7(285):285ra264 (2015) (23 pages).

Morrow, "Expensive new biologic helps children fight hypophosphatasia," Manag Care. 24(12) (2015) (7 pages).

Moss et al., "Association of inorganic-pyrophosphatase activity with human alkaline-phosphatase preparations," Biochem J. 102:53-57 (1967).

Murgu et al. "Tracheobronchomalacia and excessive dynamic airway collapse," Respirology. 11(4):388-406 (2006).

Murray, "Lectin-specific targeting of lysosomal enzymes to reticuloendothelial cells," Methods Enzymol. 149:25-42 (1987).

Murshed et al., "Unique coexpression in osteoblasts of broadly expressed genes accounts for the spatial restriction of ECM mineralization to bone," Genes Dev. 19:1093-1104 (2005).

Nahabet et al., "Postnatal pancraniosynostosis in a patient with infantile hypophosphatasia," Cleft Palate Craniofac J. 53(6):741-4, doi: 10.1597/15-027 (Nov. 2016).

Nakamura-Utsunomiya et al., "Clinical characteristics of perinatal lethal hypophosphatasia: a report of 6 cases," Clin Pediatr Endocrinol. 19(1):7-13 (2010).

Nakao et al., "The pharmacokinetics of alpha-human atrial natriuretic polypeptide in healthy subjects," Eur J Clin Pharmacol. 31(1):101-103 (1986).

Nangia et al., "Disorders of Calcium Metabolism in Newborns," Journal of Neonatology. 17(2):43-49 (2003).

Narisawa et al., "Abnormal vitamin B6 metabolism in alkaline phosphatase knock-out mice causes multiple abnormalities, but not the impaired bone mineralization," J Pathol. 193:125-133 (2001).

Narisawa et al., "Inactivation of two mouse alkaline phosphatase genes and establishment of a model of infantile hypophosphatasia," Dev Dyn. 208:432-446 (1997).

Nasu et al., "Aberrant interchain disulfide bridge of tissue-nonspecific alkaline phosphatase with an Arg433 to Cys substitution associated with severe hypophosphatasia," FEBS Journal. 273:5612-5624 (2006).

National Institute for Health and Care Excellence, "Highly Specialised Technology Evaluation: Asfotase alfa for treating paediatric-onset hypophosphatasia [ID 758]," Oct. 21, 2015, <https://www.nice.org.uk/guidance/hst6/documents/committee-papers-8> (99 pages).

NCBI Protein Database Accession No. AAC33858, <http://www.ncbi.nlm.nih.gov/protein/AAC33858>, retrieved Apr. 16, 2013 (1 page).

NCBI Protein Database Accession No. AAF64516, <http://www.ncbi.nlm.nih.gov/protein/AAF64516>, retrieved Apr. 16, 2013 (2 pages).

NCBI Protein Database Accession No. AAH21289, <http://www.ncbi.nlm.nih.gov/protein/AAH21289>, retrieved Apr. 16, 2013 (2 pages).

NCBI Protein Database Accession No. AAH66116. Retrieved on Apr. 16, 2013 (2 pages).

NCBI Protein Database Accession No. AAH90861. Retrieved on Apr. 16, 2013 (2 pages).

NCBI Protein Database Accession No. AAI10910. Retrieved on Apr. 16, 2013 (2 pages).

NCBI Protein Database Accession No. AAI18209. Retrieved on Apr. 17, 2013 (2 pages).

NCBI Protein Database Accession No. AAI26166. Retrieved on Apr. 16, 2013 (2 pages).

NCBI Protein Database Accession No. AAN64273. Retrieved on Apr. 16, 2013 (1 page).

NCBI Protein Database Accession No. NP_000469. Retrieved on Apr. 16, 2013 (3 pages).

NCBI Protein Database Accession No. NP_001036028. Retrieved on Apr. 16, 2013 (2 pages).

(56) References Cited

OTHER PUBLICATIONS

NCBI Protein Database Accession No. NP_001253798, Retrieved on Apr. 17, 2013 (2 pages).
NCBI Protein Database Accession No. NP_001622. Retrieved on Apr. 16, 2013 (3 pages).
NCBI Protein Database Accession No. NP_001623. Retrieved on Apr. 16, 2013 (3 pages).
NCBI Protein Database Accession No. NP_031457. Retrieved on Apr. 16, 2013 (3 pages).
NCBI Protein Database Accession No. NP_037191. Retrieved on Apr. 16, 2013 (3 pages).
NCBI Protein Database Accession No. NP_112603. Retrieved on Apr. 16, 2013 (3 pages).
NCBI Protein Database Accession No. NP_776412. Retrieved on Apr. 17, 2013 (2 pages).
NCBI Protein Database Accession No. NP_789828. Retrieved on Apr. 16, 2013 (3 pages).
NCBI Protein Database Accession No. P01857. Retrieved on Apr. 18, 2013 (7 pages).
NCBI Protein Database Accession No. P05186. Retrieved on Apr. 16, 2013 (19 pages).
NCBI Protein Database Accession No. P05187. Retrieved on Apr. 16, 2013 (10 pages).
NCBI Protein Database Accession No. P08289. Retrieved on Apr. 16, 2013 (5 pages).
NCBI Protein Database Accession No. P09242. Retrieved on Apr. 16, 2013 (6 pages).
NCBI Protein Database Accession No. P09487. Retrieved on Apr. 16, 2013 (4 pages).
NCBI Protein Database Accession No. P09923. Retrieved on Apr. 16, 2013 (6 pages).
NCBI Protein Database Accession No. P10696. Retrieved on Apr. 16, 2013 (7 pages).
NCBI Protein Database Accession No. Q29486. Retrieved on Apr. 16, 2013 (3 pages).
NCBI Protein Database Accession No. Q6PYX1. Retrieved on Oct. 15, 2013 (2 pages).
NCBI Protein Database Accession No. Q9N0V0. Retrieved on Apr. 16, 2013 (1 page).
NCBI Protein Database Accession No. XP_001109717. Retrieved on Apr. 17, 2013 (1 page).
Ngo et al., Chapter 14: Computational Complexity, Protein Structure Prediction, and the Levinthal Paradox. *The Protein Folding Problem and Tertiary Structure Prediction.* Merz et al. (eds.), 433, 492-495 (1994).
Nishioka et al., "Enhancement of drug delivery to bone: characterization of human tissue-nonspecific alkaline phosphatase tagged with an acidic oligopeptide," Mol Genet Metab. 88:244-255 (2006).
Nosjean et al., "Human tissue non-specific alkaline phosphatases: sugar-moiety-induced enzymic and antigenic modulations and genetic aspects," Biochem J. 321(Pt 2)(Pt 2):297-303 (1997).
Notice of Final Rejection for Korean Patent Application No. 10-2018-7028255, dated Apr. 21, 2022 (7 pages).
Notice of Final Rejection for Korean Patent Application No. 10-2018-7028255, dated Aug. 18, 2022 (7 pages).
Notice of Reasons for Rejection for Japanese Application No. 2018-508754, mailed Jun. 30, 2020 (11 pages).
Notice of Reasons for Rejection for Japanese Patent Application No. 2018-515934, mailed Jul. 28, 2020 (7 pages).
Notice of Reasons for Rejection for Japanese Patent Application No. 2019-553247, mailed Apr. 20, 2022 (5 pages).
Oda et al., "A general method for rapid purification of soluble versions of glycosylphosphatidylinositol-anchored proteins expressed in insect cells: an application for human tissue-nonspecific alkaline phosphatase," J Biochem. 126(4):694-9 (1999).
Office Action for Brazilian Patent Application No. BR112018070243-9, dated Sep. 7, 2022 (10 pages).
Office Action for Canadian Patent Application No. 2,993,358, dated Sep. 20, 2022 (6 pages).

Office Action for Chinese Patent Application No. 201680048588.5, mailed Jan. 18, 2021 (28 pages).
Office Action for Chinese Patent Application No. 201780021666.7, issued Jul. 21, 2021 (34 pages).
Office Action for Chinese Patent Application No. 201780021666.7, issued Mar. 9, 2022 (23 pages).
Office Action for Chinese Patent Application No. 201780021666.7, issued on Jun. 20, 2022 (22 pages).
Office Action for Japanese Patent Application No. 2018-551309, mailed Nov. 2, 2021 (11 pages).
Office Action for Japanese Patent Application No. 2019-548417, mailed Jan. 18, 2022 (8 pages).
Office Action for Russian Patent Application No. 2018137822, mailed Jul. 24, 2020 (20 pages).
Office Action for Russian Patent Application No. 2019134794, mailed Dec. 7, 2021 (11 pages).
Office Action for U.S. Appl. No. 11/111,664, mailed Dec. 4, 2008 (7 pages).
Office Action for U.S. Appl. No. 11/111,664, mailed May 14, 2008 (8 pages).
Office Action for U.S. Appl. No. 11/111,664, mailed Oct. 4, 2007 (11 pages).
Office Action for U.S. Appl. No. 11/484,870, mailed Aug. 11, 2009 (15 pages).
Office Action for U.S. Appl. No. 11/484,870, mailed Feb. 2, 2009 (16 pages).
Office Action for U.S. Appl. No. 11/484,870, mailed Jan. 25, 2007 (15 pages).
Office Action for U.S. Appl. No. 11/484,870, mailed Jul. 5, 2007 (13 pages).
Office Action for U.S. Appl. No. 11/484,870, mailed Jun. 25, 2008 (16 pages).
Office Action for U.S. Appl. No. 11/484,870, mailed Oct. 1, 2007 (12 pages).
Office Action for U.S. Appl. No. 12/405,920, mailed Aug. 9, 2010 (7 pages).
Office Action for U.S. Appl. No. 12/405,920, mailed Dec. 17, 2009 (14 pages).
Office Action for U.S. Appl. No. 12/793,517, mailed Aug. 16, 2010 (9 pages).
Office Action for U.S. Appl. No. 13/071,445, mailed Feb. 6, 2012 (12 pages).
Office Action for U.S. Appl. No. 13/071,445, mailed May 25, 2012 (14 pages).
Office Action for U.S. Appl. No. 17/117,099, dated Nov. 28, 2022 (200 pages).
Official Action and Translation for Japanese Application No. 2013-544989, mailed Oct. 27, 2015 (6 pages).
Official Action and Translation for Japanese Application No. 2017-539393, mailed Sep. 17, 2019 (14 pages).
Official Action for Russian Patent Application No. 2017123540, dated Jul. 8, 2019 (15 pages).
Official Notification and Search Report for Eurasian Patent Application No. 201291138, dated Jul. 16, 2013 (3 pages).
Oginni et al., "Radiological and biochemical resolution of nutritional rickets with calcium," Arch Dis Child. 88(9):812-17 (2003).
Oikawa et al., "Enzyme replacement therapy on hypophosphatasia mouse model," J Inherit Metab Dis. 37(2):309-17 (2013).
Okazaki et al., "Lethal hypophosphatasia successfully treated with enzyme replacement from day 1 after birth," Eur J Pediatr. 175(3):433-7; DOI 10.1007/s00431-015-2641-2 (Mar. 2016) (5 pages).
Opperman, "Cranial sutures as intramembranous bone growth sites," Dev Dyn. 219(4):472-85 (2000).
Orimo, "Pathophysiology of hypophosphatasia and the potential role of asfotase alfa," Ther Clin Risk Manag. 12:777-86 (May 2016).
Orimo, "The mechanism of mineralization and the role of alkaline phosphatase in health and disease," J Nippon Med Sch. 77(1):4-12 (2010).
Padidela et al., "Enzyme-replacement therapy in life-threatening perinatal hypophosphatasia in a premature infant," Endocrine Abstracts. 33:P9 (2013) (1 page).

(56)        References Cited

OTHER PUBLICATIONS

Padidela et al., "P1-118: Management of Tracheobronchomalacia During Asfotase Alfa Treatment in Infants with Perinatal-Onset Hypophosphatasia: A Case Series," European Society for Paediatric Endocrinology (ESPE), Paris, France, Sep. 10-12, 2016 (1 page).

Panesar, "Hypophosphatasia: a rare disorder," US Pharm. 42(5) (May 2017) (8 pages).

Park et al. "The effect of alendronate loaded biphasic calcium phosphate scaffolds on bone regeneration in a rat tibial defect model," Int J Mol Sci. 16(11):26738-53 (2015) (17 pages).

Park et al., "Ex vivo assessment of contractility, fatigability and alternans in isolated skeletal muscles," J Vis Exp. 69:e4198 (2012) (8 pages).

Park et al., "First Korean case of infantile hypophosphatasia with novel mutation in ALPL and literature review," Ann Clin Lab Sci. 46(3):302-7 (May 2016).

Patti et al., "Critical residues in the ligand-binding site of the *Staphylococcus aureus* collagen-binding adhesin (MSCRAMM)," J Biol Chem. 270(20):12005-11 (1995).

Pedersen et al., "Removal of N-terminal polyhistidine tags from recombinant proteins using engineered aminopeptidases," Protein Expr Purif. 15(3):389-400 (1999).

Pfeifer et al., "Intestinal secretory defects and dwarfism in mice lacking cGMP-dependent protein kinase II," Science. 274(5295):2082-2086 (1996).

Phillips et al., "A modified performance-oriented mobility assessment tool for assessing clinically relevant gait impairments and change in children with hypophosphatasia: development and validation," 7th International Conference on Children's Bone Health, Jun. 27-30, Salzburg, Austria. Bone Abstracts. 4:P136 (2015) (2 pages).

Phillips et al., "Clinical Outcome Assessments: Use of Normative Data in a Pediatric Rare Disease," Value Health. 21(5):508-514 (2018).

Phillips et al., "Gait assessment in children with childhood hypophosphatasia: impairments in muscle strength and physical function," The Endocrine Society's 97th Annual Meeting & Expo, Mar. 5-8, San Diego, California. Poster LBS-039 (2015) (2 pages).

Phillips et al., "Improved activities of daily living and physical function, with decreased pain, in children with hypophosphatasia treated for three years with asfotase alfa: results from the childhood health assessment questionnaire and the pediatric outcomes data collection instrument," The Endocrine Society's 97th Annual Meeting & Expo, Mar. 5-8, San Diego, California. Poster Abstract FRI-224 (2015) (1 page).

Phillips et al., "Physical therapy management of infants and children with hypophosphatasia, " Mol Genet Metab. 119(1-2):14-9 (Sep. 2016).

Phillips et al., "Significantly improved muscle strength, running speed, and agility in children with hypophosphatasia treated with asfotase alfa," Endocrine Society's 97th Annual Meeting and Expo, Mar. 5-8, San Diego, CA. Abstract OR29-4 (2015) (2 pages).

Potter et al., "Natriuretic peptides, their receptors, and cyclic guanosine monophosphate- dependent signaling functions," Endocr Rev. 27(1):47-72 (2006).

Pradhan et al., "Exposure-Response Modeling and Simulation to Support Evaluation of Efficacious and Safe Exposure and Dose Range for Asfotase alfa in Patients with Hypophosphatasia," ASBMR 2015 Annual Meeting Abstracts. J Bone and Med Res. SU0380:S316 (2015) (1 page).

Ramachandran et al., "Treatment of an anabolic bone deficiency in neurofibromatosis with bone morphogenetic proteins and its potential application for congenital pseudarthrosis of the tibia," J Bone Joint Surg Br. 91-B (Suppl. 1), Abstract 137 (2009).

Ratner, "Alexion pays big for Synageva's rare disease drug candidate," Nat Biotechnol. 33(7):679 (2015).

Reginato et al., "Musculoskeletal manifestations of osteomalacia and rickets," Best Pract Res Clin Rheumatol. 17(6):1063-80 (2003).

Remde et al., "Successful asfotase alfa treatment in an adult dialysis patient with childhood-onset hypophosphatasia," J Endoc Soc. 1(9):1188-93 (Aug. 2017).

Reply Brief as Filed in U.S. Appl. No. 12/638,527, dated Apr. 22, 2016 (4 pages).

Reply to Final Office Action for U.S. Appl. No. 11/111,664, dated Sep. 10, 2008 (32 pages).

Reply to Final Office Action for U.S. Appl. No. 13/071,445, dated Oct. 25, 2012 (14 pages).

Restriction Requirement for U.S. Appl. No. 12/599,679, mailed Jun. 12, 2012 (5 pages).

Rezende et al., "Inorganic pyrophosphate-phosphohydrolytic activity associated with rat osseous plate alkaline phosphatase," Cell Mol Biol. 44(2):293-302 (1998).

Rockman-Greenberg et al., "Hypophosphatasia: Enzyme Replacement with ENB-0040, a Bone- Targeted Human Recombinant Tissue Nonspecific Alkaline Phosphatase (TNSALP) Fusion Protein," American College of Medical Genetics, 16th Annual Clinical Genetics Meeting, Mar. 25-29, Tampa, Florida (2009) (1 page).

Rockman-Greenberg, "Hypophosphatasia," Pediatr Endocrinol Rev. 10 Suppl 2:380-8 (2013) (Abstract only).

Rodgers et al., "Spring-assisted cranioplasty for the correction of non-syndromic scaphocephaly: a quantitative analysis of 100 consecutive cases," Plast Reconstr Surg. 140(1):125-34 (Jul. 2017).

Rodionova et al., "Hypophosphatasia in Adults: Clinical Cases And Literature Review," Osteoporosis and Bone Diseases. 18(2):25-28 (2015) 10.14341/osteo2015225-28 (English language abstract).

Rodriguez et al., "Respiratory mechanics in an infant with perinatal lethal hypophosphatasia treated with human recombinant enzyme replacement therapy," Pediatr Pulmonol. 47(9):917-22 (2012).

Rottgers et al., "Outcomes of endoscopic suturectomy with postoperative helmet therapy in bilateral coronal craniosynostosis," J Neurosurg Pediatr. 18(3):281-6 (2016).

Rowe et al., "MEPE, a new gene expressed in bone marrow and tumors causing osteomalacia," Genomics. 67:54-68 (2000).

Rozovsky et al., "Cranial ultrasound as a first-line imaging examination for craniosynostosis," Pediatrics. 137(2):e20152230 (Feb. 2016) (9 pages).

Rush, "Childhood hypophosphatasia: to treat or not to treat," Orphanet J Rare Dis. 13(1):116 (2018) (5 pages).

Russell et al., "Inorganic pyrophosphate in plasma in normal persons and in patients with hypophosphatasia, osteogenesis imperfecta, and other disorders of bone," J Clin Invest. 50:961-969 (1971).

Sabbagh et al., "Hypophosphatemia leads to rickets by impairing caspase-mediated apoptosis of hypertrophic chondrocytes," Proc Natl Acad Sci U S A. 102(27):9637-42 (2005).

Saglam et al., "Clinical and genetic findings of Turkish hypophosphatasia cases," J Clin Res Pediatr Endocrinol. 9(3):229-236 (Sep. 2017).

Sakamoto et al., "Physiological changes and clinical implications of syndromic craniosynostosis," J Korean Neurosurg Soc. 59(3):204-13 (May 2016).

Salih et al., "Identification of the phosphorylated sites of metabolically 32P-labeled osteopontin from cultured chicken osteoblasts," J Biol Chem. 272(21):13966-73 (1997).

Salva et al., "Signaling networks in joint development," Dev Dyn. 246(4):262-74 (Apr. 2017).

Sands et al., "Enzyme replacement therapy for murine mucopolysaccharidosis type VII," J Clin Invest. 93(6):2324-31 (1994).

Saraff et al., "A diagnostic algorithm for children with low alkaline phosphatase activities: lessons learned from laboratory screening for hypophosphatasia," J Pediatr. 172:181-6 (May 2016) (7 pages).

Sather, "Case Study: 3 year old female with hypophosphatasia, treated with asfotase alfa replacement," J Pediatr Nurs. 34:104 (Abstract 008) (May 2017) (1 page).

Sawai et al., "Severe perinatal hypophosphatasia due to homozygous deletion of T at nucleotide 1559 in the tissue nonspecific alkaline phosphatase gene," Prenat Diagn. 23(9):743-6 (2003).

Schiffman et al., "The promise of global cervical-cancer prevention," N Engl J Med. 353(20):2101-2104 (2005).

Schindeler et al., "Modeling bone morphogenetic protein and bisphosphonate combination therapy in wild-type and Nf1 haploinsufficient mice," J Orthop Res. 26(1):65-74 (2008).

(56) References Cited

OTHER PUBLICATIONS

Schmidt et al., "Clinical, radiographic and biochemical characteristics of adult hypophosphatasia," Osteoporos Int. 28(9):2653-2662 (Sep. 2017).

Schmidt et al., "Hypophosphatasia: What is currently available for treatment?" Internist (Berl). 57(12):1145-1154 (Dec. 2016) (Article in German) (English abstract).

Scott, "Asfotase alfa in perinatal/infantile-onset and juvenile-onset hypophosphatasia: a guide to its use in the USA," BioDrugs. 30(1):41-8 (Feb. 2016).

Scott, "Asfotase alfa: a review in paediatric-onset hypophosphatasia," Drugs. 76(2):255-62 (Feb. 2016).

Search Report and Translation for Russian Application No. 2018109368, dated Feb. 5, 2020 (4 pages).

Seefried et al., "Bone Turnover and Mineral Metabolism in Adult Patients with Pediatric-Onset Hypophosphatasia Treated With Asfotase Alfa," The American Society for Bone and Mineral Research 2020 Annual Meeting, Sep. 11-15, virtually (2020) (1 page).

Seefried et al., "Long-term Effectiveness of Asfotase Alfa Treatment in Adults with Pediatric-onset Hypophosphatasia in Routine Clinical Practice" 22nd European Congress of Endocrinology, Sep. 5-9, virtual (2020) (1 page).

Seefried et al., "Long-term Effectiveness of Asfotase Alfa Treatment in Adults with Pediatric-onset Hypophosphatasia in Routine Clinical Practice," 2020 American Society for Bone and Mineral Research Virtual Conference, Sep. 11-15, 2020 (1 page).

Seefried et al., "Pharmacodynamic results from a phase 2a, randomized, multicenter, open-label, dose-ranging study of asfotase alfa in adults with pediatric hypophosphatasia," 100th Annual Meeting and Expo of the Endocrine Society, Mar. 17-20, 2018, Chicago, IL (1 page).

Seefried et al., "Real-world Clinical Profiles of Adults with Hypophosphatasia (HPP) from the Global HPP Registry," The American Society for Bone and Mineral Research 2020 Annual Meeting, Sep. 11-15, virtually (2020) (1 page).

Sekido et al., "Novel drug delivery system to bone using acidic oligopeptide: pharmacokinetic characteristics and pharmacological potential," J Drug Target. 9(2):111-21 (2001).

Seshia et al., "Myopathy with hypophosphatasia," Arch Dis Child. 65(1):130-1 (1990).

Shah et al., "Sudden infant death in a patient with FGFR3 P250R mutation," Am J Med Genet A. 140A(24):2794-6 (2006).

Shapiro et al., "Hypophosphatasia in adults: clinical assessment and treatment considerations," J Bone Miner Res. 32(10):1977-1980 (Oct. 2017).

Sharma et al., "Alkaline Phosphatase: An Overview," Indian J Clin Biochem. 29(3):269-278 (2014).

Sharma et al., "Bilateral femoral neck fractures in a young patient suffering from hypophosphatasia, due to a first time epileptic seizure," J Orthop Case Rep. 5(3):66-8 (2015).

Sharma, "Craniosynostosis," Indian J Plast Surg. 46(1):18-27 (2013).

Sharom et al., "Glycosylphosphatidylinositol-anchored proteins: structure, function, and cleavage by phosphatidylinositol-specific phospholipase C," Biochem Cell Biol. 80:535-549 (2002).

Sheikh et al., "A newborn with No. bones: neonatal hypophosphatasia with respiratory distress," J Pediatr. 188:306 (Sep. 2017).

Shukla et al., "RNA interference and inhibition of MEK-ERK signaling prevent abnormal skeletal phenotypes in a mouse model of craniosynostosis," Nat Genet. 39(9):1145-1150 (2007).

Shull et al., "Enzyme replacement in a canine model of Hurler syndrome," Proc Natl Acad Sci USA. 91:12937-12941 (1994).

Siller et al., "Alkaline phosphatase: discovery and naming of our favorite enzyme," J Bone Miner Res. 33(2):362-4 (2018).

Silver et al., "Pulmonary hypoplasia in neonatal hypophosphatasia," Pediatr Pathol. 8(5):483-93 (1988) (12 pages).

Simm et al., "Successful use of enzyme replacement therapy in infantile hypophosphatasia," J Paediatr Child Health. 53(9):925-926 (Sep. 2017).

Simmons, "Best Practices In: Recognizing and Diagnosing Hypophosphatasia," Clinical Endocrinology News. <https://www.mdedge.com/sites/default/files/issues/articles/Alexion_10_11_Final_Web.pdf>, published Sep. 30, 2013, retrieved on Mar. 27, 2019 (8 pages).

Siris et al., "Paget's disease of bone," Trends Endocrinol Metab. 2(6):207-12 (1991).

Skolnick et al., "From genes to protein structure and function: novel applications of computational approaches in the genomic era," Trends Biotechnol. 18(1):34-9 (2000).

Song et al., "Preliminary study on the effect of $Zn^{2+}$ on the activities of peptidase and alkaline phosphatase," Marine Sciences. 27(3):64-65 (2003) (Abstract only).

Sotillo et al., "Signs and symptoms of hypophosphatasia," Dimensions of Dental Hygiene. 15(4):44-47 (Apr. 2017) (6 pages).

Spears et al., "Deoxyuridylate effects on thymidylate synthase-5-fluorodeoxyuridylate-folate ternary complex formation," Biochem Pharmacol. 38(18):2985-2993 (1989).

Spentchian et al., "Severe hypophosphatasia: characterization of fifteen novel mutations in the ALPL gene," Hum Mutat. 22(1) (2003) (5 pages).

Srinivas et al., "Assessment of dose proportionality, absolute bioavailability, and immunogenicity response of CTLA4lg (BMS-188667), a novel immunosuppressive agent, following subcutaneous and intravenous administration to rats," Pharm Res. 14(7): 911-6 (1997).

Stahl et al., "Evidence for receptor-mediated binding of glycoproteins, glycoconjugates, and lysosomal glycosidases by alveolar macrophages," Proc Natl Acad Sci USA. 75(3):1399-1403 (1978).

Stec et al., "A revised mechanism for the alkaline phosphatase reaction involving three metal ions," J Mol Biol. 299(5):1303-11 (2000).

Stoll et al., "Severe hypophosphatasia due to mutations in the tissue-nonspecific alkaline phosphatase (TNSALP) gene," Genet Couns. 13(3):289-95 (2002).

Sturtz et al., "A study of the delivery-targeting concept applied to antineoplasic drugs active on human osteosarcoma. I. Synthesis and biological activity in nude mice carrying human osteosarcoma xenografts of gem-bisphosphonic methotrexate analogues," Eur J Med Chemistry. 27:825-33 (1992).

Suda et al., "C-type natriuretic peptide as an autocrine/paracrine regulator of osteoblast: evidence for possible presence of bone natriuretic peptide system," Biochem Biophys Res Commun. 223(1):1-6 (1996).

Sugano et al., "Successful gene therapy in utero for lethal murine hypophosphatasia," Hum Gene Ther. 23(4):399-406 (2012).

Supplementary European Search Report for European Application No. 05739065, mailed Dec. 2, 2008 (3 pages).

Supplementary European Search Report for European Application No. 08757088, dated Jun. 7, 2010 (5 pages).

Supplementary European Search Report for European Patent Application No. 11853820.6, mailed Mar. 25, 2014 (3 pages).

Symersky et al., "Structure of the collagen-binding domain from a *Staphylococcus aureus* adhesin," Nat Struct Biol. 4(10):833-838 (1997).

Takahashi et al., "Parental serum alkaline phosphatase activity as an auxiliary tool for prenatal diagnosis of hypophosphatasia," Prenat Diagn. 37(5):491-6 (May 2017).

Takano et al., "Molecular evolution of shark C-type natriuretic peptides," Zoolog Sci. 11(3):451-454 (1994).

Taketani et al. Chapter 9: Hypophosphatasia. *Human Pathobiochemistry*. T. Oohashi et al. (eds.), 91-100 (2019).

Taketani et al., "Clinical and genetic aspects of hypophosphatasia in Japanese patients," Arch Dis Child. 99(3):211-5 (2014) (6 pages).

Taketani et al., "Ex vivo expanded allogeneic mesenchymal stem cells with bone marrow transplantation improved osteogenesis in infants with severe hypophosphatasia," Cell Transplant. 24(10):1931-43 (2015).

Takinami et al., "The mutant (F310L and V365I) tissue-nonspecific alkaline phosphatase gene from hypophosphatasia," J Med Dent Sci. 51(1):67-74 (2004).

Tamura et al., "Critical roles of the guanylyl cyclase B receptor in endochondral ossification and development of female reproductive organs," Proc Natl Acad Sci USA. 101(49):17300-17305 (2004).

(56) References Cited

OTHER PUBLICATIONS

Teixeira et al., "Nitric oxide, C-type natriuretic peptide and cGMP as regulators of endochondral ossification," Dev Biol. 319(2):171-178 (2008).

Tenorio et al., "Molecular and clinical analysis of ALPL in a cohort of patients with suspicion of hypophosphatasia," Am J Med Genet A. 173(3):601-10 (Mar. 2017).

Thacher et al., "Radiographic scoring method for the assessment of the severity of nutritional rickets," J Trop Pediatr. 46(3):132-9 (2000).

The Japanese Journal of Dermatology. 115(6): 843-7 (2005) (11 pages).

Thurner et al., "Osteopontin deficiency increases bone fragility but preserves bone mass," Bone. 46(6):1564-73 (2010).

Tokumaru et al., "Skull base and calvarial deformities: association with intracranial changes in craniofacial syndromes," Am J Neuroradiol. 17(4):619-30 (1996).

Tomatsu, Declaration Under 37 C.F.R. § 1.132 for U.S. Appl. No. 11/484,870, dated Jun. 1, 2009 (3 pages).

Tomatsu, Declaration Under 37 C.F.R. § 1.132 for U.S. Appl. No. 11/484,870, dated Nov. 27, 2007 (2 pages).

Tomazos et al., "Determination of the Minimal Clinically Important Difference in the Six-Minute Walk Test for Patients with Hypophosphatasia," 55th Annual European Society for Paediatric Endocrinology Meeting, Sep. 10-12, Paris, France. 86, Abstract FC2.5, <http://abstracts.eurospe.org/hrp/0086/hrp0086FC2.5.htm> (2016) (4 pages).

Tsiantouli et al., "Hypophosphatasia," Rev Med Suisse. 13(559):855-8 (Apr. 2017) (Article in French) (English Abstract Included).

Tsuji et al., "A loss-of-function mutation in natriuretic peptide receptor 2 (Npr2) gene is responsible for disproportionate dwarfism in cn/cn mouse," J Biol Chem. 280(14):14288-14292 (2005).

Tye et al., "Delineation of the hydroxyapatite-nucleating domains of bone sialoprotein," J Biol Chem. 278(10):7949-7955 (2003).

Uludag et al., "Bone affinity of a bisphosphonate-conjugated protein in vivo," Biotechnol Prog. 16(6):1115-8 (2000).

UniProtKB Accession No. P01857. Retrieved May 2, 2018 (13 pages).

UniProtKB Accession No. P05186. Retrieved May 2, 2018 (19 pages).

Urlaub et al., "Deletion of the diploid dihydrofolate reductase locus from cultured mammalian cells," Cell. 33(2):405-412 (1983).

Urlaub et al., "Isolation of Chinese hamster cell mutants deficient in dihydrofolate reductase activity," Proc Natl Acad Sci U S A. 77(7):4216-20 (1980).

Wang et al. "The effects of tissue-non-specific alkaline phosphatase gene therapy on craniosynostosis and craniofacial morphology in the FGFR2$^{C342Y/+}$ mouse model of Crouzon craniosynostosis," Orthod Craniofac Res. 18 Suppl. 1(01):196-206 (2015).

Wang et al., "A mouse model for achondroplasia produced by targeting fibroblast growth factor receptor 3," Proc Natl Acad Sci USA. 96(8):4455-4460 (1999).

Wang et al., "Current concepts in odontohypophosphatasia form of hypophosphatasia and report of two cases," BMC Oral Health. 16(1):70 (Aug. 2016) (8 pages).

Wang et al., "Mice lacking Nf1 in osteochondroprogenitor cells display skeletal dysplasia similar to patients with neurofibromatosis type 1," Hum Mol Genet. 20(20):3910-3924 (2011).

Wang et al., "Structure-based chemical modification strategy for enzyme replacement treatment of phenylketonuria," Mol Genet Metab. 86(1-2):134-140 (2005).

Watanabe et al., "Prevalence of c.1559delT in ALPL, a common mutation resulting in the perinatal (lethal) form of hypophosphatasia in Japanese and effects of the mutation on heterozygous carriers," J Hum Genet. 56(2):166-8 (2011).

Waymire et al., "Mice lacking tissue non-specific alkaline phosphatase die from seizures due to defective metabolism of vitamin B-6," Nat Genet. 11(1):45-51 (1995).

Weber et al., "Burden of disease in adult patients with hypophosphatasia: Results from two patient-reported surveys," Metabolism. 65(10):1522-30 (Oct. 2016).

Weber et al., "Burden of disease in children with hypophosphatasia: results from patient-reported surveys," 7th International Conference on Children's Bone Health, Jun. 27-30, Salzburg, Austria. *Bone Abstracts.* 4: P119 (2015) (3 pages).

Weinberg, "An overview of infliximab, etanercept, efalizumab, and alefacept as biologic therapy for psoriasis," Clin Ther. 25(10):2487-505 (2003).

Weiss et al., "A missense mutation in the human liver/bone/kidney alkaline phosphatase gene causing a lethal form of hypophosphatasia," Proc Natl Acad Sci USA. 85(20):7666-7669 (1988).

Weiss et al., "Isolation and characterization of a cDNA encoding a human liver/bone/kidney-type alkaline phosphatase," Proc Natl Acad Sci USA. 83(19):7182-6 (1986) (6 pages).

Weiss et al., "Structure of the human liver/bone/kidney alkaline phosphatase gene," J Biol Chem. 263(24):12002-10 (1988).

Weninger et al., "Biochemical and morphological effects of human hepatic alkaline phosphatase in a neonate with hypophosphatasia," Acta Paediatr Scand. Suppl. 360:154-160 (1989).

Whisstock et al., "Prediction of protein function from protein sequence and structure," Q Rev Biophys. 36(3):307-40 (2003).

Whyte et al. "Asfotase alfa for infants and young children with hypophosphatasia: 7 year outcomes of a single-arm, open-label, phase 2 extension trial," Lancet Diabetes Endocrinol. 7(2):93-105 (2019) (52 pages).

Whyte et al. "Natural history of perinatal and infantile hypophosphatasia: a retrospective study," J Pediatr. 209:116-124.e4 (2019) (13 pages).

Whyte et al., "A retrospective, multi-national, non-interventional, natural history study of the childhood form of hypophosphatasia," ENDO 2015: The Endocrine Society Annual Meeting, Mar. 5-8, San Diego, California. Abstract LB-OR01-4 (2015) (2 pages).

Whyte et al., "Adult hypophosphatasia treated with teriparatide," J Clin Endocrinol Metab. 92(4):1203-8 (2007).

Whyte et al., "Adult hypophosphatasia with chondrocalcinosis and arthropathy: variable penetrance of hypophosphatasemia in a large Oklahoma kindred," Am J Med. 72(4):631-41 (1982).

Whyte et al., "Alkaline phosphatase: placental and tissue-nonspecific isoenzymes hydrolyze phosphoethanolamine, inorganic pyrophosphate, and pyridoxal 5'-phosphate. Substrate accumulation in carriers of hypophosphatasia corrects during pregnancy," J Clin Invest. 95(4):1440-5 (1995).

Whyte et al., "Asfotase alfa therapy for children with hypophosphatasia," JCI Insight. 1(9):e85971 (Jun. 2016) (11 pages).

Whyte et al., "Asfotase alfa treatment improves survival for perinatal and infantile hypophosphatasia," J Clin Endocrinol Metab. 101(1):334-42 (Jan. 2016) (17 pages).

Whyte et al., "Asfotase alfa: Sustained Efficacy and Tolerability in Infants and Young Children with Life-Threatening Hypophosphatasia," 2014 Pediatric Academic Societies and Asian Society for Pediatric Research Joint Meeting, May 3-6, Vancouver, BC, Canada. Poster 69 (2014) (1 page).

Whyte et al., "Enzyme replacement therapy for infantile hypophosphatasia attempted by intravenous infusions of alkaline phosphatase-rich Paget plasma: results in three additional patients," J Pediatr. 105(6):926-33 (1984).

Whyte et al., "Enzyme-replacement therapy in life-threatening hypophosphatasia," N Engl J Med. 366(10):904-13 (2012).

Whyte et al., "Hypophosphatasia (HPP) in children: enzyme replacement therapy (EzRT) using bone-targeted, tissue-nonspecific alkaline phosphatase (TNSALP)," Ann Neurol. 68(Suppl 14):S70 Abstract WIP-28 (2010) (1 page).

Whyte et al., "Hypophosphatasia: A Retrospective Natural History Study of the Severe Perinatal and Infantile Forms," 2014 European Calcified Tissue Society Congress, May 17-20, Prague, Czech Republic. Poster P364 (2014) (1 page).

Whyte et al., "Hypophosphatasia: Enzyme replacement therapy (asfotase alfa) decreases TNSALP substrate accumulation and improves functional outcomes in affected adolescents and adults," Bull Group Int Rech Sci Stomatol Odontol. 51(1):35 (2012) (1 page).

(56)           References Cited

OTHER PUBLICATIONS

Whyte et al., "Hypophosphatasia: natural history study of 101 affected children investigated at one research center," Bone. 93:125-138 (Dec. 2016).

Whyte et al., "Hypophosphatasia: validation and expansion of the clinical nosology for children from 25 years experience with 173 pediatric patients," Bone. 75:229-39 (2015).

Whyte et al., "Infantile hypophosphatasia: enzyme replacement therapy by intravenous infusion of alkaline phosphatase-rich plasma from patients with Paget bone disease," J Pediatr. 101(3):379-86 (1982).

Whyte et al., "Infantile hypophosphatasia: normalization of circulating bone alkaline phosphatase activity followed by skeletal remineralization. Evidence for an intact structural gene for tissue nonspecific alkaline phosphatase," J Pediatr. 108(1):82-8 (1986).

Whyte et al., "Markedly increased circulating pyridoxal-5'-phosphate levels in hypophosphatasia," J Clin Invest. 76(2):752-756 (1985).

Whyte et al., "Marrow cell transplantation for infantile hypophosphatasia," J Bone Miner Res. 18(4):624-36 (2003).

Whyte et al., "Rickets and osteomalacia," Medicine. 37(9):483-8 (2009).

Whyte et al., "Supplemental Data: Asfotase alfa therapy for children with hypophosphatasia," JCI Insight. 1(9):e85971 (Jun. 2016) (33 pages).

Whyte et al., "Treatment of children with hypophosphatasia (HPP) with ENB-0040: radiographic and DXA outcomes after 6 months of therapy," Horm Res Paediatr. 76(Suppl 2):26 (2011) (Abstract only).

Whyte, "Chapter 70: Hypophosphatasia: Nature's window on alkaline phosphatase function in man," Principles of Bone Biology, 2nd ed., Bilezikian, Raisz, and Rodan. 2:1229-1248 (2002).

Whyte, "Hypophosphatasia—aetiology, nosology, pathogenesis, diagnosis and treatment," Nat Rev Endocrinol. 12(4):233-46 (Apr. 2016).

Whyte, "Hypophosphatasia and the role of alkaline phosphatase in skeletal mineralization," Endocr Rev. 15(4):439-461 (1994).

Whyte, "Hypophosphatasia: an overview for 2017," Bone. 102:15-25 (Sep. 2017).

Whyte, "Hypophosphatasia: enzyme replacement therapy brings new opportunities and new challenges," J Bone Miner Res. 32(4):667-675 (Apr. 2017).

Whyte, "Physiological role of alkaline phosphatase explored in hypophosphatasia," Ann N Y Acad Sci. 1192:190-200 (2010).

Whyte, Chapter 18: Heritable Forms of Rickets and Osteomalacia. Connective Tissue and Its Heritable Disorders. Wiley-Liss, Inc., eds. R.M. Royce and B. Steinmann, 765-87 (2002).

Whyte, Chapter 207: Hypophosphatasia. The Online Metabolic and Molecular Bases of Inherited Disease. McGraw-Hill Book Company, Valle et al. (eds.) (2001) (41 pages).

Whyte, Chapter 22: Hypophosphatasia, Genetics of Bone Biology and Skeletal Disease. Rajesh V. Thakker, Michael P. Whyte, John A. Eisman and Takashi Igarashi (eds.), 337-360 (2013).

Whyte, Chapter 73: Hypophosphatasia: Nature's Window on Alkaline Phosphatase Function in Humans, Principles of Bone Biology, vol. 1, Third Edition. John P. Bilezikian, Lawrence G. Raisz and T. John Martin (eds.), 1573-98 (2008).

Wickramasinghe et al., "A case of hypophosphatasia," Ceylon Med J. 48(3):94-5 (2003) (2 pages).

Williams et al., "Solute transport in growth plate cartilage: In vitro and in vivo," Biophys J. 93(3):1039-1050 (2007).

Witkowski et al., "Conversion of a beta-ketoacyl synthase to a malonyl decarboxylase by replacement of the active-site cysteine with glutamine," Biochemistry. 38(36):11643-50 (1999).

Wroblewski et al., "Pharmacokinetics, metabolic stability, and subcutaneous bioavailability of a genetically engineered analog of DcR3, FLINT [DcR3(R218Q)], in cynomolgus monkeys and mice," Drug Metab Dispos. 31(4):502-507 (2003).

Yadav et al., "Dose response of bone-targeted enzyme replacement for murine hypophosphatasia," available in PMC Aug. 1, 2012, published in final edited form as: Bone. 49(2):250-6 (2011) (20 pages).

Yagasaki et al., "Animal Cell Technology: Basic & Applied Aspects," Proceedings of the Fifteenth Annual Meeting of the Japanese Association for Animal Cell Technology (JAACT), vol. 13, Fuchu, Nov. 11-15, 2002 (461 pages).

Yamamoto et al., "A successful treatment with pyridoxal phosphate for West syndrome in hypophosphatasia," Pediatr Neurol. 30(3):216-8 (2004).

Yamamoto et al., "Long term phenotypic correction of severe infantile hypophosphatasia in a mouse model by neonatal injection of lentiviral vector," Mol Ther. 17:S67-S68, Abstract 171 (2009) (2 pages).

Yamamoto et al., "Prolonged survival and phenotypic correction of Akp2$^{-/-}$ hypophosphatasia mice by lentiviral gene therapy," J Bone Miner Res. 26(1):135-42 (2011).

Yasoda et al., "Natriuretic peptide regulation of endochondral ossification. Evidence for possible roles of the C-type natriuretic peptide/guanylyl cyclase-B pathway," J Biol Chem. 273(19):11695-11700 (1998).

Yasoda et al., "Overexpression of CNP in chondrocytes rescues achondroplasia through a MAPK-dependent pathway," Nat Med. 10(1):80-86 (2004).

Yasoda et al., "Systemic administration of C-type natriuretic peptide as a novel therapeutic strategy for skeletal dysplasias," Endocrinology. 150(7):3138-3144 (2009).

Yoder et al., "Reduced ability of C-type natriuretic peptide (CNP) to activate natriuretic peptide receptor B (NPR-B) causes dwarfism in lbab$^{-/-}$ mice," Peptides. 29(9):1575-1581 (2008).

Yokogawa et al., "Selective delivery of estradiol to bone by aspartic acid oligopeptide and its effects on ovariectomized mice," Endocrinology. 142(3):1228-1233 (2001).

Young et al., "Structure, expression, and regulation of the major noncollagenous matrix proteins of bone," Clin Orthop Relat Res. 281:275-294 (1992).

Zaleckas et al., "Diagnosis and treatment of craniosynostosis: Vilnius team experience," Acta Med Litu. 22(2):111-21 (2015).

Zhang et al., "Engineering E. coli Alkaline Phosphatase Yields Changes of Catalytic Activity, Thermal Stability and Phosphate Inhibition," Biocatal Biotransfor. 20(6):381-389 (2002).

Zierhut et al., "Population PK-PD model for Fc-osteoprotegerin in healthy postmenopausal women," J Pharmacokinet Pharmacodyn. 35(4):379-399 (2008).

Zurutuza et al., "Correlations of genotype and phenotype in hypophosphatasia," Hum Mol Genet. 8(6):1039-1046 (1999).

Office Action for Japanese Patent Application No. 2021-506690, dated May 30, 2023 (10 pages).

Miller et al., "Genetic diversity and population structure of the endangered marsupial Sarcophilus harrisii (Tasmanian devil)," Proc Natl Acad Sci U S A. 108(30):12348-53 (Jul. 2011).

Partial Supplementary European Search Report for European Application No. 20898477.3, dated Dec. 6, 2023 (25 pages).

Alonso et al., "Loss-of-Function Mutations in the ALPL Gene Presenting with Adult Onset Osteoporosis and Low Serum Concentrations of Total Alkaline Phosphatase," J Bone Miner Res. 35(4):657-661 (Apr. 2021).

Rodriguez et al., "A Novel Mutation in ALPL Gene Causing Adult Autosomal Dominant Hypophosphatasia in a Family of Southern Spain: Phenotype Characterization," Ann Rheum Dis. 82:428-9 (May 2023).

UniProtKB Accession No. G3WYY8. Retrieved Nov. 16, 2011 (4 pages).

Official Action for Japanese Application No. 2021-506690, dated Nov. 7, 2023 (10 pages).

International Search Report and Written Opinion for International Patent Application No. PCT/US2021/055991, mailed Jan. 25, 2022 (8 pages).

Official Action for Eurasian Application No. 202391228, dated Dec. 13, 2023 (5 pages).

(56) References Cited

OTHER PUBLICATIONS

Oguchi et al., "Control of Temperature and pH Enhances Human Monoclonal Antibody Production in CHO Cell Culture," Animal Cell Technology: Basic and Applied Aspects. Springer/Dordrecht. 13:169-172 (Jan. 2003).

Koumpouras et al., "Dynamic Optimization of Bioprocesses," Applied Mathematics. 3(10A):1487-1495 (Oct. 2012).

"Common Drug Review: Pharmacoeconomic Review Report for asfotase alfa (Strensiq)," Canadian Agency for Drugs and Technologies in Health (Apr. 2017) (25 pages).

Office Action for Eurasian Application No. 202390771, dated Jan. 16, 2024 (3 pages).

Examination Report for Australian Application No. 2021337652, dated Feb. 28, 2024 (5 pages).

Sutton et al., "Atypical femoral fractures' during bisphosphonate exposure in adult hypophosphatasia" J Bone Miner Res. 27(5):987-94 (May 2012) (8 pages).

Office Action for Canadian Patent Application No. 3,173,631, dated Jan. 26, 2024 (5 pages).

"Alkaline phosphatase, tissue-nonspecific isozyme [Galeopterus variegatus]," GenBank, accession No. XP_008584004, accessed Jul. 22, 2014, (2 pages).

"Alkaline phosphatase, tissue-nonspecific isozyme isoform X3 [Erinaceus europaeus]," GenBank, accession No. XP_016048561, accessed Apr. 11, 2016, (2 pages).

Office Action for Canadian Patent Application No. 3,161,266, dated Feb. 14, 2024 (4 pages).

International Search Report and Written Opinion for International Patent Application No. PCT/US2021/048792, mailed Dec. 23, 2021 (11 pages).

Genest et al., "Physical Function and Health-Related Quality of Life in Adults Treated With Asfotase Alfa for Pediatric-Onset Hypophosphatasiam," JBMR Plus. 4(9):e10395 (Sep. 2020) (9 pages).

Genest et al., "Long-term effectiveness of Asfotase Alfa in adults with pediatric-onset Hypophosphatasia in routine clinical practice," Journal of Bone and Mineral Research. 35(Supplement_1) from ASBMR 2020 Annual Meeting (Nov. 2020) (1 page).

GE Healthcare, "Cell BoostTM 7a and 7b supplements," first published Sep. 2015 (4 pages).

Appendix for Office Action dated Feb. 11, 2025 in U.S. Appl. No. 17/117,099: "Clustal Omega (2023) was used to obtain the multiple sequence alignments provided in the office action appendix. The alignments were retrieved on Jan. 10, 2025 and Jan. 8, 2025 from https://www.ebi.ac.uk/jdispatcher/msa/clustalo (Year: 2025)" (16 pages).

"STIC search of SEQ ID No. 1," U.S. Appl. No. 13/899,359, filed May 21, 2013, dated Feb. 22, 2024 (2 pages).

Seffernick et al., "Melamine deaminase and atrazine chlorohydrolase: 98 percent identical but functionally different," J Bacteriol. 183(8):2405-10 (2001).

Broun et al., "Catalytic plasticity of fatty acid modification enzymes underlying chemical diversity of plant lipids," Science 282(5392):1315-7 (1998) (4 pages).

Dirks, "Brain tumor stem cells: Bringing order to the chaos of brain cancer," J Clin Oncology 26(17):2916-2924 (2008).

López-Lázaro, "The migration ability of stem cells can explain the existence of cancer of unknown primary site. Rethinking metastasis," Oncoscience. 2(5):467-75 (2015).

Tran et al., "Survival comparison between glioblastoma multiforme and other incurable cancers," J Clin Neurosci. 17(4):417-421 (2010).

Mabey, "Epidemiology of sexually transmitted infections: worldwide," Medicine 42(6):287-290 (2014).

"Alkaline phosphotase (EC=3.1.3.1) from *Kryptolebias marmoratus* (Mangrove killifish) (Rivulus marmoratus)," XP093139356, retrieved from EBI accession No. UNIPROTKB:A0A3Q3B3R2_KRYMA, accessed Jul. 31, 2019 (2 pages).

"Alkaline phosphatase, tissue-nonspecific isozyme isoform X4 from *Denticeps clupeoides* (denticle herring)," XP093139383, retrieved from EBI accession No. NCBI:XP_028853958, accessed Apr. 24, 2019 (2 pages).

Extended European Search Report for European Patent Application No. 20898477.3, dated Mar. 28, 2024 (30 pages).

Ishida et al., "Structure and Function of Alkaline Phosphatases," Japanese Journal of Clinical Chemistry. 33:36-44 (2004).

Hahn et al., "Chronic calcium pyrophosphate crystal inflammatory arthritis induced by extreme hypomagnesemia in short bowel syndrome," BMC Gastroenterol. 12:129 (Sep. 2012) (7 pages).

Masuda, "Pathology and treatment of pseudogout (calcium pyrophosphate crystal deposition disease; CPPD)," Gout and Nucleic Acid Metabolism. 35(1):1-7 (2011).

Michigami, "III. Hypophosphatemia and Osteomalacia 2. X-linked Hypophosphatemic Osteomalacia," The Journal of the Japanese Society of Internal Medicine. 96(4):725-730 (2007).

Stevens, Katherine, Discussion Paper: Valuation of the Child Health Utility Index 9D (CHU9D). The University of Sheffield, 2010 (34 pages).

Francis et al., "The irritable bowel severity scoring system: a simple method of monitoring irritable bowel syndrome and its progress," Aliment Pharmacol Ther. 11(2): 395-402 (Apr. 1997).

ALXN1215 (STRENSIQ for Subcutaneous Injection 12mg/0.3mL; STRENSIQ for Subcutaneous Injection 18mg/0.45mL; STRENSIQ for Subcutaneous Injection 28mg/0.7mL; STRENSIQ for Subcutaneous Injection 40mg/1mL; STRENSIQ for Subcutaneous Injection 80mg/0.8mL), "Summary of Application Documents", Part 2 "CTD Summary", 2.7 "Clinical Summary", 2.7.3 "Clinical Efficacy", 2015, pp. 1-94.

Zuqueli et al., "Effect of sodium butyrate and zinc sulphate supplementation on recombinant human IFN-β production by mammalian cell culture," Lat. Am. appl. res., Bahia Blanca 36(4):321-7 (Oct. 2006).

U.S. Appl. No. 19/326,493, Voegtli et al.

Christou et al., "Rational design of murine secreted alkaline phosphatase for enhanced performance as a reporter gene in mouse gene therapy preclinical studies," Hum Gene Ther. 22(4) (Apr. 2011) (Abstract).

Sadowski et al., "The sequence-structure relationship and protein function prediction." Curr Opin in Structural Bio. 19:357-362, 2009.

Singh et al., "Protein Engineering Approaches in the Post-Genomic Era," Curr Protein Pept Sci. 19(1):5-15 (2018).

Tang et al., "Identification of Dehalobacter reductive dehalogenases that catalyse dechlorination of chloroform, 1, 1, 1-trichloroethane and 1, 1-dichloroethane." J. Bacterial. 183(8):2405-2410, 2001.

Uki et al., "A brief cancer pain assessment tool in Japanese: the utility of the Japanese Brief Pain Inventory—BPI-J," J Pain Symptom Manage. 16(6):364-73 (Dec. 1998).

"Clinical research on the use of IoT in the "cancer field", which is probably the most advanced in Japan~Visualizing the relationship between side effects and daily activity volume~," Oncoro. <https://oncolo.jp/news/180623k01> dated Jun. 23, 2018, retrieved Feb. 4, 2026 (9 Pages).

"Hypophosphatasia Diagnosis Guidelines," The Japanese Society for Pediatric Endocrinology, <https://jspe.umin.jp/medical/files/guide20190111.pdf> dated Jan. 11, 2019, retrieved Feb. 4, 2026 (23 Pages).

Office Action for Japanese Patent Application No. 2023-514927, dated Feb. 4, 2026 (7 Pages).

* cited by examiner

FIG. 2A                 FIG. 2B
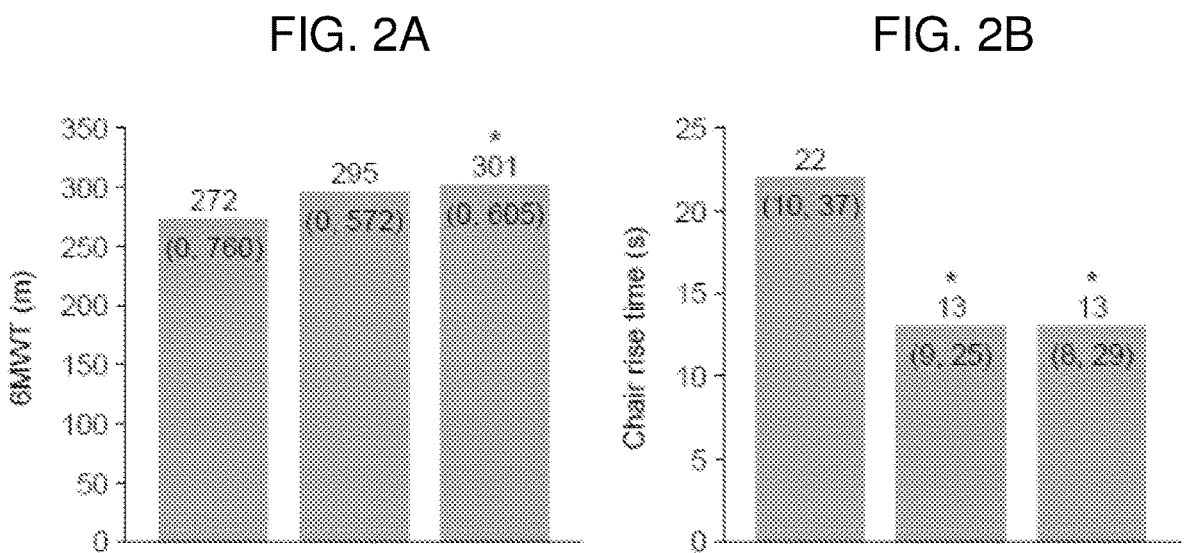
FIG. 2C                 FIG. 2D
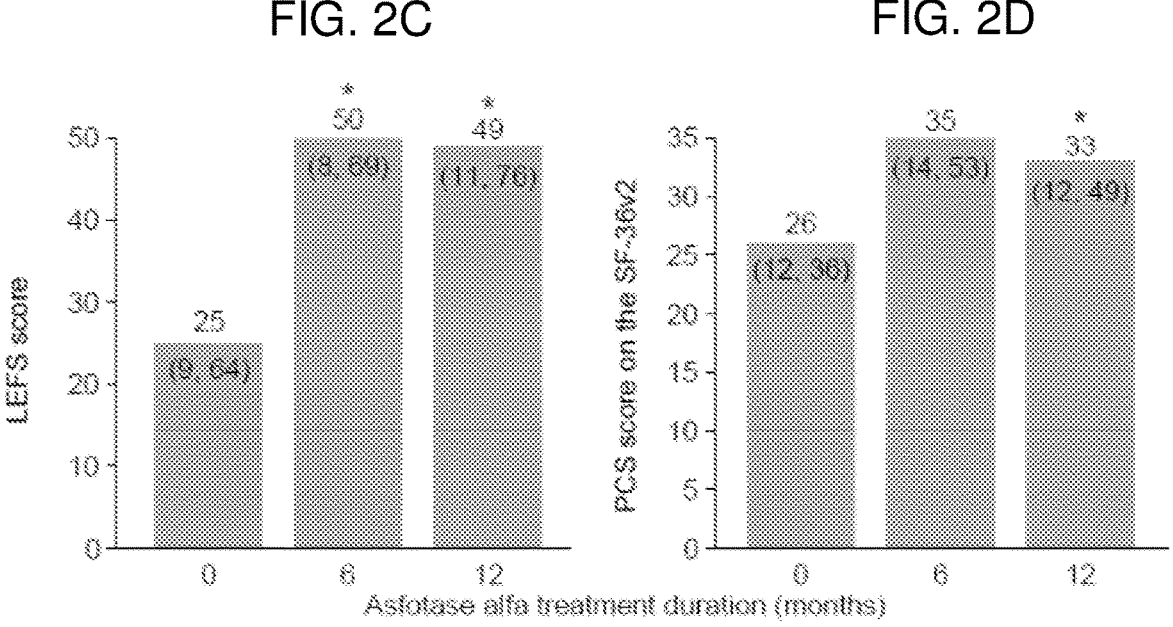

METHODS FOR TREATING BONE MINERALIZATION DISORDERS

CROSS REFERENCE TO RELATED APPLICATIONS

This application is the U.S. National Phase Application of PCT/US2021/048792, filed on Sep. 2, 2021, and claims the benefit of U.S. Provisional Application No. 63/074,917, filed Sep. 4, 2020, the contents of which is incorporated by reference herein in its entirety.

BACKGROUND

Hypophosphatasia (HPP) is a rare, serious, genetic disorder caused by loss of-function mutation(s) in the gene encoding tissue non-specific alkaline phosphatase (TNALP). Hypophosphatasia across patient ages is characterized by interdependent clinical manifestations emanating from a failure to mineralize bone matrix due to elevated concentrations of the TNALP substrate PPi. Elevations in extracellular PPi inhibit bone mineralization by blocking hydroxyapatite crystal growth, causing a pronounced accumulation of unmineralized bone matrix. HPP is characterized by defective bone mineralization and impaired phosphate and calcium regulation as a direct result of deficient TNALP, which can lead to progressive damage to vital organs along with other clinical sequelae including deformity and softness of bones (rickets and osteomalacia), fractures and pseudofractures, pain, profound muscle weakness, respiratory failure (primarily in infants), seizures (mainly in infants), impaired renal function, impaired mobility, and dental abnormalities. In patients with perinatal/infantile onset HPP, the disease course is potentially fatal.

In patients with perinatal/infantile onset HPP, bone mineralization defects with resulting skeletal deformities and fractures and rachitic changes in the chest may lead to the inability of the rib cage to support normal respiratory function and may increase the risk of ventilator dependence and premature death. In the most severely affected patients, mortality ranges from 50% to 100%. In adults, HPP manifests with recurrent and/or poorly healing fractures and chronic pain, resulting in severely restricted quality of life and activities of daily living. Severe functional impairments are often present in adult patients with HPP, including mobility problems (ambulation and gal impairments), muscle weakness, and inability to carry out activities of daily living, reliance on mobility devices, which together strongly affect patients' quality of life. Adult patients with HPP are also often misdiagnosed for many years, yet accurate diagnosis of HPP is crucial for appropriate treatment.

In patients surviving to adolescence and adulthood, long-term clinical sequelae include recurrent and nonhealing fractures, orthopedic/dental surgical burden, weakness, arthritis, the inability to remove internal fixation devices (due to the risk of recurrent fracture), pain, impaired mobility and the requirement for ambulatory assistive devices (e.g., wheelchairs, wheeled walkers, and canes). Regardless of the age when HPP first manifests, a high burden of disease could lead to a decrease in health-related quality of life, which can further decrease over a patient's lifetime. Signs and/or symptoms of HPP may also affect mental and emotional health in children and adults with the disease, which has been associated with considerable healthcare resource utilization.

Prior to asfotase alfa (STRENSIQ®, Alexion Pharmaceuticals, Inc. Boston, MA) receiving marketing authorization (European Union, Japan, Canada, the United States, etc.) clinical management of HPP was mainly supportive and aimed at addressing symptoms (e.g., respiratory support, orthopedic intervention, and pain relief medication) of the disease, but not the underlying pathophysiology. Thus, despite symptomatic treatment, the majority of patients experienced significant morbidity (growth abnormalities and bone deformities, bone pain, fractures/pseudofractures, physical dysfunction, and/or respiratory distress).

Asfotase alfa is a human recombinant TNALP-Fc-deca-aspartate fusion protein produced by recombinant DNA technology using mammalian Chinese Hamster Ovary (CHO) cell culture. It is a soluble glycoprotein of 726 amino acids that contains the catalytic domain of human TNALP, the human immunoglobulin (Ig) G1 Fc domain, and a deca aspartate peptide domain used for bone-targeting. In patients with pediatric onset HPP, including perinatal/infantile onset and Juvenile onset (Table 1), asfotase alfa is indicated and has been approved in the US for long-term treatment of HPP.

TABLE 1

| Classifications of Hypophosphatasia | |
|---|---|
| Disease Form | Age at Onset of First Signs/Symptoms |
| Perinatal | In utero |
| Infantile | <6 months of age |
| Childhood (juvenile) | ≥6 months to <18 years of age |
| Adult | ≥18 years of age |
| Only dental manifestations | odonto hypophosphatasia |

Some adult patients experience a mild phenotype of bone mineralization that may not be property diagnosed until much later in life. Thus, there exists a need for effective methods to treat such patients with HPP and other bone mineralization disorders.

SUMMARY OF THE DISCLOSURE

In one aspect, featured is a method of treating a bone mineralization disorder in a human subject (e.g., an adult human subject) that exhibits a level in at least one biochemical, physical, quality of life, or bone metric that identifies the subject as in need of treatment for the bone mineralization disorder. The method may include administering at least a one dose of a soluble alkaline phosphatase (sALP) to the subject in a first treatment phase of a treatment regimen; monitoring the subject during the first treatment phase for changes in the at least one biochemical, physical, quality of life, or bone metric; and detecting an improvement (e.g., by 1%, 2%, 3%, 4%, 5%, 10%, 15%, 20%, 25%, 30%, 40%, 50%, 60%, 70%, 80%, 90%, 100%, or more) in the at least one biochemical, physical, quality of life, or bone metric above a predetermined threshold of the metric. The subject may then enter a first non-treatment phase of the treatment regimen during which the subject is not administered the sALP.

The method may further include monitoring the subject during the first non-treatment phase for a period of time for changes in the at least one biochemical, physical, quality of life, or bone metric; detecting a level in the at least one biochemical, physical, quality of life, or bone metric below the predetermined threshold of the metric; and administering at least one dose of the sALP to the subject in a second treatment phase of the treatment regimen. Any of the steps described above may be repeated one or more times, such that the treatment regimen includes a plurality of treatment and/or non-treatment phases.

The bone mineralization disorder may be an alkaline phosphatase deficiency, such as hypophosphatasia (HPP). The HPP may be juvenile-onset HPP. The subject may not have been previously diagnosed with HPP or may have not been diagnosed with HPP until adulthood. The subject may be naïve (e.g., has not been previously administered the sALP).

In another aspect, featured is a method of treating atypical femoral fracture (AFF) in a human subject comprising administering to the subject a treatment regimen comprising at least one dose of a sALP. The sALP may be administered in amount and for a duration sufficient to repair the AFF. The subject may exhibit a level in at least one biochemical, physical, quality of life, or bone metric that identifies the subject as in need of treatment for the AFF. The method may further include monitoring the subject during the treatment regimen for changes in the at least one biochemical, physical, quality of life, or bone metric. The method may further include detecting an improvement in the at least one biochemical, physical, quality of life, or bone metric above a predetermined threshold of the metric and entering a non-treatment phase of the treatment regimen during which the subject is not administered the sALP. The subject may have a bone mineralization disorder (e.g., an alkaline phosphatase deficiency, e.g., HPP). Alternatively, the subject may not have a bone mineralization disorder (e.g., HPP) or may not have been previously diagnosed with the disorder. The HPP may be juvenile-onset HPP. In some embodiments, the subject may not have been diagnosed with HPP until adulthood. In some embodiments, the subject may have previously been administered or is currently being administered a bisphosphonate.

In some embodiments, the alkaline phosphatase is a tissue non-specific alkaline phosphatase, a placental alkaline phosphatase, an intestinal alkaline phosphatase, an engineered alkaline phosphatase, a fusion protein including an alkaline phosphatase moiety, or a chimeric alkaline phosphatase. The alkaline phosphatase may include an amino acid sequence having at least 90%, 95%, 97%, or 99% sequence identity to SEQ ID NO: 1. For example, the alkaline phosphatase may include or consist of the amino sequence of SEQ ID NO: 1.

The biochemical metric that may be used to monitor the subject may be selected from the group consisting of plasma pyrophosphate (PPi), pyridoxyl-5'phosphate (PLP), phosphoethanolamine (PEA), and alkaline phosphatase (ALP) levels, or a combination thereof.

The quality of life metric that may be used to monitor the subject may be selected from the group consisting of EuroQol Five Dimension Questionnaire (EQ-5D), Childhood Health Assessment Questionnaire (CHAQ), Pediatric Outcomes Data Collection Instrument (PODCI), Child Health Utility Index-9D (CHU-9D), Pediatric Quality of Life Inventory (PedsQL), Lower Extremity Function Scale (LEFS), Short Form Health Survey 36 (SF-36), and Short Form Health Survey 12 (SF-12), or a combination thereof.

The physical metric that may be used to monitor the subject may be selected from the group consisting of Six Minute Walk Test (6MWT), Bruininks-Oseretsky Test of Motor Proficiency 2nd Edition (BOT-2), Bayley Scales of Infant and Toddler Development, 3rd Edition (BSID-III), Muscle Strength Grade, Handheld Dynamometry (HHD), Peabody Developmental Motor Scales, 2nd Edition (PDMS-2), gait analysis, short physical performance battery (SPPB), and Timed Up and Go (TUG) test, or a combination thereof. The SPPB may include a repeated chair stand test.

The physical metric may be monitored using a wearable device, such a wearable device that includes an accelerometer. The wearable device may be configured to be worn on the arm (e.g., wrist), leg, or torso of the subject. The wearable device may track one or more biometric indicia of the subject. For example, the biometric indicia may be selected from number of steps per day, mean heart right, highest heart rate, number of physical activity counts, mean amount of time spent at various activity levels, ratio of various activity levels, duration of various activity levels, and duration of total sleep time. The various activity levels may be selected from sedentary, light, moderate, and vigorous. The physical metric may be monitored using the wearable device for a period of at least two weeks (e.g., during a treatment phase or during a non-treatment phase, or during both phases).

During the non-treatment phase, the subject may not be administered the sALP for a period of at least 1 month., e.g., at least 6 months, e.g., at least 1 year, or longer.

During the treatment phase, the sALP may be administered at a dosage of from about 1 mg/kg/week to about 12 mg/kg/week (e.g., from about 2 mg/kg/week to about 9 mg/kg/week, e.g., from about 2.5 mg/kg/week to about 6 mg/kg/week). In some embodiments, the sALP is administered at a dosage of about 2.6 mg/kg/week, 3.6 mg/kg/week, or about 6 mg/kg/week.

The dose of the sALP may be adjusted during treatment. For example, the sALP may be administered at a dosage of about 6 mg/kg/week and then lowered to a dosage of about 3.6 mg/kg week. For example, the sALP may be administered at a dosage of about 6 mg/kg/week for about 12 weeks and then lowered to a dosage of about 3.6 mg/kg/week for about 24 weeks.

The methods described herein may be used to treat or reduce the risk of bone fracture in the subject. For example, the method may result an increase in bone healing to result in new bone at a reference point in the subject compared to the reference point in the subject before the treatment. The increase in bone healing may be an increase in opacity. The increase in opacity may be determined by radiography or computed tomography (CT). The increase in bone healing may be between two portions of a bone that has been separated by a fracture. The method may result in an average change in bone mineral density of a reference point that is undetectable or no greater than 0.01% eight months after the administration of the sALP compared to the bone mineral density of the reference point in the subject before the treatment.

In some embodiments, the method further includes treating the subject with a surgical intervention. The surgical intervention may include one or more of arthrodesis, removal of bone, insertion of bone graft material, and insertion of hardware (e.g., a screw, rod, plate, metal cage, nail, pin, or nut). The surgical intervention may be selected from the group consisting of arthroscopy of the knee, shoulder, hip, ankle, elbow, or wrist, fracture and meniscectomy, shoulder arthroscopy and decompression, carpal tunnel release, knee arthroscopy and chondroplasty, removal of support implant, knee arthroscopy and anterior cruciate ligament reconstruction, knee replacement, repair of femoral neck fracture, repair of atypical femoral fracture (AFF), repair of trochanteric fracture, debridement of skin/muscle/bone/fracture, knee arthroscopy repair of one or both menisci, hip replacement, shoulder arthroscopy/distal clavicle excision, repair of rotator cuff tendon, repair fracture of radius or ulna, laminectomy, repair of ankle fracture (bimalleolar type), shoulder arthroscopy and debridement, lumbar spinal fusion, repair fracture of the distal part of radius, low back intervertebral disc surgery, incise finger tendon sheath, repair of ankle fracture (fibula), repair of femoral shaft fracture, and repair of trochanteric fracture.

The sALP may be administered daily, weekly, biweekly, or monthly (e.g., during the treatment phase). For example, the sALP may be administered twice a week, three times a week, four times a week, five times a week, six times a week, or seven times a week. During the treatment period, the sALP may be administered for a treatment period of at least one month, at least two months, at least three months, at least four months, at least five months, at least six months, at least seven months, at least eight months, at least nine months, at least ten months, at least 11 months, at least 12 months, or longer. The non-treatment period may last at least one month, at least two months, at least three months, at least four months, at least five months, at least six months, at least seven months, at least eight months, at least nine months, at least ten months, at least 11 months, at least 12 months, or longer.

The sALP may be formulated in a pharmaceutical composition with at least one pharmaceutically acceptable carrier. The pharmaceutically acceptable carrier may include saline. For example, the pharmaceutically acceptable carrier may include sodium chloride and sodium phosphate (e.g., 150 mM sodium chloride and 25 mM sodium phosphate). The pharmaceutical composition may be administered subcutaneously, intramuscularly, intravenously, orally, nasally, sublingually, intrathecally, or intradermally.

In some embodiments of the methods described herein, the method results in an average increase in a Bruininks-Oseretsky Test of Motor Proficiency $2^{nd}$ Edition (BOT-2) running speed and agility score to about 9 or greater than about 9. The median total BOT-2 running speed and agility score of the subject may be determined relative to a BOT-2 running speed and agility medial total score of an untreated subject with HPP. The medial total BOT-2 running speed and agility score of the subject may be determined from measurements selected from the group consisting of stepping over a balance beam, shuttle run, two-legged side hop, and one-legged side hop. The method may result in an average increase in a BOT-2 strength score to about 18 or greater than about 18. The medial total BOT-2 strength score of the subject may be determined relative to a BOT-2 strength medial total score of an untreated subject with HPP. The medial total BOT-2 strength score of the subject may be determined relative to a BOT-2 strength medial total score of a healthy subject. The medial total BOT-2 strength score of the subject may be determined from measurements selected from the group consisting of sit-ups, V-ups, standing long jump, wall si, and push-ups.

In some embodiments of the methods described herein, the method may result in an improvement in walking ability relative to walking ability of a subject selected from the group consisting of a healthy subject and an untreated subject with HPP. For example, the subject may increase their average daily steps by 100, 200, 300, 400, 500, 1,000, 2,000, 3,000, 4,000, 5,000, 6,000, 7,000, 8,000, 9,000, 10,000, or more per day. The subject may exhibit decreased reliance on an assistive device for mobility (e.g., wheelchair, braces, crutches, and orthotics) after administration of the sALP.

The methods described herein may result in in an average decrease in inorganic pyrophosphate (PPi) concentration in a plasma sample from the subject relative to PPi concentrations in a plasma sample from an untreated subject with HPP. The method may result in an average decrease in pyridoxal 5'-phosphate (PLP) concentration in a plasma sample from the subject relative to PLP concentrations in a plasma sample from an untreated subject with HPP. The method may result in an average increase in alkaline phosphatase concentration in a plasma sample from the subject relative to alkaline phosphatase concentration in a plasma sample from an untreated subject with HPP.

In another aspect, the disclosure features a kit that includes a wearable device and a sALP. The wearable device may include an accelerometer. The wearable device may be configured to be worn on the wrist of a subject. The kit may further include a peripheral device (e.g., a smartphone). The peripheral device may be configured to run a software application (e.g., mobile application, e.g., smartphone application).

In another aspect, the disclosure features a method of monitoring a sALP treatment regimen of a subject by detecting a change in at least one physical metric based on biometric indicia produced by the wearable device. The biometric indicia may be selected from number of steps per day, mean heart right, highest heart rate, number of physical activity counts, mean amount of time spent at various activity levels, ratio of various activity levels, duration of various activity levels, and duration of total sleep time. The various activity levels may be selected from sedentary, light, moderate, and vigorous. The physical metric may be monitored using the wearable device for a period of at least two weeks (e.g., during a treatment phase or during a non-treatment phase, or during both phases).

In some embodiments of any of the above aspects, the dose is determined based on an actual body weight of the subject. In some embodiments of any of the above aspects, the dose is determined based on an Ideal body weight of the subject.

Definitions

The term "a" or "plurality" before a noun represents one or more of the particular noun or nouns. For example, the phrase "a mammalian cell" represents "one or more mammalian cells."

The term "about" means ±10% of the recited value. All measurements reported herein are understood to be modified by the term "about," whether or not the term is explicitly used, unless explicitly stated otherwise.

The term "asfotase alfa" (STRENSIQ®, Alexion Pharmaceuticals, Inc., Boston, MA) refers to a human recombinant TNALP-Fc-deca-aspartate fusion protein produced by recombinant DNA technology using mammalian Chinese Hamster Ovary (CHO) cell culture. Asfotase alfa is a soluble fusion glycoprotein comprised of 2 identical polypeptide chains. Each polypeptide chain contains the catalytic domain of human TNALP (Swiss-Prot, P05186), the human Ig G1 Fc domain (Swiss-Prot, P01857) (to facilitate purification), and a deca-aspartate peptide domain used for bone-targeting. The sequence of asfotase alfa is set forth in SEQ ID NO: 1. The two polypeptide chains are connected by two inter-chain disulfide bonds in the hinge region. Asfotase alfa can be expressed in an engineered CHO cell line that maintains endogenous folding, sorting, disulfide bridging, and N-linked glycosylation.

The term "bone-targeting moiety" means an amino acid sequence of at least 3 amino acid residues in length having a sufficient affinity to bone matrix such that the bone-targeting moiety, taken alone, has an in vivo binding affinity to the bone matrix that is at least about $1 \times 10^{-5}$ M or better (e.g., about $10^{-6}$ M, about $10^{-7}$ M, about $10^{-8}$ M, about $10^{-9}$ M, or better).

The term "bone mineralization disorder" refers to a disease or condition that affects normal mineralization of bone. Exemplary bone mineralization disorders are HPP (e.g., perinatal HPP, infantile HPP, childhood HPP, and odontohypophosphatasia), an HPP-like disease, calcium pyrophosphate deposition (CPPD), familial hypophosphatemia, bone fracture, osteoporosis, sclerosteosis, chondrocalcinosis, tracheobronchomalacia, neurofibromatosis 1 (NF1), and craniosynostosis. Other bone mineralization disorders are known in the art. A bone mineralization disorder may emanate a failure to mineralize bone matrix, e.g., due to elevated concentrations of the TNALP substrate PPi.

The terms "Brief Pain Inventory-Short Form" and "BPI-SF" as used interchangeably herein refer to a method to measure pain in a patient, in particular, a patient with a bone mineralization disorder, such as HPP (e.g., patients of about 13 years of age or older). The BPI-SF is a self-reported pain measure described in Cleeland & Ryan (*Ann Acad Med Singapore*, 23(2), 129-138; 1994), hereby incorporated by reference in its entirety. The BPI-SF is a questionnaire designed to assess the severity of pain and the impact of pain on daily functions. The BPI-SF consists of 11 items that utilize a numeric rating scale to assess pain severity (4 items) and pain interference (7 items) in the 24 hours prior to questionnaire administration. The BPI-SF questionnaire provides information on the intensity of pain and degree to which the pain interferes with daily functions of the patient on a numeric rating scale from 0 (no pain) to 10 (severe pain or significant interference caused by pain); lower scores indicate better quality of life outcomes and reduced pain. For instance, BPI-SF scores of the HPP adolescent and adult HPP patients are a composite of 11 pain assessments.

The terms "Bruininks-Oseretsky Test of Motor Proficiency $2^{nd}$ Edition" and "BOT-2," as used herein, refer to the second edition of a standardized test of gross and fine motor performance of a patient with a bone mineralization disorder, such as HPP (e.g., a child with HPP of about 5 years of age to about 12 years of age, an adolescent with HPP of about 13 years of age to about 17 years of age, or an adult with HPP of greater than about 18 years of age or older). See Bruininks, R. H. (2005). *Bruininks-Oseretsky Test of Motor Proficiency*, (BOT-2). Minneapolis, MN: Pearson Assessment, hereby incorporated by reference in Its entirety. The BOT-2 is administered individually to assess gross and fine motor skills of a range of patients. The BOT-2, for example, can be used to evaluate physical impairments and mobility restrictions in patients with HPP, e.g., children with HPP of about 5 years of age to about 12 years of age, adolescents with HPP of about 13 years of age to about 17 years of age, or adults with HPP of greater than about 18 years of age or older. The BOT-2 provides composite BOT-2 scores in the following exemplary areas: strength, running speed and agility, fine motor precision, fine motor integration, manual dexterity, bilateral coordination, balance, and upper-limb coordination. For example, a BOT-2 strength total score can be determined by having a patient perform sit-ups, v-ups, standing long jump, wall sit, and push-ups. A running speed and agility total score can be determined by having a patient step over a balance beam or perform a shuttle run, two-legged side hop, or one-legged side hop. Both BOT-2 total strength and BOT-2 running speed and agility total scores range from 0 to 25, in which a score of about 10 to 25 is considered representative of heathy subjects.

The term "catalytically competent," as used herein, refers to a sALP that hydrolyzes the bone mineralization inhibitor inorganic pyrophosphate (PPi) to provide inorganic phosphate (Pi), thereby decreasing the extracellular concentra-tions of PPi. Thus, the catalytically competent sALP Improves skeletal mineralization in bone by regulating the concentration of PPi.

The terms "Childhood Health Assessment Questionnaire" and "CHAQ," as used herein refer to a questionnaire that is used to assess the heath state (e.g., ability to perform activities of daily living (ADLs) and incidence of pain) of a patient of 1 to 19 years of age, such as a child, an adolescent, and an adult with a bone mineralization disorder, such as HPP. For a description of the CHAQ index, see Bruce & Fries (*J. Rheumatol.* 30(1): 167-178, 2003), hereby incorporated by reference in Its entirety. The CHAQ may be administered by interview or self-report for children greater than 8 years of age. The CHAQ includes eight sub-scales for dressing/grooming, arising, eating, walking, hygiene, reach, grip, and activities. The range of scores within each category is from 0 to 3, in which a score of 0 indicates without any difficulty; a score of 1 indicates with some difficulty; a score of 2 indicates with much difficulty; and a score of 3 indicates that the patient is unable to perform the activity. The CHAQ index may also be used to determine the presence and severity of pain.

The terms "EuroQol five dimension questionnaire" and "EQ-5D," as used herein, refer to a questionnaire that is used to assess the health state (e.g., mobility, self-care, ability to perform usual activities of school, work, or housework, ability to perform ADLs (e.g., dressing, toileting, and cooking), experience of pain or discomfort, and anxiety or depression) of a patient with a bone mineralization disorder, such as HPP (e.g., children with HPP of about 5 years of age to about 12 years of age, adolescents with HPP of about 13 years of age to about 17 years of age, or adults with HPP of greater than about 18 years of age or older. For a description of the EQ-5D index, see Reenan & Oppe (EQ-5D-3L User Guide Version 5.1, 2015), hereby incorporated by reference in its entirety. The EQ-5D may be self-administered or administered by a clinician or in an interview. The EQ-5D questionnaire includes the following five dimensions that characterize the health state of the HPP patient: mobility, self-care, ability to perform ADLs, incidence of pain or discomfort, and anxiety or depression. As described herein, the EQ-5D may be used in combination with at least one physical assessment, such as the 6MWT, to categorize an HPP patient as having a health state of level I indicating no problems with physiological condition, level II indicating some problems with physiological condition, level III indicating extreme problems with physiological condition, or level IV indicating the most extreme problems of physiological condition. The EQ-5D can also be used as part of the analysis to assess the transition of an HPP patient from one heath state to another heath state, such as from a health state of IV to III, IV to II, IV to I, III to II, III to I, or II to I. The Child Health Utility Index-9D (CHU-9D) can also be used to assess health status in HPP patients. For a description of the CHU-9D and EQ-5D indices, see Stevens (*Appl Health Econ Health Policy.* 9(3): 157-69, 2011) and PCT Publication No. WO 2018/191254, hereby incorporated by reference in Its entirety.

The term Fc means a fragment crystallizable region of an immunoglobulin, e.g., IgG1, IgG2, IgG3, or IgG4, including the CH2 and CH3 domains of the immunoglobulin heavy chain. Fc may also include any portion of the hinge region joining the Fab and Fc regions. The Fc can be derived from of any mammal, including human, and may be post-translationally modified (e.g., by glycosylation). In a non-limiting example, Fc can be the fragment crystallizable region of human IgG1.

By "fragment" is meant a portion of a polypeptide or nucleic acid molecule that contains, preferably, at least 10%, 20%, 30%, 40%, 50%, 60%, 70%, 75%, 80%, 85%, 90%, 95%, 96%, 97%, 98%, 99%, or more of the entire length of the reference nucleic acid molecule or polypeptide. A fragment may contain, e.g., 10, 15, 20, 25, 30, 35, 40, 45, 50, 55, 60, 65, 70, 75, 80, 85, 90, 95, 100, 110, 120, 130, 140, 150, 180, 170, 180, 190, 200, 210, 220, 230, 240, 250, 280, 270, 280, 290, 300, 310, 320, 330, 340, 350, 360, 370, 380, 390, 400, 500, 800, 700, 800, 900, 1,000, 1100, 1200, 1300, 1400, 1500, 1600, 1700, 1800, 1900, 2000, 2100, or more nucleotides, up to the entire length of the nucleic acid molecule, or 10, 15, 20, 25, 30, 35, 40, 45, 50, 55, 80, 85, 70, 75, 80, 85, 90, 95, 100, 110, 120, 130, 140, 150, 180, 170, 180, 190, 200, 210, 220, 230, 240, 250, 260, 270, 280, 290, 300, 400, 500, 800, 700, or more amino acid residues, up to the entire length of the polypeptide.

The terms "Hand Held Dynamometry" and "HHD" as used interchangeably herein refer to a method to measure the grip and muscle strength of a subject, in particular, a subject with HPP (e.g., a subject of about 13 years of age or older) or other bone mineralization disorder. A dynamometer can be used to assess grip strength, knee flexion, knee extension, hip flexion, hip extension, and hip abduction of a subject with HPP. For example, knee flexion and extension and also hip flexion, extension, and abduction of a subject with HPP of about 13 years of age or older can be measured using, e.g., a MICROFET2™ Dynamometer, while grip strength of the subject can be measured using, e.g., a JAMAR® Grip Dynamometer. In particular, the administrator holds the dynamometer stationary, and the subject exerts a maximal force against the dynamometer. Peak force data is collected in pounds, then converted to Newtons (N). Torque values are then calculated using limb length in N-meters. The torque value can then be compared to the value of, e.g., a normal subject of about the same age, the same gender, and/or the same height, and expressed as a percentage value to generate the HHD score of the subject.

The term "health state," as used herein, refers to the characterized physiological condition of a patient with HPP (e.g., a child with HPP of about 5 years of age to about 12 years of age, an adolescent with HPP of about 13 years of age to about 17 years of age, or an adult with HPP of greater than about 18 years of age or older) or other bone mineralization disorder. The health state of the patient can be characterized with at least one physical assessment selected from one or more of the following metrics Six Minute Walk Test (6MWT), Bruininks-Oseretsky Test of Motor Proficiency 2nd Edition (BOT-2), Bayley Scales of Infant and Toddler Development, 3rd Edition (BSID-III), Muscle Strength Grade, Handheld Dynamometry (HHD), Peabody Developmental Motor Scales, 2nd Edition (PDMS-2), gait analysis, short physical performance battery (SPPB), and Timed Up and Go (TUG) test, and/or at least one quality of life assessment selected from one or more of the following metrics: EuroQol Five Dimension Questionnaire (EQ-5D), Childhood Health Assessment Questionnaire (CHAQ), Pediatric Outcomes Data Collection Instrument (PODCI), Child Health Utility Index-9D (CHU-9D), Pediatric Quality of Life Inventory (PedsQL), Lower Extremity Function Scale (LEFS), Short Form Health Survey 38 (SF-38), and Short Form Health Survey 12 (SF-12). In particular, the health state of the patient is characterized by, e.g., the 6MWT in combination with the EQ-5D. After obtaining the results of at least one physical assessment and at least one quality of life assessment selected from the above metrics, the patient may be identified as having a health state of level I indicating no problems with physiological condition, level II indicating some problems with physiological condition, level III indicating extreme problems with physiological condition, or level IV indicating the most extreme problems of physiological condition. The metric(s) can be used to assess transition of the patient from one health state to another health state after, e.g., treatment with an sALP as described herein, such as a transition from a health state of IV to III, IV to II, IV to I, III to II, III to I, or II to I after administration of the sALP.

The terms "hypophosphatasia" and "HPP," as used herein, refer to a rare, heritable skeletal disorder caused by, e.g., one or more loss-of-function mutations in the ALPL (alkaline phosphatase, liver/bone/kidney) gene, which encodes TNALP. HPP may be further characterized as infantile HPP, childhood HPP, perinatal HPP (e.g., benign perinatal HPP or lethal perinatal HPP), odonto-HPP, adolescent HPP, or adult HPP. For instance, "childhood HPP describes a patient with HPP that is about 5 years of age to about 12 years, "adolescent HPP" describes a patient with HPP that is about 13 years of age to about 17 years, and "adult HPP" describes a patient with HPP that is about 18 years of age or older. The term "adult HPP," as used herein, refers to a condition or phenotype characterized by the presence of one or more of the following symptoms: elevated blood and/or urine levels of inorganic pyrophosphate (PPi), hypomineralization, hypercalciuria, one or more skeletal deformities, hypotonia, muscle weakness, rheumatoid complications, waddling gait, ambulatory difficulties, bone pain, pain, bone fracture, calcium pyrophosphate dihydrate crystal deposition, pseudogout, arthritis, pyrophosphate arthropathy, chondrocalcinosis, calcific periarthritis, and pseudofracture. The term "adolescent HPP," as used herein, refers to a condition or phenotype characterized by the presence of one or more of the following symptoms: elevated blood or urine levels of PPi, PEA, or PLP; osteomalacia, one or more skeletal deformities, hypotonia, muscle weakness, rheumatoid complications, arthritis, pseudogout, waddling gait, ambulatory difficulties, bone pain, pain, premature loss of teeth, hypomineralization, pulmonary hypoplasia, respiratory insufficiency, seizures, hypercalciuria, short stature, and growth delay. The term "childhood HPP," as used herein, refers to refers to a condition or phenotype characterized by the presence of one or more of the following symptoms: elevated blood or urine levels of PPi, PEA, or PLP; rickets, rachitic ribs, one or more skeletal deformities, hypotonia, muscle weakness, rheumatoid complications, arthritis, pseudogout, waddling gait, ambulatory difficulties, bone pain, pain, premature loss of teeth, hypomineralization, delayed motor development, seizures, hypercalciuria, short stature, bone fracture, pseudofracture, and growth delay.

The terms "Lower Extremity Function Scale" and "LEFS" as used interchangeably herein refer to a method to measure the functional disability in the lower extremities of a patient, in particular, a patient with HPP (e.g., patients of about 13 years of age or older) or other bone mineralization disorder. The LEFS is a self-reported measure described in Binkley et al. (*Phys Ther.* 79:371-83, 1999), hereby incorporated by reference in its entirety. Total LEFS scores range from 0 to 80 with higher scores indicative of better lower extremity functioning. A LEFS score change of about 9 points is considered a clinically meaningful change. A licensed physical therapist can administer the LEFS to a patient (e.g., an HPP patient of about 13 years of age or older) in interview format. Higher LEFS scores are indicative of improved lower extremity functioning including transitional movements (e.g., getting out of bath or rolling in bed), locomotion (e.g., waking or running on uneven ground), climbing stairs, and squatting. The LEFS can be used to evaluate the functional impairment of one or both lower extremities of a patient, including the ability to monitor the patient over time and evaluate the effectiveness of asfotase alfa treatment.

The terms "nucleic acid" or"nucleic acid molecule" means a polymeric molecule, e.g., RNA or DNA, having a sequence of two or more covalently bonded, naturally occurring or modified, nucleotides. The nucleic acid molecule may be, e.g., single or double stranded, and may include modified or unmodified nucleotides, or mixtures or combinations thereof. Various salts, mixed salts, and free acid forms of nucleic acid molecules are also included.

The terms "Pediatric Outcomes Data Collection Instrument" and "PODCI," as used herein, refer to a questionnaire used to assess overall health, incidence of pain, and ability to perform ADLs of a patient under 19 years of age, particularly in a patient with a chronic health disorder, such as a patient with HPP or other bone mineralization disorders. For a description of the PODCI, see Plint et al. (*J. Pediatr. Orthop.* 23(8): 788-790, 2003), hereby incorporated by reference in its entirety. The questionnaire may be completed by the patient or by a parent/guardian of the patient with knowledge of the patient's condition. The eight scales generated from the PODCI include the following: 1) the upper extremity and physical function scale to measure difficulty encountered in performing daily personal care and student activities; 2) the transfer and basic mobility scale to measure difficulty experienced in performing routine motion and motor activities in daily activities; 3) the sports/physical functioning scale to measure difficulty or limitations encountered in participating in more active activities or sports; 4) the pain/comfort scale to measure the level of pain experienced during the past week; 5) the treatment expectations scale to measure the long term expectations of treatment; 6) the happiness scale to measure overall satisfaction with personal looks and sense of similarity to friends and others of own age; 7) the satisfaction with symptoms scale to measure the patient's acceptance of current limitations should this be a life-long state; and 8) the global functioning scale, which is a general combined scale calculated from the first four scales listed above. Standardized scores are generated from a series of questions in the PODCI and converted to a 0 to 100 scale, in which 0 represents significant disability and 100 represents less disability.

The term "recombinant protein" is known in the art. A recombinant protein can be a glycoprotein. For example, recombinant protein or a recombinant protein variant made in a CHO cell is glycosylated, with the sugar moieties covalently attached on the protein, and is a glycoprotein. Briefly, the term "recombinant protein" can refer to a protein that can be manufactured using a cell culture system. The cells in the cell culture system can be derived from, for example, a mammalian cell, including a human cell, a CHO cell, an insect cell, a yeast cell, or a bacterial cell. In general, the cells in the cell culture contain an introduced nucleic acid encoding the recombinant protein of interest (which nucleic acid can be borne on a vector, such as a plasmid vector). The nucleic acid encoding the recombinant protein can also contain a heterologous promoter operably linked to a nucleic acid encoding the protein.

As used herein, "Six Minute Walk Test" and "6MWT" refer to a physical assessment that is a standardized test to assess walking ability of a patient with HPP (e.g., a child with HPP of about 5 years of age to about 12 years of age, an adolescent with HPP of about 13 years of age to about 17 years of age, or an adult with HPP of greater than about 18 years of age or older) or other bone mineralization disorder. In particular, walking ability refers to the ability of the patient to lift and set down each foot in turn. See the American Thoracic Society statement: guidelines for the six-minute walk test (*Amer. J. of Respiratory and Critical Care Medicine,* 188(1):111-7, 2002, hereby incorporated by reference in its entirety). The 6MWT is determined from the distance (e.g., in meters) that a patient walks on a flat, hard surface in a period of six minutes. The 6MWT distance can then be compared to the 6MWT distance of the patient at baseline, the 6MWT distance of an untreated subject (e.g., an untreated subject of about the same age, height, and/or gender), or the 6MWT distance of a healthy subject (e.g., a healthy subject of about the same age, height, and/or gender) and expressed as a percentage to determine the 6MWT value.

By "treating," "treat," and "treatment" is meant the medical management of a patient with the intent to cure, ameliorate, stabilize, reduce the likelihood of, or prevent a disease condition, such as HPP (e.g., child, adolescent, or adult HPP) or other bone mineralization disorder, or one or more symptoms thereof and/or the management of a patient exhibiting or likely to have a disease condition, such as HPP, or other bone mineralization disorder, e.g., by administering a pharmaceutical composition (e.g., an sALP as described herein). This term includes active treatment, that is, treatment directed specifically toward the Improvement or associated with the cure of a disease, pathological condition, disorder, or event, and also includes causal treatment, that is, treatment directed toward removal of the cause of the associated disease, pathological condition, disorder, or event. In addition, this term includes palliative treatment, that is, treatment designed for the relief or Improvement of at least one symptom rather than the curing of the disease, pathological condition, disorder, or event; symptomatic treatment, that is, treatment directed toward constitutional symptoms of the associated disease, pathological condition, disorder, or event; preventative treatment, that is, treatment directed to minimizing or partially or completely inhibiting the development of the associated disease, pathological condition, disorder, or event, e.g., in a patient who is not yet ill, but who is susceptible to, or otherwise at risk of, a particular disease, pathological condition, disorder, or event; and supportive treatment, that is, treatment employed to supplement another specific therapy directed toward the improvement of the associated disease, pathological condition, disorder, or event.

The terms "peptide," "polypeptide," and "protein" are used interchangeably and refer to any chain of two or more natural or unnatural amino acid residues, regardless of post-translational modification (e.g., glycosylation or phosphorylation), constituting all or part of a naturally-occurring or non-naturally occurring polypeptide or peptide, as is described herein.

The terms "sALP," "soluble alkaline phosphatase," and "extracellular domain of an alkaline phosphatase" are used interchangeably, and mean a soluble, non-membrane-bound alkaline phosphatase or a domain, biologically active fragment, or biologically active variant thereof. sALPs include, for example, an alkaline phosphatase lacking a C-terminal GPI signal sequence, and additional variants and analogs thereof which retain alkaline phosphatase activity, e.g., the ability to hydrolyze PPi or other natural or artificial substrates. This includes TNALP, PALP, GALP, and IALP domain, and biologically active fragment, or biologically active variant thereof, unless specified otherwise. A mature sALP lacks the GPI membrane anchor and the signal peptide, which is cleaved during processing.

The terms "isolated" or "purified" means separated from other naturally accompanying components. Typically, a compound (e.g., protein, polypeptide, nucleic acid, or small molecule), factor, cell, or other component is considered isolated when it is at least, e.g., 50%, 60%, 70%, 75%, 80%, 85%, 90%, 95%, 96%, 97%, 98%, or even 99%, by weight, free from proteins, antibodies, naturally-occurring organic molecules, and other components with which it is naturally associated. In some instances, the component is at least 75%, 90%, or even 99%, by weight, pure. An isolated component may be obtained by chemical synthesis, separation of the factor from natural sources, or production of the component in a recombinant host cell that does not naturally produce the component. Proteins and small molecules may be purified by one skilled in the art using standard techniques such as those described by Ausubel et al. (*Current Protocols in Molecular Biology*, John Wiley & Sons, New York, 2000). The component is preferably at least, e.g., 2, 5, or 10 times as pure as the starting material, as measured using, e.g., polyacrylamide gel electrophoresis, column chromatography, optical density, HPLC analysis, or Western analysis (Ausubel et al., 2000). Exemplary methods of purification are column chromatography, filtration, immunoprecipitation, and magnetic bead immunoaffinity purification.

The terms "pharmaceutically acceptable carrier" or"pharmaceutically acceptable excipient" is meant a carrier or excipient that is physiologically acceptable to the treated patient while retaining the therapeutic properties of the compound with which it is administered. One exemplary pharmaceutically acceptable carrier substance is physiological saline. Other physiologically acceptable carriers and their formulations are known to those skilled in the art and described, for example, in *Remington's Pharmaceutical Sciences* (Remington: The Science and Practice of Pharmacy, 22nd Ed., Allen, Ed. 2012).

The term "pharmaceutical composition" means a composition containing a polypeptide or nucleic acid molecule as described herein formulated with a pharmaceutically acceptable excipient and includes those that are manufactured or sold with the approval of a governmental regulatory agency as part of a therapeutic regimen for the treatment or prevention of a disease or event in a patient. Pharmaceutical compositions can be formulated, for example, for subcutaneous administration, intravenous administration (e.g., as a sterile solution free of particulate emboli and in a solvent system suitable for intravenous use), for oral administration (e.g., a tablet, capsule, caplet, gelcap, or syrup), or any other formulation described herein, e.g., in unit dosage form.

The terms "subject" and "patient" are used interchangeably and mean a mammal, including, but not limited to, a human or non-human mammal, such as a bovine, equine, canine, ovine, or feline.

The term "mammalian cell" is known in the art and can refer to any cell from or derived from any mammal including, for example, a human, a hamster, a mouse, a green monkey, a rat, a pig, a cow, a hamster, or a rabbit. The mammalian cell can be an immortalized cell, a differentiated cell, or an undifferentiated cell.

The term "therapeutically effective amount" means an amount of a polypeptide or nucleic acid molecule described herein that is sufficient to substantially treat, prevent, delay, suppress, or arrest any symptom of a disease or condition described herein, particularly HPP. A therapeutically effective amount of a composition described herein may depend on the severity of the disorder being treated and the condition, weight, and general state of the subject and can be determined by an ordinarily-skilled artisan with consideration of such factors. A therapeutically effective amount of a composition described herein can be administered to a subject in a single dose or in multiple doses administered over a period of time.

As used herein, when a polypeptide or nucleic acid sequence is referred to as having "at least X % sequence identity" to a reference sequence, it is meant that at least X percent of the amino acid residues or nucleotides in the polypeptide or nucleic acid are identical to those of the reference sequence when the sequences are optimally aligned. An optimal alignment of sequences can be determined in various ways that are within the skill in the art, for instance, the Smith Waterman alignment algorithm (Smith et al., *J. Mol. Biol.* 147:195-7, 1981) and BLAST (Basic Local Alignment Search Tool; Altschul et al., *J. Mol. Biol.* 215: 403-10, 1990). These and other alignment algorithms are accessible using publicly available computer software such as "Best Fit" (Smith and Waterman, *Advances in Applied Mathematics,* 482-489, 1981) as incorporated into GeneMatcher Plus™ (Schwarz and Dayhof, *Atlas of Protein Sequence and Structure*, Dayhoff, M. O., Ed., pp 353-358, 1979), BLAST, BLAST-2, BLAST-P, BLAST-N, BLAST-X, WU-BLAST-2, ALIGN, ALIGN-2, CLUSTAL, or Megalign (DNASTAR). In addition, those skilled in the art can determine appropriate parameters for measuring alignment, including any algorithms needed to achieve optimal alignment over the length of the sequences being compared.

As used herein, a "predetermined threshold" refers to a value of a metric in a subject relative to a control value (e.g., the value of the metric in a normal subject, e.g., a subject without a bone mineralization disorder (e.g., HPP), in a subject with the disease who has been treated with a sALP, or in a subject with the disease who has not yet been treated with a sALP). The normal or treated subject may have the same or similar age, weight, and/or gender. The predetermined threshold may refer to a value of a metric that falls between the measured value for a subject with a bone mineralization disorder and the corresponding value in a normal subject. For example, if a subject with a bone mineralization disorder is determined to have a score of 50 steps according to the 6MWT metric, and a normal subject has a score of 500 steps according to this metric, then the predetermined threshold may be a value that falls within the range of 50 steps to 500 steps. A predetermined threshold may also be a value of a metric that is, e.g., 10%, 20%, 30%, 40%, 50%, 60%, 70%, 80%, 90%, 100%, or more below the value for a normal or treated subject. Alternatively, the predetermined threshold may be a value of a metric that is adjusted to reflect the score of a subject treated with a sALP such that the predetermined threshold value becomes a value of the metric that is at least, e.g., 10%, 20%, 30%, 40%, 50%, 60%, 70%, 80%, 90%, 100%, greater than an initial value of the metric in the subject, e.g., before treatment with the sALP.

The words "preferred" and "preferably" refer to embodiments of the disclosed polypeptides, compositions and methods that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the disclosure.

For any method disclosed herein that includes discrete steps, the steps may be conducted in any feasible order; also, as appropriate, any combination of two or more steps may be conducted simultaneously.

The above summary is not intended to describe each disclosed embodiment or every Implementation of disclosed polypeptides, compositions and methods. The description that follows more particularly exemplifies illustrative embodiments. In several places throughout the application, guidance may be provided through lists of examples, which examples can be used in various combinations. In each instance, the recited list serves only as a representative group and should not be interpreted as an exclusive list.

All headings are for the convenience of the reader and should not be used to limit the meaning of the text that follows the heading, unless so specified.

Other features and advantages of the disclosure will be apparent from the detailed description, the drawings, and the claims.

BRIEF DESCRIPTION OF THE DRAWINGS

FIGS. 2A-2D are graphs showing physical function (FIGS. 2A-2C) and HRQoL (FIG. 2D) among adults treated with asfotase alfa for pediatric-onset HPP according to data collected at baseline, 8 months, and 12 months. A) Six-minute walk test (6MWT), n=12 B) chair rise test (part of the SPPB, n=9), C) LEFS (n=9), D) PCS scores as assessed by the SF-38v2 (n=9); asterisks denote statistical significance vs baseline.

FIGS. 11A and 11B are graphs showing grip strength in dominant (FIG. 11A) and nondominant (FIG. 11B) hand to 30 months.

DETAILED DESCRIPTION

Figure 1:
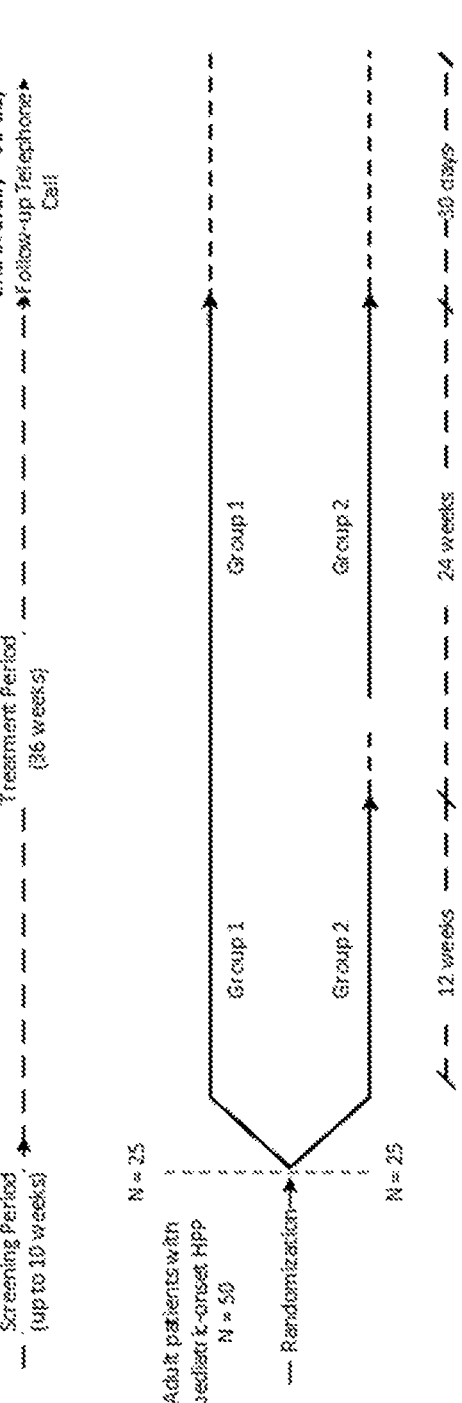
FIG. 1 shows a schematic of the study design described in Example 2. Group 1 is randomized to asfotase alfa at 6 mg/kg/week at baseline and continues on 6 mg/kg/week from week 12 through the end of treatment (week 36). Group 2 is randomized to asfotase alfa at 6 mg/kg/week at baseline and transitions to 3.6 mg/kg/week from week 12 through the end of treatment (week 36). AA=asfotase alfa; HPP=hypophosphatasia; qw=every week.

Featured are methods for treating bone mineralization disorders, such as hypophosphatasia (HPP), and symptoms thereof. HPP is a rare, heritable skeletal disease with an incidence of 1 per 100,000 births for the most severe forms of the disease. The disorder typically results from loss-of-function mutations in the gene coding for TNALP. HPP exhibits a remarkable range of symptoms and severity, from premature tooth loss to almost complete absence of bone mineralization in utero. The presentation of HPP varies markedly among subjects and also varies markedly between subject ages. Many subjects with HPP display skeletal changes, short stature, chronic pain, painful lower limbs, gait disturbance, and premature, atraumatic tooth loss. Due to the loss-of-function mutation in the endogenous TNALP, a subject with HPP requires restoration of the native ALP activity to provide normal bone matrix mineralization.

Due to the variety of phenotypes and severity within subjects, different metrics can be used to assess or monitor disease state (e.g., before, during, and after treatment). In particular, several of these metrics are specific, e.g., specific to infants or to adults. For example, radiographic changes, such as skeletal mineralization can be monitored in infants as new bones grow during development. However, an adult with a mid phenotype may exhibit normal or nearly normal mineralization characteristics. Thus, a different metric may be needed to effectively monitor treatment efficacy in these different patients. One such patient includes adult patients (i.e., those 18 years and older) who exhibit diminished quality of life and/or chronic disability due to the bone or muscle manifestations of the disease. Symptoms in adult patients include, for example, fractures and pseudofractures, chronic pain, muscle weakness, hypotonia, and/or poor physical stamina. Sometimes simple daily activities, such as sitting down, standing up, or walking, can be difficult for an adult patient. Featured herein are methods of treatment that include monitoring changes in biochemical, physical, and/or quality of life metrics in order to establish a treatment regimen for a patient with a bone mineralization disorder, such as HPP, and in particular, for an adult HPP patient.

Methods of Treatment

The methods described herein include treating a bone mineralization disorder in a human subject. The subject may exhibit a level in at least one biochemical, physical, quality of life, or bone metric (or combinations thereof) that identifies the subject as in need of treatment for the bone mineralization disorder. The method may include administering at least one dose of a sALP to the subject in a first treatment phase of a treatment regimen, monitoring the subject during the first treatment phase for changes in the at least one biochemical, physical, quality of life, or bone metric, and detecting an improvement in the at least one biochemical, physical, quality of life, or bone metric. The improvement may be above a predetermined threshold of the metric (e.g., an improvement of 10%, 20%, 30%, 40%, 50%, 60%, 70%, 80%, 90%, or more relative to an initial value of the metric in the subject prior to treatment). If the subject shows improvement, the subject may then enter a first non-treatment phase of the treatment regimen during which the subject is not administered the sALP. During the non-treatment phase, the method may further include monitoring the subject during the first non-treatment phase for a period of time for changes in the at least one biochemical, physical, quality of life, or bone metric. If the subject exhibits a decrease in the measured value of a metric, such as a decrease to or below the predetermined threshold (e.g., a decrease of 10%, 20%, 30%, 40%, 50%, 60%, 70%, 80%, 90%, or more in the value of the metric relative to the predetermined threshold), then the treatment regimen may restart (e.g., the subject is administered at least one dose of the sALP in a second, or subsequent, treatment phase of the treatment regimen). These steps may be repeated one or more times while efficacy is monitored (e.g., continuously or intermittently) throughout the course of the treatment regimen. While a predetermined threshold may be used as a cutoff for assessing whether or not to administer the sALP during a particular phase of the treatment regimen, one of skill in the art would appreciate that one may continue or discontinue treatment despite decreasing below or increasing above a predetermined threshold. For example, it may be desirable to restart dosing before a BOT-2 strength score decreases below a predetermined threshold in order to avoid a decrease below a predetermined threshold in the value of a metric in the subject (e.g., treatment can be resumed before the value of a metric reaches a value that is 1%, 2%, 5%, 10%, 15%, 20%, 25%, or 30% or more above the predetermined threshold).

Evaluation of Treatment Efficacy

A bone mineralization disorder (such as HPP, including e.g., perinatal HPP, infantile HPP, childhood HPP, and odontohypophosphatasia, and HPP-like disease, CPPD, and familial hypophosphatemia, as described herein) can be treated with an alkaline phosphatase, or a polypeptide having alkaline phosphatase activity (e.g., a sALP, e.g., a polypeptide having the sequence of SEQ ID NO: 1 or a polypeptide variant having at least 95% sequence identity to the sequence of SEQ ID NO: 1, e.g., asfotase alfa). The methods described herein are also useful for diagnosing or monitoring a subject having or being prone to develop a bone mineralization disorder, such as HPP, identifying a subject as having or being prone to develop a bone mineralization disorder, such as HPP, or testing the efficacy of treatment of a bone mineralization disorder, such as HPP. For example, a subject may be diagnosed as having or being prone to develop a bone mineralization disorder, such as HPP, if the subject is characterized as having certain characteristic biomarkers or a metric score(s). A subject may be treated with an alkaline phosphatase, or a polypeptide having alkaline phosphatase activity, (e.g., a sALP, e.g., a polypeptide having the sequence of SEQ ID NO: 1 or a variant thereof with at least 85% sequence identity thereto), and the treatment efficacy or effects may be analyzed using the characteristic biomarkers or metric score(s). A predetermined metric score may include a characteristic predetermined threshold in which increasing above or decreasing below the threshold indicates a need to stop or start administration of the sALP.

Exemplary metrics useful for evaluating the efficacy of treatment using a sALP (such as TNALP, for example the sALP fusion polypeptide of SEQ ID NO: 1 or a polypeptide variant having at least 95% sequence identity to the sequence of SEQ ID NO: 1, e.g., asfotase alfa) include biochemical metrics, physical metrics, quality of life metrics, and bone metrics. Biochemical metrics include monitoring sALP substrates, such as PPi, PEA, and PLP concentrations in the serum, plasma, the bone or muscle tissues, or the urine of the subject. Physical metrics include assessments such as the Six Minute Walk Test (6MWT), Bruininks-Oseretsky Test of Motor Proficiency 2nd Edition (BOT-2), Bayley Scales of Infant and Toddler Development, 3rd Edition (BSID-III), Muscle Strength Grade, Handheld Dynamometry (HHD), Peabody Developmental Motor Scales, 2nd Edition (PDMS-2), gait analysis, Timed Up and Go (TUG) test, and short physical performance battery (SPPB). The SPPB may include tests, such as a repeated chair stand test. The methods may include tracking metrics such as decreased reliance on assistive devices (e.g., wheelchairs, wheeled walkers, and canes). Physical metrics may be monitored by a wearable device, such as a device that tracks steps (e.g. pedometer), physical activity, heart rate (e.g., heart rate monitor), and/or sleep patterns. Bone metrics include monitoring bone morphology, bone healing, bone mineralization, and bone mineral density. Quality of life metrics include assessments, such as the EuroQol Five Dimension Questionnaire (EQ-5D), Childhood Health Assessment Questionnaire (CHAQ), Pediatric Outcomes Data Collection Instrument (PODCI), Child Heath Utility Index-9D (CHU-9D), Pediatric Quality of Life Inventory (PedsQL), Lower Extremity Function Scale (LEFS), Short Form Health Survey 38 (SF-38), and Short Form Health Survey 12 (SF-12). The methods may further include the use of one or more of the described metrics (e.g., bone healing, mineralization, bone mineral density, or plasma PPi and PLP concentrations, physical metrics, and quality of life metrics), singly or in combination, to assess treatment efficacy, in which improvements as described herein demonstrate that sALP is an effective treatment for the treated condition. Additionally, the method may further include stopping treatment if the methods are effective to treat the subject in need thereof. Furthermore, the methods may include changing the dosage and/or frequency of sALP (e.g., SEQ ID NO: 1; e.g., asfotase alfa) administration in order to determine the effective amount of sALP to administer to subject in need thereof. If the subject is not being treated for a certain period during the treatment regimen, the subject may be monitored at different time points to assess whether treatment should recommence, or the subject should remain in a nontreatment phase. These metrics are described in more detail below.

Bone Healing and Mineralization

A subject having or being prone to a bone mineralization disorder, such as HPP, can be identified for treatment with an alkaline phosphatase or a polypeptide having alkaline phosphatase activity (e.g., a sALP, e.g., a polypeptide having the sequence of SEQ ID NO: 1 or a variant thereof with at least 85% sequence identity thereto) based on a level of bone mineralization. For example, bone mineralization may be used as a metric to diagnose a subject as having a bone mineralization disorder, such as HPP, or testing the efficacy of a polypeptide described herein. In a subject with a bone mineralization disorder (e.g., HPP) administration of the sALP results in an increase in bone healing in the subject following successful treatment.

A decrease in bone healing results in loss of bone and includes decreased mineralization that results in the disunion of two or more bones. Bone healing and decreased mineralization may be compared to a reference bone. Methods for identifying a decrease in bone healing and mineralization are routine and include non-invasive techniques such as radiography and computed tomography (CT).

Typically, images of the relevant area of the subject can be taken before and at one or more time points following the sALP treatment, and the images can be compared to assess treatment efficacy. Decreased bone healing and/or mineralization can be identified as decreased opacity. Images can be taken at any time during sALP treatment, and can be timed to be, e.g., 1, 2, 3, 4, 5, or 8 day(s), week(s), or month(s), or year(s) following initiation of the sALP ERT treatment or when a decrease in efficacy is suspected. The decrease in bone healing and/or mineralization in the subject may become detectable at least 1, 2, 3, 4, 5, 8, 7, 8, 9, 10, 11, or 12 week(s) or month(s) following initiation of the sALP treatment period. The decrease in bone healing and/or mineralization in the subject may in some cases be sustained for at least 1, 2, 3, 4, 5, 8, 7, 8, 9, 10, 11, or 12 week(s), month(s), or year(s) following initiation of the sALP ERT treatment period. An increase in bone healing and mineralization may be used to determine that the sALP efficacy is restored and the bone mineralization disorder (e.g., HPP) is being efficaciously treated following therapy. If bone healing and mineralization increases to or above a predetermined threshold, then administration of the sALP may stop. However, the mineralization levels may be periodically monitored to determine if administration should be restarted.

Bone Mineral Density (BMD)

A subject having or being prone to a bone mineralization disorder, such as HPP, can be identified for treatment with an alkaline phosphatase or a polypeptide having alkaline phosphatase activity (e.g., a sALP, e.g., a polypeptide having the sequence of SEQ ID NO: 1 or a variant thereof with at least 85% sequence identity thereto) based on a BMD level. A reduction in BMD (e.g., relative to a normal subject) may be used as a metric to diagnose a subject as having a bone mineralization disorder, such as HPP.

A decrease in BMD can be used to monitor the efficacy of the sALP (e.g., the polypeptide of SEQ ID NO: 1) during the ERT. Methods for measuring BMD are known in the art and include, for instance, bone biopsy, dual-energy X-ray absorptiometry (DXA or DEXA), peripheral quantitative CT (pQCT), high-resolution pQCT (HR-pQCT), and quantitative ultrasound (QUS). Measurements can be made by any routine method, including CT Hounsfield measurement, and can use comparison of results to a normative database or control subject. BMD is sometimes reported as a Z-score or a T-score. Pre-treatment BMD values can be measured at any time during sALP ERT treatment, and can be timed to be 1, 2, 3, 4, 5, 8, 7, 8, 9, 10, 11, or 12 day(s), week(s), month(s), or year(s) following initiation of sALP ERT. The BMD value of a reference point after treatment may decrease by, e.g., 0.01%, 0.05%, 0.1%, 0.5%, or 1%. The decrease in a BMD value of a reference point after initiation of sALP treatment may also be unchanged or a change is undetectable. An increase in BMD above a predetermined threshold may be used to determine that the sALP efficacy is restored and the bone mineralization disorder (e.g., HPP) is being efficaciously treated following therapy. If restored, the subject may stop treatment and be monitored periodically for changes in BMD. If the BMD level decreases below the predetermined threshold, then therapy may be restarted.

Plasma Inorganic Pyrophosphate (PPi) and Alkaline Phosphatase (ALP) Concentrations A subject having or being prone to a bone mineralization disorder, such as HPP, can be identified for treatment with an alkaline phosphatase or a polypeptide having alkaline phosphatase activity, (e.g., a sALP, e.g., a polypeptide having the sequence of SEQ ID NO: 1 or a variant thereof with at least 85% sequence identity thereto) by determining the inorganic pyrophosphate (PPi) and/or alkaline phosphatase (ALP) concentrations in a sample, such as a plasma or urine sample, from the subject. Any method known to those of skill in the art can be used to quantify the PPi and/or ALP concentrations in a plasma sample or alternatively in a urine sample, as described in detail in Whyte et al., 1995 (J. Clin. Invest. 95(4): 1440-1445), hereby incorporated by reference in its entirety. Methods to quantify PPi concentrations in a plasma or urine sample are also described in Cheung et al., 1977 (Anal. Biochem. 83: 61-63), Cook et al., 1978 (Anal. Biochem. 91: 557-565), and Johnson et al, 1968 (Anal. Biochem. 26: 137-145), which are each hereby incorporated by reference in their entirety.

In particular, an alkaline phosphatase or a polypeptide having alkaline phosphatase activity (e.g., a sALP, e.g., a polypeptide having the sequence of SEQ ID NO: 1 or a variant thereof with at least 85% sequence identity thereto) can be administered to a subject having or being prone to a bone mineralization disorder, such as HPP, previously determined to have a plasma PPi concentration of up to about 8 μM (e.g., about 4.5 μM, about 5 μM, or about 5.5 μM or a plasma PPi concentration within the range of about 4.5 μM to about 8 μM). For example, the alkaline phosphatase or the polypeptide having alkaline phosphatase activity is administered to, e.g., an infant or child (e.g., a subject less than about 12 years of age) having a plasma PPi concentration of about 5.71 μM or greater; or an adolescent (e.g., a subject of about 13 to about 18 years of age) having a plasma PPi concentration of about 4.78 μM or greater.

In particular, the alkaline phosphatase or the polypeptide having alkaline phosphatase activity is administered to an adult (e.g., a subject of greater than about 18 years of age) having a plasma PPi concentration of about 5.82 μM or greater.

Additionally, an alkaline phosphatase or a polypeptide having alkaline phosphatase activity can be administered to a subject (e.g., a human) having or being prone to a bone mineralization disorder, such as HPP, previously determined to have a plasma ALP concentration of, e.g., about 90 U/L or less for a subject of 0 to 14 days of age; about 134 U/L or less for a subject of 15 days of age to less than 1 year of age; about 156 U/L or less for a subject of about 1 year of age to less than 10 years of age; about 141 U/L or less for a subject of about 10 years of age to less than about 13 years of age; about 82 U/L or less for a female subject of about 13 years of age to less than about 15 years of age; about 127 U/L or less for a male subject of about 13 years of age to less than about 15 years of age; about 54 U/L or less for a female subject of about 15 years of age to less than about 17 years of age; about 89 U/L or less for a male subject of about 15 years of age to less than about 17 years of age; about 48 U/L or less for a female subject of about 17 years of age or older; or about 59 U/L or less for a male subject of about 17 years of age or older.

The plasma PPi concentration and/or plasma ALP concentration of a subject (e.g., a human) having or being prone to a bone mineralization disorder, such as HPP, can be compared to the plasma PPi concentration and/or plasma ALP of a normal subject to determine a treatment effect in the subject administered an alkaline phosphatase or a polypeptide having alkaline phosphatase activity (e.g., a sALP, e.g., a polypeptide having the sequence of SEQ ID NO: 1 or a variant thereof with at least 85% sequence identity thereto). In particular, the alkaline phosphatase or the polypeptide having alkaline phosphatase activity can be administered for a treatment period of least one year (e.g., at least two years, at least three years, at least four years, at least five years, at least six years, at least seven years, at least eight years, at least nine years, at least ten years, or longer than ten years, such as for the lifetime of the subject). Alternatively, the methods can include determining the plasma PPi concentration and/or plasma ALP concentration prior to administering the alkaline phosphatase or the polypeptide having alkaline phosphatase activity to assess an effect in the subject of treatment with the alkaline phosphatase or the polypeptide having alkaline phosphatase activity.

The methods result in a decrease in PPi and/or an increase in ALP concentration in a sample (e.g., a plasma sample) from a subject (e.g., a human subject) having or being prone to a bone mineralization disorder, such as HPP. For example, treatment with an alkaline phosphatase or a polypeptide having alkaline phosphatase activity (e.g., a sALP, e.g., a polypeptide having the sequence of SEQ ID NO: 1 or a variant thereof with at least 85% sequence identity thereto) results in a decrease in PPi concentration in a sample (e.g., a plasma sample) from the subject of about 1 $\mu$M, about 1.5 $\mu$M, about 2 $\mu$M, about 2.5 $\mu$M, or about 3 $\mu$M or 25% or greater (e.g., 30%, 35%, 40%, 45%, 50%, 55%, 60%, or more than 60%). Thus, the subject exhibits a plasma PPi concentration of, e.g., about 2 $\mu$M to about 5 $\mu$M, about 3 $\mu$M to about 5 $\mu$M, about 2 $\mu$M to about 4 $\mu$M, or about 2 $\mu$M to about 3 $\mu$M after administration of the alkaline phosphatase or the polypeptide having alkaline phosphatase activity.

Likewise, treatment with alkaline phosphatase or a polypeptide having alkaline phosphatase activity results in an increase in ALP concentration in a sample (e.g., a plasma sample) from a subject (e.g., a human) having or being prone to a bone mineralization disorder, such as HPP, of 30%, 35%, 40%, 45%, 50%, 55%, 60%, or more than 60%, relative to the subject prior to administration of the alkaline phosphatase or a polypeptide having alkaline phosphatase activity. For example, administration of the alkaline phosphatase or the polypeptide having alkaline phosphatase activity increases the ALP concentration in a sample (e.g., a plasma sample) from the subject to, e.g., about 273 U/L or greater for a subject of 0 to 14 days of age; about 518 U/L or greater for a subject of 15 days of age to less than 1 year of age; about 369 U/L or greater for a of about 1 year of age to less than 10 years of age; about 460 U/L or greater for a subject of about 10 years of age to less than about 13 years of age; about 280 U/L or greater for a female subject of about 13 years of age to less than about 15 years of age; about 517 U/L or greater for a male subject of about 13 years of age to less than about 15 years of age; about 128 U/L or greater for a female subject of about 15 years of age to less than about 17 years of age; about 365 U/L or greater for a male subject of about 15 years of age to less than about 17 years of age; about 95 U/L or greater for a female subject of about 17 years of age or older; or about 164 U/L or greater for a male subject of about 17 years of age or older.

The decrease in the plasma PPi and/or increase in the ALP concentrations of the subject (e.g., a human) having or being prone to a bone mineralization disorder, such as HPP, can be sustained throughout administration of the alkaline phosphatase or the polypeptide having alkaline phosphatase activity (e.g., a sALP, e.g., a polypeptide having the sequence of SEQ ID NO: 1 or a variant thereof with at least 85% sequence identity thereto). For instance, the plasma PPi concentration decreases by about 25% and remains at $\pm$10% of the decreased plasma PPi concentration during treatment with the sALP and/or the plasma ALP concentration increases by about 50% and remains at $\pm$10% of the increased plasma ALP concentration during treatment with the alkaline phosphatase or the polypeptide having alkaline phosphatase activity.

Alternatively, when administration of an alkaline phosphatase or a polypeptide having alkaline phosphatase activity (e.g., a sALP, e.g., a polypeptide having the sequence of SEQ ID NO: 1 or a variant thereof with at least 85% sequence identity thereto) does not result in an average decrease in PPi concentrations in a plasma sample from the subject (e.g., a human) having or being prone to a bone mineralization disorder, such as HPP, by about 25% or greater, the dosage and/or frequency of sALP administration can be changed in order to determine an effective amount of the sALP for the subject.

Likewise, when administration of an alkaline phosphatase or a polypeptide having alkaline phosphatase activity does not result in an average increase in ALP concentrations in a plasma sample from the subject by about 50% or greater, the dosage and/or frequency of alkaline phosphatase or a polypeptide having alkaline phosphatase activity administration can be changed in order to determine an effective amount of the alkaline phosphatase or a polypeptide having alkaline phosphatase activity for the subject. For instance, the dosage of the alkaline phosphatase or a polypeptide having alkaline phosphatase activity can be increased from, e.g., about 0.5 mg/kg/week or about 3.5 mg/kg/week to about 3-6 mg/kg/week or about 6-9 mg/kg/week. If desired levels of PPi or ALP are achieved, then the subject may stop treatment and be monitored periodically for changes in PPi or ALP levels. For example, if PPi levels increase above and/or ALP levels decrease below a predetermined threshold, then therapy may be restarted.

Short Physical Performance Battery (SPPB)

The SPPB is designed to measure functional status and physical performance. It is a composite measurement that evaluates walking speed, standing balance, and sit-to-stand (STS) performance. The SPPB is calculated from 3 components: the ability to stand for up to 10 seconds with feet positioned in 3 ways (together side-by-side, semi-tandem, and tandem); time to complete a 3 meter or 4 meter walk; and time to rise from a chair 5 times (i.e., repeated chair stand test). The standing balance tests are scored based on the ability to maintain balance in each of these positions. The walking speed and STS tests are scored firstly on the ability to complete the tasks and secondly time taken to complete each task. Each task is scored out of 4, with the scores from the 3 tests summed to give a total of a maximum of 12 and a minimum of 0. A higher score indicates a higher level of function, while lower scores indicate a lower level of function. Lower scores on the SPPB have been shown to be predictive of an increased risk of falling, loss of independence in ADLs, decreased mobility, disability, decline in health, rehospitalization; and increased hospital length of stay, nursing home admission, and death. A change of 0.5 points on the SPPB is considered to be a small meaningful change, while a change of 1 point on the SPPB is considered to be a substantial meaningful change.

The repeated chair stand test involves activation of multiple muscles of the lower limb, most notably the knee extensor (quadriceps femoris) muscles. The repeated chair stand test has been used as a standalone assessment (e.g., the STS maneuver) that is used extensively as a measure of lower limb strength.

The SPPB score of a subject having or being prone to a bone mineralization disorder, such as HPP, can be used to assess treatment efficacy using an alkaline phosphatase, or a polypeptide having alkaline phosphatase activity, such as a sALP (e.g., a polypeptide having the sequence of SEQ ID NO: 1 or a variant thereof with at least 85% sequence identity thereto), in which improvements relative to a certain test score demonstrate that the alkaline phosphatase, or the polypeptide having alkaline phosphatase activity, is effective for treating, e.g., disability in activities of daily living (ADL) and pain associated with the bone mineralization disorder, such as HPP. In particular, a subject having or being prone to a bone mineralization disorder, such as HPP, could be tested with SPPB and to assess treatment efficacy of sALP administration.

For example, when administration of a sALP described herein to a subject having or being prone to a bone mineralization disorder, such as HPP, results in an average increase in the SPPB score to about 6 or greater than about 8, in which the subject previously had an average SPPB score of less than about 8, then the sALP is effective at treating the bone mineralization disorder, such as HPP. Alternatively, when administration of a sALP described herein does not result in an average increase in the SPPB score to about 6 or greater than about 8, the dosage and frequency of sALP administration can be changed in order to determine the effective amount of the sALP for the subject having or being prone to a bone mineralization disorder, such as HPP. For instance, the dosage of the sALP (e.g., a polypeptide having the sequence of SEQ ID NO: 1 or a variant thereof with at least 85% sequence identity thereto) can be increased from, e.g., from about 0.5-3 mg/kg/week to about 3-6 mg/kg/week or from about 3-6 mg/kg/week to about 6-9 mg/kg/wk. If the SBBP increases to above a predetermined threshold, then the subject may stop treatment and be monitored periodically for changes in their SBBP score. If the SBBP score decreases below the predetermined threshold, then the therapy may be restarted.

Timed Up-and-go (TUG) Test

The timed "Up-and-Go" (TUG) test measures, in seconds, the time taken by an individual to stand up from a standard arm chair, walk a distance of 3 meters (approximately 10 feet), turn, walk back to the chair, and sit down. This test requires patients to wear their regular footwear and use their customary walking aid (none, cane, walker). No physical assistance is given. Patients begin the test with their back against the chair, their arms resting on the armrests, and their waking aid in hand. They are instructed that, on the word "go" they are to get up and walk at a comfortable and safe pace to a line on the floor 3 m away, turn, return to the chair, and sit down again. The patient walks through the test once before being timed in order to become familiar with the test. Either a stopwatch or a wristwatch with a second hand can be used to time the test. Normal healthy elderly persons usually complete the task in 10 seconds or less. Very frail or weak elderly persons with poor mobility may take 2 minutes or more. A score of 214 seconds may indicate high risk of falls. The TUG test may be administered by a blinded rater.

The TUG score of a subject having or being prone to a bone mineralization disorder, such as HPP, can be used to assess treatment efficacy using an alkaline phosphatase, or a polypeptide having alkaline phosphatase activity, such as a sALP (e.g., a polypeptide having the sequence of SEQ ID NO: 1 or a variant thereof with at least 85% sequence identity thereto), in which improvements relative to a certain test score demonstrate that the alkaline phosphatase, or the polypeptide having alkaline phosphatase activity, is effective for treating the bone mineralization disorder, such as HPP. In particular, a subject having or being prone to a bone mineralization disorder, such as HPP, could be administered a TUG test to assess treatment efficacy of sALP administration.

For example, when administration of a sALP described herein to a subject having or being prone to a bone mineralization disorder, such as HPP, results in an average decrease in the TUG score to about 14 or less than about 14, in which the subject previously had an average TUG score of greater than about 14, then the sALP is effective at treating, e.g., disability in activities of daily living (ADL) and pain associated with a bone mineralization disorder, such as HPP. Alternatively, when administration of a sALP described herein does not result in an average decrease in the TUG score to about 14 or less than about 14, the dosage and frequency of sALP administration can be changed in order to determine the effective amount of the sALP for the subject having or being prone to a bone mineralization disorder, such as HPP. For instance, the dosage of the sALP (e.g., a polypeptide having the sequence of SEQ ID NO: 1 or a variant thereof with at least 85% sequence identity thereto) can be increased from, e.g., from about 0.5-3 mg/kg/week to about 3-6 mg/kg/week or from about 3-6 mg/kg/week to about 6-9 mg/kg/wk. If the subject's TUG test decreases below a predetermined threshold, then the subject may stop treatment and be monitored periodically for changes in the TUG test score. If the TUG score increases above the predetermined threshold, then the treatment may be restarted.

Bruininks-Oseretsky Test of Motor Proficiency $2^{nd}$ Edition (BOT-2)

An exemplary Bruininks-Oseretsky Test of Motor Proficiency $2^{nd}$ Edition (BOT-2) is described in Bruininks, R. H. (2005). *Bruininks-Oseretsky Test of Motor Proficiency*, (BOT-2), Minneapolis, MN: Pearson Assessment, hereby incorporated by reference in Ks entirety. In particular, the BOT-2 can be used to evaluate physical Impairments and mobility restrictions in a subject having or being prone to a bone mineralization disorder (e.g., HPP) to generate a BOT-2 score for the subject.

The BOT-2 includes a range of tests to evaluate physical Impairments of a subject, which can be performed with, e.g., a kit including the tests. The BOT-2 provides composite BOT-2 scores in the following areas: strength, running speed and agility, fine motor precision, fine motor integration, manual dexterity, bilateral coordination, balance, and upper-limb coordination. For example, a subject having or being prone to a bone mineralization disorder, such as HPP, can perform sit-ups, v-ups, standing long jump, wall sit, and/or push-ups to determine the BOT-2 strength score. A subject having or being prone to a bone mineralization disorder, such as HPP, can step over a balance beam and/or perform a shuttle run, two-legged side hop, and/or one-legged side hop to determine the BOT-2 running speed and agility score. A subject having or being prone to a bone mineralization disorder, such as HPP, can cut out a circle and/or connect dots to determine the BOT-2 fine motor precision score. A subject having or being prone to a bone mineralization disorder, such as HPP, can copy a star and/or copy a square to determine the BOT-2 fine motor integration score. A subject having or being prone to a bone mineralization disorder, such as HPP, can transfer pennies, sort cards, and/or string blocks to determine the manual dexterity score. A subject having or being prone to a bone mineralization disorder, such as HPP, can tap his or her foot and finger and/or perform jumping jacks to determine the BOT-2 bilateral coordination score. A subject having or being prone to a bone mineralization disorder, such as HPP, can walk forward on a line and/or stand on one leg on a balance beam to determine the BOT-2 balance score. A subject having or being prone to a bone mineralization disorder, such as HPP, can throw a ball at a target and/or catch a tossed ball to determine the BOT-2 upper-limb coordination score.

A subject having or being prone to a bone mineralization disorder, such as HPP, could perform tests in one or more of described areas (strength, running speed and agility, fine motor precision, fine motor integration, manual dexterity, bilateral coordination, balance, and upper-limb coordination) to generate a BOT-2 score indicative of physical impairments in the subject. Within each BOT-2 area (strength, running speed and agility, fine motor precision, fine motor integration, manual dexterity, bilateral coordination, balance, and upper-limb coordination), such subject could perform one or more tests to determine the BOT-2 score of the subject, e.g., the subject could perform one or more of sit-ups, v-ups, standing long jump, wall sit, and push-ups to determine the BOT-2 strength score. Thus, only one test (e.g., one test selected from the group of sit-ups, v-ups, standing long jump, wall sit, and push-ups) can be performed to determine the BOT-2 score (e.g., a BOT-2 strength score) of a subject having or being prone to a bone mineralization disorder, such as HPP, (e.g., an HPP-like disease).

Each of the BOT-2 scores (strength, running speed and agility, fine motor precision, fine motor integration, manual dexterity, bilateral coordination, balance, and upper-limb coordination) of the subject having or being prone to a bone mineralization disorder, such as HPP, can be compared to the BOT-2 score of a subject without the bone mineralization disorder, such as HPP, to, e.g., determine a baseline comparison of the BOT-2 score. Each of the BOT-2 scores (e.g., strength, running speed and agility, fine motor precision, fine motor integration, manual dexterity, bilateral coordination, balance, and upper-limb coordination) of the subject having or being prone to a bone mineralization disorder, such as HPP, can be compared to the BOT-2 score of other subjects having or being prone to the bone mineralization disorder, such as HPP, to, e.g., provide a relative BOT-2 score for the subject.

BOT-2 scores (e.g., strength, running speed and agility, fine motor precision, fine motor integration, manual dexterity, bilateral coordination, balance, and upper-limb coordination scores) range from about 0 to equal to or less than about 25, in which a score of about 10 to about 20 is considered representative of healthy subject (e.g., subject without the bone mineralization disorder, such as HPP). A subject with an average BOT-2 score (e.g., strength, running speed and agility, fine motor precision, fine motor integration, manual dexterity, bilateral coordination, balance, and upper-limb coordination scores) of less than about 10 can be treated with an alkaline phosphatase, or a polypeptide having alkaline phosphatase activity, e.g., sALP, e.g., a polypeptide having the sequence of SEQ ID NO: 1 or a variant thereof with at least 85% sequence identity thereto.

For example, a subject having or being prone to a bone mineralization disorder, such as HPP, with a BOT-2 strength score of less than 10 (e.g., about 0, about 1, about 2, about 3, about 4, about 5, about 8, about 7, about 8, about 9, or about 10) can be treated with a sALP (e.g., a polypeptide having the sequence of SEQ ID NO: 1 or a variant thereof with at least 85% sequence identify thereto) for a period of time, up to the lifetime of the subject. Likewise, a subject having or being prone to a bone mineralization disorder, such as HPP, with a BOT-2 running speed and agility score of less than 10 (e.g., about 0, about 1, about 2, about 3, about 4, about 5, about 8, about 7, about 8, about 9, or about 10) can then be treated with a sALP (e.g., a polypeptide having the sequence of SEQ ID NO: 1 or a variant thereof with at least 85% sequence identity thereto) for a period of time, up to the lifetime of the subject.

The methods can result in an improvement in the BOT-2 score (e.g., strength, running speed and agility, fine motor precision, fine motor integration, manual dexterity, bilateral coordination, balance, and/or upper-limb coordination score) of a subject having or being prone to a bone mineralization disorder, such as HPP. For example, treatment with an alkaline phosphatase, or a polypeptide having alkaline phosphatase activity, such as a sALP (e.g., a polypeptide having the sequence of SEQ ID NO: 1 or a variant thereof with at least 85% sequence identify thereto), such as treatment with a sALP for a period of time, can result in an average increase in the BOT-2 strength score to about 10 to about 20 (e.g., about 10, about 11, about 12, about 13, about 14, about 15, about 16, about 17, about 18, about 19, or about 20). Additionally, treatment with a sALP (e.g., a polypeptide having the sequence of SEQ ID NO: 1 or a variant thereof with at least 85% sequence identity thereto) can result in an average increase in the BOT-2 running speed and agility score to about 5 to about 20 (e.g., about 5, about 8, about 7, about 8, about 9, about 10, about 11, about 12, about 13, about 14, about 15, about 16, about 17, about 18, about 19, or about 20).

The increase in the BOT-2 score (e.g., strength, running speed and agility, fine motor precision, fine motor integration, manual dexterity, bilateral coordination, balance, and/or upper-limb coordination score) can be sustained throughout administration of the alkaline phosphatase, or the polypeptide having alkaline phosphatase activity, such as sALP (e.g., a polypeptide having the sequence of SEQ ID NO: 1 or a variant thereof with at least 85% sequence identity thereto), e.g., for a period of time. Likewise, the decrease in physical Impairments of muscles after administration of the alkaline phosphatase, or the polypeptide having alkaline phosphatase activity, can be sustained throughout administration of the alkaline phosphatase, or the polypeptide having alkaline phosphatase activity.

The BOT-2 scores (strength, running speed and agility, fine motor precision, fine motor integration, manual dexterity, bilateral coordination, balance, and upper-limb coordination scores) of a subject having or being prone to a bone mineralization disorder, such as HPP, can be used singly or in combination with other metrics for assessing treatment efficacy using an alkaline phosphatase, or a polypeptide having alkaline phosphatase activity, such as sALP (e.g., a polypeptide having the sequence of SEQ ID NO: 1 or a variant thereof with at least 85% sequence identity thereto), in which improvements relative to a certain test score demonstrate that the alkaline phosphatase, or the polypeptide having alkaline phosphatase activity, is effective for treating muscle impairments associated with the bone mineralization disorder, such as HPP. For example, when administration of a sALP described herein to a subject having or being prone to a bone mineralization disorder, such as HPP, results in an average increase in the BOT-2 running speed and agility score to about 5 or greater than about 5, in which the subject previously had an average BOT-2 running speed and agility score of less than about 5, then the sALP is considered to be effective at, e.g., treating physical impairments associated with a bone mineralization disorder, such as HPP.

Additionally, within each BOT-2 area (strength, running speed and agility, fine motor precision, fine motor integration, manual dexterity, bilateral coordination, balance, and upper-limb coordination), a subject having or being prone to a bone mineralization disorder, such as HPP, could perform one or more tests to determine the BOT-2 score of the subject.

Alternatively, when administration of an alkaline phosphatase, or a polypeptide having alkaline phosphatase activity, such as a sALP described herein, does not result in an average increase in the BOT-2 running speed and agility score to greater than about 5, the dosage and/or frequency of administration can be changed in order to determine the effective amount of the alkaline phosphatase, or the polypeptide having alkaline phosphatase activity, for the subject having or being prone to the bone mineralization disorder, such as HPP. For instance, the dosage of the sALP (e.g., a polypeptide having the sequence of SEQ ID NO: 1 or a variant thereof with at least 85% sequence identity thereto) can be increased from, e.g., from about 0.5-3 mg/kg/week to about 3-6 mg/kg/week or from about 3-6 mg/kg/week to about 6-9 mg/kg/wk. If the subject's BOT-2 score increases above a predetermined threshold, then the subject may stop treatment and be monitored periodically for changes in their BOT-2 score. If the BOT-2 score decreases below the predetermined threshold, then the therapy may be restarted.

36-Item Short-Form (SF-36)

Health-related quality of life refers to functioning and well-being in physical, mental, and social dimensions of lfe. The SF-36 is composed of 8 multi-item scales (35 items) assessing physical function (10 items), role limitations due to physical health problems (4 items), bodily pain (2 items), general health (5 items), vitality (4 items), social functioning (2 items), role imitations due to emotional problems (3 items), and emotional well-being (5 items). These 8 scales can be aggregated into 2 summary measures: the PCS and Mental Component Summary (MCS) scores. The 38th Item, which asks about health change, is not included in the scale or summary scores.

The SF-36 is a self-administered questionnaire. Patients complete 1 response from a range of options for each of the 38 questions. A combination of item response(s) is then aggregated to calculate a score for each of the 8 scales listed. The scores for each dimension range from 0 to 100, with higher scores indicating better health status. Body pain is also scored in this way, with higher scores indicating less pain. The 2 summary measures (PCS and MCS) are scored differently from the 8 dimension scores. These scales are scored using norm-based methods. A score of 50 reflects an average score with respect to these populations. Scores lower than 50 reflect less than average health and scores greater than 50 reflect better than average health.

The SF-36 score of a subject having or being prone to a bone mineralization disorder, such as HPP, can be used to assess treatment efficacy using an alkaline phosphatase, or a polypeptide having alkaline phosphatase activity, such as a sALP (e.g., a polypeptide having the sequence of SEQ ID NO: 1 or a variant thereof with at least 85% sequence identity thereto), in which improvements relative to a certain test score demonstrate that the alkaline phosphatase, or the polypeptide having alkaline phosphatase activity, is effective for treating, e.g., disability in activities of daily living (ADL) and pain associated with the bone mineralization disorder, such as HPP. In particular, a subject having or being prone to a bone mineralization disorder, such as HPP, could be asked one or more questions in one or more of the eight scales to arrive at an average SF-36 score and to assess treatment efficacy of sALP administration.

For example, when administration of a sALP described herein to a subject having or being prone to a bone mineralization disorder, such as HPP, results in an average increase in the SF-36 score to about 50 or greater than about 50, in which the subject previously had an average SF-36 score of less than about 50, then the sALP is effective at treating, e.g., disability in activities of daily living (ADL) and pain associated with a bone mineralization disorder, such as HPP. Alternatively, when administration of a sALP described herein does not result in an average increase in the SF-36 score to about 50 or greater than about 50, the dosage and frequency of sALP administration can be changed in order to determine the effective amount of the sALP for the subject having or being prone to a bone mineralization disorder, such as HPP. For instance, the dosage of the sALP (e.g., a polypeptide having the sequence of SEQ ID NO: 1 or a variant thereof with at least 85% sequence identity thereto) can be increased from, e.g., from about 0.5-3 mg/kg/week to about 3-6 mg/kg/week or from about 3-6 mg/kg/week to about 6-9 mg/kg/wk. If the subject's SF-36 score increases above a predetermined threshold, then the subject may stop treatment and be monitored periodically for changes in their SF-36 score. If the SF-36 score decreases below the predetermined threshold, then the therapy may be restarted.

Lower Extremity Function Scale (LEFS)

LEFS refers to a method to measure the functional disability in the lower extremities of patients, in particular, patients with HPP (e.g., patients of about 13 years of age or older). The LEFS is a self-reported measure described in Binkley et al. (*Phys Ther.* 79:371-83, 1999), hereby incorporated by reference in its entirety. Total LEFS scores range from 0 to 80 with higher scores indicative of better lower extremity functioning. A LEFS score change of about 9 points is considered a clinically meaningful change. A licensed physical therapist can administer the LEFS to HPP patients (e.g., HPP patients of about 13 years of age or older) in interview format. Higher LEFS scores are indicative of improved lower extremity functioning including transitional movements (e.g., getting out of bath or rolling in bed), locomotion (e.g., walking or running on uneven ground), climbing stairs, and squatting. The LEFS can be used to evaluate the functional impairment of one or both lower extremities of an HPP patient, including the ability to monitor the patient over time and evaluate the effectiveness of asfotase alfa treatment.

The increase in the LEFS score of the subject having a bone mineralization disorder, such as HPP, can be sustained throughout administration of the alkaline phosphatase or a polypeptide having alkaline phosphatase activity (e.g., a sALP, e.g., a polypeptide having the sequence of SEQ ID NO: 1 or a variant thereof with at least 85% sequence identity thereto), e.g., for a treatment period of at least two weeks (e.g., at least three weeks, at least four weeks, at least five weeks, at least six weeks, at least seven weeks, at least eight weeks, at least nine weeks, at least ten weeks, at least three months, at least four months, at least five months, at least six months, at least seven months, at least eight months, at least nine months, at least one year, at least two years, at least three years, at least four years, at least five years, at least six years, at least seven years, at least eight years, at least nine years, or at least ten years, or the lifetime of the subject; particularly at least six weeks). For instance, the LEFS score increases by at least 9 points and remains at ±10% of the LEFS score during treatment with the alkaline phosphatase or a polypeptide having alkaline phosphatase activity.

Alternatively, when administration of an alkaline phosphatase or a polypeptide having alkaline phosphatase activity (e.g., a sALP, e.g., a polypeptide having the sequence of SEQ ID NO: 1 or a variant thereof with at least 85% sequence identity thereto) does not result in an average increase in the LEFS score by at least 9 points, the dosage and/or frequency of alkaline phosphatase or a polypeptide having alkaline phosphatase activity administration can be changed in order to determine the effective amount of the alkaline phosphatase or a polypeptide having alkaline phosphatase activity for the subject having a bone mineralization disorder, such as HPP. For instance, the dosage of the alkaline phosphatase or a polypeptide having alkaline phosphatase activity can be increased from, e.g., from about 0.1-3 mg/kg/week or about 3-6 mg/kg/week to about 3-6 mg/kg/week or about 6-9 mg/kg/week. If the subject's LEFS score increases above a predetermined threshold, then the subject may stop treatment and be monitored periodically for changes in their LEFS score. If the LEFS score decreases below the predetermined threshold, then the therapy may be restarted.

Childhood Health Assessment Questionnaire (CHAQ)

The Childhood Health Assessment Questionnaire (CHAQ) can be administered to evaluate the health status of children having a bone mineralization disorder, such as HPP, to generate a CHAQ index score for the child, as is described in Bruce & Fries (*J. Rheumatol.* 30(1): 167-178, 2003) and Klepper (*Arthritis & Rheumatism,* 49: S5-S14, 2003), hereby incorporated by reference in their entirety. The CHAQ includes eight categories of questions for dressing/grooming, arising, eating, walking, hygiene, reach, grip, and activities, in which a parent or guardian records the amount of difficulty the child with the bone mineralization disorder, such as HPP, has in performing the respective activities. The range of scores within each category is from 0 to 3, in which a score of 0 indicates without any difficulty; a score of 1 indicates with some difficulty; a score of 2 indicates with much difficulty; and a score of 3 indicates that the child is unable to perform the activity.

Children having or being prone to a bone mineralization disorder, such as HPP, with an average CHAQ index score (e.g., indicative of disability in activities of daily living (ADL) and/or pain) greater than about 0.8 (e.g., about 0.8, about 1, about 1.2, about 1.4, about 1.6, about 1.8, about 2.0, about 2.2, about 2.4, about 2.6, about 2.8, or about 3.0) can be treated by administering an alkaline phosphatase, or a polypeptide having alkaline phosphatase activity, such as sALP (e.g., a polypeptide having the sequence of SEQ ID NO: 1 or a variant thereof with at least 85% sequence identity thereto). For example, children with an average CHAQ index score of greater than about 0.8 can be treated by administering an alkaline phosphatase, or a polypeptide having alkaline phosphatase activity, such as sALP (e.g., a polypeptide having the sequence of SEQ ID NO: 1 or a variant thereof with at least 85% sequence identity thereto)

for a period of time, up to the lifetime of the subject. Furthermore, a child having or being prone to a bone mineralization disorder, such as HPP, disclosed herein could be asked one or more questions in one or more of the eight categories (dressing/grooming, arising, eating, waking, hygiene, reach, grip, and activities) to arrive at an average CHAQ index score, and if the average CHAQ index score is greater than about 0.8, the child can be treated by administering an alkaline phosphatase, or a polypeptide having alkaline phosphatase activity, such as a sALP.

The CHAQ index score of a child having or being prone to a bone mineralization disorder, such as HPP, disclosed herein can be compared to the CHAQ index score of children without such bone mineralization disorder, such as HPP, to, e.g., determine the standard deviation of the CHAQ index score. Additionally, the CHAQ index score of a child having or being prone to a bone mineralization disorder, such as HPP, disclosed herein can be compared to the CHAQ index score of other children having or being prone to the bone mineralization disorder, such as HPP, disclosed herein to, e.g., determine the standard deviation of the CHAQ index score.

The methods can result in an improvement in the CHAQ index score (e.g., indicative of disability in ADL and/or pain) of the child having or being prone to a bone mineralization disorder, such as HPP, disclosed herein. For example, treatment with a sALP (e.g., a polypeptide having the sequence of SEQ ID NO: 1 or a variant thereof with at least 85% sequence identity thereto), such as treatment with a sALP for a period of time, up to the lifetime of the child, can result in an average decrease in the CHAQ index score to about 0 to equal to or less than about 0.5 (e.g., about 0, about 0.1, about 0.2, about 0.4, or about 0.5) in children with an HPP-like disease.

The decrease in the CHAQ index score of the child having or being prone to a bone mineralization disorder, such as HPP, can be sustained throughout administration of the alkaline phosphatase, or the polypeptide having alkaline phosphatase activity, such as sALP (e.g., a polypeptide having the sequence of SEQ ID NO: 1 or a variant thereof with at least 85% sequence identity thereto), e.g., for a period of time, up to the lifetime of the child. Likewise, the increase in ADL and/or decrease in pain of the child can be sustained throughout administration of the sALP (e.g., a polypeptide having the sequence of SEQ ID NO: 1 or a variant thereof with at least 85% sequence identity thereto), for a period of time, up to the lifetime of the child.

The CHAQ index score of a child having or being prone to a bone mineralization disorder, such as HPP, can be used to assess treatment efficacy using an alkaline phosphatase, or a polypeptide having alkaline phosphatase activity, such as sALP (e.g., a polypeptide having the sequence of SEQ ID NO: 1 or a variant thereof with at least 85% sequence identity thereto), in which improvements relative to a certain test score demonstrate that the alkaline phosphatase, or the polypeptide having alkaline phosphatase activity, is effective for treating, e.g., disability in activities of daily living (ADL) and pain associated with the bone mineralization disorder, such as HPP. In particular, a child having or being prone to a bone mineralization disorder, such as HPP, could be asked one or more questions in one or more of the eight categories (dressing/grooming, arising, eating, walking, hygiene, reach, grip, and activities) to arrive at an average CHAQ index score and to assess treatment efficacy of sALP administration. For example, when administration of a sALP described herein to a child having or being prone to a bone mineralization disorder, such as HPP, results in an average decrease in the CHAQ index score to equal to or less than about 0.5, in which the child previously had an average CHAQ index score of greater than about 0.8, then the sALP is effective at treating, e.g., disability in activities of daily living (ADL) and pain associated with a bone mineralization disorder, such as HPP. Alternatively, when administration of a sALP does not result in an average decrease in the CHAQ index score to equal to or less than about 0.5, the dosage and/or frequency of sALP administration can be changed in order to determine the effective amount of the sALP for the child having or being prone to a bone mineralization disorder, such as HPP. For instance, the dosage of the sALP (e.g., a polypeptide having the sequence of SEQ ID NO: 1 or a variant thereof with at least 85% sequence identity thereto) can be increased from, e.g., from about 0.5-3 mg/kg/week to about 3-6 mg/kg/week or from about 3-6 mg/kg/week to about 6-9 mg/kg/wk. If the CHAQ increases above a predetermined threshold, then the subject may stop treatment and be monitored periodically for changes in their CHAQ score. If the CHAQ score decreases below the predetermined threshold, then the therapy may be restarted.

Pediatric Outcomes Data Collection Instrument (PODCI)

Certain subjects having or being prone to a bone mineralization disorder, such as HPP, can be identified for treatment with an alkaline phosphatase, or a polypeptide having alkaline phosphatase activity, such as a sALP (e.g., a polypeptide having the sequence of SEQ ID NO: 1 or a variant thereof with at least 85% sequence identify thereto) using the Pediatric Outcomes Data Collection Instrument (PODCI). The PODCI can be administered to evaluate the heath status of children to generate a PODCI score for the subject, as is described in Pint et al. (*J. Pediatr. Orthop.* 23(8): 758-790, 2003). The PODCI includes eight categories of questions that can be completed by a subject having or being prone to a bone mineralization disorder, such as HPP, or by a parent/guardian of the subject. Categories that can be used to determine the PODCI of a subject having or being prone to a bone mineralization disorder, such as HPP, include the following: 1) the upper extremity and physical function scale to measure difficulty encountered in performing daily personal care and student activities; 2) the transfer and basic mobility scale to measure difficulty experienced in performing routine motion and motor activities in daily activities; 3) the sports/physical functioning scale to measure difficulty or limitations encountered in participating in more active activities or sports; 4) the pain/comfort scale to measure the level of pain experienced during the past week; 5) the treatment expectations scale to measure the long term expectations of treatment; 6) the happiness scale to measure overall satisfaction with personal looks and sense of similarity to friends and others of own age; 7) the satisfaction with symptoms scale to measure the subject's acceptance of current imitations should this be a life-long state; and 8) the global functioning scale, which is a general combined scale calculated from the first four scales listed above. In each of the categories, a standardized score is determined for the subject having or being prone to a bone mineralization disorder, such as HPP, and then converted to a 0 to 100 scale, in which 0 represents significant disability and 100 represents less disability.

A subject having or being prone to a bone mineralization disorder, such as HPP, with an average PODCI score (e.g., indicative of disability in ADL and/or pain) less than about 40 (e.g., about 5, about 10, about 15, about 20, about 25, about 30, about 35, or about 39) can be treated by administering an alkaline phosphatase, or a polypeptide having alkaline phosphatase activity, such as a sALP (e.g., a polypeptide having the sequence of SEQ ID NO: 1 or a variant thereof with at least 85% sequence identity thereto). For example, a subject with an average PODCI score of less than 40 can be treated by administering a sALP for a period of time, up to the lifetime of the subject. Furthermore, a subject having or being prone to a bone mineralization disorder, such as HPP, could be asked one or more questions in one or more of the eight scales described above (e.g., transfer and basic mobility, sports/physical functioning, and the pain/comfort scale) to arrive at an average PODCI score, and if the average PODCI score is greater than less than 40, the subject can be treated by administering a sALP.

The methods described herein can result in an increase in the PODCI score (e.g., indicative of disability in ADL and/or pain) of the subject having or being prone to a bone mineralization disorder, such as HPP. For example, treatment with an alkaline phosphatase, or a polypeptide having alkaline phosphatase activity, such as a sALP (e.g., a polypeptide having the sequence of SEQ ID NO: 1 or a variant thereof with at least 85% sequence identity thereto), such as treatment with a sALP for a period of time, up to the lifetime of the subject, can result in an average increase in the PODCI score to about 40 to about 50 (e.g., about 40, about 41, about 42, about 43, about 44, about 45, about 46, about 47, about 48, about 49, or about 50).

The increase in the PODCI score can be sustained throughout administration of the alkaline phosphatase, or the polypeptide having alkaline phosphatase activity, such as the sALP (e.g., a polypeptide having the sequence of SEQ ID NO: 1 or a variant thereof with at least 85% sequence identity thereto), e.g., for a period of time, up to the lifetime of the subject having or being prone to a bone mineralization disorder, such as HPP. Likewise, the increase in ADL and/or decrease in pain can be sustained throughout administration of the sALP (e.g., a polypeptide having the sequence of SEQ ID NO: 1 or a variant thereof with at least 85% sequence identity thereto), for a period of time, up to the lifetime of the subject.

The PODCI score of a subject having or being prone to a bone mineralization disorder, such as HPP, can be used to assess treatment efficacy using an alkaline phosphatase, or a polypeptide having alkaline phosphatase activity, such as a sALP (e.g., a polypeptide having the sequence of SEQ ID NO: 1 or a variant thereof with at least 85% sequence identity thereto), in which improvements relative to a certain test score demonstrate that the alkaline phosphatase, or the polypeptide having alkaline phosphatase activity, is effective for treating, e.g., disability in activities of daily living (ADL) and pain associated with the bone mineralization disorder, such as HPP. In particular, a subject having or being prone to a bone mineralization disorder, such as HPP, could be asked one or more questions in one or more of the eight scales (the upper extremity and physical function scale, the transfer and basic mobility scale, the sports/physical functioning scale, the pain/comfort scale, the treatment expectations scale, the happiness scale, the satisfaction with symptoms scale, and the global functioning scale) to arrive at an average PODCI score and to assess treatment efficacy of sALP administration.

For example, when administration of a sALP described herein to a subject having or being prone to a bone mineralization disorder, such as HPP, results in an average increase in the PODCI score to about 40 or greater than about 40, in which the subject previously had an average PODCI score of less than about 40, then the sALP is effective at treating, e.g., disability in activities of daily living (ADL) and pain associated with a bone mineralization disorder, such as HPP. Alternatively, when administration of a sALP described herein does not result in an average increase in the PODCI score to about 40 or greater than about 40, the dosage and frequency of sALP administration can be changed in order to determine the effective amount of the sALP for the subject having or being prone to a bone mineralization disorder, such as HPP. For instance, the dosage of the sALP (e.g., a polypeptide having the sequence of SEQ ID NO: 1 or a variant thereof with at least 85% sequence identity thereto) can be increased from, e.g., from about 0.5-3 mg/kg/week to about 3-6 mg/kg/week or from about 3-6 mg/kg/week to about 6-9 mg/kg/wk.

If the subject's PODCI score increases above a predetermined threshold, then the subject may stop treatment and be monitored periodically for changes in their PODCI score. If the PODCI score decreases below the predetermined threshold, then the therapy may be restarted.

Bayley Scales of Infant and Toddler Development, $3^{rd}$ Edition (BSID-III)

Another endpoint, the Bayley Scales of Infant and Toddler Development, $3^{rd}$ Edition (BSID-III) can be administered to evaluate the health status of a subject having or being prone to a bone mineralization disorder, such as HPP, from birth to generate a BSID-III score for the subject, as is described in Bayley. (2006). *Bayley scales of infant and toddler development: administration manual*. San Antonio, TX: Harcourt Assessment. The BSID-III includes a series of developmental play tasks that can be administered to the subject to determine the raw BSID-III score. For example, categories for determining the BSID-III score of a subject having or being prone to a bone mineralization disorder, such as HPP, (e.g., infants of about three years of age or less with HPP) can include prehension, perceptual-motor integration, motor planning and speed, visual tracking, reaching, object grasping, object manipulation, functional hand skills, responses to tactile information, movement of the limbs and torso, static positioning, dynamic movement, balance, and motor planning. The BSID-III measurements are then converted to scaled BSID-III scores, which can be used to determine the subject's performance compared to healthy, age-adjusted subjects. The BSID-III scaled score of a subject having or being prone to a bone mineralization disorder, such as HPP, (e.g., a subject with HPP) can range from 0 to 14, in which scores of about 7 to about 13 are considered the normal range for a heathy subject.

A subject having or being prone to a bone mineralization disorder, such as HPP, could perform tests in one or more of described categories (prehension, perceptual-motor integration, motor planning and speed, visual tracking, reaching, object grasping, object manipulation, functional hand skills, responses to tactile information, movement of the limbs and torso, static positioning, dynamic movement, balance, and motor planning) as an infant (e.g., at about 3 years of age or less than 3 years of age) to generate a BSID-III score indicative of delayed motor development. A subject having or being prone to a bone mineralization disorder, such as HPP, with an average BSID-III score in one or more of the described categories (prehension, perceptual-motor integration, motor planning and speed, visual tracking, reaching, object grasping, object manipulation, functional hand skills, responses to tactile information, movement of the limbs and torso, static positioning, dynamic movement, balance, and motor planning) less than about 2 as an infant can be treated by administering a sALP (e.g., a polypeptide having the sequence of SEQ ID NO: 1 or a variant thereof with at least 85% sequence identity thereto). In particular, a subject having or being prone to a bone mineralization disorder, such as HPP, with an average BSID-III score of less than about 2 as an infant can be treated by administering a sALP for a period of time, up to the lifetime of the subject.

The methods can result in an improvement in the average BSID-III score (e.g., indicative of delayed motor development) of the subject having or being prone to a bone mineralization disorder, such as HPP. For example, treatment with a sALP (e.g., a polypeptide having the sequence of SEQ ID NO: 1 or a variant thereof with at least 85% sequence identity thereto), such as treatment with a sALP for a period of time, up to the lifetime of the subject, can result in an average increase in the BSID-III score to greater than about 5 (e.g., about 5, about 8, about 7, about 8, about 9, about 10, about 11, about 12, or about 13).

The increase in the BSID-III score can be sustained throughout administration of the alkaline phosphatase, or the polypeptide having alkaline phosphatase activity, such as a sALP (e.g., a polypeptide having the sequence of SEQ ID NO: 1 or a variant thereof with at least 85% sequence identity thereto), for a period of time, up to the lifetime of the subject having or being prone to a bone mineralization disorder, such as HPP. Likewise, the increase in motor development can be sustained throughout administration of the alkaline phosphatase, or the polypeptide having alkaline phosphatase activity, such as a sALP (e.g., a polypeptide having the sequence of SEQ ID NO: 1 or a variant thereof with at least 85% sequence identity thereto), e.g., for a period of time, up to the lifetime of the subject.

The BSID-III score of a subject having or being prone to a bone mineralization disorder, such as HPP, can be used to assess treatment efficacy using an alkaline phosphatase, or a polypeptide having alkaline phosphatase activity, such as a sALP (e.g., a polypeptide having the sequence of SEQ ID NO: 1 or a variant thereof with at least 85% sequence identity thereto), in which improvements relative to a certain test score demonstrate that the alkaline phosphatase, or the polypeptide having alkaline phosphatase activity, is effective for treating, e.g., delayed motor development associated with the bone mineralization disorder, such as HPP. In particular, a subject having or being prone to a bone mineralization disorder, such as HPP, could perform tests in one or more of described categories (prehension, perceptual-motor integration, motor planning and speed, visual tracking, reaching, object grasping, object manipulation, functional hand skis, responses to tactile information, movement of the limbs and torso, static positioning, dynamic movement, balance, and motor planning) as an infant (e.g., at about three years of age or less with HPP) to arrive at an average BSID-III score and to assess treatment efficacy of sALP administration.

For example, when administration of a sALP to a child having or being prone to a bone mineralization disorder, such as HPP, results in an average increase in the BSID-III scaled score to greater than about 5, in which the child previously had an average BSID-III scaled score of less than about 2 as an infant (e.g., at about 3 years of age or less than 3 years of age), then the sALP is effective at treating, e.g., delayed motor development associated with an HPP-like disease. Alternatively, when administration of a sALP does not result in an average increase in the BSID-III scaled score to greater than about 5, the dosage and/or frequency of sALP administration can be changed in order to determine the effective amount of the sALP for the child having or being prone to a bone mineralization disorder, such as HPP. For instance, the dosage of the sALP (e.g., a polypeptide having the sequence of SEQ ID NO: 1 or a variant thereof with at least 85% sequence identity thereto) can be increased from, e.g., from about 0.5-3 mg/kg/week to about 3-6 mg/kg/week or from about 3-6 mg/kg/week to about 6-9 mg/kg/wk.

If the subject's BSID-III score increases above a predetermined threshold, then the subject may stop treatment and be monitored periodically for changes in their BSID-III score. If the BSID-III score decrease below the predetermined threshold, then the therapy may be restarted.

Peabody Developmental Motor Scales, 2nd Edition (PDMS-2)

Another endpoint, the Peabody Developmental Motor Scales, 2nd Edition (PDMS-2), can be administered to evaluate the health status of a subject having or being prone to a bone mineralization disorder, such as HPP, from birth to generate a PDMS-2 score for the subject, as is described in van Hartingsveldt et al. (*Occup. Ther. Int.* 12(1): 1-13, 2005). The PDMS-2 includes six categories of subtests to measure motor skis of the subject, such as a subject with HPP.

In particular, PDMS-2 measurements can be determined from the following subtests: 1) the locomotor subtest to measure a subject's ability to move from one place to another (measurements include crawling, waking, running, hopping, and jumping forward); 2) the reflexes subtest to measure a subject's ability to automatically react to environmental events; 3) the stationary subtest to measure a subject's ability to sustain body control within the center of gravity and retain equilibrium; 4) the object manipulation subtest to measure a subject's ability to manipulate an object, such as catching, throwing, and kicking a ball; 5) the grasping subtest to measure a subject's ability to use his or her hands, such as the ability to hold an object with one hand and actions involving the controlled use of the fingers of both hands; and 6) the visual-motor integration subtest to measure a subject's ability to use his or her visual perceptual skis to perform complex eye-hand coordination tasks, such as reaching and grasping for an object, building with blocks, and copying designs. The PDMS-2 measurement can be determined for one or more of these categories for a subject having or being prone to a bone mineralization disorder, such as HPP, and then converted into a PDMS-2 score, such as the PDMS-2 locomotor standard score ranging from 0 to 13, in which the range of healthy subjects (e.g., subjects without the bone mineralization disorder, such as HPP) is from about 7 to about 13.

A subject having or being prone to a bone mineralization disorder, such as HPP, with an average PDMS-score (e.g., indicative of delayed motor development) can be treated by administering a sALP (e.g., a polypeptide having the sequence of SEQ ID NO: 1 or a variant thereof with at least 85% sequence identity thereto).

The methods described herein can result in an improvement in the PDMS-2 score (e.g., indicative of delayed motor development) of the subject having or being prone to a bone mineralization disorder, such as HPP. For example, treatment with an alkaline phosphatase, or a polypeptide having alkaline phosphatase activity, such as a sALP (e.g., a polypeptide having the sequence of SEQ ID NO: 1 or a variant thereof with at least 85% sequence identity thereto), can result in an average increase in the PDMS-2 score to about 7 to about 13 (e.g., about 7, about 8, about 9, about 10, about 11, about 12, or about 13).

The increase in the PDMS-2 score can be sustained throughout administration of the alkaline phosphatase, or the polypeptide having alkaline phosphatase activity, such as sALP (e.g., a polypeptide having the sequence of SEQ ID NO: 1 or a variant thereof with at least 85% sequence identity thereto), for an elongated time, e.g., for a period of time, up to the lifetime of the subject having or being prone to a bone mineralization disorder, such as HPP. Likewise, the increase in motor development can be sustained throughout administration of the sALP (e.g., a polypeptide having the sequence of SEQ ID NO: 1 or a variant thereof with at least 85% sequence identity thereto) for a period of time, up to the lifetime of the subject having or being prone to a bone mineralization disorder, such as HPP.

The PDMS-2 score of a subject having or being prone to a bone mineralization disorder, such as HPP, can be used to assess treatment efficacy using an alkaline phosphatase, or a polypeptide having alkaline phosphatase activity, such as a sALP (e.g., a polypeptide having the sequence of SEQ ID NO: 1 or a variant thereof with at least 85% sequence identity thereto), in which improvements relative to a certain test score demonstrate that the alkaline phosphatase, or the polypeptide having alkaline phosphatase activity, is effective for treating, e.g., delayed motor development associated with the bone mineralization disorder, such as HPP. For example, a child having or being prone to a bone mineralization disorder, such as HPP, could perform tests in one or more of described categories (locomotor, reflexes, stationary, object manipulation, grasping, and visual-motor) at about 5 years of age or less than 5 years of age to arrive at an average PDMS-2 score and to assess treatment efficacy of sALP administration.

For example, when administration of a sALP to a child having or being prone to a bone mineralization disorder, such as HPP, results in an average increase in the PDMS-2 standard score to about 7, in which the child previously had an average PDMS-2 standard score of about 5, then the sALP is effective at treating, e.g., delayed motor development associated with an HPP-like disease. Alternatively, when administration of a sALP does not result in an average increase in the PDMS-2 standard score to about 7, the dosage and/or frequency of sALP administration can be changed in order to determine the effective amount of the sALP for the child. For instance, the dosage of the sALP (e.g., a polypeptide having the sequence of SEQ ID NO: 1 or a variant thereof with at least 85% sequence identity thereto) can be increased from, e.g., from about 0.5-3 mg/kg/week to about 3-6 mg/kg/week or from about 3-6 mg/kg/week to about 6-9 mg/kg/wk. If the subject's PDMS-2 score increases above a predetermined threshold, then the subject may stop treatment and be monitored periodically for changes in their PDMS-2 score. If the PDMS-2 score decreases below the predetermined threshold, then the therapy may be restarted.

Six Minute Walk Test (6MWT)

A subject having a bone mineralization disorder, such as HPP, can be identified for treatment with an alkaline phosphatase or a polypeptide having alkaline phosphatase activity (e.g., a sALP, e.g., a polypeptide having the sequence of SEQ ID NO: 1 or a variant thereof with at least 85% sequence identity thereto) using the 6MWT. In particular, the 6MWT can be used to evaluate walking ability in an adult having a bone mineralization disorder, such as HPP, to generate a 6MWT value for the adult. The 6MWT can be performed indoors or outdoors using a flat, straight, enclosed corridor (e.g., of about 30 meters in length) with a hard surface. A stopwatch or other timer can be used to track the time and a mechanical counter or other device can be used to determine the distance (e.g., in meters) that the subject having a bone mineralization disorder, such as HPP, walks. For instance, the length of the corridor can be marked every three meters to determine the number of meters walked by the subject having a bone mineralization disorder, such as HPP, with the turnaround point at 30 meters and the starting line also marked. The distance waked by the subject having a bone mineralization disorder, such as HPP, in six minutes can then be compared to the predicted number of meters walked, e.g., by a normal subject of about the same age, the same gender, and/or the same height, and expressed as a percentage value to generate the 6MWT value of the subject. The 6MWT value of the subject having a bone mineralization disorder, such as HPP, can be compared to the 6MWT value at baseline of the subject. Additionally, the 6MWT value of the subject having a bone mineralization disorder, such as HPP, can be compared to the 6MWT value of a normal subject.

A subject having a bone mineralization disorder, such as HPP, with an average 6MWT of less than about 80% of the predicted 6MWT value (e.g., relative to a normal subject of about the same age, the same gender, and/or the same height) can be treated with an alkaline phosphatase or a polypeptide having alkaline phosphatase activity (e.g., a sALP, e.g., a polypeptide having the sequence of SEQ ID NO: 1 or a variant thereof with at least 85% sequence identity thereto), such as by administering an alkaline phosphatase or a polypeptide having alkaline phosphatase activity for a treatment period of at least two weeks (e.g., at least three weeks, at least four weeks, at least five weeks, at least six weeks, at least seven weeks, at least eight weeks, at least nine weeks, at least ten weeks, at least three months, at least four months, at least five months, at least six months, at least seven months, at least eight months, at least nine months, at least one year, at least two years, at least three years, at least four years, at least five years, at least six years, at least seven years, at least eight years, at least nine years, or at least ten years, or the lifetime of the subject; particularly at least six weeks). For example, a subject having a bone mineralization disorder, such as HPP, with an average 6MWT of less than about 80% of the predicted 6MWT value (e.g., about 50%, about 55%, about 60%, about 65%, about 70%, or about 75% of the predicted 6MWT value) can be treated with an alkaline phosphatase or a polypeptide having alkaline phosphatase activity for a treatment period of at least two weeks (e.g., at least three weeks, at least four weeks, at least five weeks, at least six weeks, at least seven weeks, at least eight weeks, at least nine weeks, at least ten weeks, at least three months, at least four months, at least five months, at least six months, at least seven months, at least eight months, at least nine months, at least one year, at least two years, at least three years, at least four years, at least five years, at least six years, at least seven years, at least eight years, at least nine years, or at least ten years, or the lifetime of the subject; particularly at least six weeks).

The methods can result in an improvement in the 6MWT value of a subject having a bone mineralization disorder, such as HPP. For example, treatment with an alkaline phosphatase or a polypeptide having alkaline phosphatase activity (e.g., a sALP, e.g., a polypeptide having the sequence of SEQ ID NO: 1 or a variant thereof with at least 85% sequence identity thereto), such as treatment with an alkaline phosphatase or a polypeptide having alkaline phosphatase activity for a treatment period of at least two weeks (e.g., at least three weeks, at least four weeks, at least five weeks, at least six weeks, at least seven weeks, at least eight weeks, at least nine weeks, at least ten weeks, at least three months, at least four months, at least five months, at least six months, at least seven months, at least eight months, at least nine months, at least one year, at least two years, at least three years, at least four years, at least five years, at least six years, at least seven years, at least eight years, at least nine years, or at least ten years, or the lifetime of the subject; particularly at least six weeks), can result in an average increase in the 6MWT value to about 80% or greater of the predicted 6MWT value of the subject (e.g., about 82%, about 84%, about 86%, about 88%, about 90%, about 92%, about 94%, about 96%, about 98%, or more of the predictive 6MWT value).

The increase in the 6MWT value of the subject having a bone mineralization disorder, such as HPP, can be sustained throughout administration of the alkaline phosphatase or a polypeptide having alkaline phosphatase activity (e.g., a sALP, e.g., a polypeptide having the sequence of SEQ ID NO: 1 or a variant thereof with at least 85% sequence identity thereto), e.g., for a treatment period of at least two weeks (e.g., at least three weeks, at least four weeks, at least five weeks, at least six weeks, at least seven weeks, at least eight weeks, at least nine weeks, at least ten weeks, at least three months, at least four months, at least five months, at least six months, at least seven months, at least eight months, at least nine months, at least one year, at least two years, at least three years, at least four years, at least five years, at least six years, at least seven years, at least eight years, at least nine years, or at least ten years, or the lifetime of the subject; particularly at least six weeks). For instance, the 6MWT value increases to greater than about 80% of the predicted 6MWT value of the subject having a bone mineralization disorder, such as HPP, and remains at ±10% of the increased 6MWT value during treatment with the alkaline phosphatase or a polypeptide having alkaline phosphatase activity.

Likewise, the Improvement in waking ability of the subject having a bone mineralization disorder, such as HPP, can be sustained throughout administration of the alkaline phosphatase or a polypeptide having alkaline phosphatase activity, e.g., for a treatment period of at least two weeks (e.g., at least three weeks, at least four weeks, at least five weeks, at least six weeks, at least seven weeks, at least eight weeks, at least nine weeks, at least ten weeks, at least three months, at least four months, at least five months, at least six months, at least seven months, at least eight months, at least nine months, at least one year, at least two years, at least three years, at least four years, at least five years, at least six years, at least seven years, at least eight years, at least nine years, or at least ten years, or the lifetime of the subject; particularly at least six weeks). For instance, the subject having a bone mineralization disorder, such as HPP, exhibits decreased reliance on an assistive mobility device, such as a walker, a wheelchair, braces, crutches, or orthotics, during treatment with the sALP.

Alternatively, when administration of an alkaline phosphatase or a polypeptide having alkaline phosphatase activity (e.g., a sALP, e.g., a polypeptide having the sequence of SEQ ID NO: 1 or a variant thereof with at least 85% sequence identity thereto) does not result in an average increase in the 6MWT value to greater than 80% of the predicted 6MWT value (e.g., of a normal subject of about the same age, same gender, and/or height), the dosage and/or frequency of alkaline phosphatase or a polypeptide having alkaline phosphatase activity administration can be changed in order to determine the effective amount of the alkaline phosphatase or a polypeptide having alkaline phosphatase activity for the subject having a bone mineralization disorder, such as HPP. For instance, the dosage of the alkaline phosphatase or a polypeptide having alkaline phosphatase activity can be increased from, e.g., from about 0.1-3 mg/kg/week or about 3-6 mg/kg/week to about 3-6 mg/kg/week or about 6-9 mg/kg/week. If the subject's 6MWT score increases above a predetermined threshold, then the subject may stop treatment and be monitored periodically for changes in their 6MWT score. If the 6MWT score decreases below the predetermined threshold, then the therapy may be restarted.

Handheld Dynamometry (HHD)

The grip and muscle strength of a subject having or being prone to a bone mineralization disorder, such as HPP, can be assessed using Hand Held Dynamometry (HHD). For example, knee flexion and extension and also hip flexion, extension, and abduction of a subject having or being prone to a bone mineralization disorder, such as HPP, can be measured using, e.g., a MICROFET2™ Dynamometer, while grip strength of the subject can be measured using, e.g., a Jamar Grip Dynamometer. In particular, the administrator holds the dynamometer stationary, and the subject exerts a maximal force against the dynamometer. Peak force data is collected in pounds, then converted to Newtons (N). Torque values are then calculated using limb length in N-meters. The torque value can then be compared to the torque value of, e.g., a normal subject of about the same age, the same gender, and/or the same height, and expressed as a percentage value to generate the HHD value of the subject.

A subject having a bone mineralization disorder, such as HPP, with an average HHD value of less than about 80% of the predicted HHD value (e.g., relative to a normal subject of about the same age, the same gender, and/or the same height) can be treated with an alkaline phosphatase or a polypeptide having alkaline phosphatase activity (e.g., a sALP, e.g., a polypeptide having the sequence of SEQ ID NO: 1 or a variant thereof with at least 85% sequence identity thereto), such as by administering an alkaline phosphatase or a polypeptide having alkaline phosphatase activity for a treatment period of at least two weeks (e.g., at least three weeks, at least four weeks, at least five weeks, at least six weeks, at least seven weeks, at least eight weeks, at least nine weeks, at least ten weeks, at least three months, at least four months, at least five months, at least six months, at least seven months, at least eight months, at least nine months, at least one year, at least two years, at least three years, at least four years, at least five years, at least six years, at least seven years, at least eight years, at least nine years, or at least ten years, or the lifetime of the subject; particularly at least six weeks). For example, a subject having a bone mineralization disorder, such as HPP, with an average HHD of less than about 80% of the predicted HHD value (e.g., about 30%, about 35%, about 40%, about 45%, about 50%, about 55%, about 60%, about 65%, about 70%, or about 75% of the predicted HHD value) can be treated with an alkaline phosphatase or a polypeptide having alkaline phosphatase activity for a treatment period of at least two weeks (e.g., at least three weeks, at least four weeks, at least five weeks, at least six weeks, at least seven weeks, at least eight weeks, at least nine weeks, at least ten weeks, at least three months, at least four months, at least five months, at least six months, at least seven months, at least eight months, at least nine months, at least one year, at least two years, at least three years, at least four years, at least five years, at least six years, at least seven years, at least eight years, at least nine years, or at least ten years, or the lifetime of the subject; particularly at least six weeks).

The methods can result in an improvement in the HHD value of a subject having a bone mineralization disorder, such as HPP. For example, treatment with an alkaline phosphatase or a polypeptide having alkaline phosphatase activity (e.g., a sALP, e.g., a polypeptide having the sequence of SEQ ID NO: 1 or a variant thereof with at least 85% sequence identity thereto), such as treatment with an alkaline phosphatase or a polypeptide having alkaline phosphatase activity for a treatment period of at least two weeks (e.g., at least three weeks, at least four weeks, at least five weeks, at least six weeks, at least seven weeks, at least eight weeks, at least nine weeks, at least ten weeks, at least three months, at least four months, at least five months, at least six months, at least seven months, at least eight months, at least nine months, at least one year, at least two years, at least three years, at least four years, at least five years, at least six years, at least seven years, at least eight years, at least nine years, or at least ten years, or the lifetime of the subject; particularly at least six weeks), can result in an average increase in the HHD value to about 80% or greater of the predicted HHD value of the subject (e.g., about 83%, about 85%, about 87%, about 90%, about 93%, about 95%, about 97%, or about 100%, or about 100% of the predictive HHD value).

The increase in the HHD value of the subject having a bone mineralization disorder, such as HPP, can be sustained throughout administration of the alkaline phosphatase or a polypeptide having alkaline phosphatase activity (e.g., a sALP, e.g., a polypeptide having the sequence of SEQ ID NO: 1 or a variant thereof with at least 85% sequence identity thereto), e.g., for a treatment period of at least two weeks (e.g., at least three weeks, at least four weeks, at least five weeks, at least six weeks, at least seven weeks, at least eight weeks, at least nine weeks, at least ten weeks, at least three months, at least four months, at least five months, at least six months, at least seven months, at least eight months, at least nine months, at least one year, at least two years, at least three years, at least four years, at least five years, at least six years, at least seven years, at least eight years, at least nine years, or at least ten years, or the lifetime of the subject; particularly at least six weeks). For instance, the HHD value increases to greater than about 80% of the predicted HHD value of the subject having a bone mineralization disorder, such as HPP, and remains at ±10% of the increased HHD value during treatment with the alkaline phosphatase or a polypeptide having alkaline phosphatase activity.

Alternatively, when administration of an alkaline phosphatase or a polypeptide having alkaline phosphatase activity (e.g., a sALP, e.g., a polypeptide having the sequence of SEQ ID NO: 1 or a variant thereof with at least 85% sequence identity thereto) does not result in an average increase in the HHD value to greater than 80% of the predicted HHD value (e.g., of a subject having a bone mineralization disorder, such as HPP, of about the same age, same gender, and/or height), the dosage and/or frequency of alkaline phosphatase or a polypeptide having alkaline phosphatase activity administration can be changed in order to determine the effective amount of the alkaline phosphatase or a polypeptide having alkaline phosphatase activity for the subject having a bone mineralization disorder, such as HPP. For instance, the dosage of the alkaline phosphatase or a polypeptide having alkaline phosphatase activity can be increased from, e.g., from about 0.1-3 mg/kg/week or about 3-6 mg/kg/week to about 3-6 mg/kg/week or about 6-9 mg/kg/week. If the subject's HHD score increases above a predetermined threshold, then the subject may stop treatment and be monitored periodically for changes in their HHD score. If the HHD score decreases below the predetermined threshold, then the therapy may be restarted.

Wearable Device

The methods described herein may be performed in conjunction with a wearable device. A wearable device may be used to monitor biometric or biochemical indicia during a treatment regimen. For example, the wearable device may be used to monitor the treatment efficacy and assist in determining whether administration of the sALP should be stopped once efficacy is achieved or restarted if efficacy is not maintained based on a change in the biometric or biochemical indicia.

A wearable device is a device containing at least one sensor (e.g., one or more, e.g., 2, 3, 4, 5, 8, 7, 8, 9, 10, or more sensors) and is configured to be worn on the subject being treated, e.g., on the arm, leg, or torso of the subject. The wearable device may be worn on the wrist of the subject. The sensor can be any sensor known in the art, and may be, e.g., a position or movement sensor, such as an accelerometer. In some instances, the one or more sensors may be selected from the group consisting of a movement sensor, an orientation sensor, an accelerometer, a gyroscope, a micro-electro-mechanical systems (MEMS) sensor (e.g., MEMS accelerometer), a G-sensor, a tilt sensor, a rotation sensor, a pressure sensor, a temperature sensor, a moisture sensor, an electromyography (EMG) sensor, a light detecting sensor, such as a LIDAR sensor, an EIM sensor, and combinations thereof.

The wearable device may contain a chemical sensor to sense biochemical biomarkers (e.g., PPi, PLP, PEA) in the subject.

The wearable device may be configured to establish a baseline measurement of biometric indicia selected from steps, gait, activity, ballistocardiography, heart rate, heart rate volume, relative stroke volume, respiration rate, rotation, balance, pressure, relative humidity, body composition, temperature, pulse transit time, blood pressure, pulse oxygenation, and blood pressure. The sensors and indicia described herein may be used to monitor one or more biometric indicia selected from number of steps per day, mean heart right, highest heart rate, number of physical activity counts, mean amount of time spent at various activity levels, ratio of various activity levels, duration of various activity levels, and duration of total sleep time. The various activity levels may be selected from sedentary, light, moderate, and vigorous. The indicia may be measured for any predetermined amount of time during the treatment regimen, such as 1 day, 2 days, 3 days, 4 days, 5 days, 6 days, 7 days, 2 weeks, 3 weeks, 4 weeks, 2 months, 3 months, 4 months, 5 months, 6 months, 7 months, 8 months, 9 months, 10 months, 11 months, 12 months, or longer.

The wearable device may be part of a kit that includes the wearable device and a sALP. The wearable device may include an accelerometer. The wearable device may be configured to be worn on the wrist of a subject. The kit may further include a peripheral device (e.g., a smartphone). The peripheral device may be configured to run a software application (e.g., mobile application).

The wearable device may be used in a method of monitoring a sALP treatment regimen of a subject by detecting a change in at least one physical metric based on biometric indicia produced by the wearable device. The biometric indicia may be selected from number of steps per day, mean heart right, highest heart rate, number of physical activity counts, mean amount of time spent at various activity levels, ratio of various activity levels, duration of various activity levels, and duration of total sleep time. The various activity levels may be selected from sedentary, light, moderate, and vigorous. The physical metric(s) may be monitored using the wearable device for a period of at least two weeks or more (e.g., during a treatment phase or during a non-treatment phase, or during both phases).

In conjunction with the methods described herein, the subject may use a wearable device to monitor one or more of the biometric indicia described herein (e.g., steps per day, mean heart rate, number of physical activity counts) and may continue to wear the device for a predetermined period of time (e.g., two weeks or more). The subject may then begin a treatment regimen with a sALP (such as TNALP, for example the sALP fusion polypeptide of SEQ ID NO: 1 or a polypeptide variant described herein, such as a variant having at least 95% sequence identity to the sequence of SEQ ID NO: 1, e.g., asfotase alfa) for the treatment of a bone mineralization disorder, such as HPP. The sALP may be administered during the first phase of the treatment regimen, and the biometric indicia may be tracked daily over time. When the biometric indicia indicate an improvement in the condition of the subject, such as an increase above a predetermined threshold (e.g., a certain number of steps per day or mean heart rate), it may be determined that the treatment is or has been efficacious in improving or restoring normal physical in the subject. The subject may then enter a non-treatment phase of the treatment regimen in which the sALP is not administered. The subject may continue to wear the wearable device to monitor the biometric indicia. If the biometric indicia indicate a deterioration in the condition of the subject, such as a decrease in the value of a measured metric (e.g., a value decrease below the predetermined threshold), then it may be determined that the subject should re-enter a treatment phase of the treatment regimen, in which the sALP therapy is administered again.

The wearable device may be configured as a system that further includes a peripheral electronic device, such as a smartphone or a cloud-based database. As data is continuously monitored and measured by the wearable device, the data collected by the device may be transmitted to the peripheral device and stored on the peripheral device or on a cloud-based storage medium. The peripheral device may be configured to run a software application (e.g., smartphone application) that provides navigable information to the subject in order to track changes in the subject's physiological indicia during the course of treatment (e.g., improvement over time). The data can also be transmitted to a third party, e.g., a clinician administering the sALP therapy to the subject, in order to monitor the treatment progress of the subject.

Treating Bone Fracture

In some embodiments of the method, sALP (such as TNALP, for example the sALP fusion polypeptide of SEQ ID NO: 1 or a polypeptide variant described herein, such as a variant having at least 95% sequence identity to the sequence of SEQ ID NO: 1, e.g., asfotase alfa) is administered to a patient in an amount that is therapeutically effective to treat bone manifestations of a bone mineralization disorder, e.g., HPP. For example, the subject may have, e.g., spine curvature, kyphosis, osteoporosis, weakened vertebral bones, thinning of the ribs, rotation of the vertebrae, vertebral wedging, erosion of vertebrae. rotational or angular spinal deformity, dural ectasia, incomplete bone mineralization, elevated blood and/or urine levels of phosphoethanolamine (PEA), hypomineralization, hypercalciuria, short stature, skeletal deformity, waddling gait, bone pain, bone fracture, weakness, and calcium pyrophosphate dihydrate crystal deposition.

In some embodiments of the method, sALP (such as TNALP, for example the sALP fusion polypeptide of SEQ ID NO: 1 or a polypeptide variant having at least 80, 85%, 90%, 95%, 97%, 99%, or 100% sequence identity to the sequence of SEQ ID NO: 1, e.g., asfotase alfa) is administered to a patient in an amount that is therapeutically effective to treat at least one symptom of dystrophic scoliosis, for example neurofibromatosis (NF1)-related dystrophic scoliosis, e.g., shorter and more sharply angulated curves than seen in non-dystrophic scoliosis, bone abnormalities including thinning of the ribs, weakened vertebral bones, significant rotation of the vertebrae, vertebral wedging, and erosion of the vertebrae by the spinal fluid.

In one embodiment of the method, sALP (such as TNALP, for example the sALP fusion polypeptide of SEQ ID NO: 1 or a polypeptide variant having at least 80, 85%, 90%, 95%, 97%, 99%, or 100% sequence identity to the sequence of SEQ ID NO: 1, e.g., asfotase alfa) is administered to a patient in an amount that is therapeutically effective to induce bone healing. Examples of inducing bone healing includes treating a bone fracture and arthrodesis, the surgical fusion of two joints. For example, the method is useful to promote spinal fusion. Spinal fusion surgery can be used to eliminate bone-on-bone friction and/or to relive nerve compression that cause pain and other symptoms. Surgical bone fusion can also be used on fingers, ankles, and feet, for instance.

In some embodiments of the method, sALP (such as TNALP, for example the sALP fusion polypeptide of SEQ ID NO: 1 or a polypeptide variant described herein, such as a variant having at least 95% sequence identity to the sequence of SEQ ID NO: 1, e.g., asfotase alfa) is administered to a patient who has undergone an orthopedic surgery. The surgery may include at least one implant or hardware inserted during the surgery. The patient may have a disease or disorder, or may have one or more bone related conditions, such as spine curvature, kyphosis, osteoporosis, weakened vertebral bones, thinning of the ribs, rotation of the vertebrae, vertebral wedging, erosion of vertebrae. rotational or angular spinal deformity, dural ectasia, incomplete bone mineralization, elevated blood and/or urine levels of phosphoethanolamine (PEA), hypomineralization, hypercalciuria, short stature, skeletal deformity, wadding gait, bone pain, bone fracture, weakness, and calcium pyrophosphate dihydrate crystal deposition. In some embodiments, the patient has hardware inserted into bone that fails. The patient may have had one or more orthopedic surgeries (e.g., revision surgeries) in which implant fixation has failed. For example, the patient may have, or may be in need of, a craniofacial implant, dental implant, spinal implant, joint replacement part for hip, knee, shoulder, spine, elbow, or wrist, or a bone fixation material, such as a nail, screw, pin, nut, rod, and plate. The patient may also be in need of a revision surgery, in which a craniofacial implant, dental implant, spinal implant, joint replacement part for hip, knee, shoulder, spine, elbow, or wrist, or a bone fixation material, such as a nail, screw, pin, nut, rod, and plate, has failed.

Orthopedic surgeries that may include an implant or hardware include, for example, surgeries to the hand or upper extremity, shoulder, elbow, joint (e.g., total joint reconstruction, e.g., arthroplasty), foot, ankle, spine, musculoskeletal oncology related surgery, sports injury related surgery, trauma, and the like. Other common orthopedic surgeries that may include the use of hardware or an implant include, for example, arthroscopy of the knee, shoulder, hip, ankle, elbow, or wrist, fracture and meniscectomy, shoulder arthroscopy and decompression, carpal tunnel release, knee arthroscopy and chondroplasty, removal of support implant, knee arthroscopy and anterior cruciate ligament reconstruction, knee replacement, repair of femoral neck fracture, repair of atypical femoral fracture, repair of trochanteric fracture, debridement of ski/muscle/bone/fracture, knee arthroscopy repair of one or both menisci, hip replacement, shoulder arthroscopy/distal clavicle excision, repair of rotator cuff tendon, repair fracture of radius (bone)/ulna, laminectomy, repair of ankle fracture (bimalleolar type), shoulder arthroscopy and debridement, lumbar spinal fusion, repair fracture of the distal part of radius, low back intervertebral disc surgery, incise finger tendon sheath, repair of ankle fracture (fibula), repair of femoral shaft fracture, and repair of trochanteric fracture. A patient who has undergone any of the foregoing orthopedic procedures may be treated with a sALP according to the methods described herein in order to improve the repair of the bone or to improve fixation of the implant or hardware.

The sALP may be used for repair of bone trauma or a bone defect that may have resulted from surgery or disease. The damaged or fragmented bone tissue may be reconstructed using an implant or hardware and supplemented by administration of a sALP before, during, or after a surgery to repair the defect. The implant or hardware, in combination with sALP administration, may further provide the necessary mechanical support for the remaining pieces of bone fragments at the site of damage and simultaneously allow blood and bone forming cells from adjacent tissues to penetrate the implant for improved healing. For example, the methods described herein can be used to repair calvarial bone defects after neurosurgical operations and traumas, in reconstructions of bony orbital floors and jaw bones. The methods described herein can also be used in orthopedics and spine surgery, as well as in fixation of fragmented pieces of bone and cosmetic surgeries. In the presence of long bones weakened by diseases, or when parts of the cortical bone are lost, the Implant can be used to reinforce the long bones and cover openings where cortical bone is lost.

The sALP may be used for repair of an atypical fracture, such as atypical femoral fracture (AFF), which is a transverse fracture of the femoral shaft. The AFF may be caused by use (e.g., long term use) of bisphosphonate, e.g., for the treatment of osteoporosis. The sALP may be used to treat AFF in a subject (e.g., adult subject) with HPP (e.g., pediatric-onset HPP) or without HPP. In an alternative embodiment, the sALP is used to treat NF1 and NF1-related skeletal manifestations/complications, such as tibial dysplasia, pseudoarthrosis, vertebral scalloping, scoliosis and others. The treatment of NF1, NF1 related skeletal manifestations/complications, and/or other poorly healing fractures can be separate from or in addition to treatment of AFF. The sALP (such as TNALP, for example the sALP fusion polypeptide of SEQ ID NO: 1 or a polypeptide variant described herein, such as a variant having at least 95% sequence identity to the sequence of SEQ ID NO: 1, e.g., asfotase alfa) may be administered to the subject, e.g., at a dosage of about 6 mg/kg/week. Administration of the sALP may lead to transient increase of one or more metabolites or biomarkers (e.g., bone turnover markers), such as parathyroid hormone, procollagen type 1 N-propeptide (PINP), osteocalcin, and bone alkaline phosphatase (BAP). The transient increase may be sustained for at least, e.g., 1 week, 2 weeks, 3 weeks, 1 month, 2 months, 3 months, 4 months, 5 months, or 6 months or more. Following the transient increase, the level of the biomarker may decrease back to baseline. This may indicate bone turnover and facilitation of bone remodeling in the subject. The fracture may be monitored for healing for a period of time (e.g., 1 week, 2 weeks, 3 weeks, 1 month, 2 months, 3 months, 4 months, 5 months, or 6 months or more) until sufficient healing is observed, at which time the treatment may conclude. After resolution of the fracture, a lower dosage (e.g., 3 mg/kg/week) may be administered or less frequent dosing (e.g., bimonthly or monthly administration, such as at a dosage of 0.5 mg/kg to 50 mg/kg) may be administered. The subject may engage in physical therapy following treatment in order to resume normal activity levels. In some cases, the subject may continue therapy for an extended duration (e.g., for life) in order to minimize recurrence of fracture or side effects related to anti-drug antibodies.

The methods described herein may also be used with bones of reduced quality (e.g., osteoporotic bone) or in revision surgeries (e.g., they can be used to replace previously inserted Implants). The sALP (such as TNALP, for example the sALP fusion polypeptide of SEQ ID NO: 1 or a polypeptide variant described herein, such as a variant having at least 95% sequence identity to the sequence of SEQ ID NO: 1, e.g., asfotase alfa) can be used, for example, in osteosynthesis to internally stabilize and/or join bones, e.g., fractured (broken) bones, either in conjunction with mechanical stabilizing devices, such as metal plates, pins, rods, or wires, or individually.

The methods described herein may also be used to treat a bone defect in a patient with a fracture requiring compression. In particular, the sALP can be administered in conjunction with an implant that may be used to provide compressive fixation in a patient.

Bones that can be treated according to the methods described herein include, for example, subarticular fracture, a defect of the spine or vertebra, or a defect of the radius, ulna, fibula, clavicle, humerus, pelvis, femur, patella, tibia, talus, calcaneus, navicular, cuneiforms, metatarsals, metacarpals, phalanges, scapula, ankle, maxilla, or mandible. The Implant or hardware can be positioned in proximity to the bone defect (e.g., positioning the Implant so that it contacts the intraosseous space of a bone). The sALP (such as TNALP, for example the sALP fusion polypeptide of SEQ ID NO: 1 or a polypeptide variant described herein, such as a variant having at least 95% sequence identity to the sequence of SEQ ID NO: 1, e.g., asfotase alfa) may be administered at any time before, during, or after administration of the implant or hardware. The sALP may be coated on the implant or hardware.

Treatment methods of the disclosure also include maxillomandibular or craniofacial fixation, temporary fixation for repairing a bone defect in a staged reconstruction, glenoid or humeral fixation, patellar fixation, or spine fixation. For example, in spinal surgeries, the implant may be placed within a pedicle, used to anchor an interbody device, used to anchor spinal fusion plates and spacer replacement, used in an osteoporotic vertebra, or positioned in proximity to the spinous processes of adjacent vertebrae. The method may also include the insertion of a rod, pin, nail, or mesh or bone plate in proximity to the bone defect. The sALP may be administered at any time before, during, or after the surgery. The sALP may be coated on any implant or hardware.

Particular bone defects that may be treated using the methods described herein include, e.g., any bone deficient region, such as a void, gap, recess, or other discontinuity in a bone. The bone defect may be due to, for example, disease or trauma. The implants or hardware described herein can be applied, for example, in the repair of periodontal defects, in craniofacial or maxillofacial surgery or reconstruction, in cosmetic surgery, in hand surgery, in joint reconstruction, in fracture repair, in orthopedic surgical procedures, and in spinal fusion. The implants may also be used, for example, in osteosynthesis to internally stabilize and/or join bones, e.g., fractured (broken) bones, either in conjunction with other mechanical devices, such as washers, metal plates, pins, rods, or wires, or individually. For example, the implants can be used with a washer to provide compressive fixation of bone defects and bone fractures. In particular, the methods are useful for the treatment of defects or breaks in large bones. Non-limiting examples of bone fractures include, e.g., stable fractures, transverse fractures, oblique fractures, spiral fractures, comminuted fractures and open and displaced fractures. Exemplary large bones that may require fracture fixation include, e.g., the femur, tibia, fibula, humerus, ulna, radius, ribs, innominate bone (hip bone), and sternum. For each of these surgeries, the sALP may be administered at any time before, during, or after the surgery.

Surgical Intervention

Administration of sALP (such as TNALP, for example the sALP fusion polypeptide of SEQ ID NO: 1, or a polypeptide variant having at least 95% sequence identity to the sequence of SEQ ID NO: 1, e.g., asfotase alfa) in any of the disclosed methods can occur in conjunction with a physical intervention, for instance, surgical intervention. Surgical intervention can be used for arthrodesis, removal of bone, insertion of bone graft material, or setting a fractured bone. Surgical intervention can include instrumentation (e.g., implantation of hardware, such as screws, rods, plates, and metal cages) to aid in bone fusion. Surgical intervention can include traditional open surgery, such as open neck or open back surgery, a minimally invasive surgery, or a combination thereof.

Alkaline Phosphatase

Asfotase alfa is a human TNALP (hTNALP; SEQ ID NO: 1) fusion polypeptide. In particular, asfotase alfa (SEQ ID NO: 1) can be used effectively to treat at least one symptom of a bone mineralization disorder, such as HPP.

Given the results described herein, the treatment methods are not linked to administration of a particular alkaline phosphatase (ALP) or nucleic acid sequence encoding an ALP. Alkaline phosphatases encompass a group of enzymes that catalyze the cleavage of a phosphate moiety (e.g., hydrolysis of pyrophosphate, PPi). There are four known mammalian alkaline phosphatase (ALP) isozymes: tissue nonspecific alkaline phosphatase (TNALP; described further below), placental alkaline phosphatase (PLALP) (e.g., Accession Nos. P05187, NP_112603, and NP_001623), germ cell alkaline phosphatase (GALP) (e.g., Accession No. P10696), and intestinal alkaline phosphatase (IALP) (e.g., Accession Nos. P09923 and NP_001622). In addition to the exemplary ALPs discussed herein, any polypeptide having the identical or similar catalytic site structure and/or enzymatic activity of ALP can be used (e.g., as a sALP or a sALP fusion polypeptide as defined herein) in a method disclosed herein. Bone delivery conjugates including sALP are further described in PCT Publication Nos: WO 2005/103263 and WO 2008/138131.

TNALPs that can be used according to the methods described herein include, e.g., human TNALP (Accession Nos. NP_000489, AAI0910, AAH90881, AAH68116, AAH21289, and AAI26188), rhesus TNALP (Accession No. XP_01109717), rat TNALP (Accession No. NP_037191), dog TNALP (Accession No. AAF64516), pig TNALP (Accession No. AAN64273), mouse (Accession No. NP_031457), cow TNALP (Accession Nos. NP_789828, NP_778412, AAM 8209, and AAC33858), and cat TNALP (Accession No. NP_001038028). In particular, TNALP can be a recombinant human TNALP (e.g., SEQ ID NO: 1, asfotase alfa; see U.S. Pat. Nos. 7,763,712 and 7,960,529) used in a method disclosed herein. The TNALP can also be one that exhibits at least about 95% sequence identity to the polypeptide or nucleic acid sequence of the above-noted TNALPs.

Soluble Alkaline Phosphatases

An ALP that can be used in the methods described herein includes soluble (e.g., extracellular or non-membrane-bound) forms of any of the alkaline phosphatases described herein. The sALP can be, for example, a soluble form of human tissue non-specific alkaline phosphatase (human TNALP (hTNALP)). The methods are not limited to a particular sALP and can include any sALP that is physiologically active toward, e.g., phosphoethanolamine (PEA), inorganic pyrophosphate (PPi), and pyridoxal 5'-phosphate (PLP). In particular, a sALP is one that is catalytically competent to improve skeletal mineralization in bone. The methods further include nucleic acids encoding the sALPs described herein that can be used in a method described herein.

TNALP is a membrane-bound protein anchored by a glycolipid moiety at the C-terminal (Swiss-Prot, P05186). This glycolipid anchor (GPI) is added post-translationally after the removal of a hydrophobic C-terminal end, which serves both as a temporary membrane anchor and as a signal for the addition of the GPI. While the GPI anchor is located in the cell membrane, the remaining portions of TNALP are extracellular. In particular, TNALP (e.g., human TNALP (hTNALP)) can be engineered to replace the first amino acid of the hydrophobic C-terminal sequence (an alanine) with a stop codon, thereby producing an engineered hTNALP that contains all amino acid residues of the native anchored form of TNALP and lacks the GPI membrane anchor. One skilled in the art will appreciate that the position of the GPI membrane anchor will vary in different ALPs and can include, e.g., the last 10, 12, 14, 16, 18, 20, 21, 22, 23, 24, 25, 26, 27, 28, 29, 30, 32, 34, 36, 38, 40, 45, 50, or more amino acid residues on the C-terminus of the polypeptide. Recombinant sTNALP can include, e.g., amino acids 1 to 502 (18 to 502 when secreted), amino acids 1 to 501 (18 to 501 when secreted), amino acids 1 to 504 (18 to 504 when secreted), amino acids 1 to 505 (18-505 when secreted), or amino acids 1 to 502. Thus, the C-terminal end of the native ALP can be truncated by certain amino acids without affecting ALP activity.

In addition to the C-terminal GPI anchor, TNALP also has an N-terminal signal peptide sequence. The N-terminal signal peptide is present on the synthesized protein when it is synthesized but cleaved from TNALP after translocation into the ER. The sALPs include both secreted (i.e., lacking the N-terminal signal) and non-secreted (i.e., having the N-terminal signal) forms thereof. One skilled in the art will appreciate that the position of the N-terminal signal peptide will vary in different alkaline phosphatases and can include, for example, the first 5, 8, 10, 11, 12, 13, 14, 15, 16, 17, 18, 19, 20, 21, 22, 23, 24, 25, 27, 30, or more amino acid residues on the N-terminus of the polypeptide. One of skill in the art can predict the position of a signal sequence cleavage site, e.g., by an appropriate computer algorithm such as that described in Bendtsen et al. (*J. Mol. Biol.* 340(4):783-795, 2004) and available on the Web at www.cbs.dtu.dk/services/SignalP/.

The methods can also be performed using sALP consensus sequences derived from the extracellular domain of ALP isozymes (e.g., TNALP, PALP, GCALP, IALP, etc.). Thus, similar to sTNALP discussed above, the present disclosure also provides other soluble human ALP isozymes, i.e., without the peptide signal, preferably comprising the extracellular domain of the ALPs. The sALPs also include polypeptide sequences satisfying a consensus sequence derived from the ALP extracellular domain of human ALP isozymes and of mammalian TNALP orthologs (human, mouse, rat, cow, cat, and dog) or a consensus derived from the ALP extracellular domain of just mammalian TNALP orthologs (human, mouse, rat, cow, cat, and dog). The sALPs also include those which satisfy similar consensus sequences derived from various combinations of these TNALP orthologs or human ALP isozymes. Such consensus sequences are given, for example, in VD 2008/138131.

sALPs of the present methods can include not only the wild-type sequence of the sALPs described above, but any polypeptide having at least 50% (e.g., 55%, 60%, 65%, 70%, 75%, 80%, 85%, 86%, 87%, 88%, 89%, 90%, 91%, 92%, 93%, 94%, 95%, 96%, 97%, 98%, 99%, or more) sequence identity to these alkaline phosphatases (e.g., the sALP fusion polypeptide of SEQ ID NO: 1 or a polypeptide variant having at least 95% sequence identity to the sequence of SEQ ID NO: 1, e.g., asfotase alfa). Examples of mutations that can be introduced into an ALP sequence are described in US Publication No. 2013/0323244. A sALP can optionally be glycosylated at any appropriate one or more amino acid residues. In addition, an sALP can have at least 50% (e.g., 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or more) sequence identity to any of the sALPs described herein (such as TNALP, for example the sALP fusion polypeptide of SEQ ID NO: 1 or a polypeptide variant having at least 95% sequence identity to the sequence of SEQ ID NO: 1, e.g., asfotase alfa). A sALP can have 1, 2, 3, 4, 5, 8, 7, 8, 9, 10, or more additions, deletions, or substitutions relative to any of the sALPs described herein (such as TNALP, for example the sALP fusion polypeptide of SEQ ID NO: 1 or a polypeptide variant having at least 95% sequence identity to the sequence of SEQ ID NO: 1, e.g., asfotase alfa).

sALP Fusion Polypeptides

Any of the sALPs (such as TNALP, for example the sALP fusion polypeptide of SEQ ID NO: 1 or a polypeptide variant having at least 95% sequence identity to the sequence of SEQ ID NO: 1, e.g., asfotase alfa), linkers, spacers (e.g., Fc regions), and bone-targeting moieties described herein can be combined in a fusion polypeptide, which includes the structures Z-sALP-Y-spacer-X-Mn-V, Z-Mn-X-spacer-Y-sALP-V, Z-sALP-Y-M-X-spacer-V, and Z-M-X-sALP-Y-spacer-V. In particular, the structure of the sALP fusion polypeptide can be Z-sALP-Y-spacer-X-M-V or Z-Wn-X-spacer-Y-sALP-V. The sALP of the sALP fusion polypeptide can be the full-length ALP or functional fragments of ALPs, such as the soluble, extracellular domain of the ALP, as is described herein (e.g., TNALP, PALP, GCALP and IALP).

Any one of X, Y, Z, and V and/or the spacer can be absent or a inker region including an amino acid sequence of at least one amino acid. For example, X, Y, Z, and V may be a dipeptide sequence (e.g., leucine-lysine or aspartic acid-isoleucine), such as a two-residue linker at the Y position (e.g., leucine-lysine) or a two residue linker at the X position (e.g., aspartic acid-isoleucine). For example, sALP fusion polypeptides can have the structure hTNALP-Fc-D10 (e.g., a sALP fusion polypeptide including the amino acid sequence of SEQ ID NO: 1 or a polypeptide variant having at least 95% sequence identity to the sequence of SEQ ID NO: 1, e.g., asfotase alfa).

The linker region can be of any sequence and length that allows the sALP to remain biologically active, e.g., not sterically hindered. Exemplary linker lengths are between 1 and 200 amino acid residues, e.g., 1-5, 6-10, 11-15, 16-20, 21-25, 26-30, 31-35, 38-40, 41-45, 48-50, 51-55, 58-0, 61-65, 68-70, 71-75, 76-80, 81-85, 86-90, 91-95, 96-100, 101-110, 111-120, 121-130, 131-140, 141-150, 151-160, 161-170, 171-180, 181-190, or 191-200 amino acid residues. For instance, inkers include or consist of flexible portions, e.g., regions without significant fixed secondary or tertiary structure. Exemplary flexible linkers are glycine-rich inkers, e.g., containing at least 50%, 60%, 65%, 70%, 75%, 80%, 85%, 90%, 95%, or even 100% glycine residues. Linkers can also contain, e.g., serine residues. In some cases, the amino acid sequence of linkers consists only of glycine and serine residues. A linker can optionally be glycosylated at any appropriate one or more amino acid residues. Additionally, a inker as described herein can include any other sequence or moiety, attached covalently or non-covalently. The linker can also be absent, in which the spacer (e.g., the Fc region) and the sALP are fused together directly, with no intervening residues.

Useful spacers include, but are not limited to, polypeptides comprising an Fc region. For example, a sALP can be a fusion polypeptide including an Fc region of an immunoglobulin at the N-terminal or C-terminal domain. An immunoglobulin molecule has a structure that is well known in the art. It includes two light chains (~23 kD each) and two heavy chains (~50-70 kD each) joined by inter-chain disulfide bonds. Immunoglobulins are readily cleaved proteolytically (e.g., by papain cleavage) into Fab (containing the light chain and the VH and CH1 domains of the heavy chain) and Fc (containing the CH2 and CH3 domains of the heavy chain, along with adjoining sequences). Useful Fc fragments as described herein include the Fc fragment of any immunoglobulin molecule, including IgG, IgM, IgA, IgD, or IgE, and their various subclasses (e.g., IgG-1, IgG-2, IgG-3, IgG-4, IgA-1, IgA-2), from any mammal (e.g., human). For instance, the Fc fragment is human IgG-1. The Fc fragments can include, for example, the CH2 and CH3 domains of the heavy chain and any portion of the hinge region. The Fc region can optionally be glycosylated at any appropriate one or more amino acid residues known to those skilled in the art. Engineered, e.g., non-naturally occurring, Fc regions can be incorporated into the sALP fusion polypeptides described herein, e.g., those described in MD 2005/007809. An Fc fragment as described herein can have 1, 2, 3, 4, 5, 8, 7, 8, 9, 10, 11, 12, 13, 14, 15, 16, 17, 18, 19, 20, 25, 30, 35, 40, 50, or more additions, deletions, or substitutions relative to any of the Fc fragments described herein.

Wn can be a bone-targeting moiety, e.g., having a series of consecutive aspartate (D) or glutamate (E) residues, in which n=1 to 50, e.g., n=3-30, e.g., 5-15, e.g., 1, 2, 3, 4, 5, 8, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 36, 38, 39, 40, 41, 42, 43, 44, 45, 46, 47, 48, 49, or 50. The bone-targeting moiety, if present, can be positioned anywhere in the fusion polypeptide, e.g., at or near the N-terminal or C-terminal end, and/or in the inker region. For instance, the bone-targeting moiety can be present at the C-terminal end of a sALP fusion polypeptide. sALPs and fusion polypeptides can also lack a bone-targeting moiety.

Additional amino acid residues can be introduced into the polypeptide according to the cloning strategy used to produce the fusion polypeptides. For instance, the additional amino acid residues do not provide an additional GPI anchoring signal so as to maintain the polypeptide in a soluble form. Furthermore, any such additional amino acid residues, when incorporated into the polypeptide of the methods, do not provide a cleavage site for endoproteases of the host cell. The likelihood that a designed sequence would be cleaved by the endoproteases of the host cell can be predicted as described, e.g., by Ikezawa (*Biol. Pharm. Bull.* 25:409-417, 2002).

The sALP fusion polypeptides (such as a TNALP, for example the sALP fusion polypeptide of SEQ ID NO: 1 or a polypeptide variant having at least 95% sequence identity to the sequence of SEQ ID NO: 1, e.g., asfotase alfa) can be associated into dimers or tetramers. For example, two sALP-Fc monomers can be covalently linked through two disulfide bonds located in the hinge regions of the Fc fragments. Additionally, the sALP fusion polypeptide (e.g., a sALP or a sALP fusion polypeptide) can be glycosylated or PEGylated.

Production of Nucleic Acids and Polypeptides

The nucleic acids encoding sALPs (such as TNALP, for example the sALP fusion polypeptide of SEQ ID NO: 1 or a polypeptide variant having at least 95% sequence identity to the sequence of SEQ ID NO: 1, e.g., asfotase alfa) can be produced by any method known in the art. Typically, a nucleic acid encoding the desired fusion polypeptide is generated using molecular cloning methods, and is generally placed within a vector, such as a plasmid or virus. The vector is used to transform the nucleic acid into a host cell appropriate for the expression of the fusion polypeptide. Representative methods are disclosed, for example, in Maniatis et al. (Cold Springs Harbor Laboratory, 1989). Many cell types can be used as appropriate host cells, although mammalian cells are preferable because they are able to confer appropriate post-translational modifications. Host cells can include, e.g., Chinese Hamster Ovary (CHO) cell, L cell, C127 cell, 3T3 cell, BHK cell, COS-7 cell or any other suitable host cell known in the art. For example, the host cell is a Chinese Hamster Ovary (CHO) cell (e.g., a CHO-DG44 cell).

The sALPs (such as TNALP, for example the sALP fusion polypeptide of SEQ ID NO: 1 or a polypeptide variant having at least 95% sequence identity to the sequence of SEQ ID NO: 1, e.g., asfotase alfa) can be produced under any conditions suitable to effect expression of the sALP polypeptide in the host cell. Such conditions include appropriate selection of a media prepared with components such as a buffer, bicarbonate and/or HEPES, ions like chloride, phosphate, calcium, sodium, potassium, magnesium, iron, carbon sources like simple sugars, amino acids, potentially lipids, nucleotides, vitamins and growth factors like insulin; regular commercially available media like alpha-MEM, DMEM, Ham's-F12, and IMDM supplemented with 2-4 mM L-glutamine and 5% Fetal bovine serum; regular commercially available animal protein free media like Hyclone™ SFM4CHO, Sigma CHO DHFR–, Cambrex POWER™ CHO CD supplemented with 2-4 mM L-glutamine. These media are desirably prepared without thymidine, hypoxanthine and L-glycine to maintain selective pressure, allowing stable protein-product expression.

Treatment of a Patient with sALP

The patient to whom sALP is administered can be of any age. In some particular embodiments, the subject may be an adult older than about 18 years of age. The patient may be afflicted with at least one symptom of a bone mineralization disorder, such as HPP. The patient may be in need of induced bone healing and/or mineralization. For instance, the patient may be afflicted with one or more bone fractures or pseudofractures. The patient may exhibit poor muscle tone or hypotonia and may have difficulty with daily activities, such as sitting, standing, or waking. The patient may be one that has not been diagnosed with HPP and/or has never received a sALP therapy.

US 12,611,447 B2

51
52

Administration and Dosage

In any of the disclosed methods, any amount of a pharmaceutical composition (e.g., including a sALP or sALP fusion polypeptide, such as TNALP, for example the sALP polypeptide of SEQ ID NO: 1 or a polypeptide variant described herein, such as a variant having at least 80, 85%, 90%, 95%, 97%, 99%, or 100% sequence identity to the sequence of SEQ ID NO: 1, e.g., asfotase alfa) can be administered to a patient. The dosages will depend on many factors including the mode of administration and the age of the patient. Typically, the amount of the composition (e.g., a sALP or sALP fusion polypeptide, such as TNALP, for example the sALP polypeptide of SEQ ID NO: 1 or a polypeptide variant having at least 95% sequence identity to the sequence of SEQ ID NO: 1, e.g., asfotase alfa) contained within a single dose will be an amount that is effective to treat a patient described herein without inducing significant toxicity.

For example, in any of the disclosed methods the sALP (such as TNALP, for example the sALP polypeptide of SEQ ID NO: 1 or a polypeptide variant having at least 95% sequence identity to the sequence of SEQ ID NO: 1, e.g., asfotase alfa) described herein can be administered to a patient in individual doses ranging, e.g., from 0.01 mg/kg to 500 mg/kg (e.g., from 0.05 mg/kg to 500 mg/kg, from 0.1 mg/kg to 20 mg/kg, from 5 mg/kg to 500 mg/kg, from 0.1 mg/kg to 100 mg/kg, from 10 mg/kg to 100 mg/kg, from 0.1 mg/kg to 50 mg/kg, from 0.5 mg/kg to 25 mg/kg, from 1.0 mg/kg to 10 mg/kg, from 1.5 mg/kg to 5 mg/kg, or from 2.0 mg/kg to 3.0 mg/kg, e.g., about 2.1 mg/kg, 2.2 mg/kg, 2.3, mg/kg, 2.4 mg/kg, 2.5 mg/kg, 2.6 mg/kg, 2.7 mg/kg, 2.8 mg/kg, 2.9 mg/kg, 3.0 mg/kg, 3.1 mg/kg, 3.2 mg/kg, 3.3 mg/kg, 3.4 mg/kg, 3.5 mg/kg, 3.6 mg/kg, 3.7 mg/kg, 3.8 mg/kg, 3.9 mg/kg, 4.0 mg/kg) or from 1 µg/kg to 1,000 µg/kg (e.g., from 5 µg/kg to 1,000 µg/kg, from 1 µg/kg to 750 µg/kg, from 5 µg/kg to 750 µg/kg, from 10 µg/kg to 750 µg/kg, from 1 µg/kg to 500 µg/kg, from 5 µg/kg to 500 µg/kg, from 10 µg/kg to 500 µg/kg, from 1 µg/kg to 100 µg/kg, from 5 µg/kg to 100 µg/kg, from 10 µg/kg to 100 µg/kg, from 1 µg/kg to 50 µg/kg, from 5 µg/kg to 50 µg/kg, or from 10 µg/kg to 50 µg/kg). Any of the foregoing doses can be administered once per day. Any of the foregoing doses can be administered once per week.

Exemplary doses of a sALP include, e.g., 0.01, 0.05, 0.1, 0.5, 1, 2, 2.5, 5, 10, 20, 25, 50, 100, 125, 150, 200, 250, or 500 mg/kg; or 1, 2, 2.5, 5, 10, 20, 25, 50, 100, 125, 150, 200, 250, 500, 750, 900, or 1,000 µg/kg. For al dosages or ranges recited herein, the term "about" can be used to modify these dosages by ±10% of the recited values or range endpoints. In particular, compositions (e.g., including sALP (such as TNALP, for example the sALP polypeptide of SEQ ID NO: 1 or a polypeptide variant having at least 95% sequence identity to the sequence of SEQ ID NO: 1, e.g., asfotase alfa)) in accordance with the present disclosure can be administered to a patient in doses ranging from about 0.001 mg/kg/day to about 500 mg/kg/day, about 0.01 mg/kg/day to about 100 mg/kg/day, or about 0.01 mg/kg/day to about 20 mg/kg/day. For example, the sALP compostions (such as TNALP, for example the sALP polypeptide of SEQ ID NO: 1 or a polypeptide variant having at least 95% sequence identity to the sequence of SEQ ID NO: 1, e.g., asfotase alfa) can be administered to a patient in a weekly dosage ranging, e.g., from about 0.5 mg/kg/week to about 140 mg/kg/week, e.g., about 0.8 mg/kg/week to about 50 mg/kg/week, or about 1 mg/kg/week to about 10 mg/kg/week (e.g., about 3 or about 6 or about 9 mg/kg/week). In particular, the sALP (such as TNALP, for example the sALP polypeptide of SEQ ID NO: 1 or a polypeptide variant having at least 95% sequence identity to the sequence of SEQ ID NO: 1, e.g., asfotase alfa) can be administered at a dosage of 2 mg/kg three times a week (total dose about 6 mg/kg/week), 1 mg/kg six times a week (total dose about 6 mg/kg/week), 3 mg/kg three times a week (total dose 9 mg/kg/week), 0.5 mg/kg three times a week (total dose of 1.5 mg/kg/week), or 9.3 mg/kg three times a week (total dose about 28 mg/kg/week). The dosage will be adapted by the clinician in accordance with conventional factors such as, for instance, the extent of the bone mineralization disorder, such as the need for bone healing, and different parameters from the patient.

Dosages of pharmaceutical compositions including sALPs (such as TNALP, for example the sALP polypeptide of SEQ ID NO: 1 or a polypeptide variant having at least 95% sequence identity to the sequence of SEQ ID NO: 1, e.g., asfotase alfa) can be provided in either a single or multiple dosage regimens. Doses can be administered, e.g., hourly, bihourly, daily, bidaily, twice a week, three times a week, four times a week, five times a week, six times a week, weekly, biweekly, monthly, bimonthly, or yearly. Alternatively, doses can be administered, e.g., twice, three times, four times, five times, six times, seven times, eight times, nine times, 10 times, 11 times, or 12 times per day. In particular, the dosing regimen is three times a week. The duration of the dosing regimen can be, e.g., 1, 2, 3, 4, 5, 8, 7, 8, 9, 10, 11, 12, 13, 14, 15, 16, 17, 18, 19, 20, 21, 22, 23, 24, 25, 26, 27, 28, 29, or 30 day(s), week(s), or month(s). The dosing regimen can begin before, during, or after a physical intervention, such as a surgical intervention. The amount, frequency, and duration of dosage will be adapted by the clinician in accordance with conventional factors such as the extent of the bone mineralization disorder and different parameters from the patient.

For example, a sALP or sALP fusion polypeptide (such as TNALP, for example the sALP polypeptide of SEQ ID NO: 1 or a polypeptide variant having at least 95% sequence identity to the sequence of SEQ ID NO: 1, e.g., asfotase alfa) can be formulated as a solution for injection, which is a clear, colorless to slightly yellow, aqueous solution, pH 7.4. The sALP (such as TNALP, for example the sALP polypeptide of SEQ ID NO: 1 or a polypeptide variant having at least 95% sequence identity to the sequence of SEQ ID NO: 1, e.g., asfotase alfa) may be formulated at a concentration of, for instance, 12 mg/0.3 mL, 18 mg/0.45 mL, 28 mg/0.7 mL, 40 mg/1 ml, or 80 mg/0.8 mL. In particular, the composition can be formulated as a 40 mg/ml solution for injection, in which each ml of solution contains 40 mg of sALP (e.g., each vial contains 0.3 ml solution and 12 mg of sALP (40 mg/ml), each vial contains 0.45 ml solution and 18 mg of sALP (40 mg/ml), each vial contains 0.7 ml solution and 28 mg of sALP (40 mg/ml), or each vial contains 1.0 ml solution and 40 mg of asfotase alfa (40 mg/ml)). A sALP (such as TNALP, for example the sALP polypeptide of SEQ ID NO: 1 or a polypeptide variant having at least 95% sequence identity to the sequence of SEQ ID NO: 1, e.g., asfotase alfa) can be formulated as a solution for injection at a concentration of 100 mg/ml, in which each 1 ml of solution contains 100 mg of sALP or sALP polypeptide (e.g., each vial contains 0.8 ml solution and 80 mg of asfotase alfa (100 mg/ml)).

For example, the recommended dosage of a sALP (such as TNALP, for example the sALP polypeptide of SEQ ID NO: 1 or a polypeptide variant having at least 95% sequence identity to the sequence of SEQ ID NO: 1, e.g., asfotase alfa) is 2 mg/kg of body weight administered subcutaneously three times per week, or a dosage regimen of 1 mg/kg of body weight administered subcutaneously six times per week. Additional dosage information is provided below (Tables 2-1, 2-2, and 2-3).

In some embodiments as described herein, the dose may be determined based on an actual body weight of the subject. In some embodiments, the dose may be determined based on an ideal body weight of the subject. Actual body weight refers to the true weight of the subject. Ideal body weight refers to a calculated body weight of the subject, which is an adjusted weight that takes into account the physical variables of the subject, such as, age, gender, height, body frame size, wrist size, and the like. Suitable formulas for calculating ideal body weight are known in the art, e.g., the G. J. Hamwi Formula, B. J. Devine Formula, J. D. Robinson Formula, and the D. R. Miler Formula.

TABLE 2-1

Dosing of Asfotase Alfa 2 mg/kg Three Times Per Week

| Body Weight (kg)* | Dose to Inject | Volume to Inject | Vial Configuration |
|---|---|---|---|
| 3 | 6 mg | 0.15 mL | 18 mg/0.45 mL |
| 4 | 8 mg | 0.2 mL | 18 mg/0.45 mL |
| 5 | 10 mg | 0.25 mL | 18 mg/0.45 mL |
| 6 | 12 mg | 0.3 mL | 18 mg/0.45 mL |
| 7 | 14 mg | 0.35 mL | 18 mg/0.45 mL |
| 8 | 16 mg | 0.4 mL | 18 mg/0.45 mL |
| 9 | 18 mg | 0.45 mL | 18 mg/0.45 mL |
| 10 | 20 mg | 0.5 mL | 28 mg/0.7 mL |
| 15 | 30 mg | 0.75 mL | 40 mg/mL |
| 20 | 40 mg | 1 mL | 40 mg/mL |
| 25 | 50 mg | 1.25 mL | Two 28 mg/0.7 mL vials |
| 30 | 60 mg | 1.5 mL | Two 40 mg/mL vials |
| 35 | 70 mg | 1.75 mL | Two 40 mg/mL vials |
| 40 | 80 mg | 0.8 mL | 80 mg/0.8 mL |
| 50 | 100 mg | 1 mL | Two 80 mg/0.8 mL vials |
| 60 | 120 mg | 1.2 mL** | Two 80 mg/0.8 mL vials |
| 70 | 140 mg | 1.4 mL** | Two 80 mg/0.8 mL vials |
| 80 | 160 mg | 1.6 mL** | Two 80 mg/0.8 mL vials |

TABLE 2-2

Dosing of Asfotase Alfa 1 mg/kg Six Times Per Week

| Body Weight (kg)* | Dose to Inject | Volume to Inject | Vial Configuration |
|---|---|---|---|
| 3 | 3 mg | 0.08 mL | 18 mg/0.45 mL |
| 4 | 4 mg | 0.1 mL | 18 mg/0.45 mL |
| 5 | 5 mg | 0.13 mL | 18 mg/0.45 mL |
| 6 | 6 mg | 0.15 mL | 18 mg/0.45 mL |
| 7 | 7 mg | 0.18 mL | 18 mg/0.45 mL |
| 8 | 8 mg | 0.2 mL | 18 mg/0.45 mL |
| 9 | 9 mg | 0.23 mL | 18 mg/0.45 mL |
| 10 | 10 mg | 0.25 mL | 18 mg/0.45 mL |
| 15 | 15 mg | 0.38 mL | 18 mg/0.45 mL |
| 20 | 20 mg | 0.5 mL | 28 mg/0.7 mL |
| 25 | 25 mg | 0.63 mL | 28 mg/0.7 mL |
| 30 | 30 mg | 0.75 mL | 40 mg/mL |
| 35 | 35 mg | 0.88 mL | 40 mg/mL |
| 40 | 40 mg | 1 mL | 40 mg/mL |
| 50 | 50 mg | 0.5 mL | 80 mg/0.8 mL |
| 60 | 60 mg | 0.6 mL | 80 mg/0.8 mL |
| 70 | 70 mg | 0.7 mL | 80 mg/0.8 mL |
| 80 | 80 mg | 0.8 mL | 80 mg/0.8 mL |
| 90 | 90 mg | 0.9 mL | Two 80 mg/0.8 mL vials |
| 100 | 100 mg | 1 mL | Two 80 mg/0.8 mL vials |

TABLE 2-3

Dosing of Asfotase Alfa 3 mg/kg Three Times Per Week (Only for Perinatal/Infantile-Onset HPP)

| Body Weight (kg)* | Dose to Inject | Volume to Inject | Vial Configuration |
|---|---|---|---|
| 3 | 9 mg | 0.23 mL | 18 mg/0.45 mL |
| 4 | 12 mg | 0.3 mL | 18 mg/0.45 mL |
| 5 | 15 mg | 0.38 mL | 18 mg/0.45 mL |
| 6 | 18 mg | 0.45 mL | 18 mg/0.45 mL |
| 7 | 21 mg | 0.53 mL | 28 mg/0.7 mL |
| 8 | 24 mg | 0.6 mL | 28 mg/0.7 mL |
| 9 | 17 mg | 0.68 mL | 28 mg/0.7 mL |
| 10 | 30 mg | 0.75 mL | 40 mg/mL |
| 15 | 45 mg | 1.13 mL*** | Two 28 mg/0.7 mL vials |
| 20 | 60 mg | 1.5 mL*** | Two 40 mg/mL vials |
| 25 | 75 mg | 1.88 mL*** | Two 40 mg/mL vials |

In some instances, administration of the sALP (such as TNALP, for example the sALP polypeptide of SEQ ID NO: 1 or a polypeptide variant having at least 95% sequence identity to the sequence of SEQ ID NO: 1, e.g., asfotase alia) according to the disclosure can result in one or more of an increase in bone healing in the patient and/or a change in bone mineral density that is undetectable or increased.

In any of the aspects disclosed herein, the patient exhibits tolerability to administration of the sALP (such as TNALP, for example the sALP polypeptide of SEQ ID NO: 1 or a polypeptide variant having at least 95% sequence identity to the sequence of SEQ ID NO: 1, e.g., asfotase alfa), such as a lack of or decreased incidence of adverse events selected from the group consisting of injection site erythema, decrease in hemoglobin, pyrexia, pneumonia, upper respiratory tract infection, otitis media, vomiting, constipation, diarrhea, tooth loss, nasopharyngitis, rash, dental carries, and irritability.

In any of the aspects disclosed herein, the sALP (such as TNALP, for example the sALP polypeptide of SEQ ID NO: 1 or a polypeptide variant having at least 95% sequence identity to the sequence of SEQ ID NO: 1, e.g., asfotase alfa) is formulated in a pharmaceutical composition, with at least one pharmaceutically acceptable carrier, such as saline (e.g., sodium chloride and sodium phosphate). For example, the at least one pharmaceutically acceptable carrier can include 150 mM sodium chloride and 25 mM sodium phosphate.

In any of the above aspects, the sALP (such as TNALP, for example the sALP polypeptide of SEQ ID NO: 1 or a polypeptide variant having at least 95% sequence identity to the sequence of SEQ ID NO: 1, e.g., asfotase alfa) is physiologically active toward PEA, PPi, and PLP, catalytically competent to improve skeletal mineralization in bone, and/or is the soluble extracellular domain of an alkaline phosphatase.

Formulations

The pharmaceutical compositions including sALPs (such as TNALP, for example the sALP polypeptide of SEQ ID NO: 1 or a polypeptide variant having at least 95% sequence identity to the sequence of SEQ ID NO: 1, e.g., asfotase alfa) can be formulated according to standard methods. Pharmaceutical formulation is a well-established art, and is further described in, e.g., Gennaro (2000) *Remington: The Science and Practice of Pharmacy,* 20th Edition, Lippincott, Williams & Wilkins (ISBN: 0683306472); Ansel at al. (1999) *Pharmaceutical Dosage Forms and Drug Delivery Systems,* 7th Edition, Lippincott Williams & Wilkins Publishers (ISBN: 0683305727); and Kibbe (2000) *Handbook of Pharmaceutical Excepients,* American Pharmaceutical Association, 3rd Edition (ISBN: 091733098X). For instance, a sALP composition (such as TNALP, for example the sALP polypeptide of SEQ ID NO: 1 or a polypeptide variant having at least 95% sequence identity to the sequence of SEQ ID NO: 1, e.g., asfotase alfa) can be formulated, for example, as a buffered solution at a suitable concentration and suitable for storage at 2-8° C. (e.g., 4° C.). A composition can also be formulated for storage at a temperature below 0° C. (e.g., −20° C. or −80° C.). A composition can further be formulated for storage for up to 2 years (e.g., one month, two months, three months, four months, five months, six months, seven months, eight months, nine months, 10 months, 11 months, 1 year, 1% years, or 2 years) at 2-8° C. (e.g., 4° C.). Thus, the compositions described herein can be stable in storage for at least 1 year at 2-8° C. (e.g., 4° C.).

The pharmaceutical compositions including sALPs (such as TNALP, for example the sALP polypeptide of SEQ ID NO: 1 or a polypeptide variant having at least 95% sequence identity to the sequence of SEQ ID NO: 1, e.g., asfotase alfa) can be in a variety of forms. These forms include, e.g., liquid, semi-solid and solid dosage forms, such as liquid solutions (e.g., injectable and infusible solutions), dispersions or suspensions, tablets, pills, powders, liposomes and suppositories. The preferred form depends, in part, on the intended mode of administration and therapeutic application.

For example, compositions intended for systemic or local delivery can be in the form of injectable or infusible solutions. Accordingly, the compositions including sALPs (such as TNALP, for example the sALP polypeptide of SEQ ID NO: 1 or a polypeptide variant having at least 95% sequence identity to the sequence of SEQ ID NO: 1, e.g., asfotase alfa) can be formulated for administration by a parenteral mode (e.g., subcutaneous, intravenous, intraperitoneal, or intramuscular injection).

The pharmaceutical compositions including sALPs (such as TNALP, for example the sALP fusion polypeptide of SEQ ID NO: 1 or a polypeptide variant having at least 95% sequence identity to the sequence of SEQ ID NO: 1, e.g., asfotase alfa) can be formulated as a solution, microemulsion, dispersion, liposome, or other ordered structure suitable for stable storage at high concentration. Sterile injectable solutions can be prepared by incorporating a composition described herein in the required amount in an appropriate solvent with one or a combination of ingredients enumerated above, as required, followed by filter sterilization. Generally, dispersions are prepared by incorporating a composition described herein into a sterile vehicle that contains a basic dispersion medium and the required other ingredients from those enumerated above. In the case of sterile powders for the preparation of sterile injectable solutions, methods for preparation include vacuum drying and freeze-drying that yield a powder of a composition described herein plus any additional desired ingredient (see herein) from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition a reagent that delays absorption, for example, monostearate salts, and gelatin.

The pharmaceutical compositions described herein can also be formulated in immunoliposome compositions. Such formulations can be prepared by methods known in the art such as, e.g., the methods described in Epstein et al. (1985) *Proc Natl Aced Sci USA* 82:3688; Hwang et al. (1980) *Proc*

*Natl Acad Sci USA* 77:4030; and U.S. Pat. Nos. 4,485,045 and 4,544,545. Liposomes with enhanced circulation time are disclosed in, e.g., U.S. Pat. No. 5,013,556.

Pharmaceutical compositions including sALPs (such as TNALP, for example the sALP polypeptide of SEQ ID NO: 1 or a polypeptide variant having at least 95% sequence identity to the sequence of SEQ ID NO: 1, e.g., asfotase alfa) can also be formulated with a carrier that will protect the composition (e.g., a sALP polypeptide or sALP fusion polypeptide) against rapid release, such as a controlled release formulation, including Implants and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are known in the art. See, e.g., J. R. Robinson (1978) *Sustained and Controlled Release Drug Delivery Systems*, Marcel Dekker, Inc., New York.

When compostons are to be used in combination with a second active agent, the compositions can be co-formulated with the second agent, or the compositions can be formulated separately from the second agent formulation. For example, the respective pharmaceutical compositions can be mixed, e.g., just prior to administration, and administered together or can be administered separately, e.g., at the same or different times.

Carriers/Vehicles

Preparations containing a sALP (such as TNALP, for example the sALP polypeptide of SEQ ID NO: 1 or a polypeptide variant having at least 95% sequence identity to the sequence of SEQ ID NO: 1, e.g., asfotase alfa) can be provided to a patient, such as a patient having at least one symptom of a bone mineralization disorder (e.g., HPP) in combination with pharmaceutically acceptable sterile aqueous or non-aqueous solvents, suspensions or emulsions. Examples of non-aqueous solvents are propylene glycol, polyethylene glycol, vegetable oil, fish oil, and injectable organic esters. Aqueous carriers include water, water-alcohol solutions, emulsions or suspensions, including saline and buffered medical parenteral vehicles including sodium chloride solution, Ringers dextrose solution, dextrose plus sodium chloride solution, Ringer's solution containing lactose, or fixed oils. For example, the pharmaceutically acceptable carrier can include sodium chloride and/or sodium phosphate, in which the composition includes, e.g., about 150 mM sodium chloride and/or about 25 mM sodium phosphate, pH 7.4.

Intravenous vehicles can include fluid and nutrient replenishers, electrolyte replenishers, such as those based upon Ringers dextrose, and the like. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, can be present in such vehicles. A thorough discussion of pharmaceutically acceptable carriers is available in *Remington's Pharmaceutical Sciences* (Mack Pub. Co., N.J. 1991).

Timing of Treatment Phase

The methods described herein include administering a sALP therapy during a treatment regimen that may contain a treatment phase (e.g., one or more treatment phases), which involves administering a sALP to a subject in need thereof, and a non-treatment phase (e.g., one or more non-treatment phases), in which sALP administration is discontinued. For example, a subject may be administered a sALP during a first treatment phase that lasts at least 1 day, 2 days, 3 days, 4 days, 5 days, 6 days, 7 days, 2 weeks, 3 weeks, 4 weeks, 2 months, 3 months, 4 months, 5 months, 6 months, 12 months, 2 years, 3 years, 4 years, 5 years, 6 years, 7 years, 8 years, 9 years, 10 years, or longer. During the first treatment phase, the subject may be administered the sALP, e.g., one or more times per day, week, month, or year.

Periodically, during the first treatment phase, the subject may be monitored with at least one biochemical, physical, quality of life, or bone metric, e.g., as described herein. When the measured value of the metric reaches a predetermined threshold (e.g., an Improvement by at least about 1%, 2%, 3%, 4%, 5%, 10%, 20%, 30%, 40%, 50%, or more, or an improvement to, e.g., 10%, 20%, 30%, 40%, 50%, 60%, 70%, 80%, 90%, 95%, 97%, 99%, or 100% of the corresponding value of a normal subject), then it may be determined that the subject can discontinue therapy and can enter a non-treatment phase of the treatment regimen. The non-treatment phase may last at least 1 day, 2 days, 3 days, 4 days, 5 days, 6 days, 7 days, 2 weeks, 3 weeks, 4 weeks, 2 months, 3 months, 4 months, 5 months, 6 months, 12 months, 2 years, 3 years, 4 years, 5 years, 6 years, 7 years, 8 years, 9 years, 10 years, or longer.

Periodically, during the non-treatment phase, the subject may be monitored with at least one biochemical, physical, quality of Ife, or bone metric, e.g., as described herein. When the measured value of the metric decreases to or below the predetermined threshold (e.g., an decrease by 1%, 2%, 3%, 4%, 5%, 10%, 20%, 30%, 40%, 50%, or more, or a decrease to, e.g., 90%, 80%, 70%, 60%, 50% or less, of the corresponding value of a normal subject), then it may be determined that the subject should re-enter a treatment phase of the treatment regimen, in which a sALP is again administered. If the subject does not decrease below the predetermined threshold, then the subject may remain in the non-treatment phase of the treatment regimen. It will be understood that the length of time of each treatment or non-treatment phase can vary for any given patient depending on a variety of factors, such as the metric and/or predetermined threshold used. Thus, the length of the phases may be determined empirically and may be different or the same from each other. For example, a first treatment phase may be longer or shorter than a second treatment phase.

EXAMPLES

The following examples are intended as illustration only, are not meant to limit the disclosure in any way.

Example 1. Dose-Ranging Clinical Study in Adults

Asfotase alfa was administered at 3.5 mg/kg in a dose ranging study that included 8 adolescent patients and 13 adult patients with HPP aged ≥13 to ≤65 years at study entry. Thirteen patients were randomized to receive asfotase alfa (7 patients to receive 2.1 mg/kg/qw and 8 patients to receive 3.5 mg/kg/qw) and 8 were randomized to the untreated control group. All patients in the combined treatment group (2.1 mg/kg/qw and 3.5 mg/kg/qw) experienced an approximately 2 fold greater decrease in plasma PPi levels compared with the control group after 24 weeks of treatment (mean change of −2.100 µM versus −1.052 µM in control patients); however, this difference was not statistically significant (p=0.0715) because a control patient who received a high dose of vitamin D and had an elevated Baseline PPi value (12.1 µM) experienced a decrease in plasma PPi. When this patient was excluded from the Full Analysis Set (FAS), statistical significance was demonstrated (p=0.0044). After the initial 24 weeks of treatment, all patients received a total weekly dose of 3.5 mg/kg for an additional 24 weeks. The mean (SD) change in plasma PPi from Baseline to the last overall exposure for al patients at a dose of 3.5 mg/kg/qw was −1.859 µM (2.8071).

Of the 13 patients who received asfotase alfa, 10 patients were adults (the majority [76.9%] aged >50 years). Adult patients (n=5) who received a total weekly dose of 3.5 mg/kg exhibited a decrease in plasma PPi levels after 24 weeks of treatment (mean change of −2.258 µM). Asfotase alfa was generally well tolerated by all 19 patients during this study.

Example 2. Clinical Study in Adults with Functional Impairments

Hypophosphatasia presents a wide spectrum of clinical manifestations in adults. Adult patients with HPP are often misdiagnosed for many years, yet accurate diagnosis of HPP is crucial for appropriate treatment (Hogler et al. *BMC Musculoskelet Disord.* 20:80, 2019). As a result, inappropriate therapies (e.g., high-dose vitamin D, excessive calcium supplementation, parathyroid hormone analogs, and (bisphosphonates) may be ineffective or even worsen clinical conditions and signs and symptoms (Conti et al. *Clin Cases Miner Bone Metab.* 14:230-234, 2017). In addition, severe functional impairments are often present in patients with HPP, including mobility problems (ambulation and gait impairments), muscle weakness, and inability to carry out ADLs, altogether affecting patients' quality of life. Long-term clinical sequelae include recurrent and nonhealing fractures, orthopedic/dental surgical burden, weakness, arthritis, the inability to remove internal fixation devices (due to the risk of recurrent fracture), pain, and the requirement for ambulatory assistive devices (e.g., wheelchairs, wheeled walkers, and canes) (Kishnani et al. Annual Meeting of the Endocrine Society; 2019; New Orleans). Regardless of the age when HPP first manifests, a high burden of disease could lead to a decrease in health-related quality of Ife, which can further decrease over a patient's lifetime (Szabo et al. *Orphanet J Rare Dis.* 14:85, 2019; Weber et al. *Metab.: clin. and exper.* 85(10):1522-1530, 2016). Signs and/or symptoms of HPP may also affect mental and emotional health in children and adults with the disease, which has been associated with considerable healthcare resource utilization (Colazo J M, Hu J R, Dahir K M, Simmons J H. Neurological symptoms in Hypophosphatasia. Osteoporos Int. 2019; 30(2):469-480; Jenkins-Jones et al. *Annual Meeting of the Amer. Soc. Bone and Mineral Res.;* 2018; Montréal, QC, Canada).

In adult patients with a high disease burden (i.e., pediatric-onset HPP with delayed diagnosis), multiple lower extremity fractures are often reported (typically femoral or metatarsal fractures or pseudofractures; uni-/bilateral, in the lateral or medial subtrochanteric diaphysis) with poor healing that can cause severe aching, tenderness, limited mobility, and poor quality of Ife (Genest et al. *Osteoporos Int.* 29:1815-1825, 2018; Marini et al. *Clin Cases Miner Bone Metab.* 14:324-328, 2017. Patients have also reported chronic muscle pain, reduced muscular strength and performance related to muscle weakness, and bone pain without fractures (Conti et al. *Clin Cases Miner Bone Metab.* 14:230-234, 2017).

Up until now, most of the attention has been dedicated to diagnosing and treating pediatric patients. In fact, there is a significant gap in functional outcomes data in adult patients including those with pediatric-onset HPP, who most likely did not receive any diagnosis until significant complications occurred or were not deemed appropriate for an ERT such as asfotase alfa. This study will provide additional data on the effect of asfotase alfa in adult patients with pediatric-onset HPP who present with significant physical functional limitations due to their disease. This study will also explore the effects of a lower dosage regimen of asfotase alfa following a loading dosage regimen of 6 mg/kg/gw.

TABLE 3

| Objectives and Endpoints | |
|---|---|
| Objectives | Endpoints |
| Primary (evaluate in patients in Group 1 [patients administered asfotase alfa 6 mg/kg/qw for a total of 36 weeks] ONLY) | |
| Evaluate the effect of asfotase alfa on plasma concentrations of PPi at Week 36 | Change from Baseline to Week 36 in plasma concentrations of PPi |
| Key Secondary (evaluate in patients in Group 1 [patients administered asfotase alfa 6 mg/kg/qw for a total of 36 weeks]] or Group 2 [patients administered asfotase alfa 6 mg/kg/qw for 12 weeks followed by 3.6 mg/kg/qw for 24 weeks] as indicated) | |
| Evaluate the effect of asfotase alfa on the plasma concentrations of PPi in Group 2 at Week 36 | Change from Baseline to Week 36 in plasma concentrations of PPi in Group 2 |
| Evaluate the effect of asfotase alfa on the SF-36 PCS score in Groups 1 and 2 at Week 36 | Change from Baseline to Week 36 in the SF-36 PCS score in Groups 1 and 2 |
| Evaluate the effect of asfotase alfa on the repeated chair stand test (a component of the SPPB) in Groups 1 and 2 at Week 36 | Change from Baseline to Week 36 in the repeated chair stand test (a component of the SPPB) in Groups 1 and 2 |
| Other Secondary (evaluate in patients in Group 1 [patients administered asfotase alfa 6 mg/kg/qw fora total of 36 weeks]] or Group 2 [patients administered asfotase alfa 6 mg/kg/qw for 12 weeks followed by 3.6 mg/kg/qw for 24 weeks] as indicated) | |
| Evaluate the effect of asfotase alfa on the physical function and pain in Groups 1 and 2 at Week 36 | Change from Baseline to Week 36 in Groups 1 and 2 in the following: TUG test BPI - Question 3 (Worst Pain) score LEFS score |
| Evaluate the effect of asfotase alfa on the repeated chair stand test (a component of the SPPB) in Groups 1 and 2 at Week 24 | Change from Baseline to Week 24 in the repeated chair stand test (a component of the SPPB) in Groups 1 and 2 |
| Evaluate the effect of asfotase alfa on the SF-36 PCS score in Groups 1 and 2 at Week 24 | Change from Baseline to Week 24 in the SF-36 PCS score in Groups 1 and 2 |
| Safety (evaluate in all patients) | |
| Evaluate the safety, tolerability, and immunogenicity-potential of asfotase alfa for up to 36 weeks | Incidence of TEAEs, TESAEs, and AESIs (IARs, including hypersensitivity reactions and ISRs); lipodystrophy; ectopic calcification; immunogenicity (e.g., ADA results); physical examination; vital signs findings; and clinical laboratory results |
| Exploratory (evaluate in patients in Group 1 [patients administered asfotase alfa 6 mg/kg/qw for a total of 36 weeks]] or Group 2 [patients administered asfotase alfa 6 mg/kg/qw for 12 weeks followed by 3.6 mg/kg/qw for 24 weeks] as indicated) | |
| Evaluate the serum activity of asfotase alfa in Groups 1 and 2 at Weeks 12, 24, and 36 | Change from Baseline to Weeks 12, 24, and 36 in the serum activity of asfotase alfa in Groups 1 and 2 |
| Evaluate the effect of asfotase alfa on the plasma levels of PL and PLP in Groups 1 and 2 at Weeks 12, 24, and 36 | Change from Baseline to Weeks 12, 24, and 36 in the ratio of PLP to PL in Groups 1 and 2 |
| Evaluate the effect of asfotase alfa on the plasma concentrations of PPi in Groups 1 and 2 at Week 12 | Change from Baseline to Week 12 in plasma levels of PPi in Groups 1 and 2 |
| Evaluate the effect of asfotase alfa on the repeated chair stand test (a component of the SPPB) in Groups 1 and 2 at Week 12 | Change from Baseline to Week 12 in the repeated chair stand test (a component of the SPPB) in Groups 1 and 2 |
| Evaluate the effect of asfotase alfa on the SF-36 PCS score in Groups 1 and 2 at Week 12 | Change from Baseline to Week 12 in the SF-36 PCS score in Groups 1 and 2 |
| Evaluate the effect of asfotase alfa on physical function and pain in Groups 1 and 2 at Weeks 12 and 24 | Change from Baseline to Week 12 and Week 24 in Groups 1 and 2 in the following: TUG test BPI - Question 3 (Worst Pain) score LEFS score |
| Assess the effect of asfotase alfa on bone quality/microarchitecture in Groups 1 and 2 at Week 36 | Change from Baseline to Week 36 in HR-pQCT (total, trabecular, and cortical volumetric BMD, cortical thickness, stiffness, trabecular number, trabecular separation, and trabecular thickness) |
| Assess the effect of asfotase alfa on markers of bone turnover in Groups 1 and 2 at Weeks 12 and 36 | Change from Baseline to Weeks 12 and 36 in osteocalcin, P1NP, and sCTX in Groups 1 and 2 |
| Assess the effect of asfotase alfa on health-related quality of life in Groups 1 and 2 at Weeks 12, 24, and 36 | Change from Baseline to Weeks 12, 24, and 36 in the SF-36 total score in Groups 1 and 2 |

TABLE 3-continued

| Objectives and Endpoints | |
| --- | --- |
| Objectives | Endpoints |
| Evaluate the proportion of healed fractures or pseudofractures in patients with delayed healing[a] of fractures or pseudofractures of the lower extremity(ies) in Groups 1 and 2 at Week 36 | Proportion of healed fractures by X-ray evaluation in patients with delayed healing of active fractures or pseudofractures at Week 36 in Groups 1 and 2 |
| Evaluate time to fracture healing in patients with delayed healing[a] of fractures or pseudofractures of the lower extremity(ies) in Groups 1 and 2 at Weeks 12, 24, and 36 | Time to union/healing of fracture by X-ray evaluation at Weeks 12, 24, and 36 in Groups 1 and 2 |
| Assess the effect of asfotase alfa on PGI-I in Groups 1 and 2 at Week 36 | In Groups 1 and 2: PGI-I score at Week 36 Proportion of patients who reported a status of "very much better" and "much better" at Week 36 in the PGI-I questionnaire |

[a]Delayed healing is defined as an active fracture or pseudofracture without evidence of healing for at least 3 months prior to screening Abbreviations:

ADA = antidrug antibody;

AESI = adverse event of special interest;

BMD = bone mineral density;

BPI = Brief Pain Inventory;

HR-pQCT = high-resolution peripheral quantitative computed tomography;

IAR = injection-associated reaction;

ISR = injection-site reaction;

LEFS = Lower Extremity Functional Scale;

P1NP = N-terminal propeptide of type I procollagen;

PCS = Physical Component Summary;

PGI-I = Patients' Global Impression of Improvement;

PL = pyridoxal;

PLP = pyridoxal 5'-phosphate;

PPi = inorganic pyrophosphate;

qw = every week;

sCTX = serum C-telopeptide cross-link of type 1 collagen;

SF-36 = 36-item Short-Form survey;

SPPB = Short Physical Performance Battery;

TEAE = treatment-emergent adverse event;

TESAE = treatment-emergent serious adverse event;

TUG = timed up-and-go.

Overall Design:

Eligible patients will be randomly assigned in a 1:1 ratio to either Group 1 (n=25) or Group 2 (n=25). All patients will begin dosing with asfotase alfa 6 mg/kg/qw at Week 1. At Week 13, patients in Group 1 will continue to receive asfotase alfa 6 mg/kg/qw for 24 weeks and patients in Group 2 will begin dosing with asfotase alfa 3.6 mg/kg/qw for 24 weeks. Specific dosing timepoints will be provided in the Study Operations Manual. Approximately 36 (75%) patients are expected to complete the study.

Number of Patients:

Approximately 50 patients will be randomized (25 patients to Group 1 and 25 patients to Group 2) across multiple geographic regions.

Treatment Groups and Duration:

Asfotase alfa will be suppled as a sterile, aqueous solution in an 80-mg vial (100 mg/mL) dosage strength and will be administered subcutaneously for a total weekly dose of 6 mg/kg (2 mg/kg 3 times per week) or a total weekly dose of 3.6 mg/kg (1.2 mg/kg 3 times per week). If more frequent dosing is indicated (e.g., based on weight or tolerability issues due to an injection-associated reaction or injection site reaction), the patient may transition to a 6 times per week dosing schedule.

The total duration of the study is anticipated to be approximately 50 weeks: an up to 10-week Screening Period, a 38-week Treatment Period, and a 30-day follow-up telephone call.

Schema

The flow diagram for the study design is illustrated in FIG. 1.

TABLE 4

| Schedule of Activities | | | | | | | | | | | | | | | |
|---|---|---|---|---|---|---|---|---|---|---|---|---|---|---|---|
| | Screening Period | Base-line Period | Treatment Period | | | | | | | | | | | | Follow-up[3] |
| Visit location | In Clinic | In Clinic | In Clinic | Remote | In Clinic | Remote | In Clinic | Remote Visit[1] | In Clinic | Remote | In Clinic | Remote | In Clinic | In Clinic | Remote |
| | 1 | 2 | 3 | 4-9 | 10 | 11-13 | 14 | 15-21 | 22 | 23-25 | 26 | 27-37 | 38[2] | ET | 39/EOS |
| Week(s) | -10 to -1 | 0 | 1 | 2-7 | 8 | 9-11 | 12 | 13-19 | 20 | 21-23 | 24 | 25-35 | 36 | NA | 40 |
| Windows (in days) | NA | ±7 | ±7 | NA | ±7 | NA | ±7 | NA | ±7 | NA | ±7 | NA | ±7 | NA | NA |
| Eligibility | | | | | | | | | | | | | | | |
| Informed consent | X | | | | | | | | | | | | | | |
| Inclusion/exclusion | X | X | | | | | | | | | | | | | |
| Screening laboratory tests | X | | | | | | | | | | | | | | |
| Medical history[4] | X | | | | | | | | | | | | | | |
| Demographics[5] | X | | | | | | | | | | | | | | |
| HPP diagnosis[6] | X | | | | | | | | | | | | | | |
| HPP gene mutation analysis[7] | X | | | | | | | | | | | | | | |
| Renal impairment (eGFR) | X | | | | | | | | | | | | | | |
| Randomization | | | | | | | | | | | | | | | |
| Randomization | | X | | | | | | | | | | | | | |
| Study Administrative | | | | | | | | | | | | | | | |
| Physical examination[8] | X | X | | | X | | X | | | | X | | X | X | |
| Vital signs[9] | X | X | X | | X | | X | | X | | X | | X | X | |
| Body weight[10] | X | X | X | | X | | X | | X | | X | | X | X | |
| Serum pregnancy test[11] | X | X | X | | X | | X | | X | | X | | X | X | |
| Urine pregnancy test[11] | | | | X | | | | X | | | | X | | | |
| Administration of Study Drug[12] | | | | | | | | | | | | | | | |
| Asfotase alfa | | | X | X | X | X | X | X | X | X | X | X | X | X | |
| Safety Assessments/Laboratory Analyses[13] | | | | | | | | | | | | | | | |
| Radiographic imaging[14] | X | X | | | | | X | | | | X | | X | X | |
| Chemistry[15] | X | X | | | X | | X | | | | X | | X | X | |
| 25-hydroxy vitamin D | X | X | | | | | X | | | | X | | X | X | |
| Ophthalmological examination[16] | | X | | | | | X | | | | | | X | X | |
| Renal ultrasound | | X | | | | | X | | | | | | X | X | |
| PTH | X | X | | | | | X | | | | | | X | X | |
| HR-pQCT[17] | | X | | | | | | | | | | | X | X | |
| Tryptase for serious IAR[18] | | | X | X | X | X | X | X | X | X | X | X | X | X | |
| Adverse event review and evaluation | | | | | | <<monitor continuously>> | | | | | | | | | |
| Biomarker Analyses | | | | | | | | | | | | | | | |
| Bone turnover marker analyses (osteocalcin, P1NP, sCTX) | | X | | | | | X | | | | | | X | X | |
| PK/PD/ADA Analyses[19] | | | | | | | | | | | | | | | |
| PD (PPi, PL, and PLP) | | X | | | X | | X | | X | | X | | X | X | |
| PK | | X | | | X | | X | | X | | X | | X | X | |
| ADA | | X | | | X | | X | | X | | X | | X | X | |

TABLE 4-continued

Schedule of Activities

| | Screening Period | Base-line Period | | | | | Treatment Period | | | | | | | | Follow-up[3] |
|---|---|---|---|---|---|---|---|---|---|---|---|---|---|---|---|
| | | | | | | | Visit location | | | | | | | | |
| | In Clinic | In Clinic | In Clinic | Remote | In Clinic | Remote | In Clinic | Remote Visit[1] | In Clinic | Remote | In Clinic | Remote | In Clinic | In Clinic | Remote |
| | 1 | 2 | 3 | 4-9 | 10 | 11-13 | 14 | 15-21 | 22 | 23-25 | 26 | 27-37 | 38[2] | ET | 39/EOS |
| | | | | | | | | Week(s) | | | | | | | |
| | -10 to -1 | 0 | 1 | 2-7 | 8 | 9-11 | 12 | 13-19 | 20 | 21-23 | 24 | 25-35 | 36 | NA | 40 |
| | | | | | | | | Windows (in days) | | | | | | | |
| | NA | ±7 | ±7 | NA | ±7 | NA | ±7 | NA | ±7 | NA | ±7 | NA | ±7 | NA | NA |
| Outcomes Assessments | | | | | | | | | | | | | | | |
| BPI | | X | | | | | X | | | | X | | X | X | |
| SF-36 | | X | | | | | X | | | | X | | X | X | |
| SPPB | | X | | | | | X | | | | X | | X | X | |
| TUG test | | X | | | | | X | | | | X | | X | X | |
| LEFS | | X | | | | | X | | | | X | | X | X | |
| PGI-I | | | | | | | | | | | | | X | X | |
| Other | | | | | | | | | | | | | | | |
| 30-day phone call | | | | | | | | | | | | | | | X |
| Concomitant medication/ nonpharmacologic therapies and procedures review | | | | | | | <<monitor continuously>> | | | | | | | | |
| Use of assistive devices review | | | | | | | <<monitor continuously>> | | | | | | | | |
| Patient diaries | | | | | | | <<monitor continuously>> | | | | | | | | |

Abbreviations:
ADA = antidrug antibody;
ALP = alkaline phosphatase;
BPI = Brief Pain Inventory;
eGFR = estimated glomerular filtration rate;
EOS = end-of-study;
ET = early termination;
HPP = hypophosphatasia;
HR-pQCT = high-resolution peripheral quantitative computed tomography;
IAR = injection-associated reaction;
LEFS = Lower Extremity Functional Scale;
NA = not applicable;
P1NP = N-terminal propeptide of type I procollagen;
PD = pharmacodynamic;
PGI-I = Patient's Global Impression of Improvement;
PK = pharmacokinetic;
PL = pyridoxal;
PLP = pyridoxal 5'-phosphate;
PPi = inorganic pyrophosphate;
PTH = parathyroid hormone;
sCTX = serum C-telopeptide cross-link of Type 1 Collagen;
SF-36 = 36-item Short-Form survey;
SPPB = Short Physical Performance Battery;
TUG = timed up-and-go;
ULN = upper limit of normal.
[1]Visits will be conducted at the investigational site with certain visits being a patient dosing at home.
[2]If a patient discontinues from the study prior to Week 36, all assessments at this visit should be conducted if possible, with the exception of study drug administration. To facilitate scheduling of required study assessments at each visit, the study visit may be shortened or prolonged, as necessary, as long as the specified order of assessments pertaining to laboratory sampling (e.g., PK/PD/ADA, serum pregnancy) and vital signs evaluation are followed. Order of assessments will be specified in the Study Operations Manual.
[3]The follow-up telephone call will occur 30 days after the last dose of study drug (Week 36). For patients who discontinue from the study prior to Week 36, the 30-day follow-up telephone call should be conducted (unless the patient withdraws consent to participate in the study). Female patients of childbearing potential will be followed for birth control and pregnancy information. Any reported pregnancies in female patients or female partners of male patients will be followed until the outcome of the pregnancy is known.
[4]Medical history includes general medical history and HPP-specific medical history, including details of pediatric-onset disease. Details of loss of adult teeth will be assessed as part of medical history. Complete medical history will be collected at Baseline and patients will be queried to determine if there is any change to medical history since the previous visit at subsequent in-clinic study visits.
[5]Demographics will be collected as permitted by region and may include date of birth, age, sex, ethnicity, and race.
[6]Clinical diagnosis of pediatric-onset HPP based on signs and symptoms consistent with HPP, confirmed by the following:
a. Documented ALPL gene mutation(s) from a certified laboratory;
b. Serum ALP level below the age- and sex-adjusted normal range, and a PLP greater than 2 × ULN, at screening.

TABLE 4-continued

Schedule of Activities

| | | | | | | | Treatment Period | | | | | | | Follow-up[3] |
|---|---|---|---|---|---|---|---|---|---|---|---|---|---|---|
| Screening Period | Baseline Period | | | | | | | | | | | | | |
| | | | | | | | Visit location | | | | | | | |
| In Clinic | In Clinic | In Clinic | Remote | In Clinic | Remote | In Clinic | Remote Visit[1] | In Clinic | Remote | In Clinic | Remote | In Clinic | In Clinic | Remote |
| 1 | 2 | 3 | 4-9 | 10 | 11-13 | 14 | 15-21 | 22 | 23-25 | 26 | 27-37 | 38[2] | ET | 39/EOS |
| | | | | | | | Week(s) | | | | | | | |
| -10 to -1 | 0 | 1 | 2-7 | 8 | 9-11 | 12 | 13-19 | 20 | 21-23 | 24 | 25-35 | 36 | NA | 40 |
| | | | | | | | Windows (in days) | | | | | | | |
| NA | ±7 | ±7 | NA | ±7 | NA | ±7 | NA | ±7 | NA | ±7 | NA | ±7 | NA | NA |

[7]If the results of HPP gene mutation analysis are not already available in the patient's medical records, it should be performed within the first 2 weeks of the Screening Period.
[8]Physical examination will include assessment of general appearance; skin; head, ear, eye, nose, and throat; neck; lymph nodes; chest; heart; abdominal cavity; limbs; central nervous system; musculoskeletal. At the Screening and Baseline Visits, a complete physical examination will be performed. At timepoints specified in Schedule of Activities (Table 4), abbreviated physical examinations (based on the patient's signs and symptoms) will be performed. All physical examinations (complete and abbreviated) will include weight (using a calibrated scale) and examination of asfotase alfa injection sites for potential injection-site reaction(s). The Screening and Baseline Visit physical examinations will also include an assessment of height.
[9]Vital signs include blood pressure, heart rate, respiratory rate, and temperature (whether temporal, oral, or axillary). On dosing days in the clinic, vital signs should be taken within 10 minutes before study drug injection. Please ensure that the method of obtaining the patient's temperature is consistent throughout the study.
[10]On dosing days in the clinic, body weight measurement will be required prior to dosing to confirm correct dose.
[11]Urine and serum pregnancy testing are required for female patients of childbearing potential only. Serum pregnancy testing is required at the timepoints specified in Schedule of Activities (Table 4) and will be conducted during in-clinic study visits. Urine pregnancy testing, obtained at timepoints specified in schedule of activities, will be conducted by patients at home.
[12]Study drug will be administered in clinic at timepoints specified in the Schedule of Activities (Table 4). All other dosing may occur in the clinic or at home at the discretion of the Investigator.
[13]All blood samples for clinical chemistry laboratory assessments must be collected prior to study drug administration.
[14]All patients will have had an X-ray to assess for fracture(s) or pseudofracture(s) of the lower extremit(ies) during the Screening Period. During the study, X-rays are only required for patients with documented fracture(s) or pseudofracture(s) at randomization or patients with suspected new fracture(s) during study conduct.
[15]List of parameters included under clinical chemistry described below.
[16]A full ophthalmological examination will be performed at the timepoints specified in the Schedule of Activities. The examination will assess for papilledema and signs of ectopic calcification and will include assessments of visual acuity; adnexa; and slit-lamp biomicroscopy with examination of anterior chamber, lens, conjunctiva, cornea, and fundus. The ophthalmological examination should be performed by a blinded qualified ophthalmologist. Sites will be provided ophthalmologic worksheets required to complete the full exam. Ophthalmology exams may be performed by a qualified optometrist (e.g., Doctor of Optometry) as long as the optometrist works under the supervision of an ophthalmologist.
[17]High-resolution peripheral quantitative computed tomography will be available to all the patients. If patients are willing and able to undergo this imaging assessment, their travel will be arranged to the investigational sites that have the capability for this diagnostic imaging. Also, if an HR-pQCT was performed for a patient within 3 months of the Screening Visit, it may be considered as a baseline assessment.
[18]Serum sample for tryptase will be collected predose on Day 1. Samples will be drawn only if the patient has no active allergies at the time and will only be analyzed if the patient experiences a subsequent IAR. For acute or severe IARs (e.g., with signs and symptoms of hypersensitivity, irrespective of the time from administration of study drug to onset), additional blood and urine samples must be collected to assess the reaction as described herein. For systemic hypersensitivity reactions, additional blood and urine samples must be collected to assess the reaction.
[19]Serum sample for PK/PD/ADA analysis must be obtained 15 to 30 minutes prior to asfotase alfa dosing.

The administration of asfotase alfa according to the treatment regimen described herein is anticipated to significantly benefit adult patients with pediatric-onset HPP with functional impairments due to chronic disease.

Scientific Rationale for Study Design

The scientific rationale for each aspect of the study design is discussed below.

This study is being conducted in adult patients with pediatric-onset HPP with high disease burden (confirmed via specific inclusion criteria), a population for which there is a paucity of functional outcomes data.

Asfotase alfa 6 mg/kg is the label-recommended dose that has an established efficacy and safety profile.

Asfotase alfa 3.6 mg/kg is similar to a dose (3.5 mg/kg) evaluated in a dose-ranging study that included 6 adolescent patients and 13 adult patients with HPP aged ≥13 to ≤65 years at study entry. In this study, the 3.6 mg/kg dose will be evaluated in a larger cohort of adult patients with pediatric-onset HPP with a high disease burden (defined via specific inclusion criteria).

The functional assessments (e.g., 36-item Short-Form survey [SF-36] Physical Component Summary [PCS] and repeated chair stand test [a component of the Short Physical Performance Battery (SPPB)]) that will be used in this study are validated subjective and objective outcome measures that have been evaluated in conditions/diseases reported to impair functional mobility and affect ADLs (e.g., rheumatoid arthritis, osteoarthritis, chronic musculoskeletal pain, and X-linked hypophosphatemia).

The cutoff scores for the key secondary functional endpoints that are validated subjective and objective outcome measures (SF-36 PCS score <40 and repeated chair stand test [a component of the SPPB] time of >13 seconds) were determined based on a comprehensive review of cumulative data reported both in conditions/diseases noted to impair functional mobility or ADLs and in a healthy population.

Asfotase Alfa Dosing

Asfotase alfa 3.6 mg/kg/qw will be administered to patients in Group 2 for 24 weeks (from Week 13 through Week 36), after receiving 6.0 mg/kg/qw for the first 12 weeks. Dose reduction to 3.6 mg/kg/qw is anticipated to sustain reductions in plasma PPi levels from Week 13 through Week 36.

Asfotase alfa 3.5 mg/kg was administered daily in Study ENB-009-10 (e.g., 0.5 mg/kg 7 times per week). In this study, asfotase alfa 3.6 mg/kg was selected to allow for convenient dosing of 3 times per week (i.e., 1.2 mg/kg 3 times per week). It should be noted that there may be some instances when more frequent dosing (i.e., 6 times per week) is indicated.

Type of Patient and Disease Characteristics

Clinical diagnosis of pediatric-onset HPP based on signs and symptoms consistent with HPP, confirmed by the following:

Documented ALPL gene mutation(s) from a certified laboratory;

Serum alkaline phosphatase (ALP) level below the age- and sex-adjusted normal range, AND a pyridoxal 5'-phosphate (PLP) greater than 2×the upper limit of normal, at screening Body mass index <35 kg/m$^2$ at Baseline Functional impairment, as evidenced by a repeated chair stand test (a component of the SPPB) time of >13 seconds and a SF-36 PCS score <40 at screening. A maximum of 4 patients who are unable to complete the repeated chair stand test (a component of the SPPB) will be eligible for the study Patients must have a past medical history that includes at least 1 nonvertebral fracture (or pseudofracture) incurred without evidence of significant trauma Patients with current unhealed fracture(s) or pseudofracture(s) (e.g., femoral, tibial, fibular, metatarsal) of the lower extremity(ies) must have documentation of these fractures for at least 3 months duration prior to screening (with or without surgical intervention).

Study Drug(s) Administered

Asfotase alfa will be supplied as a sterile, aqueous solution in an 80-mg vial (100 mg/mL) dosage strength with an extractable volume of 0.8 mL. Additional details are provided in Table 5.

TABLE 5

| Study Drug Administered | |
|---|---|
| | Investigational Product |
| Product name: | Asfotase alfa |
| Dosage form: | Liquid |
| Unit dose: | Group 1: 6 mg/kg/qw for 36 weeks |
| | Group 2: 6 mg/kg/qw for 12 weeks, then 3.6 mg/kg/qw for 24 weeks |
| Route of administration: | SC |
| Physical description: | Clear to slightly opalescent, colorless to pale yellow, sterile aqueous solution at 100 mg/mL asfotase alfa, 25 mM sodium phosphate, 150 mM sodium chloride, pH 7.4 in a single-use glass vial |
| Manufacturer: | Alexion Pharmaceuticals, Inc. |

Abbreviations:

SC = subcutaneous;

qw = every week.

Study Drug Preparation and Administration

Patients randomized to Group 1 or Group 2 will commence with thrice weekly dosing. The number of vials used to prepare SC injections of asfotase alfa will be determined based on the patient's weight (Table 6 and Table 8).

If a patient who is receiving 6 mg/kg/qw weighs ≥90 kg, that patient must transition to a 6 times per week dosing schedule (Table 7). If more frequent dosing is indicated (e.g., based on weight or tolerability issues due to an IAR/ISR as assessed by the investigator), the patient must transition to a 6 times per week dosing schedule (Table 7 and Table 9). Additional dose adjustments may also be considered for lack of efficacy or safety-related reasons. The specified dose volume can be withdrawn from the drug product vial using a sterile disposable 1 mL syringe for injection. Study drug should be administered SC using aseptic technique.

TABLE 6

Weight-Based Dosing for Administration of Asfotase Alfa 6 mg/kg/week (2 mg/kg Three Times per Week)

| Body Weight (kg) | Dose to Inject (mg) | Volume to Inject (mL) | Vial Configuration |
|---|---|---|---|
| 40 | 80 | 0.80 | 80 mg/0.8 mL |
| 50 | 100 | 1.00 | Two (2) 80 mg/0.8 mL vials |
| 60 | 120 | 1.20$^a$ | Two (2) 80 mg/0.8 mL vials |
| 70 | 140 | 1.40$^a$ | Two (2) 80 mg/0.8 mL vials |
| 80 | 160 | 1.60$^a$ | Two (2) 80 mg/0.8 mL vials |

$^a$When preparing a volume for injection greater than 1 mL, split the volume equally between 2 syringes, and administer 2 injections at 2 separate injection sites about 1 inch (2.54 cm) apart.

TABLE 7

Weight-Based Dosing for Administration of Asfotase Alfa 6 mg/kg/week (1 mg/kg Six Times per Week)

| Body Weight (kg) | Dose to Inject (mg) | Volume to Inject (mL) | Vial Configuration |
|---|---|---|---|
| 40 | 40 | 0.40 | 80 mg/0.8 mL |
| 50 | 50 | 0.50 | 80 mg/0.8 mL |
| 60 | 60 | 0.60 | 80 mg/0.8 mL |
| 70 | 70 | 0.70 | 80 mg/0.8 mL |
| 80 | 80 | 0.80 | 80 mg/0.8 mL |
| 90 | 90 | 0.90 | Two (2) 80 mg/0.8 mL vials |
| 100 | 100 | 1.00 | Two (2) 80 mg/0.8 mL vials |
| 110 | 110 | 1.10$^a$ | Two (2) 80 mg/0.8 mL vials |
| 120 | 120 | 1.20$^a$ | Two (2) 80 mg/0.8 mL vials |
| 130 | 130 | 1.30$^a$ | Two (2) 80 mg/0.8 mL vials |

$^a$When preparing a volume for injection greater than 1 mL, split the volume equally between 2 syringes, and administer 2 injections at 2 separate injection sites about 1 inch (2.54 cm) apart.

TABLE 8

Weight-Based Dosing for Administration of Asfotase Alfa 3.6 mg/kg/week (1.2 mg/kg Three Times per Week)

| Body Weight (kg) | Dose to Inject (mg) | Volume to Inject (mL) | Vial Configuration |
|---|---|---|---|
| 40 | 48 | 0.48 | 80 mg/0.8 mL |
| 50 | 60 | 0.60 | 80 mg/0.8 mL |
| 60 | 72 | 0.72 | 80 mg/0.8 mL |
| 70 | 84 | 0.84 | Two (2) 80 mg/0.8 mL vials |
| 80 | 96 | 0.96 | Two (2) 80 mg/0.8 mL vials |
| 90 | 108 | 1.08$^a$ | Two (2) 80 mg/0.8 mL vials |
| 100 | 120 | 1.20$^a$ | Two (2) 80 mg/0.8 mL vials |
| 110 | 132 | 1.32$^a$ | Two (2) 80 mg/0.8 mL vials |
| 120 | 144 | 1.44$^a$ | Two (2) 80 mg/0.8 mL vials |
| 130 | 156 | 1.56$^a$ | Two (2) 80 mg/0.8 mL vials |

$^a$When preparing a volume for injection greater than 1 mL, split the volume equally between 2 syringes, and administer 2 injections at 2 separate injection sites about 1 inch (2.54 cm) apart.

TABLE 9

| Weight-Based Dosing for Administration of Asfotase Alfa 3.6 mg/kg/week (0.6 mg/kg Six Times per Week) | | | |
|---|---|---|---|
| Body Weight (kg) | Dose to Inject (mg) | Volume to Inject (mL) | Vial Configuration |
| 40 | 24 | 0.24 | 80 mg/0.8 mL |
| 50 | 30 | 0.30 | 80 mg/0.8 mL |
| 60 | 36 | 0.36 | 80 mg/0.8 mL |
| 70 | 42 | 0.42 | 80 mg/0.8 mL |
| 80 | 48 | 0.48 | 80 mg/0.8 mL |
| 90 | 54 | 0.54 | 80 mg/0.8 mL |
| 100 | 60 | 0.60 | 80 mg/0.8 mL |
| 110 | 66 | 0.66 | 80 mg/0.8 mL |
| 120 | 72 | 0.72 | 80 mg/0.8 mL |
| 130 | 78 | 0.78 | 80 mg/0.8 mL |

Dose Modification

After the initial 12 weeks of treatment, patients in Group 2 will transition to a dosage regimen of 3.6 mg/kg/qw. Dose modifications may be permitted if a patient experiences worsening of HPP-related signs and symptoms relative to pretreatment baseline after a dose reduction to 3.6 mg/kg/qw, a dose increase to 6 mg/kg/qw is permitted.

Efficacy Assessments

Plasma Inorganic Pyrophosphate

Hypophosphatasia across patient ages is characterized by interdependent clinical manifestations, emanating from a failure to mineralize bone matrix due to elevated concentrations of the TNALP substrate PPi. Elevations in extracellular PPi inhibit bone mineralization by blocking hydroxyapatite crystal formation, causing a pronounced accumulation of unmineralized bone matrix resulting in osteomalacia (softening of bones) in patients of all ages, skeletal deformities of rickets (abnormal mineralized bone, dysmorphic long bones, and ribs), and subsequent growth abnormalities in infants and children. Administration of asfotase alfa is expected to hydrolyze PPi, releasing Pi for combination with calcium, thereby promoting growth of hydroxyapatite crystal and bone mineralization and restoring the normal skeletal phenotype.

Blood samples for the measurement of plasma PPi can be collected at various timepoints, such as those indicated in Table 4, to assess potential substrates of asfotase alfa activity.

Short Physical Performance Battery

The SPPB was designed to measure functional status and physical performance. It is a composite measurement that evaluates walking speed, standing balance, and sit-to-stand (STS) performance. The SPPB is calculated from 3 components: the ability to stand for up to 10 seconds with feet positioned in 3 ways (together side-by-side, semi-tandem, and tandem); time to complete a 3 meter or 4 meter walk; and time to rise from a chair 5 times (e.g., repeated chair stand test). The standing balance tests are scored based on the ability to maintain balance in each of these positions. The walking speed and STS tests are scored firstly on the ability to complete the tasks and secondly time taken to complete each task. Each task is scored out of 4, with the scores from the 3 tests summed to give a total of a maximum of 12 and a minimum of 0. A higher score indicates a higher level of function, while lower scores indicate a lower level of function. Lower scores on the SPPB have been shown to be predictive of an increased risk of falling, loss of independence in ADLs, decreased mobility, disability, decline in health, rehospitalization; and increased hospital length of stay, nursing home admission, and death. A change of 0.5 points on the SPPB is considered to be a small meaningful change, while a change of 1 point on the SPPB is considered to be a substantial meaningful change (Treacy et al., *J Physiother.* 64(1):61, 2018).

The repeated chair stand test involves activation of multiple muscles of the lower limb, most notably the knee extensor (quadriceps femoris) muscles (Bohannon et al. *Isokinet Exerc Sci.* 18(4):235-240, 2010). The repeated chair stand test has been used as a standalone assessment (e.g., the STS maneuver) that is used extensively as a measure of lower limb strength. Several variations of the STS test exist; however, the repeated chair stand component of the SPPB will be used in this study.

The SPPB can be administered at various timepoints, such as those indicated in Table 4, by a blinded rater.

36-Item Short-Form

Health-related quality of life refers to functioning and well-being in physical, mental, and social dimensions of life. The SF-36 is composed of 8 multi-item scales (35 items) assessing physical function (10 items), role limitations due to physical health problems (4 items), bodily pain (2 items), general health (5 items), vitality (4 items), social functioning (2 items), role limitations due to emotional problems (3 items), and emotional well-being (5 items). These 8 scales can be aggregated into 2 summary measures: the PCS and Mental Component Summary (MCS) scores. The 36th item, which asks about health change, is not included in the scale or summary scores (Farivar et al. *Health Qual Life Outcomes* 5:54, 2007).

The SF-36 is a self-administered questionnaire. Patients complete 1 response from a range of options for each of the 36 questions. A combination of item response(s) is then aggregated to calculate a score for each of the 8 scales listed. The scores for each dimension range from 0 to 100, with higher scores indicating better health status. Body pain is also scored in this way, with higher scores indicating less pain. The 2 summary measures (PCS and MCS) are scored differently from the 8 dimension scores. These scales are scored using norm-based methods. A score of 50 reflects an average score with respect to these populations. Scores lower than 50 reflect less than average health and scores greater than 50 reflect better than average health (Stewart et al. Aust J Physiother. 53:208, 2007). The SF-36 questionnaire can be administered at various timepoints, such as those indicated in Table 4.

Timed Up-and-Go Test

The timed "Up-and-Go" (TUG) test measures, in seconds, the time taken by an individual to stand up from a standard arm chair, walk a distance of 3 meters (approximately 10 feet), turn, walk back to the chair, and sit down. This clinical test, developed in a medical setting, requires patients to wear their regular footwear and use their customary walking aid (none, cane, walker). No physical assistance is given. Patients begin the test with their back against the chair, their arms resting on the armrests, and their walking aid in hand. They are instructed that, on the word "go" they are to get up and walk at a comfortable and safe pace to a line on the floor 3 m away, turn, return to the chair, and sit down again. The patient walks through the test once before being timed in order to become familiar with the test. Either a stopwatch or a wristwatch with a second hand can be used to time the test. Normal healthy elderly persons usually complete the task in 10 seconds or less. Very frail or weak elderly persons with poor mobility may take 2 minutes or more. A score of ≥14 seconds has been shown to indicate high risk of falls (Lysack C. et al. Household and Neighborhood Safety, Mobility. 2nd ed. St. Elsevier; 2010). The TUG test will be administered by a blinded rater at various timepoints, such as those indicated in Table 4.

Brief Pain Inventory—Question 3 (Worst Pain) Score

The Brief Pain Inventory (BPI), previously known as the Brief Pain Questionnaire, is a self-administered questionnaire that was originally designed to assess cancer pain. It is now also used as a generic pain questionnaire for other chronic pain conditions. It is available in short- (9 items) and long-(17 items) form. The BPI short-form is more frequently used and is what is referred to when the BPI is cited in research.

The first, optional item is a screening question about the respondent's pain on the day. The questionnaire is then composed of pain drawing diagrams, 4 items about pain intensity (worst pain, least pain, average pain, pain right now), 2 items on pain relief treatment or medication, and 1 item on pain interference, with 7 subitems (general activity, mood, walking ability, normal walk, relations with other people, sleep, and enjoyment of life).

The BPI gives 2 main scores: a pain severity score and a pain interference score. The pain severity score is calculated from the 4 items about pain intensity. Each item is rated from 0, no pain, to 10, pain as bad as you can imagine; and contributes with the same weight to the final score, ranging from 0 to 40. The pain interference score corresponds to the item on pain interference. The 7 subitems are rated from 0, does not interfere, to 10, completely interferes; and contributes with the same weight to the final score, ranging from 0 to 70. The first item, pain drawing diagrams (painful and most painful areas), and the items on pain relief treatment or medication (list of the treatments and amount of relief) do not contribute to the scoring. It takes approximately 5 minutes to complete the BPI (Poquet et al. *J Physiother.* 62:52, 2016). The BPI can be administered at various timepoints, such as those indicated in Table 4.

Lower Extremity Functional Scale Score

The Lower Extremity Functional Scale (LEFS) is a patient-reported measure to examine the functional status in the presence of lower extremity musculoskeletal problems. The LEFS consists of 20 items, with scores ranging from 0 (extreme difficulty/unable to perform activity) to 4 (no difficulty). The total score can be obtained by summing the scores of the individual items. The maximum score of 80 indicates no functional limitations and the minimum score of 0 indicates extreme limitations (Mehta et al. *J orthopaed. and sports phys. ther.* 46:200-216, 2016). The LEFS can be administered at various timepoints, such as those indicated in Table 4.

Radiographic Assessment of Fracture Healing

The study will evaluate the proportion of healed fractures or pseudofractures in patients with delayed healing of fractures or pseudofractures of the lower extremity(ies) via radiographic evaluation. Radiographic bone healing is defined as observation of signs of cortical bridging by callus and/or almost complete obliteration of the fracture line. The radiographic union scale in tibial fractures (RUST) score uses these radiographic signs to assess healing. The RUST and modified RUST (mRUST) are based on scores assigned for callus formation and fracture line visibility at each of the 4 visible cortices in 2 radiographs. An mRUST score of "1" is assigned when there is "no callus"; a score of "2" is assigned when "callus is present"; a score of "3" is assigned when there is a presence of "bridging callus"; and a score of "4" is assigned when the bone is "remodeled" and "fracture is not visible" (Leow et al. *Bone Joint Res.* 5:116-121, 2016; Litrenta et al. *J Orthop Trauma* 29:516-520, 2015; Whelan et al. *J Trauma.* 68:629-632, 2010). An mRUST score of 3 will be considered as evidence of healing in this study.

Radiographs will be adjudicated by a blinded panel of experts (e.g., radiologists, orthopedic surgeons). Radiographic imaging can be performed at various timepoints, such as the timepoints indicated in Table 4.

Use of Assistive Devices

Hypophosphatasia is associated with a high fracture and orthopedic/dental surgical burden, pain, impaired mobility, need for assistive walking devices, decreased functional status, and impairments in ADLs in children and adults (Berkseth et al. *Bone.* 54:21-27, 2013; Coe et al. *J. Bone Joint Surg. Surg.* American volume. 68:981-990, 1986; Weber et al. *Metabolism: clinical and experimental.* 65:1522-1530, 2016). This study will assess the reasons for use of assistive devices including pain, weakness, fatigue, balance, fear of falling, or fear of fracture. The information of types of devices used (e.g., crutches, wheelchair dependent [full time], wheelchair dependent [part time], walker, cane, leg braces, ramps, modification to bath/shower, grab bar/railings, or other assistive devices) can also be collected. The use of assistive devices can be monitored continuously throughout the study.

High-Resolution Peripheral Quantitative Computed Tomography

High-resolution peripheral quantitative computed tomography (HR-pQCT) is a noninvasive, low-radiation method for assessing bone microarchitecture and volumetric bone mineral density (BMD) in cortical and trabecular compartments of the distal radius and distal tibia. Its application in clinical research has helped the understanding of differences in bone structure across a wide range of bone metabolic disorders, fracture risk, and the response of bone to different osteoporosis therapies (Cheung et al. *Current oseteopor. reports.* 11:136-146, 2013). Microarchitecture analysis using this methodology provides a better understanding of possible trabecular and cortical bone compromise due to disease-related components. High resolution peripheral quantitative computed tomography will be available to all the patients. HR-pQCT can be performed to assess total, trabecular, and cortical volumetric BMD, cortical thickness, stiffness, trabecular number, trabecular separation, and trabecular thickness, such as at the timepoints indicated in Table 4.

Patient's Global Impressions of Improvement

The Patient's Global Impressions of Improvement (PGI-I) is a 1-item questionnaire that is used to assess a patient's overall perception of their condition relative to baseline. A patient is requested to rate the perceived change in his/her condition in response to therapy or intervention (Yalcin et al. Am J Obstet Gynecol. 189:98-101, 2003). The PGI-I assessment can be administered at various timepoints, such as the timepoints indicated in Table 4.

Safety Assessments

Medical History and Demographic Information

Demographic information will include date of birth, age, sex, ethnicity, and race. Medical history will include age at onset of earliest signs or symptoms of HPP, and specific signs or symptoms at diagnosis and at enrollment including skeletal, neurologic, constitutional/metabolic, muscular, dental, respiratory, renal, and rheumatic. Medical history and demographic information can be obtained at various timepoints, such as the timepoints indicated in Table 4.

Physical Examination

Physical examination will include assessment of general appearance; skin; head, ear, eye, nose, and throat; neck; lymph nodes; chest; heart; abdominal cavity; limbs; central nervous system; musculoskeletal. An abbreviated physical examination will encompass an assessment of the patient's signs and symptoms. All physical examinations (complete and abbreviated) will include weight (using a calibrated scale) and the examination of asfotase alfa injection sites for potential reaction(s). Full and abbreviated physical examinations can be performed at various timepoints, such as the timepoints indicated in Table 4.

Vital Signs

Vital signs include systolic and diastolic blood pressure (millimeters of mercury [mm Hg]), heart rate (beats/minute), respiratory rate (breaths/minute), and temperature (degrees Celsius [° C.] or degrees Fahrenheit [° F.]). On dosing days in the clinic, vital signs can be taken within 10 minutes before administration of the study drug. Vital signs can be performed at various timepoints, such as the timepoints indicated in Table 4.

Pharmacodynamics

Samples for the measurement of plasma PPi and PLP can be collected to assess potential substrates of asfotase alfa activity 15 to 30 minutes prior to asfotase alfa dosing. Pyridoxal (PL) can be measured independently and can be reported as a ratio of PLP/PL. Pyridoxal 5-phosphate is a substrate for asfotase alfa and results in formation of PL through the dephosphorylation activity. Thus, the ratio of PLP/PL is expected to be higher pretreatment and lower with treatment with asfotase alfa as more PLP is dephosphorylated to PL (Akiyama et al. *Mol Genet Metab.* 125:174-180, 2018). The changes in PL reflect asfotase alfa activity when analyzed as a ratio with PLP. The actual date and time (24-hour clock) of each sample collection will be recorded.

Blood samples for the measurement of plasma PPi, PLP, and PL can be collected at various timepoints, such as the timepoints indicated in Table 4.

Biomarkers

Hypophosphatasia is characterized by interdependent clinical manifestations, emanating from a failure to mineralize bone matrix due to elevated concentrations of the TNALP substrates, including PPi and PLP. Failure to mineralize bone matrix results in osteomalacia (softening of bones). Bone turnover markers such as osteocalcin, N-terminal propeptide of type I procollagen (P1NP), and serum C-telopeptide cross-link of type 1 collagen (sCTX) are a series of protein or protein derivative biomarkers released during bone remodeling due to activity of osteoblasts or osteoclasts. Bone turnover markers respond rapidly to changes in bone physiology; therefore, they have utility in determining patient response to and compliance with therapies for bone metabolic disorders (Greenblatt et al. *Clin Chem.* 63:484-474, 2017).

Blood samples for bone turnover marker analysis (osteocalcin, P1NP, and sCTX) can be collected at various timepoints, such as the timepoints indicated in Table 4.

Efficacy Analyses

Primary Analysis

A primary endpoint of this study is the change from Baseline to Week 36 in plasma concentrations of PPi in Group 1. A primary analysis for the primary endpoint can be performed using a MMRM model, fitted for treatment groups and visits to estimate the change at each postbaseline timepoint. The primary hypothesis can test the within group change from Baseline at Week 36.

Secondary Analyses

Key Secondary

Change from Baseline to Week 36 in plasma concentrations of PPi in Group 2 and change from Baseline to Week 36 in the repeated chair stand test (a component of the SPPB) and SF-36 PCS score in Groups 1 and 2 can be analyzed in the same manner as for PPi (primary analysis).

A subgroup analysis can be performed for patients with presence of any type of fractures at randomization (fracture or pseudofracture) (yes versus no).

Key secondary endpoints can be ordered and tested in sequence to control overall type 1 error rate in the order of: (1) PPi for Group 2, (2) SF-36 PCS for Group 1, (3) SF-36 PCS for Group 2, (4) the repeated chair stand test (a component of the SPPB) for Group 1, and (5) the repeated chair stand test (a component of the SPPB) for Group 2.

Other Secondary

Analysis of the following endpoints can be performed in Groups 1 and 2 in the same manner as for the change from Baseline to Week 36 in plasma concentrations of PPi (key secondary endpoint):

Change from Baseline to Week 24 in the repeated chair stand test (a component of the SPPB)

Change from Baseline to Week 24 in SF-36 PCS score

A statistical analysis similar to that performed for the primary endpoint will be performed for the following endpoints:

Change from Baseline to Week 36 in TUG test

Change from Baseline to Week 36 in BPI

Change from Baseline to Week 36 in LEFS scores

Exploratory Analyses

For change from Baseline to Week 12, 24, and 36 for exploratory endpoints, analysis can be performed in the same manner as for the change from Baseline to Week 36 for PPi.

The proportion of healed fractures or pseudofractures at Week 36 can be summarized using counts and percentages. Time to union or fracture healing can be analyzed using the Kaplan-Meier method.

Change from Week 12 to Week 36 in PPi can be derived for the assessment of durability. The PLP-to-PL ratio may be determined.

For the PK profile of asfotase alfa, individual serum asfotase alfa activity-time data, and actual blood sampling times can be listed with observed and change in activity-time profiles plotted. A summary of serum asfotase alfa activity can be provided using descriptive statistics with mean activity-time profiles plotted and compared between the 2 treatment groups.

Example 3. Physical Function and HRQoL in Adults Treated with Asfotase Alfa for Pediatric-Onset HPP Data on adults (≥18 years old) with pediatric-onset HPP who had received asfotase alfa for at least 12 months were collected during routine clinical practice at the Orthopedic Institute of the Julius-Maximilians-University of Würzburg (NCT03418389). Physical function was assessed using the Short Physical Performance Battery (SPPB), the Lower Extremity Functional Scale (LEFS) and the 6-minute walk test (6MWT); pain was evaluated using the PainQuest instrument. The 36-item Short-Form Health Survey version 2 (SF-36v2) was used to assess HRQoL. Change from baseline to 12 months in the scores for each tool was analyzed. Safety concerns during this period were also captured.

Of the 14 patients included (11 female, 3 male), median (min, max) age at start of treatment with asfotase alfa was 53 (20, 78) years for women and 46 (19, 57) years for men. Median (min, max) height was 160 (135, 167) cm for women and 176 (170, 180) cm for men. All patients had heterozygous mutations in the ALPL gene. Of the 12 patients with data on the 6MWT, median (min, max) distance walked increased significantly from 272 (0, 760) m to 301 (0, 605) m after 12 months of treatment (FIG. 2A). Median (min, max) scores on the chair rise test, a part of the SPPB, improved significantly from 22 seconds at baseline to 13 seconds after 12 months of treatment (n=9; FIG. 2B). Significant improvements in LEFS and SF-36v2 Physical Component Summary scores were observed after 12 months of treatment (n=9; FIGS. 2C and 2D). Changes in grip force (n=12) or pain (n=8) were variable over the 12 months of treatment. The safety profile of asfotase alfa in this population was similar to that reported in previous clinical studies. While only a small number of patients were evaluated, this real-world adult treatment cohort showed improvements in physical functioning and in HRWoL from asfotase alfa treatment over six or 12 months.

Example 4. Wearable Device to Track Treatment

A Phase 4 clinical trial can be performed in conjunction with a wearable device configured to be worn on the wrist of each subject being treated. The wearable device contains an accelerometer and can be used to track steps and physical activity of the subject. The wearable device may be used to monitor biometric indicia during the treatment regimen and may be used to monitor the treatment efficacy and assist in determining whether administration of the sALP should be stopped once efficacy is achieved, or restarted if efficacy is not maintained, based on a change in the biometric indicia.

The wearable device may be configured as a system that further includes a peripheral electronic device, such as a smartphone or a cloud-based database. As data is continuously monitored and measured by the wearable device, the data collected by the device may be transmitted to the peripheral device and stored on the peripheral device or on a cloud-based storage medium. The peripheral device may be configured to run a software application (e.g., smartphone application) that provides navigable information to the subject in order to track changes in the subject's physiological indicia during the course of treatment (e.g., improvement over time). The data can also be transmitted to a third party, e.g., a clinician administering the sALP therapy to the subject, in order to monitor the treatment progress of the subject.

Study Endpoints

Exemplary endpoints and their rationale are listed in the table below:

TABLE 10

Wearable Device Endpoints

| Proposed Endpoint | Rationale |
|---|---|
| Change relative to baseline in mean daily physical activity counts | Provide an objective measure of overall physical activity and ambulation over time |
| Ratio of mean daily activity counts collected during the most active 30 minutes of the subject's day between defined intervals and baseline | Provide an objective estimate of an individual's maximal physical exertion potential over time |
| Change relative to baseline in mean daily time spent at various activity levels (sedentary, light, moderate, vigorous) during the non-sleeping timeframe | Provide an objective estimate of the distribution of an individual's activity across various intensity states over time |
| Change relative to baseline in mean daily active to sedentary ratio | Provide an objective measure of an individual's overall physical activity and ambulation over time |

TABLE 10-continued

Wearable Device Endpoints

| Proposed Endpoint | Rationale |
|---|---|
| Change relative to baseline in mean daily duration of activity bouts at various activity intensity thresholds | Provide an objective estimate of the distribution of an individual's activity across various intensity states over time |
| Change relative to baseline in mean daily duration of total sleep time | Provide an objective measure of changes in an individual's sleep duration over time |
| Change relative to baseline in mean activity (counts per minute) during sleep | Provide an objective measure of sleep quality and sleep disturbances over time |

Link Between Proposed Endpoints and Clinical Outcomes of Interest

For patients with HPP, particularity older and mobile patients, particularity adult patients, treatment goals include improved functional status (changes in endurance, strength, and gait improvements), reduced fatigue, and reduced joint pain. The digital endpoints are designed to measure aggregate levels of activity that are hypothesized to change over time in response to improvements in the treatment goals outlined. Various studies have shown associations between accelerometer derived measures and pain symptoms in certain populations. Similarity, accelerometer-based measures have been shown to correlate with functional measures, such as the Six Minute Walk Test (6MWT).

Device Option-Actigraph Insight Watch

Accelerometry monitors are commercially available. The Actigraph Insight Watch is a medical-grade 510(k) cleared, Class II, wrist-worn device containing a tri-axial accelerometer. The battery and storage on this device allow for 30 days of continuous data capture and on-device storage at the default sampling rate of 32 Hz. Data transfer between the device and the cloud is conducted via the Centrepoint Data Hub that securely transfers data either via Bluetooth or USB from the device to the Centrepoint Cloud. Data stored within the Centrepoint cloud can be directly downloaded by study administrators via the Centrepoint Web Portal, or retrieved via web API (application programming interface) with the appropriate security credentials. A suite of accelerometer-based endpoints are computed by Actigraph using published and publicly available algorithms including Energy expenditure, MET Rates, Physical activity, Activity bouts, Sedentary bouts, Sleep latency, Total sleep time, Wake after sleep onset, and Sleep efficiency. Moreover, raw 3-axis accelerometer data is available via the web API allowing for the development of alternative endpoints and statistical measures not computed by Actigraph. The Actigraph Insight watch offers standard wristwatch fittings, allowing participants or study administrators to exchange the provided wrist band depending on style or material preferences. The device should blind study participants to any data recorded, and only display the time of day, date, and remaining battery life of the device, in order to avoid biasing the wearer's behavior. Additionally, such device use may encompass intermittent data collection to more effectively follow the lengthy timeline for bone growth over weeks and months.

Advantages of the Actigraph Insight Watch include:

The Insight Watch is a device that offers the participant experience of a commercial wearable device.

The battery life and on-device storage are sufficient for the expected collection time, minimizing participant burden of transferring data during the study Raw device data is available via API Data flow procedures are well established, secure, and offer multiple avenues for export Actigraph devices can be utilized for data collection

Example 5. Treating an Adult HPP Patient with Painful Lower Limbs

An adult male subject presents with an elevated inorganic pyrophosphate (PPi) concentration of about 5.82 μM, and an average BOT-2 strength score of less than 10. The subject is 24 years old and is experiencing painful lower limbs and gait disturbance. The subject may be diagnosed with HPP and selected for treatment. The subject can be subjected to an X-ray and a bone mineral density test, both of which may show reduced bone mineralization in the legs.

A pharmaceutical formulation containing the polypeptide of SEQ ID NO: 1 can be formulated at 0.1 mg/mL. The formulation can be injected subcutaneously into the subject once a week for 8 weeks at a dosage of 3.5 mg/kg/week. The subject can be evaluated for treatment efficacy after the 8 week treatment regimen. The subject may notice a reduction in bone pain and normalization of gait. The subject can be subjected to follow-up X-rays and bone mineral density tests, which may show normalization of bone mineralization relative to before treatment. The PPi concentration of the subject can be reduced to under 5 μM, and his BOT-2 strength score can improve to 12, indicative of a treatment effect by the polypeptide. The subject then discontinues treatment.

Six months after discontinuing treatment, the subject begins to experience painful lower limbs and gait disturbance. The PPi concentration is elevated to about 5.82 μM and has an average BOT-2 strength score of less than 10. The subject then enters a phase of the treatment regimen in which administration of the sALP is restarted. Following one month of the second treatment phase, the painful lower limbs and gait disturbance subsides.

Example 6. Treating an Adolescent Female with Tooth Loss and Chronic Pain

An adolescent female subject presents with an elevated inorganic pyrophosphate (PPi) concentration of about 4.78 μM and an average 6MWT of less than about 70% of the predicted 6MWT value. The subject is 14 years old and is experiencing tooth loss and chronic pain. The subject may be diagnosed with HPP and selected for treatment. The subject can be subjected to an X-ray and a bone mineral density test, both of which may show may bone mineralization in her teeth and femurs.

The subject is equipped with a wearable device configured for her wrist. The wearable device tracks her physical activity for a period of two weeks. She averages 3,000 steps per day and two periods per day of at least 5 minutes in which her heart rate is elevated by at least 10%. She then begins asfotase alfa treatment at a high or low dose.

A pharmaceutical formulation containing the polypeptide of SEQ ID NO: 1 can be formulated at 0.5 mg/mL. The formulation can be injected subcutaneously into the subject once a week for 4 weeks at a dosage of 2.5 mg/kg/week. The subject can be evaluated for treatment efficacy after the 4 week treatment regimen. The subject may notice a reduction in chronic pain. The subject can be subjected to follow-up X-rays and bone mineral density tests, which may show normalization of bone mineralization in her femurs relative to before treatment. The PPi concentration of the subject can be reduced to under 4 μM, and her 6MWT score improves to about 85% of the predicted value, indicative of a treatment effect by the polypeptide. The wearable device, which is worn for two weeks (weeks 3 and 4 of the treatment regimen) shows that her steps per day may increase to about 8,000 steps per day and 8 periods per day of at least 5 minutes in which her heart rate is elevated by at least 10%. The subject may wear the wearable device for one or more two-week periods, followed by evaluation. It may be determined that she can stop administration of the sALP and be monitored periodically for any evidence of symptom recurrence.

Example 7. Bone Turnover and Mineral Metabolism in Adult Patients with Pediatric-Onset HPP Treated with Asfotase Alfa We evaluated changes in bone turnover markers in adults with pediatric-onset HPP treated with asfotase alfa. We performed an observational study of patients 218 years (y) with pediatric-onset HPP receiving asfotase alfa for 12 months (m) for routine care at 1 center. Data were obtained from 14 patients, ages 19-78y (median 52y), with compound heterozygous ALPL mutations and histories of skeletal (at least 1 fracture) and other HPP manifestations were studied. At baseline, serum concentrations of pyridoxal 5'-phosphate (PLP) were a median of 286 ng/mL and decreased significantly (n=12, P=0.005) in 12 m of treatment to 8.5 ng/mL (normal: 5-30). Significant reductions occurred in urine phosphoethanolamine (PEA)/creatinine ratio (n=11, P=0.008), with decrease from 54.9 mmol/mol creatinine at baseline to 22.4 mmol/mol creatinine at 12 m (normal: 2.3-11.3). Temporary increase of parathyroid hormone 1-84 at 3 m of treatment was not accompanied by changes in calcium or phosphate. Significant transient increases in procollagen type 1 N-propeptide (PINP) at 3 m and osteocalcin at 3 m and 6 m were observed; both reverted to near baseline by 12 m. Numeric increases in N-telopeptide of type 1 collagen (NTx) and tartrate-resistant acid phosphatase 5b (TRAP 5b) were not statistically significant.

The first systematic evaluation of bone turnover markers during asfotase alfa treatment reflects that, beyond significantly reducing PLP and PEA and improving bone mineralization, asfotase alfa facilitates bone remodeling in adults with pediatric-onset HPP.

Example 8. Treating an Adult HPP Patient with Atypical Femoral Fracture (AFF)

An adult male subject (52 years old) with pediatric-onset HPP presents with an AFF but has no other bone mineralization defects. The subject can be prescribed a treatment of asfotase alfa to be administered at 6 mg/kg/week, or at a lower dose, for three months. The subject can be monitored monthly for fracture healing. After three months, if the fracture shows moderate but incomplete healing, the treatment can be extended for an additional three months at the same dosage. The AFF can be monitored during treatment until resolution. After resolution, a lower dosage would be tried. Typically, therapy is recommended for the life of the patient to minimize any potential anti-drug antibody issues.

Example 9. Treating an Adult Patient with AFF

An adult female subject (45 years old), without HPP, being treated with a bisphosphonate presents with an AFF. The subject can be prescribed a treatment of asfotase alfa to be administered at 6 mg/kg/week for six months. The subject can be monitored monthly for fracture healing. After three months, if the fracture shows complete healing, the therapy could be terminated early. The patient can be prescribed three months of physical therapy and may be able to resume normal physical activities by six months after the onset of injury.

Example 10. Physical Function and Health-Related Quality of Life in Adults Treated with Asfotase Alfa for Pediatric-Onset HPP

Materials and Methods

Study Design

This was an observational, retrospective and prospective, single-center study of adults (aged ≥18 years) diagnosed with pediatric-onset HPP who had received asfotase alfa treatment during routine clinical practice for at least 30 months.

Study Population

Adults with pediatric-onset HPP (confirmed by low alkaline phosphatase level and/or mutation of the alkaline phosphatase gene (ALPL), and clinical signs and/or symptoms consistent with HPP), who had received asfotase alfa for at least 30 months were included. Informed consent was provided by all individuals before enrollment in the study. HPP care and asfotase alfa treatment were administered according to clinical practice, including continuous prescriptions of physiotherapy and manual therapy analogous to previously established individual requirements. The starting dose of asfotase alfa was determined by the treating physician. The recommended dosing regimen for asfotase alfa is a subcutaneous injection of either 2 mg/kg body weight 3 times a week, or 1 mg/kg body weight 6 times a week.

Data Collection

Data were collected retrospectively from patients' electronic and hard copy medical records for a look-back period corresponding to the time from study enrollment to the earliest documented date of HPP diagnosis (or birth, as applicable) on demographics, age at HPP onset and HPP-related manifestations. Data collected both retrospectively and prospectively included clinical symptoms, physical function assessments, HRQoL assessments, adverse events (AEs) and asfotase alfa treatment information. Data collection was based on available information from assessments commonly conducted in this patient group at the Investigator's site (i.e., no investigations were performed outside the standard of care). Baseline clinical evaluations were typically captured within the 6 months before initiation of enzyme replacement therapy. Follow-up assessments, including data collection, were regularly scheduled at 3, 6, 12, 18, 24, and 30 months of treatment.

Detailed Description of Procedures

Short Physical Performance Battery (SPPB)

The SPPB is a summary performance measure consisting of 4 m walking velocity at usual pace, a timed repeated chair stand and 3 increasingly difficult standing balance tests (not yet performed). Each performance measure was assigned to a categorical score ranging from 0 (inability to complete the test) to 4 (optimal performing). A summary score ranging from 0 (worst performers) to 12 (best performers) was calculated by summing the 3 component scores.

4M-Gait Speed

The 4M-Gait Speed is part of the SPPB. The participant had also to be able to walk unassisted without the use of a cane or walker. Gait speed was determined indoor on a flat surface marked at start and 4 meters from the start. The patient was instructed to walk at their usual pace from a standing start, walking past the 4 m mark without hesitation. The stopwatch was started if the physician said "go" and stopped when the first feet was across the finish line. This test was repeated for 2 more times. The faster of the two tests was used to calculate the walking speed.

Chair-Rise-Test

The Chair-Rise-Test was a measurement to test the strength and endurance. A chair with a straight back and without arm rests was used (seat height 43 cm=17 inch). The participant was seated in the middle of the chair, the legs were flexed 90°, and the arms were crossed in front of the chest during the test. The feet kept flat on the floor. The stopwatch was started if the physician said "go". The participant rose to a full standing position and sat back down completely as fast as possible. This procedure was performed five times. The watch was stopped when the participant was in the last standing position.

6-Minute-Walk-Test

The 6MWT was conducted to assess the maximum distance that a person can walk within a 6 minute timeframe. The walking course had to be 30 m in length. The length of the corridor was marked every meter. The turnaround points were marked with a cone or anything else. A starting line, which marked the beginning and end of each 60 m round were marked on the floor using brightly colored tape.

Handheld Dynamometry

Grip Strength was measured in the dominant and non-dominant hand using a hand-held dynamometer. A total of three procedures were conducted per each hand reciprocally right and left. The pause took 20 seconds between the measurements. The test was administered while the participant was sitting down on a chair without arm rests. The grip strength with the dominant hand was measured first. The elbow was flexed to 90° and the wrist was in a comfortable position (approximately 0-30° wrist extension). Any contraindications against test performance were noted.

Variables

Physical Function

Physical function of the patients was assessed using validated qualitative and quantitative measures. Primary outcome measures were: the 6-Minute Walk Test (6MWT), Timed Up and-Go (TUG) test, the Short Physical Performance Battery (SPPB; a summary performance measure consisting of a balance test, 4 m usual gait speed test and a repeated chair rise test) and handheld dynamometry (grip strength) test. The Lower Extremity Functional Scale (LEFS) was a secondary outcome measure of physical function. If applicable, it was documented whether the patient required an assistive device (e.g., crutches or a walker) to complete these assessments.

Health Related Quality of Life and Pain

HRQoL was assessed as a secondary outcome using the 36-item Short-Form Health Survey version 2 (SF-36v2). Prevalence of pain was assessed using the following five categories: never, rarely, sometimes, frequently, or persistently. If pain was present, pain intensity was quantitated using a 10-item Likert scale. Information on patients' use of pain medication was also collected.

Injection Site Reactions and Safety Reporting

All patients were advised to continuously monitor injection sites and document any local or systemic observations they may have made themselves in association with the injections. All serious and non-serious AEs reported by the patient and/or identified in response to open-ended questions from the treating physician or revealed by observation, physical examination or other study procedures were documented in the patient's study records/source documents.

Data Analysis

The SPSS Statistics 25 (SPSS Inc., an IBM Company, Chicago, IL, USA) statistical software was used for the data analyses. Quantitative variables were presented as median with interquartile range (IQR) or mean with standard deviation (SD). They were tested for normal distribution using the Shapiro-Wilk test. Owing to significant deviations from normal distribution, further analyses were performed using non-parametric methods. Comparisons between baseline and 3, 6, 12, 18, 24, and 30 months of treatment for each variable were assessed using the Wilcoxon matched pairs test; only patients who had data for both of the time points being compared were included in the statistical analyses. For qualitative variables, absolute and percentage frequencies were given. All tests were two-sided with a significance level of 5%. Because the present analysis was primarily descriptive, no alpha adjustment for multiple testing was applied. Representation of longitudinal results only included those patients with available data for all 4 time points.

Results

Figure 5:
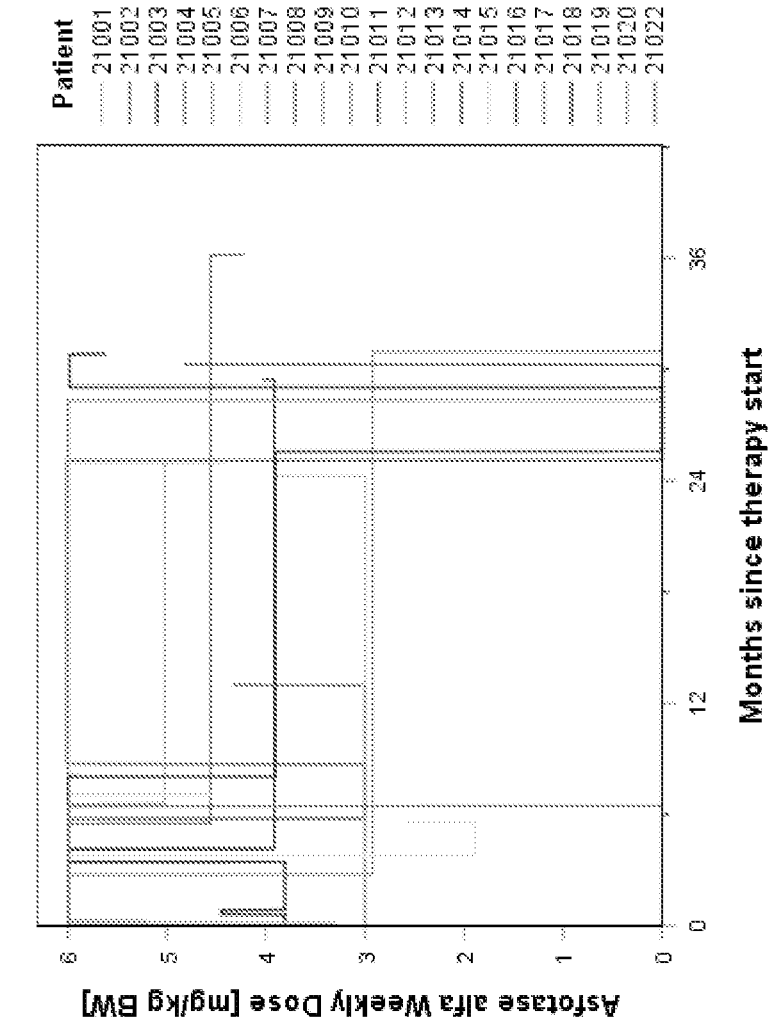
FIG. 5 is a graph showing asfotase alfa weekly dose changes in (mg/kg body weight).
Figure 6:
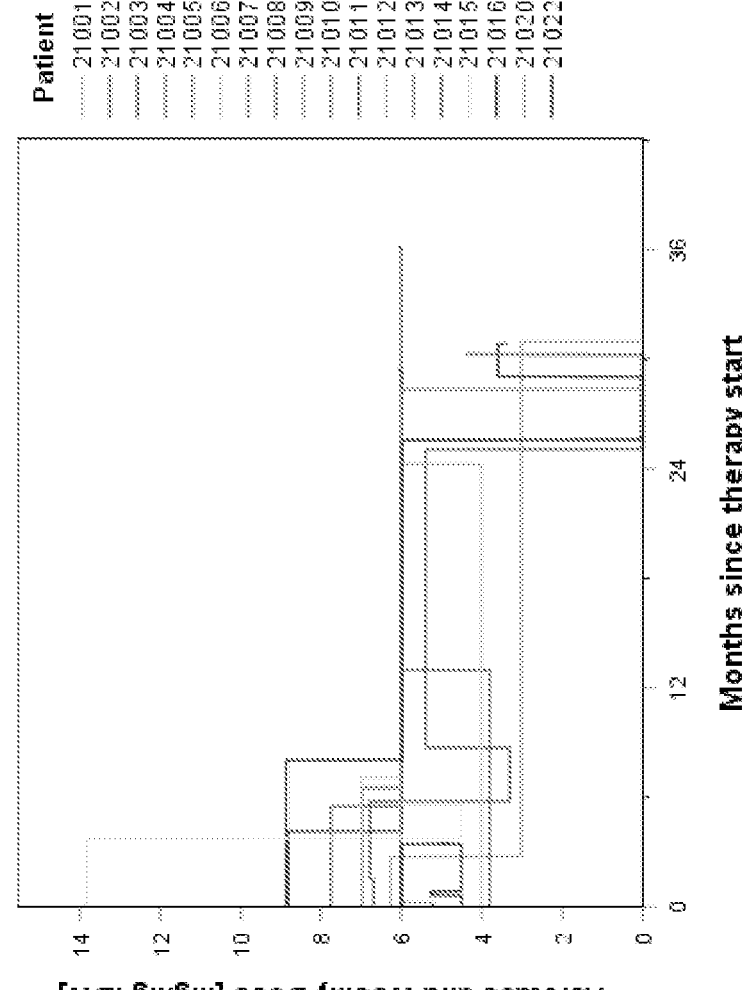
FIG. 6 is a graph showing asfotase alfa weekly dose changes in (mg/kg ideal body weight).

At start of therapy, 21 patients received a weekly median dose (mg/kg BW) of asfotase alfa of 6.0 mg, range 3.0 mg-6.0 mg (mean mg/kg BW 5.4±1.1). This corresponds to a weekly median dose of 6.3 mg/kg ideal body weight (iBW). Most patients (n=19) received asfotase alfa injections on 3 days per week, two patients received injections 4 days per week. Thirteen patients received a total of 6 syringes per week, 4 patients received 3 syringes, 2 patients received 9 syringes, and 1 patient each received 2 or 4 syringes, respectively. The median body weight for calculating the asfotase alfa dose was 65.0 kg, range 46.0-123.0 kg, mean weight was 73.2*21.0 kg. Up to 5 changes in a single patient of the weekly asfotase alfa dose were made during the treatment period. In 17 patients it was at least 1 change, a further change occurred in 9 patients, 3 patients had 3 changes, 2 patients had 2 changes and in 1 patient there were 5 changes of the weekly asfotase alfa dose. Details about changes in asfotase alfa weekly dose (mg/kg BW) are presented in FIG. 5. Asfotase alfa weekly dose changes in mg/kg iBW are shown in FIG. 6. Changes in dosing were made according to best clinical practice at the decision of the treating physician. Actual body weight (BW) refers to the true weight of the subject. Ideal body weight (iBW) refers to a calculated body weight of the subject, which is an adjusted weight that takes into account the physical variables of the subject, such as, age, gender, height, body frame size, wrist size, and the like.

Patient Demographics and Baseline Clinical Characteristics

In total, 14 patients were included in the analysis (11 women, 3 men; their mean age (SD) was 51 (17) years, ranging from 19 to 78 years (Table 11)). All patients were unrelated, had compound heterozygous ALPL mutations, and had a documented bone manifestation of the disease (including a history of at least one fracture) in addition to other HPP-related manifestations. Twelve patients were initiated on an asfotase alfa dosage of approximately 6.0 mg/kg/week; two patients who were concerned about potential side effects were initiated on 3.0 mg/kg/week. In all patients, the weekly dose was administered on three injection days. Dosing was adjusted as deemed clinically necessary during the 30 months of treatment.

TABLE 11

Patient demographics and baseline clinical characteristics

| Characteristic | Patients (N = 14) |
|---|---|
| Sex, n (%) | |
| Women | 11 (79) |
| Age at baseline, years | |
| Mean (SD) | 51 (17) |
| Range | 19-78 |
| Mean height, cm (SD) | |
| Men | 175 (5) |
| Women | 157 (9) |
| Mean weight, kg (SD) | |
| Men | 98 (18) |
| Women | 73 (22) |
| Mean BMI, kg/m² (SD) | |
| Men | 32 (7) |
| Women | 30 (8) |
| Compound heterozygous mutations of ALPL, n (%) | 14 (100) |
| Mean ALP activity level at baseline, IU/L (SD)[a] | |
| Men | 14 (4) |
| Women | 18 (7) |
| Mean PLP activity at baseline, ng/mL (SD)[b] | 451 (390) |
| Mean PEA/creatinine ratio at baseline, mmol/mol creatinine[c] | 76 (59) |
| Menopause status (women only) | |
| Postmenopausal (n, %)[d] | 5 (45) |
| History of HPP-related manifestations, n (%)[e] | |
| Dental | 14 (100) |
| Fractures | 14 (100) |
| Muscular | 14 (100) |
| Neurological | 6 (43) |
| Renal | 3 (21) |
| Rheumatic | 3 (21) |
| Skeletal | 14 (100) |
| Pain | 14 (100) |

ALP = alkaline phosphatase;
ALPL = alkaline phosphatase gene;
BMI = body mass index;
HPP = hypophosphatasia;
PEA = phosphoethanolamine;
PLP = pyridoxal 5'-phosphate;
SD = standard deviation.
[a]Reference ranges for ALP: 53-128 IU/L (men), 42-98 IU/L (women).
[b]Reference range for PLP: 5-30 ng/mL.
[c]Reference range for PEA/creatinine ratio: 2.3-11.3 mmol/mol creatinine; data were unavailable for three patients.
[d]Calculated as proportion of female patients; data were unavailable for one patient.
[e]Calculated as proportion of patients for whom data were available.
[f]Excluding fractures. Skeletal diagnoses included bowing of the long bones, congenital club foot, craniosynostosis, scoliosis, and kyphosis.

Physical Function

6 Minute Walk Test

Figure 3B:
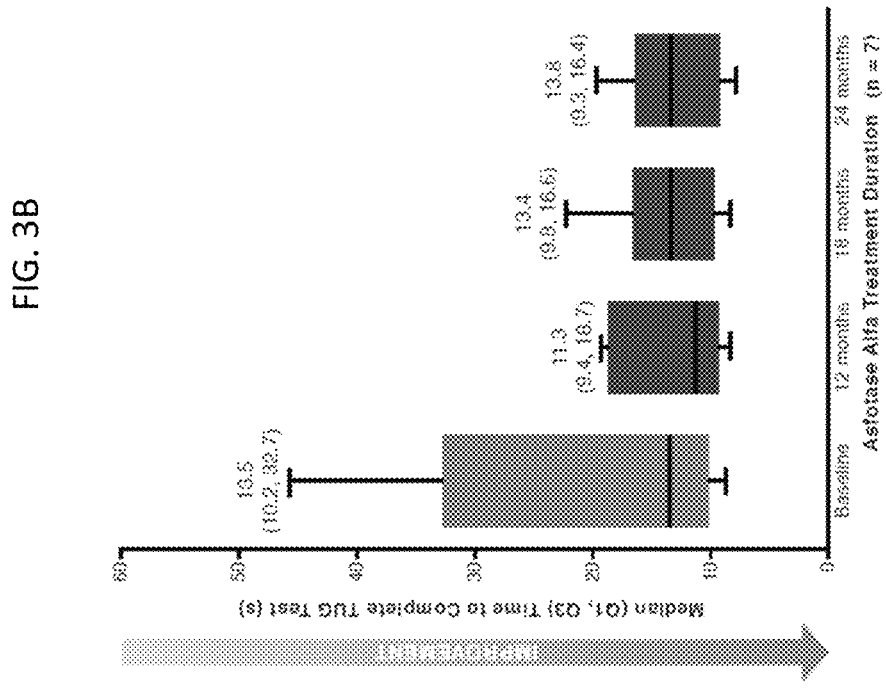
FIGS. 3A-3D are a set of graphs showing primary outcomes of physical function as assessed by 6MWT distance (FIG. 3A), TUG test time (FIG. 3B), 4 m gait speed (FIG. 3C), and repeated chair rise test (FIG. 3D), among adults treated with asfotase alfa for pediatric-onset HPP at baseline, 12, 18, and 24 months of treatment. *p<0.05 vs baseline. The lower and upper boundaries of blue boxes represent the 25th and 75th percentiles, respectively. The horizontal black lines represent the median and whiskers represent the maximum and minimum values. 6MWT (n=13); TUG test (n=7); 4 m gait speed (n=9); repeated chair rise (n=8). 6MWT=8-Minute Walk Test; HPP=hypophosphatasia; IQR= interquartile range; SPPB=Short Physical Performance Battery; TUG=Timed Up-and-Go.
Figure 3A:
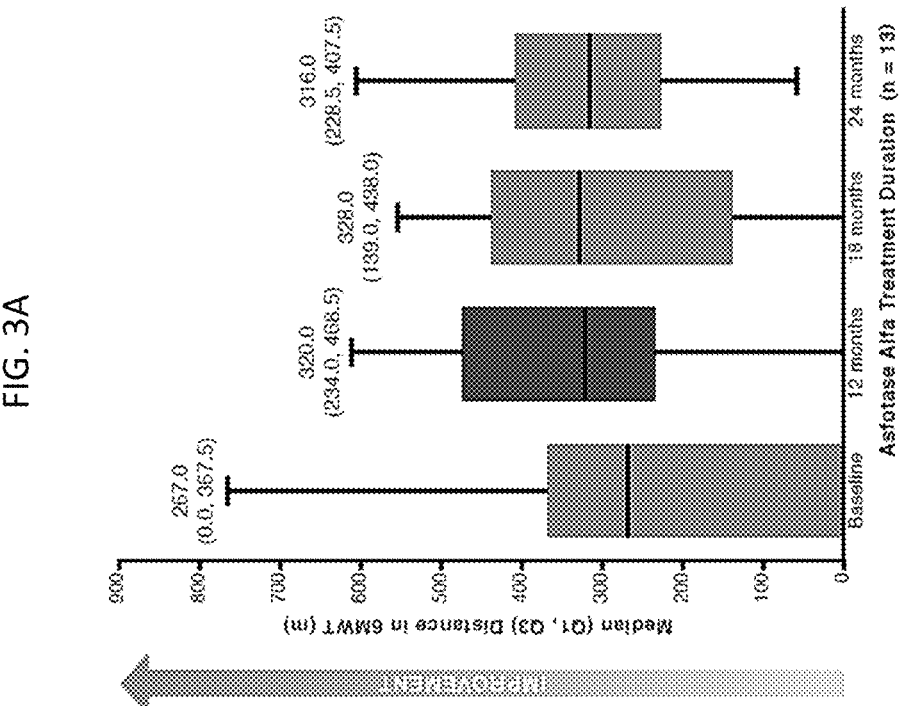
Figure 7:
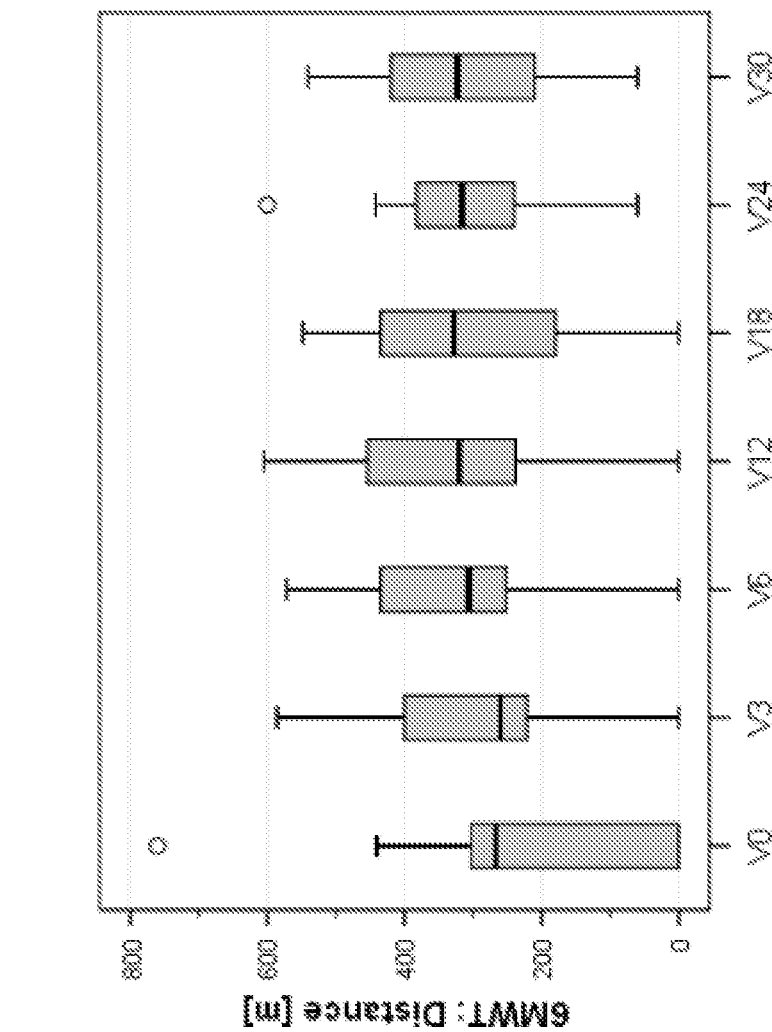
FIG. 7 is a graph showing 6MWT data as in FIG. 3A to 30 months.

Of the 14 patients in this study, 13 completed 6MWT assessments at each timepoint. At baseline, the median (IQR) distance walked was 267 (0-368) m (mean [SD], 237 [223] m), which increased to 320 (234-469) m at 12 months of treatment (mean [SD], 335 [159] m) (FIG. 3A). The change in median 6MWT distance walked between baseline and 12 months was 53 m (p=0.023), which corresponded to a 20% improvement. The median changes between baseline and 3 months and between baseline and 6 months of treatment were −7 m and 39 m, respectively. The change in 6MWT distance from baseline to 18 and 24 months was not significantly different (p=0.221 and p=0.060, respectively). The median distance was similar at 12 and 24 months (p=0.115), and 30 months (p=0.133) (FIG. 7)

Seven of the evaluable patients required assistive devices to complete the 6MWT at baseline (three patients used crutches; four used a rolling walker). Two of these patients were able to complete the test unassisted later during the course of the study; one patient was able to complete the test unassisted from 3 months onwards, and another patient was able to complete the 12-month assessment without assistive devices. None of the patients who walked unassisted at baseline required assistance at any point during the study.

Timed Up-and-go Test

In total, nine patients were able to perform the TUG test at all timepoints. The median (IQR) time to complete the TUG test was 14.4 (10.7-28.9) s at baseline and decreased to 11.3 (9.4-16.9) s after 12 months of treatment (FIG. 3B). The change in median time to complete the test between baseline and 12 months of treatment corresponded to a 22% improvement and was statistically significant (p=0.008). Median (IQR) time to complete the test at 3 months and 6 months of treatment was 13.6 (10.9-20.3) s and 12.2 (10.1-17.8) s respectively; this change was statistically significant when comparing baseline and 6 months of treatment (p=0.021). One patient required an assistive device to complete this test at baseline, but no longer did so at 3 months of treatment.

Figure 10:
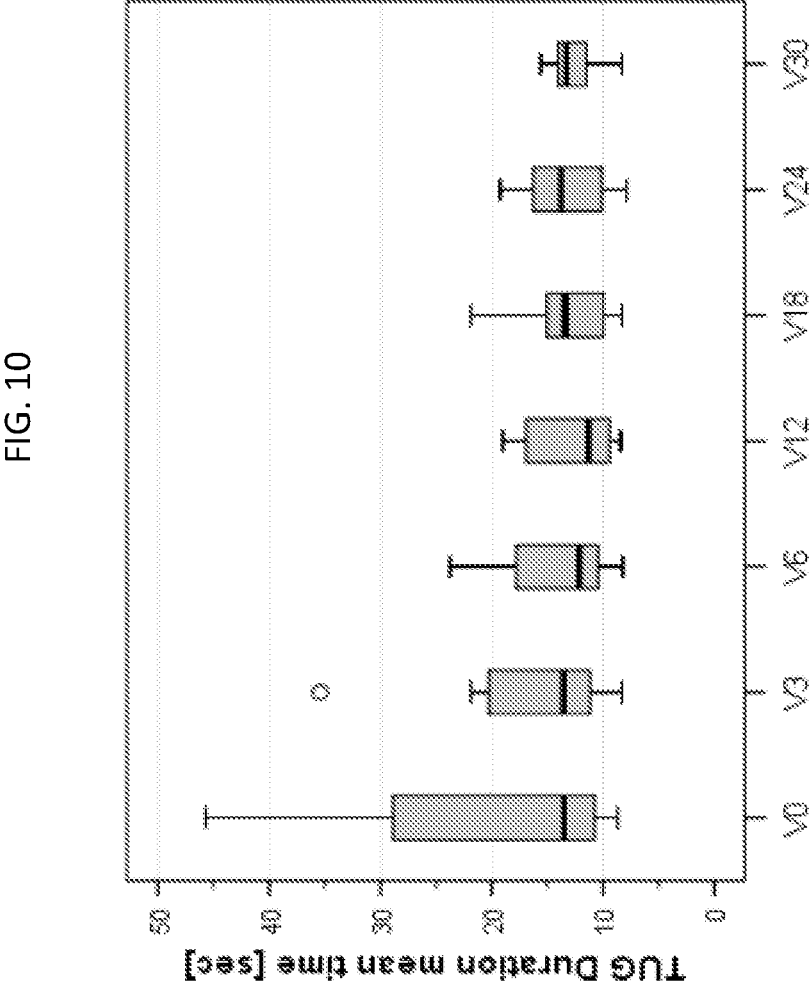
FIG. 10 is a graph showing TUG test time data as in FIG. 3B to 30 months.

Significant differences in TUG duration were observed from baseline to 12, 18, and 24 months (p=0.008, p=0.018, and p=0.013, respectively). Early improvements in median time to complete the TUG test at 12 months remained stable from 12 through 24 months of treatment (p=0.382). Thirty month duration was similar to 24 months (FIG. 10).

Short Physical Performance Battery

Figure 3D:
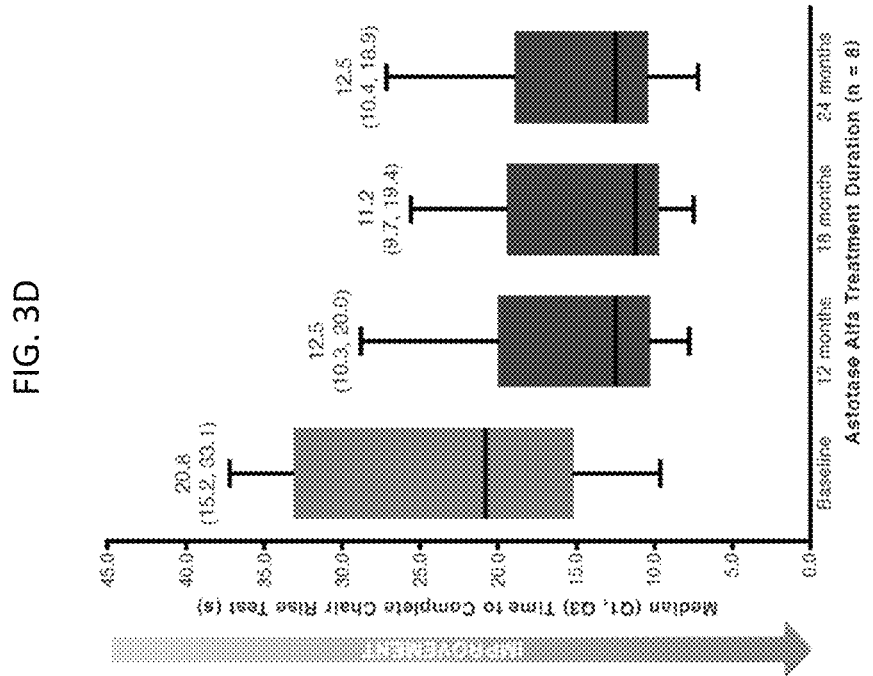
Figure 3C:
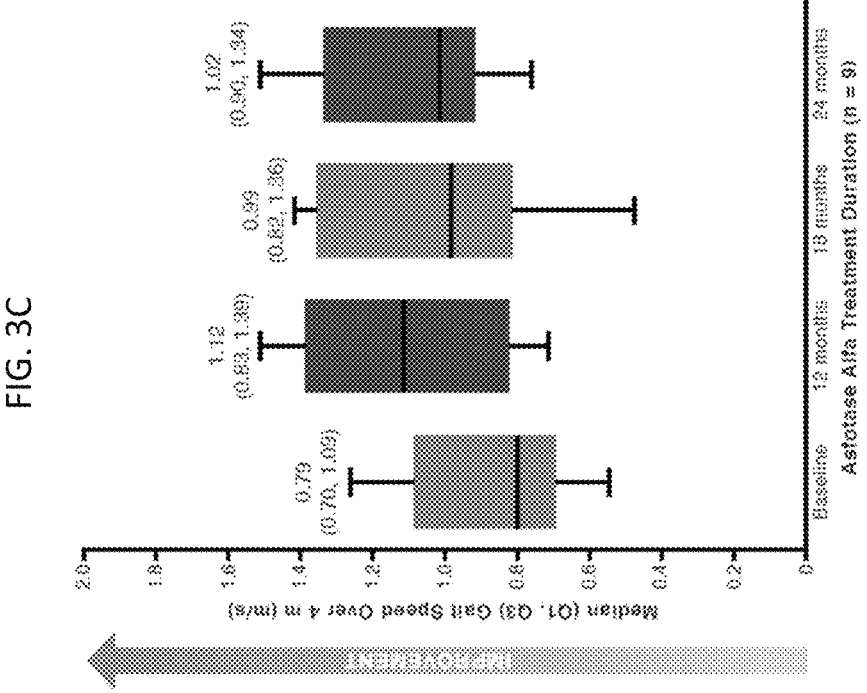

In total, 10 patients completed the 4 m gait speed test, semi-tandem stand and tandem stand components of the SPPB at baseline and at follow up visits; 9 patients completed the repeated chair rise test at all timepoints. Median (IQR) speed to walk 4 m was 0.8 (0.7-1.1) m/s at baseline and 1.1 (0.8-1.4) m/s at 12 months of treatment (FIG. 3C). The change in median usual gait speed was significant when comparing baseline with 12 months of treatment (p=0.007) and corresponded to a 38% improvement. At 3 months and 6 months of treatment, median (IQR) gait speed was 1.1 (0.7-1.2) m/s and 1.0 (0.8-1.3) m/s, respectively.

Figure 8A:
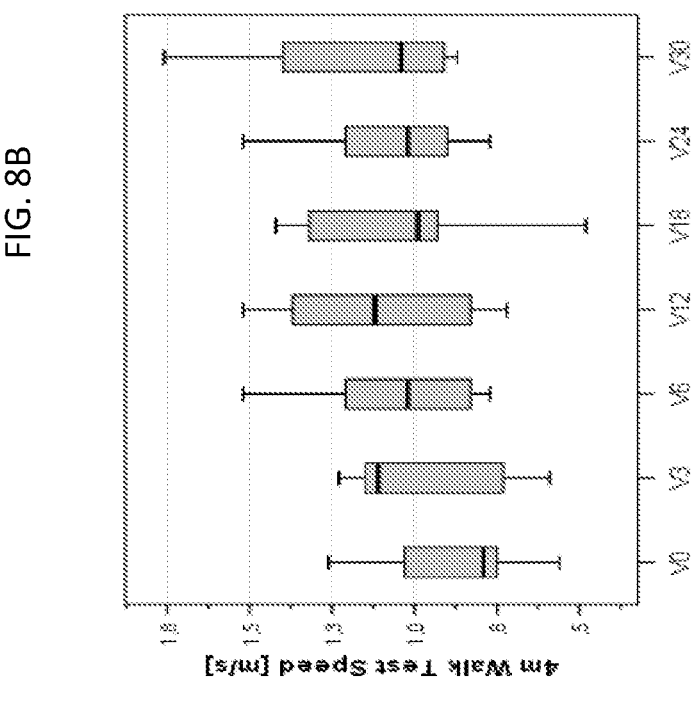
FIGS. 8A and 8B are graphs showing 4 m walk test mean time (FIG. 8A) and mean speed (FIG. 8B) as in FIG. 3C to 30 months.
Figure 8B:
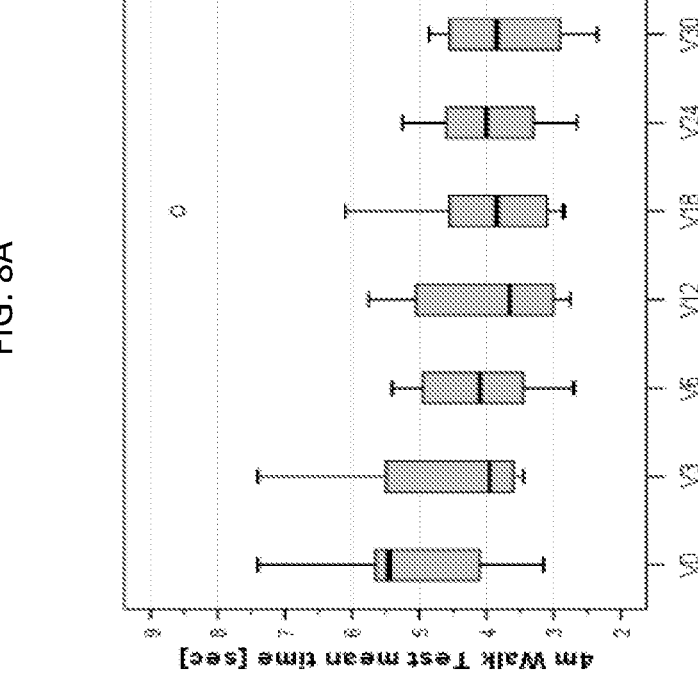

Significant differences in gait speed were observed from baseline to 12 months (p=0.007) and to 24 months (p=0.017), while the change from baseline to 18 months was not significantly different (p=0.173). A slight decrease in median gait speed from 12 to 24 months was not statistically significant (p=0.610). The median walking speed increased significantly at 30 months (p=0.012) from baseline (FIGS. 8A and 8B).

Four patients required an assistive device to complete this assessment at baseline; two of these completed the task unassisted as of 3 months of treatment, and another patient no longer required an assistive device to complete the test after 6 months of treatment. Median (IQR) time to complete the repeated chair rise test was 22.2 (16.2-30.8) s at baseline and 13.0 (10.8-22.4) s at 12 months of treatment (FIG. 3D). Changes compared with baseline were significant at 3, 6 and 12 months of treatment (all p=0.008) and corresponded to a 41% improvement.

Significant differences in chair rise time were observed from baseline to 12, 18, and 24 months (p=0.008, p=0.012, and p=0.008, respectively). Early improvements in median chair rise time at 12 months remained stable from 12 to 24 months of treatment (p=0.398). Chair rise time at 30 months was similar to that at 24 months.

At baseline, all patients were able to hold the semi-tandem stand for 10 seconds. One patient was not able to complete this task at 3 months of treatment but was able to do so at 6 months and 12 months of treatment.

Figure 9:
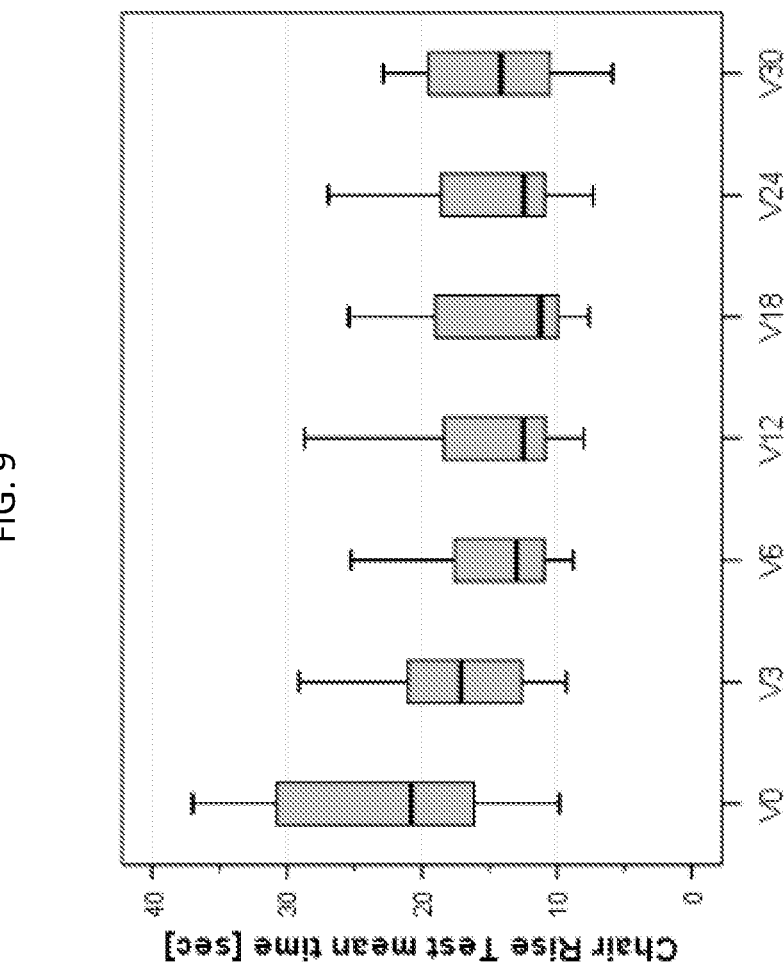
FIG. 9 is a graph showing repeated chair rise test data as in FIG. 3D to 30 months.

At baseline, eight patients were able to hold the tandem stand for 10 seconds. The two patients who were not able to complete the task were able to do so after 12 months of treatment. One patient who was able to complete the task at baseline was unable to do so after 12 months of treatment. 30 month data is shown in FIG. 9.

Additional Physiotherapy

Additional physiotherapy was also investigated for effects. Data were available in 16 patients; out of those there were 15 patients receiving physiotherapy, 8 patients receiving massage, 5 patients receiving manual therapy, 4 patients receiving thermotherapy, and 2 patients received lymphatic drainage (see Table 12).

Regarding walking ability, 13 patients out of 21 (61.9%) needed assistance for walking and 8 patients (38.1%) were able to walk unassisted at baseline.

At month 3 there were 8 patients (38.1%) needing assistance for walking and 11 patients (52.4%) were able to walk unassisted. Data were missing in 2 patients.

At month 6 and month 12 there were 6 patients (28.6%) needing assistance for walking and 14 patients (66.7%) were able to walk unassisted. Data were missing in 1 patient.

At month 18 there were 4 patients (19.0%) needing assistance for walking and 12 patients (57.1%) were able to walk unassisted. Data were missing in 5 patients.

At month 24 there were 5 patients (23.8%) needing assistance for walking and 11 patients (52.4%) were able to walk unassisted. Data were missing in 5 patients.

At month 30 there were 5 patients (23.8%) needing assistance for walking and 9 patients (42.9%) were able to walk unassisted. Data were missing in 7 patients. A summary of assistive devices used is shown in Table 12.

Fourteen patients out of 21 stated that they participated in sports; 4 patients reported participation rarely, 8 patients reported participation at least once a week, and 2 patients reported participation at least twice a week.

TABLE 12

Assistive devices used for walking

| | Visit | | | | | | | | | | | | | |
| | Baseline | | Month 3 | | Month 6 | | Month 12 | | Month 18 | | Month 24 | | Month 30 | |
| Device | N | % | N | % | N | % | N | % | N | % | N | % | N | % |
|---|---|---|---|---|---|---|---|---|---|---|---|---|---|---|
| Crutches | 8 | 38.1 | 4 | 19.0 | 4 | 19.0 | 2 | 9.5 | 1 | 4.8 | 1 | 4.8 | 1 | 4.8 |
| Walker | 1 | 4.8 | 1 | 4.8 | 1 | 4.8 | 1 | 4.8 | 0 | 0 | 2 | 9.5 | 1 | 4.8 |
| Wheelchair | 4 | 19.0 | 3 | 14.3 | 1 | 4.8 | 3 | 14.3 | 3 | 14.3 | 1 | 4.5 | 2 | 9.5 |
| Walking stick | 0 | 0 | 0 | 0 | 0 | 28.6 | 0 | 0 | 0 | 0 | 1 | 4.8 | 1 | 4.8 |
| | | | | | | | | | | | | | | |
| Total | 13 | 61.9 | 8 | 38.1 | 6 | 0 | 6 | 28.6 | 4 | 19.0 | 5 | 23.8 | 5 | 23.8 |
| Missing | 8 | 38.1 | 13 | 61.9 | 15 | 71.4 | 15 | 71.4 | 17 | 81.0 | 16 | 76.2 | 16 | 76.2 |

Grip Strength (Dominant Hand)

Grip strength measurements were available for 12 of the 14 patients at all timepoints. Median (IQR) grip strength was 22.7 (11.6-25.3) kg at baseline and 22.5 (14.3-25.4) kg at 12 months of treatment. At 3 months and 6 months of treatment median (IQR) grip strength was 22.8 (12.4-25.1) kg and 22.7 (13.6-25.7) kg respectively. Although changes were significant at 6 months (p=0.031) and 12 months of treatment (p=0.048) compared with baseline, the change corresponded to just a 1% improvement. The effect size was small, and changes are therefore unlikely to be clinically significant.

A statistically significant change in grip strength of the dominant hand could be observed when comparing baseline to month 6 (p=0.033), to month 18 (p=0.008), to month 24 (p=0.015), and to month 30 (p=0.028). At month 3 and 23, the difference was not statistically significant.

Figures 11A, 11B:
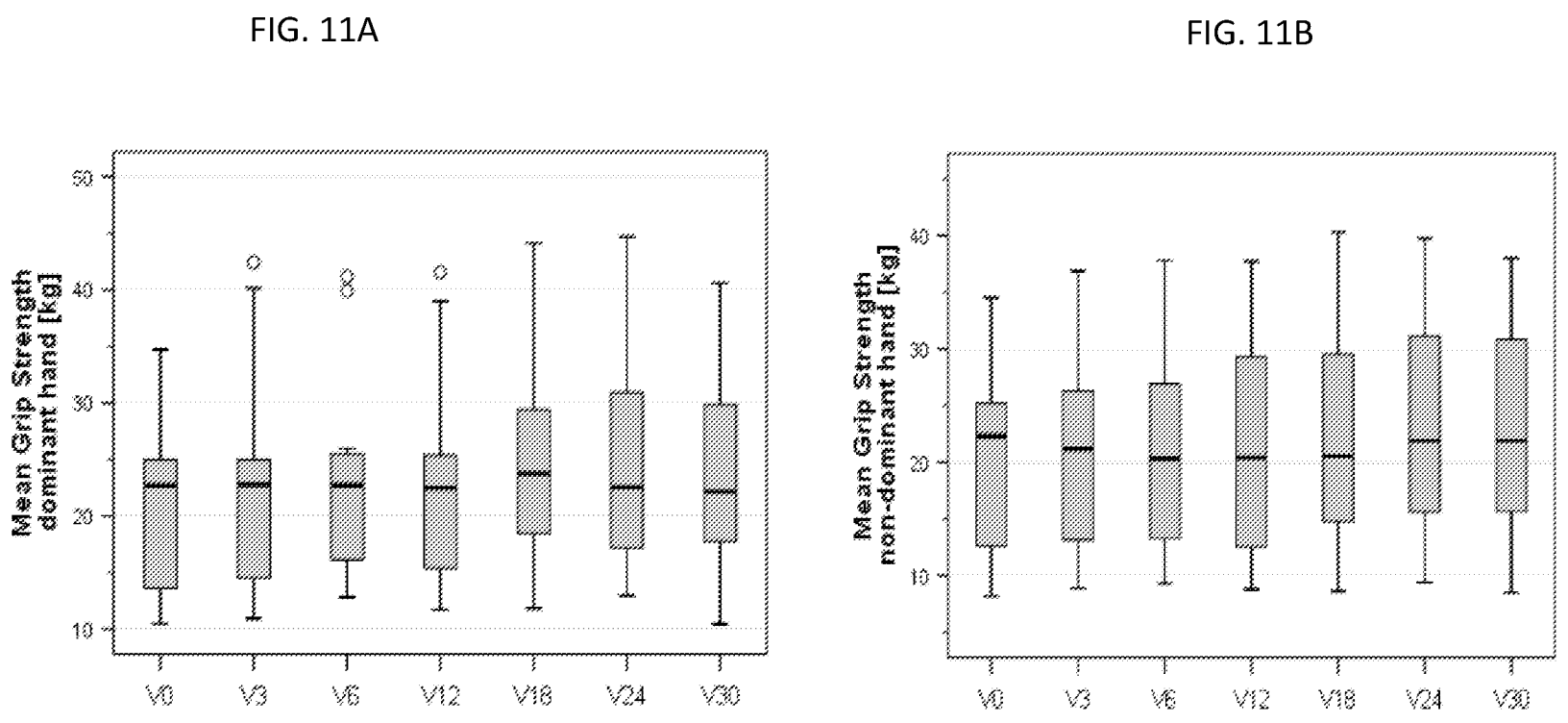

In all patients, there was an increase in grip strength of the dominant hand in 10 patients at month 3 and month 12, in 13 patients at month 6 and 18, in 11 patients at month 24, and again in 10 patients at month 30. In 9 patients at month 3 and 12, in 6 patients at month 6, in 2 patients at month 18, in 4 patients at month 24 and in 3 patients at month 30 there was a worsening of grip strength (FIGS. 11A and 11B).

Lower Extremity Functional Scale (LEFS)

Figure 4B:
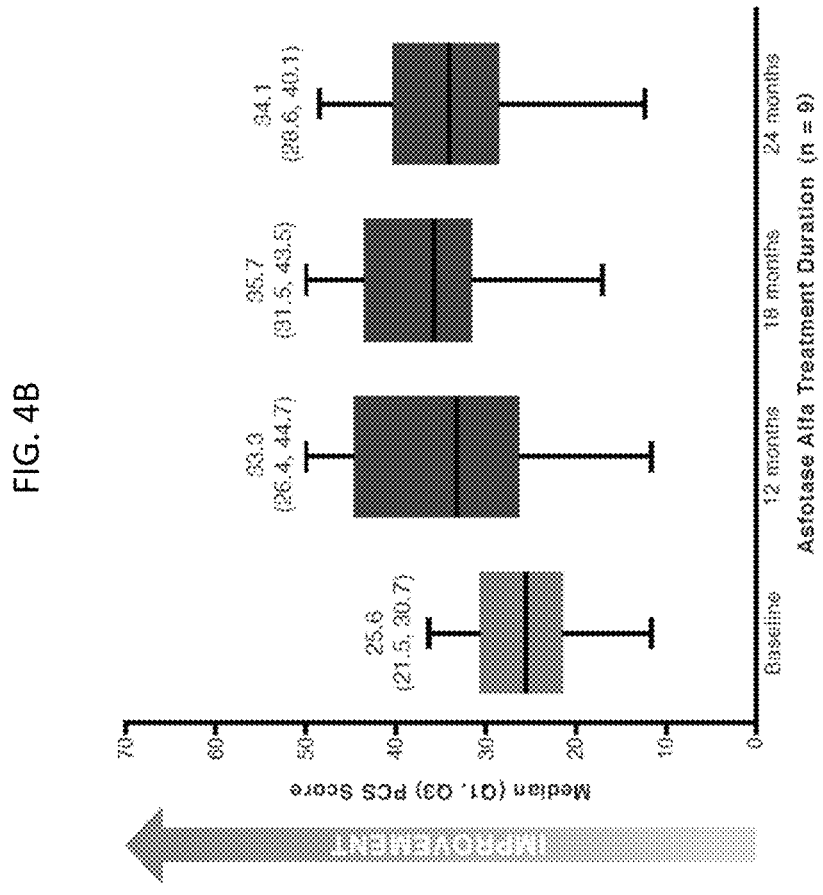
FIGS. 4A-4D are a set of graphs showing secondary outcome measures of patient-reported physical function and burden of disease as assessed by the LEFS (FIG. 4A), SF-38v2 (FIGS. 4B and 4C), and pain intensity questionnaire (FIG. 4D) among adults with pediatric-onset HPP treated with asfotase alfa for pediatric-onset HPP at baseline, 12, 18, and 24 months of treatment. *p<0.05 vs baseline. The lower and upper boundaries of blue boxes represent the 25th and 75th percentiles, respectively. The horizontal black lines represent the median and whiskers represent the maximum and minimum values. LEFS score (n=10), PCS (n=9), MCS (n=9), pain intensity questionnaire: baseline (n=13), 3 months (n=11), 8 months (n=11), 12 months (n=13), 24 months (n=5). HPP=hypophosphatasia; LEFS=Lower Extremely Functional Scale; MCS=Mental Component Summary; PCS=Physical Component Summary; SF-38v2=38-item Short-Form Health Survey version 2.
Figure 4A:
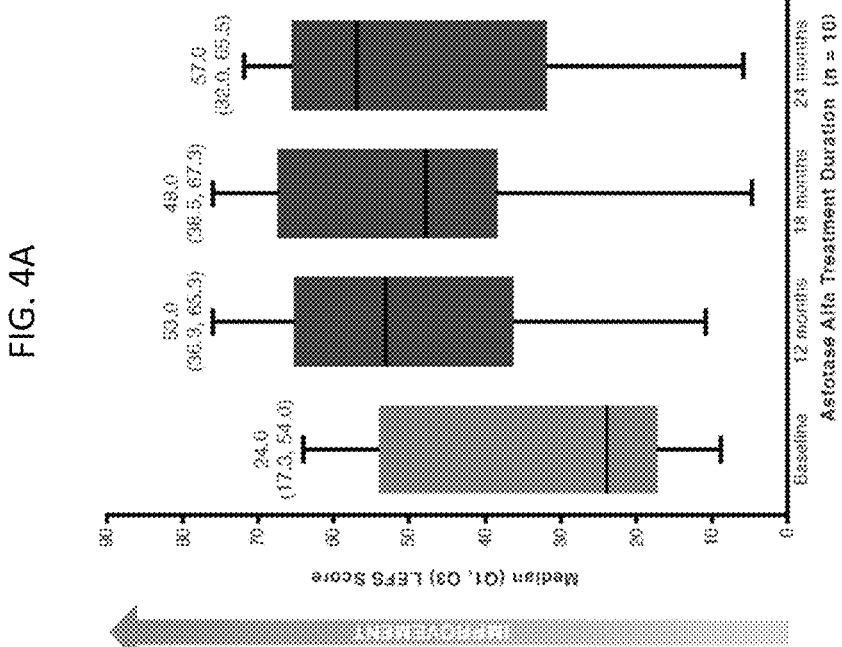

Ten of the 14 patients included in this study had LEFS data for all timepoints. At baseline, median (IQR) LEFS score was 24 (17-54) points, which increased to 53 (36-65) points at 12 months of treatment (FIG. 4A). The change in score between baseline and 12 months of treatment was significant (p=0.002) and corresponded to a 121% improvement, which indicates an improvement in the ability to carry out day-to-day activities. Median (IQR) LEFS score was 44 (31-56) points at 3 months of treatment and 52 (36-63) points at 6 months of treatment (p=0.009 and p=0.010 respectively, compared with baseline).

Significant differences in LEFS scores were observed from baseline to 12, 18, and 24 months (p=0.002, p=0.004, and p=0.004, respectively). Early improvements in median LEFS scores at 12 months remained stable from 12 to 24 months of treatment (p=0.813).

Figure 14:
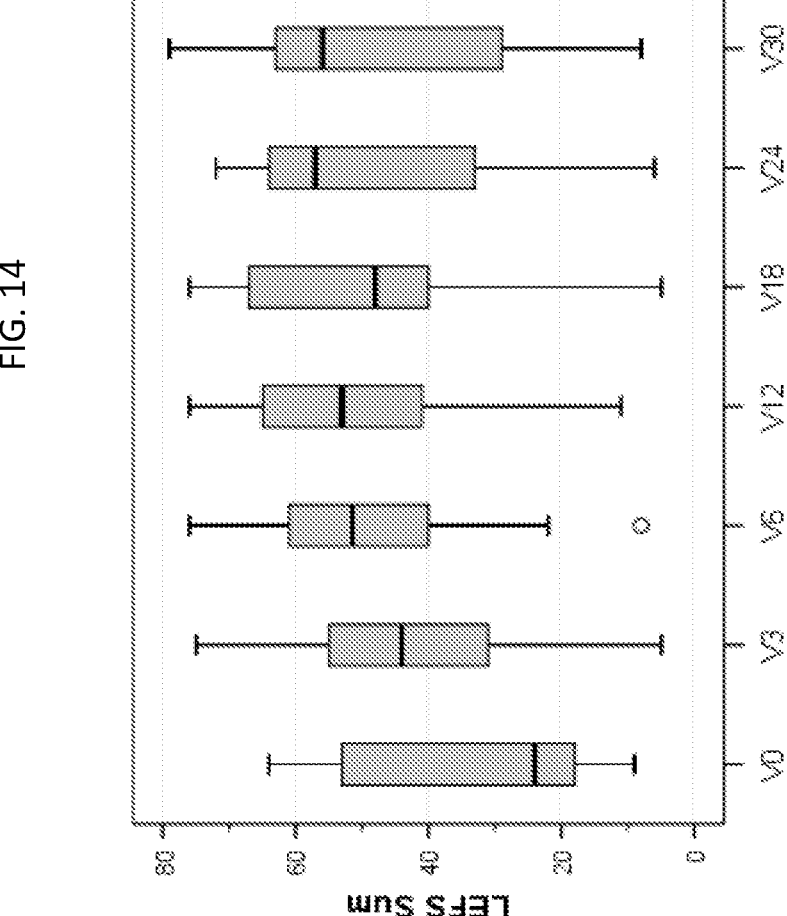
FIG. 14 is a graph showing LEFS scores as in FIG. 4A to 30 months.

The median as well as the mean LEFS sum score increased strongly at all visits compared to baseline. The increase in the LEFS sum score was significant at all timepoints tested (3, 6, 12, 18, 24, and 30 months) compared to baseline (Wilcoxon signed ranks test, p=0,005, p=0.001, p=0.000, p=0.002, p=0.002, and p=0,006, respectively) (FIG. 14).

Health Related Quality of Life and Pain

36-Item Short-Form Health Survey Version 2

Figure 4D:
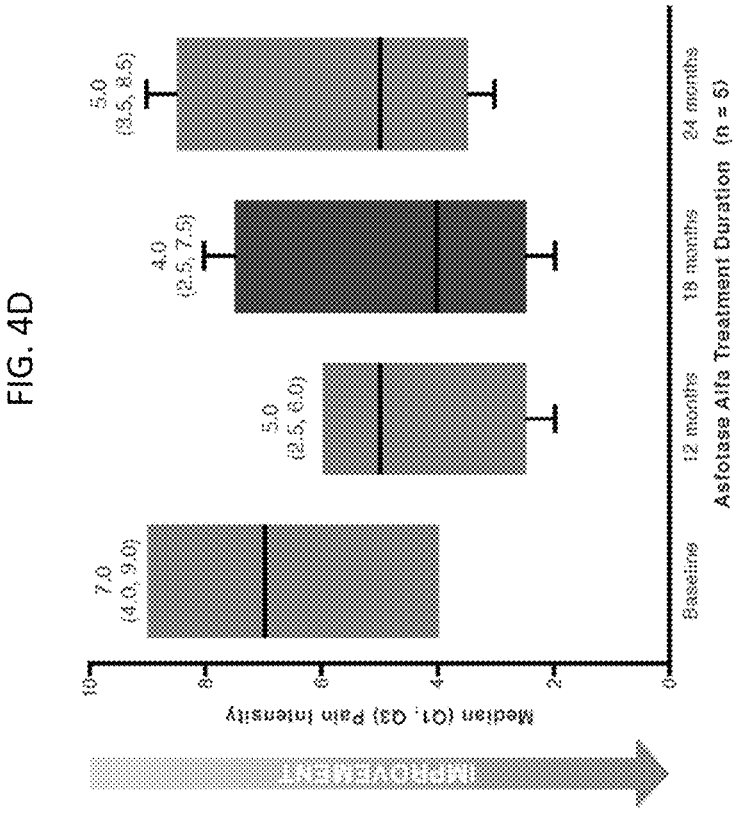
Figure 4C:
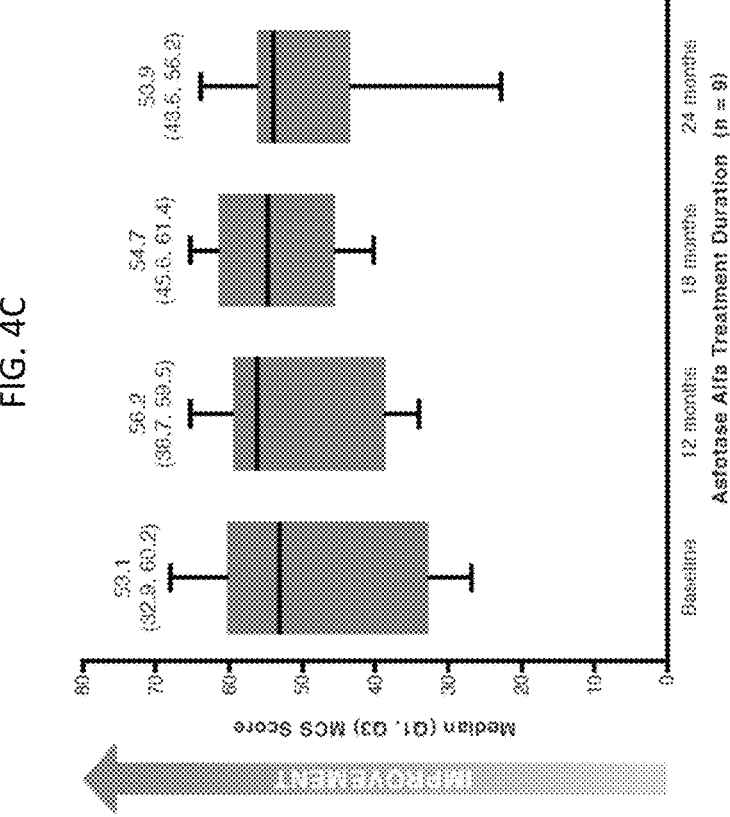

In total, 9 patients completed the SF-36v2 at all four time points. At baseline, the median (IQR) Physical Component Summary (PCS) score was 26 (21-31), which increased to 33 (26-45) at 12 months of treatment (p=0.010) (FIG. 4B); a 27% improvement. Changes were also significant between baseline and 3 months (p=0.028). The median (IQR) Mental Component Summary (MCS) score was 53 (33-60) at baseline, and 56 (39-60) at 12 months of treatment (FIG. 4C); an improvement of 5%. No statistically significant changes were observed at any of the time points compared with baseline for the MCS score.

Figure 12:
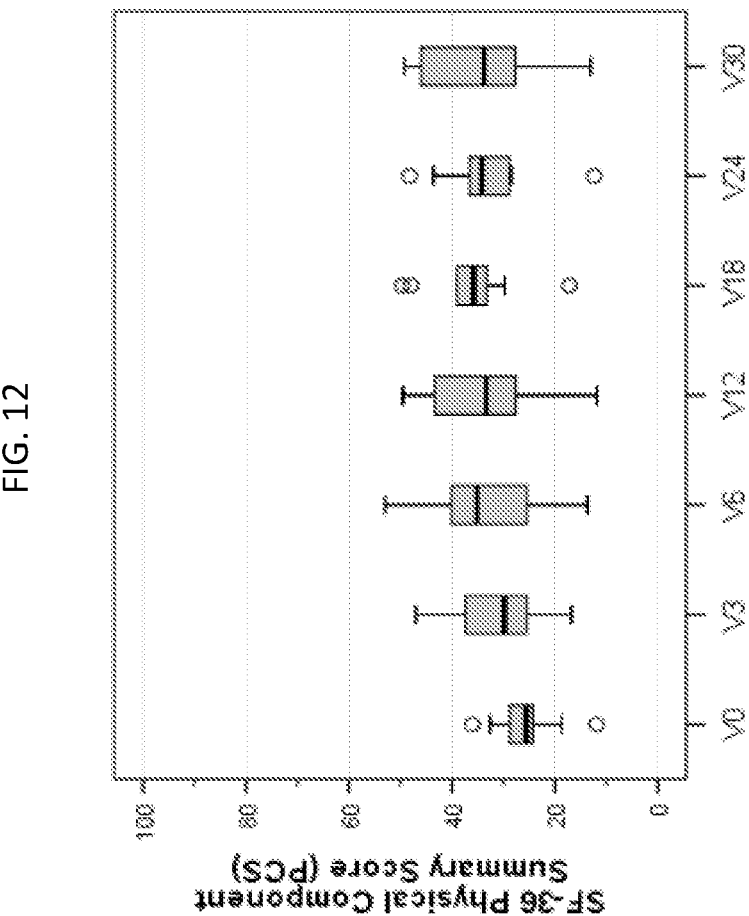
FIG. 12 is a graph showing SF-38v2 (PCS) scores as in FIG. 4B to 30 months.

Significant differences in PCS scores were observed from baseline to 12, 18, and 24 months (p=0.010, p=0.003, and p=0.003, respectively). Early improvements in SF-36v2 PCS scores at 12 months remained stable from 12 to 24 months of treatment (p=0.422). 30-month PCS scores are shown in FIG. 12 and were similar to 24 months.

No significant differences in MCS scores were observed from baseline to 12, 18, and 24 months (p=1.000, p=0.131, and p=0.424). Median SF-36v2 MCS scores were similar at 12 and 24 months of treatment.

Pain

Information on categorical prevalence of pain (categorized as never, rarely, sometimes, frequently, or persistently) was available for all 14 patients at baseline, for 12 patients at 3 months and 6 months and for 13 patients at 12 months. Except for one patient at baseline, all patients reported to be affected by pain at any given time point. At baseline, 9/14 patients (64%) reported experiencing persistent or frequent pain; this proportion decreased to 3/12 patients (25%) at 6 months, and 5/13 patients (38%) at 12 months. Data on pain intensity were available for 13 patients at baseline, 11 patients at 3 months and 6 months, and for 13 patients at 12 months; if pain was present, its intensity was quantitated using a 10-item Likert scale (1=minimal pain, 10=maximum possible pain). Median (IQR) pain intensity at baseline was 6 (4-8.25) points, which decreased to 5 (4-6) points at 12 months of treatment (FIG. 4D); a 17% improvement. At 3 months and 6 months of treatment, median (IQR) pain intensity was 5 (4-7) points and 4 (3.5-5.75) points respectively. Changes in median pain intensity from baseline to 3 months and 12 months of treatment were not statistically significant; however, a significant decrease in pain intensity compared with baseline was observed at 6 months of treatment (p=0.036).

Twelve patients had pain medication data available at baseline; all of them were using pain medication before initiating asfotase alfa treatment. Eight of these patients used pain medications daily, and six patients used a combination of pain medications. At 6 months of treatment, two of these patients were able to discontinue use of pain medication; one of these patients was not using pain medication at 12 months. Over the course of the study, four patients reduced their use of pain medication from daily use to an on-demand basis.

A statistically significant reduction in pain level was observed at 18 months (p=0.011); however, the reduction in pain level at 12 months (p=0.139) and 24 months (p=0.380) was not statistically significant. Changes in pain level were variable between 12 and 24 months.

Figure 13:
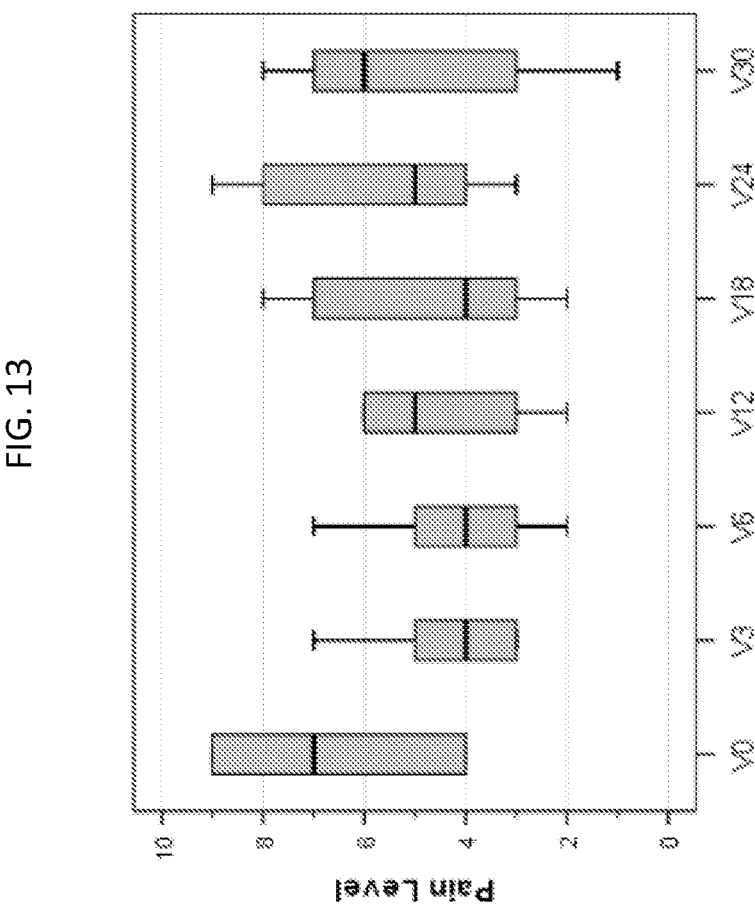
FIG. 13 is a graph showing pain levels as in FIG. 4D to 30 months.

At 30 months, it was noted that the number of patients reporting pain decreased over time for almost all pain locations except forearm (FIG. 13).

Injection Site Reactions and Safety Reporting

Retrospective assessment of available patient records and longitudinal photo documentation of injection sites and injection site reactions showed that half of the patients (n=7) self-administered asfotase alfa injections, and half had their partner or a friend administer the drug.

Although patients were advised to rotate their use of four subcutaneous injection sites including abdomen, thigh, upper arm and gluteal area, only one patient continually used all injection sites. Eight patients used 3 different sites; three patients used 2 sites; and two patients tolerated injections only in a single injection site (one used the abdomen; one used the gluteal area).

In total, 11 of the 14 patients noted reddening and/or tenderness at injection sites with variable intensity and duration at some time during the first 3 months of treatment; this increased to 13 patients by 12 months of treatment. Affected injection sites were the abdomen (n=12), thighs (n=4) and upper arm (n=3). Comparing available photographs over the course of the study revealed that five patients exhibited faint initial signs of soft tissue distension during the first 3 months of treatment, including bulging of subcutaneous fat tissue suggesting lipohypertrophy; upon palpation no bulky fat masses were identified, but rather sagging of the skin suggesting dystrophy of the subcutaneous fat tissue providing insufficient suspension for overlying skin. Of the 11 women included in this study, such alterations were visible at the abdomen in nine of these patients at 12 months of treatment; all of these patients had extensive abdominal fat tissue before treatment. None of these soft tissue distensions receded over time; nevertheless, these findings did not lead to treatment interruption or termination. No tissue distension was observed at any injection sites of the two women who were not obese (one of whom didn't inject in the abdomen). No relevant tissue distension was seen in men, even though two of them had extensive abdominal fat tissue.

In addition to injection site reactions a total of 46 AEs were recorded in the patients being treated with asfotase alfa for 12 months; all patients experienced at least one AE. The majority of these events (n=33) were not, or were unlikely to be, related to asfotase alfa treatment; they were rather associated with underlying disease and/or comorbidities, such as degenerative disease of the spine, lower back pain/lumbago, knee osteoarthritis, myogelosis (muscle tension/stiffness), greater trochanteric pain syndrome, and skin irritation. The 13 AEs reported as possibly related to treatment with asfotase alfa were fatigue (n=2), weight gain (n=2), headache (n=2), back pain, increase in pain, performance loss in daily activities, insufficiency fracture, raised intraocular pressure, small bowel ileus, and skin irritation (n=1 each).

Discussion

This study of a real-world cohort suggests that asfotase alfa is effective in improving physical functioning and HRQoL in adults with pediatric-onset HPP. The study also highlights the relevance of specific assessment tools to evaluate the effectiveness of treatment and monitoring improvements in patients over time.

More females (n=16) than males (n=5) were part of this 30-months analysis. Mean age in females was 52.0 years, and mean age in males was 38.4 years. Mean BMI was 30.0 kg/m2, range 18.0-50.5 kg/m2 at baseline. There was no significant change between baseline and V3, V6 or V12, and V18, but there was a significant increase in BMI when comparing V0 vs V24 and V30 with p=0.003 each. In addition, a significant increase in weight could be noted when comparing V0 vs V24 and vs V30 with p=0.002 each.

Assessment of physical constitution revealed significant changes in phase angle (significant increase at V18 with p=0.002), nutrition body cell mass (significant decrease at V12 with p=0.044 and at V18 with p=0.023), nutrition muscle mass (significant increase at V18 with p=0.034), and nutrition fat mass (significant increase at V18 with p=0.039, V24 with p=0.028 and V30 with p=0.037).

In the 6MWT, the observed changes in walking distance were not statistically significant for V18 and V30, however the change was statistically significant at all other visits (V3, p=0.012; V6, p=0.004; V12, p=0.002, V24, p=0.019). Regarding the use of assistive devices at V18 and V24 (18 and 24 months), the number of patients needing assistive devices decreased; 3 patients (18.8%) out of 16 needed assistive devices; no patient worsened during the course of the study.

In 11 patients there was an improvement in the 4 m walk test speed at V3, 13 patients improved at V6 (they were faster), 14 patients improved at V12, 8 patients improved at V18, 10 patients improved at V24 and in 9 patients an improvement could be observed at V30 compared to baseline. Median walking speed increased significantly at all visits, except V18: V3 (p=0.021), V6 (p=0.008), V12 (p=0.001), V24 (p=0.010), and V30 (p=0.012).

In the Chair Rise Test, almost all patients showed an improvement; time to rise was shorter at all visits compared to baseline with the exception of 1 patient at V3, who worsened. Results were statistically significant when comparing median time at baseline against median time at all visits V3, V6, V12, V18, V24 and V30 with p=0.002, p=0.001, p=0.001, p=0.008, p=0.005 and p=0.008, respectively.

The decrease in TUG duration was statistically significant at all visits V3, V6, V12, V18, V24 and V30 compared to baseline with p=0.004, p=0.002, p=0.001, p=0.012, p=0.008, and p=0.028, respectively. Eleven patients improved (time shortened) at V3, 13 patients improved at V6, 14 patients improved at V12, 8 patients improved at V18, 9 patients approved at V24, and 8 patients improved at V30 compared to baseline. At V3 in 3 patients and at V6, V24 and V30 in 1 patient, the TUG duration was longer.

A statistically significant change in grip strength of the dominant hand could be observed when comparing baseline to V6 (p=0.033), to V18 (p=0.008), to V24 (p=0.015), and to V30 (p=0.028). At V3 and V12, the difference was not statistically significant. The improvement of grip strength of the non-dominant hand was statistically significant only when comparing baseline vs V24 with p=0.011.

Data related to the overall self-reported health perception were not consistent but changed across visits. For example, at V3 versus baseline an improvement in the overall self-reported health perception could be recorded in 12 patients, in 5 patient there was no change and 1 patient worsened. At V18 eight patients reported an improvement, 3 patients felt no change and 2 patients said their health status had worsened. At V30, there was an improvement in 6 patients, in 3 patients there was no change and 4 patients felt worse.

There was a numerical improvement of the item physical functioning at all visits compared to visit 0 and this improvement was statistically significant with p=0.002, p=0.001, p=0.001, p=0.003, p=0.005, and p=0.005, respectively.

There was again a numerical improvement of the item physical role functioning at V6, V12 and V18 compared to visit 0 and this improvement was statistically significant (p=0.009, p=0.036, p=0.016, respectively).

The improvement in the median bodily pain subscale was statistically significant when comparing baseline to V3, V6, V12, and V18 with p=0.044, p=0.030, p=0.002, and p=0.027, respectively.

A significant increase (improvement) in health perception could be shown between visit 0 and V3, V6, V18, V24 and V30 with p=0.013, p=0.001, p=0.004, p=0.011, and p=0.023, respectively but not at V12

An improvement in vitality could be shown in 14, 15, 13, 11 and 8 patients at the respective visit V compared to baseline. This improvement in vitality was statistically significant when comparing baseline versus visits V3, V6, V12, V18 and V24 with p=0.006, p=0.001, p=0.013, p=0.005, and p=0.036, but not at V30.

A significant improvement between visit 0 and V6, V12, and V18 (p=0.002, p=0.014, p=0.007) could be demonstrated. At those visits, 12 out of 17 patients (V6), 12 out of 18 patients (V12), and 10 out of 14 patients (V18) reported an improvement in social functioning.

There was a statistically significant improvement in mental health as reported by 13 patients out of 18 each at V6 and V12, and in 11 patients out of 14 at V18 compared to baseline (p=0.024, p=0.014, and p=0.048, respectively).

There was a significant improvement in the physical components summary score at all visits compared to baseline (p=0.003, p=0.006, p=0.002, p=0.003, and p=0.001). In contrast, the change related to the mental component summary scores was not statistically significant at any visit.

The median as well as the mean LEFS sum score increased strongly at all visits compared to baseline. The increase in the LEFS sum score was significant at all timepoints tested compared to baseline (p=0.005, 0.001, p=0.000, p=0.002, p=0.002, and p=0,006).

Individual pain questionnaire: The decrease in pain level was statistically significant (p=0.015 and p=0.027) when comparing baseline against V6 and V18. In addition, it could be noted that the number of patients reporting pain decreased overtime for almost all pain locations except forearm.

Analgesics were taken by almost all patients throughout the course of the study, and up to 4 different analgesics were taken.

From the results presented herewith, asfotase alfa was shown to be effective over the course of the study in improving physical performance as well as in increasing QoL in most patients.

Assessments of physical function and HRQoL in this study population before initiation of asfotase alfa treatment indicate a high disease burden in adult patients with pediatric-onset HPP, compared with healthy adult populations of a similar age. For example, the mean±SD 6MWT distance that patients achieved at baseline in this study was considerably less than in a population of 444 healthy adults (237±223 m vs 571±90 m, respectively). Similarly, median TUG test time at baseline was longer than that observed in a cohort of healthy adults in their 50s (14.4 s vs 9.9 s, respectively); as was median grip strength (22.7 kg in this study at baseline vs 27 kg [women] and 46 kg [men] in a healthy North American and European population of a similar age). Median PCS score on the SF-36v2 test at baseline was also substantially lower than is observed in that country's general population (26 vs 49, respectively); however, baseline median MCS scores in these populations were not remarkably different.

Of the primary outcome measures of physical function (6MWT, TUG test, SPPB and grip strength), both the 6MWT and TUG, as well as two of the three components of the SPPB, showed statistically significant improvements from baseline to sometime during 12 months of treatment, which showed the effectiveness of asfotase alfa in improving the functional health of adult patients with pediatric-onset HPP. Minimum clinically important differences (MCIDs) for adults with HPP have been established for the 6MWT (31 m); in this study, the median 6MWT distance increased by a clinically meaningful 39 m at 6 months, and 53 m at 12 months of treatment compared with baseline. Although improvements observed by 6 months were not significant, statistically significant improvements were noted at 12 months. Similarly, usual gait speed increased during treatment and this improvement reached statistical significance at 12 months of treatment. In addition, improvements in physical function were observed in the TUG test time and the chair rise test. Time to perform these tests decreased significantly by as early as 6 months of treatment for the TUG test, and 3 months of treatment for the repeated chair rise test.

Grip strength has been recommended as a measure of muscle strength in pediatric patients with HPP, and it has previously been used in studies of pediatric cohorts; however, evidence of its use as a measure in adult populations is scarce and its usefulness is uncertain. Changes in grip strength observed during the course of treatment in this study were not clinically significant, and not as substantial as improvements in hip extensor and hip abductor strength that were reported in a clinical study of patients receiving asfotase alfa. Assessing muscle strength in these patients is likely biased by various confounding factors including pain and bone and joint issues. Therefore, it remains to be determined how best to measure muscular force and performance in these patients.

Statistically significant improvements were also recorded on the LEFS, the secondary outcome measure of physical function in this study. LEFS score increased significantly by as early as 3 months of asfotase alfa treatment and was sustained at all follow-up timepoints compared with baseline. These increases were substantially more than the MCID of 9 points calculated by Binkley et al for a population of patients with lower-extremity musculoskeletal dysfunction, and those observed in a clinical trial population of adults receiving asfotase alfa over a similar timeframe, and showed an improvement in patients' ability to carry out day-to-day tasks.

Improvements in physical well-being were also reflected by the significant improvements in the secondary outcome measures of HRQoL. Improvements in median SF-36v2 PCS score during the course of the study were statistically significant at 3 months and 12 months of asfotase alfa treatment compared with baseline. This indicates an overall improvement in physical health, comprehensively assessing domains of physical functioning, physical role functioning, bodily pain and general health. Although the median MCS score (which encompasses measures of vitality, social functioning, emotional role functioning and mental health) also increased slightly at all time points compared with baseline, this was not significant. Given that several studies have described the mental and emotional impact of HPP on adult patients, the similarity in the MCS scores observed among the general population and this study cohort at baseline suggest that the SF-36v2 may not be an accurate measure of mental well-being in patients with HPP.

The negative impact of pain on HRQoL is well-established. All patients included in this study had experienced pain; however, although median pain intensity reported across the cohort decreased significantly by 6 months of asfotase alfa treatment, pain intensity increased again by 12 months of treatment. Given that marked improvements were observed in physical function during this timeframe, it is possible that this may be owing to patients becoming more active during the course of their treatment. A 5-year study of the efficacy of asfotase alfa in adult and adolescent patients with HPP found that greater reductions in pain levels were observed after 5 years of treatment; therefore, it is also possible that the follow-up period in this interim analysis was too short to observe any meaningful decrease in pain.

Patient perception of overall pain may also change overtime and this assessment tool may not be sufficiently specific to observe consistent changes in pain associated with HPP in adults. A similar frequency of AEs and safety events were reported in the current study as observed in clinical trials, in which asfotase alfa was well tolerated; no new safety signals emerged from this study. Injection site reactions appear to be quite common, specifically reddening and tenderness at injection sites. In addition, soft tissue alterations at abdominal injection sites, including lipodystrophy with skin sagging resembling lipohypertrophy are common and women with extended abdominal fat tissue appear to be prone to develop these.

Together, these results indicate that asfotase alfa is an effective treatment for improving physical functioning and HRQoL of adult patients with HPP, and demonstrate a favorable safety profile.

Several of the physical function and HRQoL assessments used in this study have been recommended for the treatment monitoring of adult patients with HPP, including the 6MWT and SF-36v2. Results of this study suggest that specific measures of physical function and HRQoL used in this analysis, including the 6MWT, TUG test, the repeated chair rise test of the SPPB, the LEFS and the PCS component of the SF-36v2, can and should be used to measure the effectiveness of asfotase alfa, some as early as three months after treatment initiation. Of these assessments, the LEFS showed the largest percentage improvement between baseline and 12 months of treatment in this patient population, indicating that LEFS may be the most suitable scale for evaluating treatment effectiveness with regards to functional performance in adult patients. These tests should be considered by clinicians as part of routine practice to monitor early treatment response in adults with HPP, especially because they are practical and easy to implement in a clinical environment with minimal technical equipment and training. These measurements can also be helpful to monitor long-term effectiveness of treatment, e.g., monitoring patients on treatment for more than 12 months.

In addition to these data on validated assessments of physical function and HRQoL, all 14 patients included in this study notably had a history of dental abnormalities. This highlights the importance of good dental networks within communities, to ensure that diseases of bone metabolism (including HPP), are recognized early and appropriate follow-up care can be implemented. Such an approach is especially important considering that dentists may often be among the first healthcare providers in the clinical pathway for patients with HPP and other diseases of bone metabolism.

Additionally, 53% of the patients included in this study had a c.571G>A mutation of the ALPL gene. While diligent assessment of familial history did not reveal any kinship among participants, this could not be ruled out because a haplotyping approach was not applied. Nevertheless, a similar proportion of individuals (55%) were found to carry this mutation in a comparable HPP cohort, confirming that this mutation is common among HPP patients of European ancestry. These results establish a starting point of how to monitor treatment in these patients, specifically what can be expected regarding treatment effectiveness and clinical improvement and what to focus on to reduce adverse events.

CONCLUSION

These data from a real-world cohort of adult patients with pediatric-onset HPP suggest that asfotase alfa can be effective in improving physical functioning and HRQoL, and details the relevance and suitability of specific practical assessment tools, including the 6MWT, the repeated chair rise component of the SPPB, the TUG test, the LEFS and the PCS component of the SF-36v2 to evaluate the effectiveness of asfotase alfa and monitor improvements in patients over time.

A 30-month analysis of this non-interventional study evaluated the data of routine application of asfotase alfa in patients with pediatric onset HPP in routine clinical practice. Effectiveness and safety were observed in these clinical trial results.

This study suggests that patients treated with asfotase alfa showed an improvement in physical performance (6MWT, 4 m Walk test speed, chair rise test, TUG, grip force of the dominant hand). There was also an improvement in QoL measured with the SF36 questionnaire and the LEFS that was statistically significant. Furthermore, pain levels and the intake of analgesics decreased. Finally, it was noted that the asfotase alfa dose could be reduced in most of the patients.

Overall, the results from the physical performance tests as well as from the QoL questionnaires suggest effectiveness of the treatment. Furthermore, these assessment tools can also be used to assess treatment timing, such as when to treat or when treatment regimens need to be modified to improve effect or to reduce treatment dose without loss of improvement.

Example 11. Monitoring Treatment of an Adult HPP Patient with Painful Lower Limbs An adult male subject presents with an elevated inorganic pyrophosphate (PPi) concentration of about 5.82 µM, an average BOT-2 strength score of less than 10, and a TUG test score of about 14.4. The subject is 46 years old and is experiencing painful lower limbs and gait disturbance. The subject may be diagnosed with HPP and selected for treatment. The subject can be subjected to an X-ray and a bone mineral density test, both of which may show reduced bone mineralization in the legs.

A pharmaceutical formulation containing the polypeptide of SEQ ID NO: 1 can be formulated at 0.1 mg/mL. The formulation can be injected subcutaneously into the subject once a week for 12 weeks at a dosage of 6 mg/kg/week. The subject can be evaluated for treatment efficacy after the 12-week treatment regimen. The subject may notice a reduction in bone pain and normalization of gait. The subject can be subjected to follow-up X-rays and bone mineral density tests, which may show normalization of bone mineralization relative to before treatment. The PPi concentration of the subject can be reduced to under 5 µM, his BOT-2 strength score can improve to 12, and his TUG test score can decrease to 11.3, indicative of a treatment effect by the polypeptide. The subject then discontinues treatment, or, alternatively, receives treatment if and when symptoms arise again.

OTHER EMBODIMENTS

The foregoing detailed description and examples have been given for clarity of understanding only. No unnecessary limitations are to be understood therefrom. The disclosure is not limited to the exact details shown and described, for variations apparent to one skilled in the art will be included within the disclosure defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the disclosure. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. All numerical values, however, inherently contain a range necessarily resulting from the standard deviation found in their respective testing measurements.

The complete disclosures of all patents, patent applications including provisional patent applications, publications including patent publications and nonpatent publications, and electronically available material (including, for example, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. The foregoing detailed description and examples have been given for clarity of understanding only. No unnecessary limitations are to be understood therefrom. The disclosure is not limited to the exact details shown and described, for variations apparent to one skilled in the art will be included within the embodiments defined by the claims.

The invention claimed is:

1. A method of treating a mild phenotype of hypophosphatasia (HPP) in a human subject, wherein the subject exhibits a level in mean daily activity of at least one physical metric that identifies the subject as in need of treatment for the HPP, the method comprising:
(a) administering at least one dose of a soluble alkaline phosphatase (sALP) having at least 90% sequence identity to SEQ ID NO: 1 to the subject in a first treatment phase of a treatment regimen;
(b) intermittently or continuously monitoring the subject during the first treatment phase for changes in the at least one physical metric, wherein the physical metric is monitored using a wearable device; and
(c) detecting an improvement in the at least one physical metric above a predetermined threshold of the metric and entering a first non-treatment phase of the treatment regimen during which the subject is not administered the sALP.

2. The method of claim 1, further comprising:
(d) monitoring the subject during the first non-treatment phase for a period of time for changes in the at least one physical metric;
(e) detecting a level in the at least one physical metric below the predetermined threshold of the metric;
(f) administering at least one dose of the sALP to the subject in a second treatment phase of the treatment regimen; and
(g) repeating steps (a)-(f) one or more times.

3. The method of claim 1, wherein:
(a) the HPP is juvenile-onset HPP;
(b) the subject has not been previously diagnosed with HPP;
(c) the subject was not diagnosed with HPP until adulthood; or
(d) the subject is an adult.

4. The method of claim 1, wherein:
(a) the subject has not been previously administered the sALP;
(b) the method treats or reduces the risk of bone fracture in the subject; and/or
(c) the alkaline phosphatase comprises or consists of an amino acid sequence having at least 95% sequence identity to SEQ ID NO: 1.

5. The method of claim 1, wherein
the physical metric is selected from the group consisting of Bruininks-Oseretsky Test of Motor Proficiency 2nd Edition (BOT-2), Bayley Scales of Infant and Toddler Development, 3rd Edition (BSID-III), Muscle Strength Grade, Handheld Dynamometry (HHD), Peabody Developmental Motor Scales, 2nd Edition (PDMS-2), gait analysis, short physical performance battery (SPPB), and Timed Up and Go (TUG) test.

6. The method of claim 5, wherein:
(a) the SPPB comprises a repeated chair stand test;
(b) the wearable device comprises an accelerometer; and/or
(c) the wearable device is configured to be worn on the wrist, arm, leg, or torso of the subject; and/or
(d) the wearable device tracks one or more biometric indicia selected from number of steps per day, mean heart right, highest heart rate, number of physical activity counts, mean amount of time spent at various activity levels, ratio of various activity levels, duration of various activity levels, and duration of total sleep time.

7. The method of claim 6, wherein:
(a) the various activity levels are selected from sedentary, light, moderate, and vigorous; and/or
(b) the physical metric is monitored using the wearable device for a period of at least two weeks during step (b).

8. The method of claim 1, wherein in step (c), the subject is not administered the sALP for a period of:
(a) at least 1 month;
(b) at least 6 months; or
(c) at least 1 year.

9. The method of claim 1, wherein:
(I) the sALP is administered at a dosage of:
(a) about 1 mg/kg/week to about 12 mg/kg/week;
(b) about 2 mg/kg/week to about 9 mg/kg/week;
(c) about 2.5 mg/kg/week to about 6 mg/kg/week;
(d) about 2.6 mg/kg/week, 3.6 mg/kg/week, or about 6 mg/kg/week;
(e) about 6 mg/kg/week and then lowered to a dosage of about 3.6 mg/kg week;
or (f) about 6 mg/kg/week for about 12 weeks and then lowered to a dosage of about 3.6 mg/kg/week for about 24 weeks; and/or
(II)
(a) the sALP is administered daily or weekly;
(b) the sALP is administered twice a week, three times a week, four times a week, five times a week, six times a week, or seven times a week;
(c) during step (II)(a), the sALP is administered for a treatment period of at least one month, at least two months, at least three months, at least four months, at least five months, at least six months, at least seven months, at least eight months, at least nine months, at least ten months, at least 11 months, at least 12 months, or longer; and/or
(d) the sALP is formulated in a pharmaceutical composition with at least one pharmaceutically acceptable carrier selected from the group consisting of saline, sodium chloride, and sodium phosphate, wherein the pharmaceutical composition is administered subcutaneously, intramuscularly, intravenously, orally, nasally, sublingually, intrathecally, or intradermally.

10. The method of claim 9, wherein:

(a) the at least one pharmaceutically acceptable carrier comprises 150 mM sodium chloride and 25 mM sodium phosphate; and/or (b) the pharmaceutical composition is administered subcutaneously.

11. The method of claim 4, wherein the method results in:

(a) an increase in bone healing to result in new bone at a reference point in the subject compared to the reference point in the subject before the treatment; and/or (b) an average change in bone mineral density of a reference point that is undetectable or no greater than 0.01% eight months after the administration of the sALP compared to the bone mineral density of the reference point in the subject before the treatment.

12. The method of claim 1, further comprising treating the subject with a surgical intervention.

13. The method of claim 12, wherein:

(a) the surgical intervention comprises one or more of arthrodesis, removal of bone, insertion of bone graft material, and insertion of hardware; and/or (b) the surgical intervention is selected from the group consisting of arthroscopy of the knee, shoulder, hip, ankle, elbow, or wrist, fracture and meniscectomy, shoulder arthroscopy and decompression, carpal tunnel release, knee arthroscopy and chondroplasty, removal of support implant, knee arthroscopy and anterior cruciate ligament reconstruction, knee replacement, repair of femoral neck fracture, repair of atypical femoral fracture, repair of trochanteric fracture, debridement of skin/muscle/bone/fracture, knee arthroscopy repair of one or both menisci, hip replacement, shoulder arthroscopy/distal clavicle excision, repair of rotator cuff tendon, repair fracture of radius or ulna, laminectomy, repair of ankle fracture (bimalleolar type), shoulder arthroscopy and debridement, lumbar spinal fusion, repair fracture of the distal part of radius, low back intervertebral disc surgery, incise finger tendon sheath, repair of ankle fracture (fibula), repair of femoral shaft fracture, and repair of trochanteric fracture.

14. The method of claim 1, wherein the method results in:

(a) an average increase in a Bruininks-Oseretsky Test of Motor Proficiency $2^{nd}$ Edition (BOT-2) running speed and agility score to about 9 or greater than about 9;

(b) an improvement in walking ability relative to walking ability of a subject selected from the group consisting of a healthy subject and an untreated subject with HPP;

(c) an average decrease in inorganic pyrophosphate (PPi) concentration in a plasma sample from the subject relative to PPi concentrations in a plasma sample from an untreated subject with HPP;

(d) an average decrease in pyridoxal 5'-phosphate (PLP) concentration in a plasma sample from the subject relative to PLP concentrations in a plasma sample from an untreated subject with HPP; and/or (e) an average increase in alkaline phosphatase concentration in a plasma sample from the subject relative to alkaline phosphatase concentration in a plasma sample from an untreated subject with HPP.

15. The method of claim 1, further comprising monitoring the subject during the first treatment phase for changes in at least one biochemical, quality of life, or bone metric.

16. The method of claim 15, wherein:

(a) the biochemical metric is selected from the group consisting of plasma pyrophosphate (PPi), pyridoxyl-5'phosphate (PLP), phosphoethanolamine (PEA), and alkaline phosphatase (ALP) levels; and/or (b) the quality of life metric is selected from the group consisting of EuroQol Five Dimension Questionnaire (EQ-5D), Childhood Health Assessment Questionnaire (CHAQ), Pediatric Outcomes Data Collection Instrument (PODCI), Child Health Utility Index-9D (CHU-9D), Pediatric Quality of Life Inventory (PedsQL), Lower Extremity Function Scale (LEFS), Short Form Health Survey 36 (SF-36), and Short Form Health Survey 12 (SF-12).

17. The method of claim 4, wherein the alkaline phosphatase comprises or consists of an amino acid sequence having at least 97% sequence identity to SEQ ID NO: 1.

18. The method of claim 17, wherein the alkaline phosphatase comprises or consists of an amino acid sequence having at least 99% sequence identity to SEQ ID NO: 1.

19. The method of claim 18, wherein the alkaline phosphatase comprises or consists of the amino acid sequence of SEQ ID NO: 1.

* * * * *

SEQUENCE LISTING

```
<160> NUMBER OF SEQ ID NOS: 1

<210> SEQ ID NO 1
<211> LENGTH: 726
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Synthetic Construct

<400> SEQUENCE: 1

Leu Val Pro Glu Lys Glu Lys Asp Pro Lys Tyr Trp Arg Asp Gln Ala
1               5                   10                  15

Gln Glu Thr Leu Lys Tyr Ala Leu Glu Leu Gln Lys Leu Asn Thr Asn
            20                  25                  30

Val Ala Lys Asn Val Ile Met Phe Leu Gly Asp Gly Met Gly Val Ser
            35                  40                  45

Thr Val Thr Ala Ala Arg Ile Leu Lys Gly Gln Leu His His Asn Pro
        50                  55                  60

Gly Glu Glu Thr Arg Leu Glu Met Asp Lys Phe Pro Phe Val Ala Leu
65                  70                  75                  80

Ser Lys Thr Tyr Asn Thr Asn Ala Gln Val Pro Asp Ser Ala Gly Thr
                85                  90                  95

Ala Thr Ala Tyr Leu Cys Gly Val Lys Ala Asn Glu Gly Thr Val Gly
            100                 105                 110

Val Ser Ala Ala Thr Glu Arg Ser Arg Cys Asn Thr Thr Gln Gly Asn
        115                 120                 125

Glu Val Thr Ser Ile Leu Arg Trp Ala Lys Asp Ala Gly Lys Ser Val
    130                 135                 140

Gly Ile Val Thr Thr Thr Arg Val Asn His Ala Thr Pro Ser Ala Ala
145                 150                 155                 160

Tyr Ala His Ser Ala Asp Arg Asp Trp Tyr Ser Asp Asn Glu Met Pro
                165                 170                 175

Pro Glu Ala Leu Ser Gln Gly Cys Lys Asp Ile Ala Tyr Gln Leu Met
            180                 185                 190

His Asn Ile Arg Asp Ile Asp Val Ile Met Gly Gly Gly Arg Lys Tyr
            195                 200                 205

Met Tyr Pro Lys Asn Lys Thr Asp Val Glu Tyr Glu Ser Asp Glu Lys
        210                 215                 220

Ala Arg Gly Thr Arg Leu Asp Gly Leu Asp Leu Val Asp Thr Trp Lys
225                 230                 235                 240

Ser Phe Lys Pro Arg Tyr Lys His Ser His Phe Ile Trp Asn Arg Thr
                245                 250                 255
```

```
Glu Leu Leu Thr Leu Asp Pro His Asn Val Asp Tyr Leu Leu Gly Leu
            260                 265                 270

Phe Glu Pro Gly Asp Met Gln Tyr Glu Leu Asn Arg Asn Asn Val Thr
            275                 280                 285

Asp Pro Ser Leu Ser Glu Met Val Val Val Ala Ile Gln Ile Leu Arg
        290                 295                 300

Lys Asn Pro Lys Gly Phe Phe Leu Leu Val Glu Gly Gly Arg Ile Asp
305                 310                 315                 320

His Gly His His Glu Gly Lys Ala Lys Gln Ala Leu His Glu Ala Val
                325                 330                 335

Glu Met Asp Arg Ala Ile Gly Gln Ala Gly Ser Leu Thr Ser Ser Glu
            340                 345                 350

Asp Thr Leu Thr Val Val Thr Ala Asp His Ser His Val Phe Thr Phe
            355                 360                 365

Gly Gly Tyr Thr Pro Arg Gly Asn Ser Ile Phe Gly Leu Ala Pro Met
        370                 375                 380

Leu Ser Asp Thr Asp Lys Lys Pro Phe Thr Ala Ile Leu Tyr Gly Asn
385                 390                 395                 400

Gly Pro Gly Tyr Lys Val Val Gly Gly Glu Arg Glu Asn Val Ser Met
                405                 410                 415

Val Asp Tyr Ala His Asn Asn Tyr Gln Ala Gln Ser Ala Val Pro Leu
            420                 425                 430

Arg His Glu Thr His Gly Gly Glu Asp Val Ala Val Phe Ser Lys Gly
            435                 440                 445

Pro Met Ala His Leu Leu His Gly Val His Glu Gln Asn Tyr Val Pro
        450                 455                 460

His Val Met Ala Tyr Ala Ala Cys Ile Gly Ala Asn Leu Gly His Cys
465                 470                 475                 480

Ala Pro Ala Ser Ser Leu Lys Asp Lys Thr His Thr Cys Pro Pro Cys
                485                 490                 495

Pro Ala Pro Glu Leu Leu Gly Gly Pro Ser Val Phe Leu Phe Pro Pro
            500                 505                 510

Lys Pro Lys Asp Thr Leu Met Ile Ser Arg Thr Pro Glu Val Thr Cys
            515                 520                 525

Val Val Val Asp Val Ser His Glu Asp Pro Glu Val Lys Phe Asn Trp
        530                 535                 540

Tyr Val Asp Gly Val Glu Val His Asn Ala Lys Thr Lys Pro Arg Glu
545                 550                 555                 560

Glu Gln Tyr Asn Ser Thr Tyr Arg Val Val Ser Val Leu Thr Val Leu
                565                 570                 575

His Gln Asp Trp Leu Asn Gly Lys Glu Tyr Lys Cys Lys Val Ser Asn
            580                 585                 590

Lys Ala Leu Pro Ala Pro Ile Glu Lys Thr Ile Ser Lys Ala Lys Gly
            595                 600                 605

Gln Pro Arg Glu Pro Gln Val Tyr Thr Leu Pro Pro Ser Arg Glu Glu
        610                 615                 620

Met Thr Lys Asn Gln Val Ser Leu Thr Cys Leu Val Lys Gly Phe Tyr
625                 630                 635                 640

Pro Ser Asp Ile Ala Val Glu Trp Glu Ser Asn Gly Gln Pro Glu Asn
                645                 650                 655

Asn Tyr Lys Thr Thr Pro Pro Val Leu Asp Ser Asp Gly Ser Phe Phe
            660                 665                 670
```

-continued

```
Leu Tyr Ser Lys Leu Thr Val Asp Lys Ser Arg Trp Gln Gln Gly Asn
        675             680             685

Val Phe Ser Cys Ser Val Met His Glu Ala Leu His Asn His Tyr Thr
    690             695             700

Gln Lys Ser Leu Ser Leu Ser Pro Gly Lys Asp Ile Asp Asp Asp Asp
705             710             715             720

Asp Asp Asp Asp Asp Asp
            725
```